US012497614B2

(12) United States Patent
D'Souza et al.

(10) Patent No.: US 12,497,614 B2
(45) Date of Patent: Dec. 16, 2025

(54) COMPOSITIONS AND METHODS FOR EDITING BETA-GLOBIN FOR TREATMENT OF HEMAGLOBINOPATHIES

(71) Applicant: Vertex Pharmaceuticals Incorporated, Boston, MA (US)

(72) Inventors: Sanjay D'Souza, Cambridge, MA (US); Jason West, Lexington, MA (US); Brenda K. Eustace, Boston, MA (US); Sudipta Mahajan, Boston, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 162 days.

(21) Appl. No.: 17/554,682

(22) Filed: Dec. 17, 2021

(65) Prior Publication Data

US 2022/0228142 A1 Jul. 21, 2022

Related U.S. Application Data

(60) Provisional application No. 63/126,843, filed on Dec. 17, 2020.

(51) Int. Cl.

| | |
|---|---|
| ***C12N 15/113*** | (2010.01) |
| ***A61K 40/10*** | (2025.01) |
| ***A61K 40/40*** | (2025.01) |
| ***A61P 7/06*** | (2006.01) |
| ***A61P 37/06*** | (2006.01) |
| ***C12N 9/22*** | (2006.01) |
| ***C12N 15/11*** | (2006.01) |

(52) U.S. Cl.

CPC ............ *C12N 15/113* (2013.01); *A61K 40/10* (2025.01); *A61K 40/40* (2025.01); *A61P 7/06* (2018.01); *A61P 37/06* (2018.01); *C12N 9/22* (2013.01); *C12N 15/111* (2013.01); *A61K 2239/31* (2023.05); *A61K 2239/38* (2023.05); *C12N 2310/20* (2017.05); *C12N 2750/14143* (2013.01); *C12N 2800/80* (2013.01)

(58) Field of Classification Search

CPC ....... C12N 15/113; C12N 9/22; C12N 15/111; A61P 7/06

See application file for complete search history.

(56) References Cited

U.S. PATENT DOCUMENTS

| | | | |
|---|---|---|---|
| 6,825,351 | B2 | 11/2004 | McEachern et al. |
| 6,835,731 | B2 | 12/2004 | Bridger et al. |
| 6,893,821 | B2 | 5/2005 | Raz et al. |
| 7,402,607 | B2 | 7/2008 | Smith et al. |
| 9,592,232 | B2 | 3/2017 | Charifson et al. |
| 9,944,912 | B2 | 4/2018 | Joung et al. |
| 10,526,591 | B2 | 1/2020 | Joung et al. |
| 2018/0030438 | A1 | 2/2018 | Porteus et al. |
| 2018/0100148 | A1 | 4/2018 | Vakulskas et al. |
| 2018/0142222 | A1 | 5/2018 | Sternberg et al. |
| 2018/0194782 | A1 | 7/2018 | Finlay et al. |
| 2018/0200387 | A1 | 7/2018 | Porteus |
| 2019/0010196 | A1 | 1/2019 | Durocher et al. |
| 2019/0010471 | A1 | 1/2019 | Zhang et al. |
| 2019/0177710 | A1 | 6/2019 | Lee |
| 2020/0149020 | A1 | 5/2020 | Cereseto et al. |
| 2023/0022146 | A1* | 1/2023 | D'Souza ............... C12N 15/111 |

FOREIGN PATENT DOCUMENTS

| | | | |
|---|---|---|---|
| WO | WO-03024949 | A1 | 3/2003 |
| WO | WO-2015148863 | A2 | 10/2015 |
| WO | WO-2016073990 | A2 | 5/2016 |
| WO | WO-2016154579 | A2 | 9/2016 |
| WO | WO-2017053729 | A1 | 3/2017 |
| WO | WO-2018149888 | A1 | 8/2018 |
| WO | WO-2019138082 | A1 | 7/2019 |
| WO | WO-2019185920 | A1 | 10/2019 |
| WO | WO-2020057481 | A1 | 3/2020 |
| WO | WO-2020257325 | A1 | 12/2020 |
| WO | WO-2022133246 | A1 | 6/2022 |

OTHER PUBLICATIONS

He et al., DOI: https://doi.org/10.21203/rs.3.rs-68414/v1, Publication Date: Sep. 9, 2020 (Year: 2020).*

HBB gene sequence downloaded from: https://www.ncbi.nlm.nih.gov/nuccore/V00499 (Year: 1980).*

Anzalone, A. et al. "Search-and-replace genome editing without double-strand breaks or donor DNA". Nature (Dec. 2019); 576(7785): 149-157. Epub Oct. 21, 2019.

Arnoult, N. et al. "Regulation of DNA repair pathway choice in S and G2 phases by the NHEJ inhibitor CYREN". Nature (Sep. 2017); 549(7673): 548-552. Epub Sep. 28, 2017.

Botuyan, M. et al. "Structural basis for the methylation state-specific recognition of histone H4-K20 by 53BP1 and Crb2 in DNA repair". Cell (Dec. 29, 2006); 127(7): 1361-1373.

Broxmeyer, H.E. et al. "Rapid mobilization of murine and human hematopoietic stem and progenitor cells with AMD3100, a CXCR4 antagonist". The Journal of Experimental Medicine (Apr. 18, 2005); 201(8): 1307-1318.

Calsou, P. et al. "The DNA-dependent protein kinase catalytic activity regulates DNA end processing by means of Ku entry into DNA". Journal of Biological Chemistry (Mar. 19, 1999); 274(12): 7848-7856.

(Continued)

*Primary Examiner* — Peter J Reddig
*Assistant Examiner* — Cheng Lu
(74) *Attorney, Agent, or Firm* — McNeill PLLC

(57) ABSTRACT

The disclosure features systems and methods for correcting a mutation in the human beta-globin (HBB) gene in a cell or population of cells. The disclosure also features methods of increasing repair of a DNA double stranded break (DSB) in an HBB gene by the homology-directed repair (HDR) pathway. The disclosure also features compositions for use in the methods.

24 Claims, 31 Drawing Sheets

Specification includes a Sequence Listing.

(56) References Cited

OTHER PUBLICATIONS

Canny, M.D. et al. "Inhibition of 53BP1 favors homology-dependent DNA repair and increases CRISPR-Cas9 genome-editing efficiency". Nature Biotechnology (Jan. 2018); 36(1): 95-102. Epub Nov. 27, 2017.

CAS 1169562-71-3 RN, STN, "Benzofuro[3,2-d]pyrimidin-4(3H)-one, 8-chloro-2-(2S)-2-pyrrolidinyl-,hydrochloride (1 :? ) (CA Index Name)"; entered Jul. 27, 2009, received Oct. 27, 2022, 1 page.

CAS 159182-43-1 RN, STN, "Benzenesulfonamide, 4-[[(hexylamino)carbonyl]amino]-N-[4-[2-[(2S)-2-hydroxy-3-(4-hydroxyphenoxy)propyl]amino]ethyl]phenyl]—(CA Index Name)"; entered Nov. 24, 1994, received Oct. 27, 2022, 1 page.

CAS 312756-74-4 RN, STN, "Benzamide, 4-bromo-N-(4-bromophenyl)-3-[[(phenylmethyl)amino]sulfonyl]—(CA Index Name)"; entered Jan. 4, 2001, received Oct. 27, 2022, 1 page.

CAS 503468-95-9 RN, STN, "4H-1-Benzopyran-4-one, 8-(4-dibenzothienyl)-2-(4-morpholinyl)—(CA Index Name)"; entered Apr. 18, 2003, received Oct. 27, 2022, 1 page.

CAS 912444-00-9 RN, STN, "1H-Benzimidazole-7-carboxamide, 2-[(2R)-2-methyl-2-pyrrolidinyl]—(CA Index Name)"; entered Nov. 5, 2006, received Oct. 27, 2022, 1 page.

Chapman, J.R. et al. "Playing the end game: DNA double-strand break repair pathway choice". Molecular Cell (Aug. 24, 2012); 47(4): 497-510.

Cox, D.B. et al. "Therapeutic genome editing: prospects and challenges". Nature Medicine (Feb. 2015); 21(2): 121-131. Epub Feb. 5, 2015.

De Montalembert, M. "Management of sickle cell disease". Bmj. (Sep. 8, 2008); 337.

Dever, D.P. et al. "CRISPR/Cas9 β-globin gene targeting in human haematopoietic stem cells". Nature (Nov. 2016); 539(7629): 384-389. Epub Nov. 7, 2016.

Devine, S. et al. "Rapid mobilization of functional donor hematopoietic cells without G-CSF using AMD3100, an antagonist of the CXCR4/SDF-1 interaction". Blood, The Journal of the American Society of Hematology (Aug. 15, 2008); 112(4): 990-998.

Escribano-Diaz, C. et al. "A cell cycle-dependent regulatory circuit composed of 53BP1-RIF1 and BRCA1-CtIP controls DNA repair pathway choice". Molecular Cell (Mar. 7, 2013); 49(5): 872-883.

Feng, L. et al. "RIF1 counteracts BRCA1-mediated end resection during DNA repair". Journal of Biological Chemistry (Apr. 19, 2013); 288(16): 11135-11143.

Fradet-Turcotte, A. et al. "53BP1 is a reader of the DNA-damage-induced H2A Lys 15 ubiquitin mark". Nature (Jul. 2013); 499(7456): 50-54. Epub Jun. 12, 2013.

Gene ID 3043 "HBB hemoglobin subunit beta [ *Homo sapiens* (human) ]" updated Oct. 22, 2022, 13 pages.

Gottlieb, T.M. et al. "The DNA-dependent protein kinase: requirement for DNA ends and association with Ku antigen". Cell (Jan. 15, 1993); 72(1): 131-142.

Guo, X. et al. "Acetylation of 53BP1 dictates the DNA double strand break repair pathway". Nucleic Acids Research (Jan. 25, 2018); 46(2): 689-703.

Hoban, M.D. et al. "CRISPR/Cas9-mediated correction of the sickle mutation in human CD34+ cells". Molecular Therapy (Sep. 1, 2016); 24(9): 1561-1569.

International Preliminary Report on Patentability for International Application No. PCT/US2020/038203, dated Dec. 21, 2021, 13 pages.

International Search Report and Written Opinion for International Application No. PCT/US2020/038203, mailed Nov. 17, 2020, 22 pages.

International Search Report and Written Opinion for International Application No. PCT/US2021/064085, mailed Apr. 11, 2020, 12 pages.

Invitation to Pay Additional Fees for International Application No. PCT/US2020/038203, mailed Sep. 22, 2020, 17 pages.

Ismail, I.H. et al. "SU11752 inhibits the DNA-dependent protein kinase and DNA double-strand break repair resulting in ionizing radiation sensitization". Oncogene (Jan. 2004); 23(4): 873-882. Epub Aug. 8, 2003.

Iwabuchi, K. et al. "Two cellular proteins that bind to wild-type but not mutant p53". Proceedings of the National Academy of Sciences (Jun. 21, 1994); 91(13): 6098-6102.

Izzard, R.A. et al. "Competitive and noncompetitive inhibition of the DNA-dependent protein kinase". Cancer Research (Jun. 1, 1999); 59(11): 2581-2586.

Kashishian, A. et al. "DNA-dependent protein kinase inhibitors as drug candidates for the treatment of cancer". Molecular Cancer Therapeutics (Dec. 2003); 2(12): 1257-1264. Epub Jan. 5, 2004.

Leahy, J.J. et al. "Identification of a highly potent and selective DNA-dependent protein kinase (DNA-PK) inhibitor (NU7441) by screening of chromenone libraries". Bioorganic & Medicinal Chemistry Letters (Dec. 20, 2004); 14(24): 6083-6087.

Martin, R.M. et al. "Highly efficient and marker-free genome editing of human pluripotent stem cells by CRISPR-Cas9 RNP and AAV6 donor-mediated homologous recombination". Cell Stem Cell (May 2, 2019); 24(5): 821-828.

Morton, J. et al. "Granulocyte-colony-stimulating factor (G-CSF)-primed allogeneic bone marrow: significantly less graft-versus-host disease and comparable engraftment to G-CSF-mobilized peripheral blood stem cells". Blood, The Journal of the American Society of Hematology (Dec. 1, 2001); 98(12): 3186-3191.

Noon, A.T. et al. "53BP1-dependent robust localized KAP-1 phosphorylation is essential for heterochromatic DNA double-strand break repair". Nature Cell Biology (Feb. 2010); 12(2): 177-184.

Paulsen, B.S. et al. "Ectopic expression of RAD52 and dn53BP1 improves homology-directed repair during CRISPR-Cas9 genome editing". Nature Biomedical Engineering (Nov. 2017); 1(11): 878-888. Epub Oct. 9, 2017.

Sheth, S. et al. "Sickle cell disease: time for a closer look at treatment options?". British Journal of Haematology (Aug. 2013); 162(4): 455-464.

Smith, T. et al. "Economic analysis of a randomized clinical trial to compare filgrastim-mobilized peripheral-blood progenitor-cell transplantation and autologous bone marrow transplantation in patients with Hodgkin's and non-Hodgkin's lymphoma". Journal of Clinical Oncology (Jan. 1997); 15(1): 5-10.

Tasan, I. et al. "Use of genome-editing tools to treat sickle cell disease". Human Genetics (Sep. 2016); 135(9): 1011-28. Epub Jun. 1, 2016.

Vakulskas, C.A. et al. "A high-fidelity Cas9 mutant delivered as a ribonucleoprotein complex enables efficient gene editing in human hematopoietic stem and progenitor cells". Nature Medicine (Aug. 2018); 24(8): 1216-1224; including Supplementary Information.

Weinert, B. et al. "Timed inhibition of CDC7 increases CRISPR-Cas9 mediated templated repair". Nature Communications (Apr. 30, 2020); 11(1): 1-5. Epub.

Wilson, A. et al. "Hematopoietic stem cells reversibly switch from dormancy to self-renewal during homeostasis and repair". Cell (Dec. 12, 2008); 135(6): 1118-1129.

Yoo, S. et al. "Geometry of a complex formed by double strand break repair proteins at a single DNA end: recruitment of DNA-PKcs induces inward translocation of Ku protein". Nucleic Acids Research (Dec. 1, 1999); 27(24): 4679-4686.

Yu, C. et al. "Small molecules enhance CRISPR genome editing in pluripotent stem cells". Cell Stem Cell (Feb. 5, 2015); 16(2): 142-147.

Zimmermann, M. et al. "53BP1: pro choice in DNA repair". Trends in Cell Biology (Feb. 1, 2014); 24(2): 108-117. Epub Oct. 4, 2013.

* cited by examiner

BM 16 Wks NGS

16 Wks BM NGS

COMPOSITIONS AND METHODS FOR EDITING BETA-GLOBIN FOR TREATMENT OF HEMAGLOBINOPATHIES

CROSS-REFERENCE TO RELATED APPLICATIONS

This application claims priority to U.S. Provisional Patent Application No. 63/126,843, filed Dec. 17, 2020, the contents of which are incorporated herein by reference.

INCORPORATION-BY-REFERENCE OF SEQUENCE LISTING

The contents of the file named "VTEX_003_001US_SeqListing_ST25", which was created on Jan. 3, 2022, and is 96041 bytes in size are hereby incorporated by reference in their entirety.

BACKGROUND

Hemoglobin (Hb) carries oxygen from the lungs to tissues in erythrocytes or red blood cells (RBCs). During prenatal development and until shortly after birth, hemoglobin is present in the form of fetal hemoglobin (HbF), a tetrameric protein composed of two alpha (a)-globin chains and two gamma (γ)-globin chains. HbF is largely replaced by adult hemoglobin (HbA), a tetrameric protein in which the γ-globin chains of HbF are replaced with beta (β)-globin chains, through a process known as globin switching. HbF is more efficient than HbA at carrying oxygen. The average adult makes less than 1% HbF out of total hemoglobin. The α-hemoglobin gene is located on chromosome 16, while the β-hemoglobin gene (HBB), A gamma ($\gamma^A$)-globin chain (HBG1, also known as gamma globin A), and G gamma ($\gamma^G$-globin chain (HBG2, also known as gamma globin G) are located on chromosome 11 within the globin gene cluster (i.e., globin locus).

Hemoglobinopathies include anemias of genetic origin that result in decreased production and/or increased destruction of red blood cells. These disorders also include genetic defects that result in the product of abnormal hemoglobins with an associated inability to maintain oxygen concentration. Many of these disorders are referred to as β-hemoglobinopathies because of their failure to produce normal β-globin protein in sufficient amounts or failure to produce normal β-globin protein entirely. For example, β-thalassemias result from a partial or complete defect in the expression of the β-globin gene, leading to deficient or absent HbA. Sickle cell disease (SCD) results from a point mutation in the β-globin structural gene, leading to production of an abnormal hemoglobin (HbS).

The SCD mutation is a point mutation (GAG-GTG) on HBB that results in substitution of valine for glutamic acid at amino acid position 6 (E6V) in the protein. The mutation is also referred to as an E7V mutation because it occurs at the $7^{th}$ position in the initial translation product, prior to removal of the amino-terminal methionine. The valine at position 6 of the β-hemoglobin chain is hydrophobic and causes a change in conformation of the β-globin protein when it is not bound to oxygen. This change of conformation causes HbS proteins to polymerize in the absence of oxygen, leading to deformation (i.e., sickling) of RBCs. SCD is inherited in an autosomal recessive manner, so that only patients with two HbS alleles have the disease. Heterozygous subjects have sickle cell trait, and may suffer from anemia and/or painful crises if they are severely dehydrated or oxygen deprived.

Delivery of a corrected HBB gene via gene therapy has been investigated in clinical trials. However, this approach carries at least a theoretical risk of insertional mutagenesis. Transplantation with hematopoietic stem cells from an HLA-matched allogeneic stem cell donor has been demonstrated to cure SCD, but this procedure involves risks including the possibility of graft vs. host disease after transplantation. In addition, matched allogeneic donors often cannot be identified. Thus, there is a need for improved methods of managing these and other hemoglobinopathies.

SUMMARY OF DISCLOSURE

In some aspects, the disclosure provides a system for correcting an E6V mutation in human beta-globin (HBB) in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a single guide RNA (sgRNA) comprising a spacer sequence corresponding to a target sequence adjacent a PAM, the target sequence comprising a target site within intron 1 of HBB; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a single guide RNA (sgRNA) comprising a spacer sequence corresponding to a target sequence adjacent a PAM, the target sequence comprising a target site within intron 1 of HBB; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a single guide RNA (sgRNA) comprising a spacer sequence corresponding to a target sequence adjacent a PAM, the target sequence comprising a target site within intron 1 of HBB; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In some aspects, the target site is about 70 to about 200 bp downstream the E6V mutation. In some aspects, the target site is about 90, 95, 100, 105, 110, 115, 120, 125, 130, 135, 140, 145 or 150 bp downstream the E6V mutation. In some aspects, target sequence comprises a nucleotide sequence selected from SEQ ID NO: 1 and SEQ ID NO: 49. In some aspects, the target sequence consists of the nucleotide sequence of SEQ ID NO: 1. In other aspects, the target sequence consists of the nucleotide sequence of SEQ ID NO: 49.

In some aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6.

In other aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6.

In yet other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In further aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In any of the foregoing or related aspects, the codon encoding E6 is selected from GAA and GAG. In some aspects, the nucleotide sequence of (c) comprises one or more silent mutations relative to the HBB gene.

In some aspects, the nucleotide sequence of (c) comprises a nucleotide sequence having at least 90% sequence identity to a nucleotide sequence selected from SEQ ID NO: 6 or SEQ ID NO: 19. In some aspects, the nucleotide sequence of (c) comprises a nucleotide sequence having at least 90% sequence identity to a nucleotide sequence selected from SEQ ID NO: 6, SEQ ID NO: 19 and SEQ ID NO: 56. In some aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 6. In some aspects, the nucleotide sequence of (c) comprises a nucleotide sequence having 91%, 92%, 93%, 94%, 95%, 96%, 97%, 98% or 99% sequence identity to the nucleotide sequence of SEQ ID NO: 19. In some aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 56. In other aspects, the nucleotide sequence of (c) comprises the nucleotide sequence of SEQ ID NO: 6. In yet other aspects, the nucleotide sequence of (c) comprises the nucleotide sequence of SEQ ID NO: 19. In yet other aspects, the nucleotide sequence of (c) comprises the nucleotide sequence of SEQ ID NO: 56.

In further aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence having at least 90% sequence identity to the nucleotide sequence of SEQ ID NO: 6.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence a nucleotide sequence having at least 90% sequence identity to the nucleotide sequence of SEQ ID NO: 6, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence a nucleotide sequence having at least 90% sequence identity to the nucleotide sequence of SEQ ID NO: 6, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In any of the foregoing or related aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 6. In some aspects, the nucleotide sequence of (c) comprises the nucleotide sequence of SEQ ID NO: 6.

In further aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence having at least 90% sequence identity to the nucleotide sequence of SEQ ID NO: 56.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence a nucleotide sequence having at least 90% sequence identity to the nucleotide sequence of SEQ ID NO: 56, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence a nucleotide sequence having at least 90% sequence identity to the nucleotide sequence of SEQ ID NO: 56, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In any of the foregoing or related aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 56. In some aspects, the nucleotide sequence of (c) comprises the nucleotide sequence of SEQ ID NO: 56.

In other aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence having at least 90% sequence identity to the nucleotide sequence of SEQ ID NO: 19.

In yet other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence having at least 90% sequence identity to the nucleotide sequence of SEQ ID NO: 19, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence having at least 90% sequence identity to the nucleotide sequence of SEQ ID NO: 19, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In any of the foregoing or related aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 19. In some aspects, the nucleotide sequence of (c) comprises the nucleotide sequence of SEQ ID NO: 19.

In any of the foregoing or related aspects, the nucleic acid of (c) comprises a nucleotide sequence of about 0.5 kb to about 5.5 kb in length, about 1 kb to about 5 kb, about 1.5 kb to about 4.6 kb, about 2 kb to about 4.6 kb, about 2.5 kb to about 4.6 kb, about 3 kb to about 4.6 kb, or about 3.5 kb to about 4.6 kb. In other aspects, the nucleic acid of (c) comprises a nucleotide sequence of about 4 k to about 4.6 kb. In yet other aspects, the nucleic acid of (c) comprises a nucleotide sequence of less than about 5 kb.

In some aspects, the nucleotide sequence of (c) comprises a mutation to delete the PAM.

In some aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;
(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and
(c) a recombinant vector comprising a nucleic acid for correcting the E6V mutation, the nucleic acid comprising a nucleotide sequence with at least 90% sequence identity to the nucleotide sequence of SEQ ID NO: 8.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;
(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and
(c) a recombinant vector comprising a nucleic acid for correcting the E6V mutation, the nucleic acid comprising a nucleotide sequence with at least 90% sequence identity to the nucleotide sequence of SEQ ID NO: 8, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;
(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and
(c) a recombinant vector comprising a nucleic acid for correcting the E6V mutation, the nucleic acid comprising a nucleotide sequence with at least 90% sequence identity to the nucleotide sequence of SEQ ID NO: 8, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In some aspects, the nucleotide sequence of (c) is 91%, 92%, 93%, 94%, 95%, 96%, 97%, 98%, 99%, or 100% identical to SEQ ID NO: 8.

In some aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;
(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and
(c) a recombinant vector comprising a nucleic acid for correcting the E6V mutation, the nucleic acid comprising a nucleotide sequence with at least 90% sequence identity to the nucleotide sequence of SEQ ID NO: 57.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;
(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and
(c) a recombinant vector comprising a nucleic acid for correcting the E6V mutation, the nucleic acid comprising a nucleotide sequence with at least 90% sequence identity to the nucleotide sequence of SEQ ID NO: 57, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence with at least 90% sequence identity to the nucleotide sequence of SEQ ID NO: 57, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In some aspects, the nucleotide sequence of (c) is 91%, 92%, 93%, 94%, 95%, 96%, 97%, 98%, 99%, or 100% identical to SEQ ID NO: 57.

In other aspects, the disclosure provides a system for correcting an E6V mutation in HBB in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence with at least 90% sequence identity to the nucleotide sequence of SEQ ID NO: 20.

In yet other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence with at least 90% sequence identity to the nucleotide sequence of SEQ ID NO: 20, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence with at least 90% sequence identity to the nucleotide sequence of SEQ ID NO: 20, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In some aspects, the nucleotide sequence of (c) is 91%, 92%, 93%, 94%, 95%, 96%, 97%, 98%, 99%, or 100% identical to SEQ ID NO: 20.

In any of the foregoing or related aspects, the recombinant vector is an AAV vector. In some aspects, the AAV vector is about 2.5 kb-4.6 kb in length. In some aspects, the AAV vector is an AAV type 6 (AAV6). In some aspects, the AAV vector comprises 5' and 3' inverted terminal repeats (ITRs) derived from AAV type 2 (AAV2). In some aspects, the 5' ITR comprises SEQ ID NO: 5 and the 3' ITR comprises SEQ ID NO: 7.

In other aspects, the disclosure provides a system for correcting an E6V mutation in human beta-globin (HBB) in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide of SEQ ID NO: 1; and (c) an AAV vector comprising a nucleotide sequence having at least 90% sequence identity to the nucleotide sequence of SEQ ID NO: 9.

In further aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) an AAV vector comprising a nucleotide sequence having at least 90% sequence identity to the nucleotide sequence of SEQ ID NO: 9, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) an AAV vector comprising a nucleotide sequence having at least 90% sequence identity to the nucleotide sequence of SEQ ID NO: 9, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In some aspects, the nucleotide sequence of (c) is 91%, 92%, 93%, 94%, 95%, 96%, 97%, 98%, 99%, or 100% identical to the sequence of SEQ ID NO: 9.

In other aspects, the disclosure provides a system for correcting an E6V mutation in human beta-globin (HBB) in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide of SEQ ID NO: 1; and (c) an AAV vector comprising a nucleotide sequence having at least 90% sequence identity to the nucleotide sequence of SEQ ID NO: 58.

In further aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) an AAV vector comprising a nucleotide sequence having at least 90% sequence identity to the nucleotide sequence of SEQ ID NO: 58, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) an AAV vector comprising a nucleotide sequence having at least 90% sequence identity to the nucleotide sequence of SEQ ID NO: 58, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In some aspects, the nucleotide sequence of (c) is 91%, 92%, 93%, 94%, 95%, 96%, 97%, 98%, 99%, or 100% identical to the sequence of SEQ ID NO: 58.

In yet other aspects, the disclosure provides a system for correcting an E6V mutation in human beta-globin (HBB) in a cell or population of cells, the system comprising:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide of SEQ ID NO: 49; and (c) an AAV vector comprising a nucleotide sequence having at least 90% sequence identity to the nucleotide sequence of SEQ ID NO: 21.

In other aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) an AAV vector comprising a nucleotide sequence having at least 90% sequence identity to the nucleotide sequence of SEQ ID NO: 21, wherein the sgRNA combines with the Cas9 endonuclease to induce a DSB at the target site in the HBB gene, and wherein HDR of the DSB results in exchange of the region of the HBB gene encoding the E6V mutation with the nucleic acid, thereby correcting the E6V mutation in the HBB gene in the cell or population of cells.

In further aspects, the disclosure provides a method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) an AAV vector comprising a nucleotide sequence having at least 90% sequence identity to the nucleotide sequence of SEQ ID NO: 21, thereby correcting the E6V mutation in the HBB gene in the cell or population of cells. In some aspects, the sgRNA combines with the Cas9 endonuclease to induce a DSB at the target site in the HBB gene and HDR of the DSB results in exchange of the region of the HBB gene encoding the E6V mutation with the nucleic acid.

In some aspects, the nucleotide sequence of (c) is 91%, 92%, 93%, 94%, 95%, 96%, 97%, 98%, 99%, or 100% identical to the sequence of SEQ ID NO: 21.

In any of the foregoing or related aspects, the Cas9 endonuclease is a *S. pyogenes* Cas9 (SpCas9) endonuclease. In some aspects, the SpCas9 endonuclease is a high fidelity SpCas9 endonuclease. In some aspects, the high fidelity SpCas9 endonuclease comprises a R691A mutation. In some aspects, the high fidelity SpCas9 endonuclease comprises at least one NLS. In some aspects, the at least one NLS is an sv40 NLS.

In any of the foregoing or related aspects, the systems or methods comprise the Cas9 endonuclease as a polypeptide. In some aspects, the system comprises a ribonucleoprotein complex of the sgRNA and the Cas9 endonuclease. In some aspects, the Cas9 endonuclease forms a ribonucleoprotein complex with the sgRNA. In other aspects, the systems or methods comprise the mRNA encoding the Cas9 endonuclease. In yet other aspects, the systems or methods comprise the recombinant expression vector comprising a nucleotide sequence encoding the Cas9 endonuclease.

In some aspects, the Cas9 endonuclease and the sgRNA are introduced by electroporation of the cell or the population of cells. In some aspects, the recombinant expression vector or the AAV comprising the nucleic acid is introduced before or after the electroporation. In some aspects, the Cas9 endonuclease and the sgRNA are contacted with the cell or the population of cells by electroporation. In some aspects, the recombinant expression vector or the AAV comprising the nucleic acid for correcting the E6V mutation is contacted with the cell or the population of cells before or after the electroporation.

In any of the foregoing or related aspects, the system comprises the Cas9 endonuclease as a polypeptide, the sgRNA as an RNA, and the recombinant vector or AAV comprising the nucleic acid of (c). In some aspects, the system comprises a ribonucleoprotein complex comprising the Cas9 endonuclease and the sgRNA.

In any of the foregoing or related aspects, the system comprises the Cas9 endonuclease as a polypeptide, a recombinant expression vector comprising a nucleotide sequence encoding the sgRNA, and the recombinant vector or AAV comprising the nucleic acid of (c). In some aspects, the nucleotide sequence encoding the sgRNA and the nucleic acid of (c) are provided in the same recombinant expression vector. In other aspects, the nucleotide sequence encoding the sgRNA and the nucleic acid of (c) are provided in different recombinant expression vectors.

In any of the foregoing or related aspects, the system comprises an mRNA comprising a nucleotide sequence encoding the Cas9 endonuclease, the sgRNA as an RNA, and the recombinant vector or AAV comprising the nucleic acid of (c).

In any of the foregoing or related aspects, the system comprises an mRNA comprising a nucleotide sequence encoding the Cas9 endonuclease, a recombinant expression vector (e.g., AAV) comprising a nucleotide sequence encoding the sgRNA, and the recombinant vector or AAV comprising the nucleic acid of (c). In some aspects, the nucleotide sequence encoding the sgRNA and the nucleic acid of (c) are provided in the same recombinant expression vector. In other aspects, the nucleotide sequence encoding the sgRNA and the nucleic acid of (c) are provided in different recombinant expression vectors.

In any of the foregoing or related aspects, the system comprises a recombinant expression vector (e.g., AAV) comprising a nucleotide sequence encoding the Cas9 endonuclease, the sgRNA as an RNA, and the recombinant vector or AAV comprising the nucleic acid of (c).

In any of the foregoing or related aspects, the system comprises a recombinant expression vector (e.g., AAV) comprising a nucleotide sequence encoding the Cas9 endonuclease, a recombinant expression vector (e.g., AAV) comprising a nucleotide sequence encoding the sgRNA, and the recombinant vector or AAV comprising the nucleic acid of (c). In some aspects, the nucleotide sequence encoding the Cas9 endonuclease and the nucleotide sequence encoding the sgRNA are provided in the same recombinant expression vector (e.g., AAV). In other aspects, the nucleotide sequence encoding the Cas9 endonuclease and the nucleotide sequence encoding the sgRNA are provided in different recombinant expression vectors (e.g., AAV). In some aspects, the nucleotide sequence encoding the sgRNA and the nucleic acid of (c) are provided in the same recombinant expression vector. In other aspects, the nucleotide sequence encoding the sgRNA and the nucleic acid of (c) are provided in different recombinant expression vectors.

In any of the foregoing or related aspects, the method comprises contacting the cell or the population of cells with the Cas9 endonuclease as a polypeptide, the sgRNA as an RNA, and the recombinant vector or AAV comprising the nucleic acid of (c). In some aspects, the method comprises contacting the cell or the population of cells with a ribonucleoprotein complex comprising the Cas9 endonuclease and the sgRNA. In some aspects, the cell or the population of cells is simultaneously contacted with the ribonucleoprotein complex and the recombinant vector or the AAV comprising the nucleic acid of (c). In other aspects, the cell or the population of cells is sequentially contacted with the ribonucleoprotein complex and the recombinant vector or the AAV comprising the nucleic acid of (c), e.g., the cell or the population of cells is contacted with the recombinant vector or the AAV prior to or subsequent to the contacting with the ribonucleoprotein complex. In some aspects, the cell or the population of cells is contacted with the ribonucleoprotein complex by electroporation. In some aspects, the recombinant expression vector or the AAV comprising the nucleic acid of (c) is introduced before, during, or after the electroporation.

In any of the foregoing or related aspects, the method comprises contacting the cell or the population of cells with the Cas9 endonuclease as a polypeptide, a recombinant expression vector comprising a nucleotide sequence encoding the sgRNA, and the recombinant vector or AAV comprising the nucleic acid of (c). In some aspects, the nucleotide sequence encoding the sgRNA and the nucleic acid of (c) are provided in the same recombinant expression vector. In some aspects, contacting with the Cas9 endonuclease and the recombinant expression vector comprising the nucleotide sequence encoding the sgRNA and the nucleic acid of (c) is performed simultaneously or sequentially. In other aspects, the nucleotide sequence encoding the sgRNA and the nucleic acid of (c) are provided in different recombinant expression vectors. In some aspects, contacting with the Cas9 endonuclease, the recombinant expression vector comprising the nucleotide sequence encoding the sgRNA, and the recombinant vector or AVV encoding the nucleic acid of (c) is performed simultaneously or sequentially.

In any of the foregoing or related aspects, the method comprises contacting the cell or the population of cells with an mRNA comprising a nucleotide sequence encoding the Cas9 endonuclease, the sgRNA as an RNA, and the recombinant vector or AAV comprising the nucleic acid of (c). In some aspects, the cell or the population of cells is contacted with the Cas9 endonuclease, the sgRNA, and the recombinant vector or AAV comprising the nucleic acid of (c) either simultaneously or sequentially.

In any of the foregoing or related aspects, the method comprises contacting the cell or the population of cells with an mRNA comprising a nucleotide sequence encoding the Cas9 endonuclease, a recombinant expression vector (e.g., AAV) comprising a nucleotide sequence encoding the sgRNA, and the recombinant vector or AAV comprising the nucleic acid of (c). In some aspects, the nucleotide sequence encoding the sgRNA and the nucleic acid of (c) are provided in the same recombinant expression vector. In other aspects, the nucleotide sequence encoding the sgRNA and the nucleic acid of (c) are provided in different recombinant expression vectors. In some aspects, contacting with the mRNA and the recombinant expression vector(s) is performed sequentially or simultaneously.

In any of the foregoing or related aspects, the method comprises contacting the cell or the population of cells with a recombinant expression vector (e.g., AAV) comprising a nucleotide sequence encoding the Cas9 endonuclease, the sgRNA as an RNA, and the recombinant vector or AAV comprising the nucleic acid of (c). In some aspects, contacting with the recombinant expression vector (e.g., AAV), the sgRNA, and the recombinant vector or AAV comprising the nucleic acid is performed simultaneously or sequentially.

In any of the foregoing or related aspects, the method comprises contacting the cell or the population of cells with a recombinant expression vector (e.g., AAV) comprising a nucleotide sequence encoding the Cas9 endonuclease, a recombinant expression vector (e.g., AAV) comprising a nucleotide sequence encoding the sgRNA, and the recombinant vector or AAV comprising the nucleic acid of (c). In some aspects, the nucleotide sequence encoding the Cas9 endonuclease and the nucleotide sequence encoding the sgRNA are provided in the same recombinant expression vector (e.g., AAV). In some aspects, the nucleotide sequence encoding the Cas9 endonuclease and the nucleotide sequence encoding the sgRNA are provided in different recombinant expression vectors (e.g., AAV). In other aspects, the nucleic acid of (c) and the nucleotide sequence encoding the sgRNA are provided in the same recombinant expression vector or AAV. In some aspects, contacting with the recombinant expression vector(s) comprising the nucleotide sequence encoding the Cas9 endonuclease, the nucleotide sequence encoding the sgRNA, and the nucleic acid of (c) is performed simultaneously or sequentially.

In any of the foregoing or related aspects, the cell is a hematopoietic stem or progenitor cell (HSPC) or the population of cells comprises HSPCs. In some aspects, the cell is a long-term HSPC (LT-HSPC) or the population of cells comprises long-term HSPC (LT-HSPC). In some aspects, the HSPC or LT-HSPC is a CD34-expressing cell. In some aspects, the cell or population of cells is isolated from a tissue sample obtained from a human donor having sickle cell disease. In some aspects, the tissue sample is a peripheral blood sample. In some aspects, the human donor is administered one or more HSPC mobilizing agent(s) prior to obtaining the tissue sample. In some aspects, the one or more HSPC mobilizing agent(s) are selected from Plurexifor and granulocyte colony stimulating factor (GCSF).

In any of the foregoing or related aspects, when the system is introduced to the cell or population of cells, the sgRNA combines with the Cas9 endonuclease to induce a double-strand break (DSB) at the target site in the HBB gene, and wherein homology directed repair (HDR) of the DSB results in exchange of the region of the HBB gene encoding the E6V mutation with the nucleic acid for correcting the E6V mutation. In some aspects, the frequency of HDR in the population of cells is at least about 15%, 20%, 25%, 30%, 35%, 40%, 45%, 50%, 55%, or 60%. In some aspects, a frequency of INDELs at the target site in the population of cells is reduced by at least 2-fold relative to a population of cells introduced without the nucleic acid. In some aspects, off-target gene editing is not detectable as measured by frequency of INDELs induced at one or more genomic sites predicted to be off-target sites. In some aspects, the frequency of INDELs at the one or more genomic sites predicted to be off-target sites is less than about 1%, about 0.5%, or about 0.1%. In some aspects, the frequency of INDELs is measured using a method described herein (e.g., NGS).

In any of the foregoing or related aspects, cleavage of one or more predicted off-target sites in the cell or population of cells is reduced relative to a cell or population of cells contacted with a wild-type *S. pyogenes* Cas9. In some aspects, cleavage of one or more predicted off-target sites is reduced by at least about 50% relative to a cell or population of cells contacted with a wild-type *S. pyogenes* Cas9.

In any of the foregoing or related aspects, the frequency of HDR in the population of cells is at least about 15%, 20%, 25%, 30%, 35%, 40%, 45%, 50%, 55%, or 60%. In some aspects, a frequency of INDELs at the target site in the population of cells is reduced by at least 2-fold relative to a population of cells introduced without the nucleic acid for correcting the E6V mutation.

In any of the foregoing or related aspects, the methods disclosed herein further comprise contacting the cell or the population of cells with one or more inhibitors selected from: a 53BP1 inhibitor and an inhibitor of DNA-PK. In some aspects, the 53BP1 inhibitor comprises:

(i) a 53BP1 binding polypeptide that inhibits 53BP1 recruitment to the DSB in the cell;

(ii) a 53BP1 binding polypeptide comprising an amino acid sequence selected from: SEQ ID NOs: 11, 30, 33, 36, 39 and 42;

(iii) a nucleic acid comprising a nucleotide sequence encoding a 53BP1 binding polypeptide that inhibits 53BP1 recruitment to the DSB site in the cell;

(iv) a nucleic acid comprising a nucleotide sequence selected from: SEQ ID NOs: 10, 29, 32, 35, 38, 41 and 43;

(v) a recombinant vector comprising the nucleotide sequence encoding a 53BP1 binding polypeptide that inhibits 53BP1 recruitment to the DSB site in the cell; or (vi) a recombinant vector comprising a nucleotide sequence selected from: SEQ ID NOs: 28, 31, 34, 37 and 40. In some aspects, the DNA-PK inhibitor targets the DNA-PK catalytic subunit (DNA-PKcs). In some aspects, the DNA-PK inhibitor is selected from: Nu7441, Compound 284, or Compound 987. In some aspects, the cell or the population of cells is contacted with the DNA-PK inhibitor at a concentration of 0.5, 0.6, 0.7, 0.8, 0.9, 1.0, 1.1, 1.5, 2.0, 2.5, 3.0, 3.5, 4.0, 4.5, or 5.0 μM. In some aspects, the frequency of HDR of the DSB in the population of cells is increased by at least 1.1 fold, 1.2-fold, 1.3-fold, 1.4-fold, 1.5-fold, 1.6-fold, 1.7-fold, 1.8-fold, 1.9-fold, or 2-fold relative to a population of cells not contacted with the one or more inhibitors. In some aspects, the frequency of INDELs at the target site in the population of cells is decreased by about 2-fold relative to a population of cells not contacted with the one or more inhibitors. In some aspects, the DNA-PK inhibitor does not increase off-target editing (as compared to an otherwise identical method that does not comprise contacting the cell or population of cells with a DNA-PK inhibitor).

In any of the foregoing or related aspects, the method comprises contacting the cell or the population of cells with the Cas9 endonuclease as a polypeptide, the sgRNA as an RNA, the recombinant vector or AAV comprising the nucleic acid, and the one or more inhibitors (e.g., a 53BP1 inhibitor and/or a DNA-PK inhibitor). In some aspects, the method comprises contacting the cell or the population of cells with a ribonucleoprotein complex comprising the Cas9 endonuclease and the sgRNA; the recombinant vector or AAV comprising the nucleic acid; and the one or more inhibitors. In some aspects, the cell or the population of cells is simultaneously or sequentially contacted with the ribonucleoprotein complex, the recombinant vector or the AAV comprising the nucleic acid, and the one or more inhibitors. In some aspects, the cell or the population of cells is contacted with the ribonucleoprotein complex by electroporation. In some aspects, the recombinant expression vector or the AAV comprising the nucleic acid is introduced before, during, or after the electroporation. In some aspects, the one or more inhibitors is introduced before, during, or after the electroporation.

In any of the foregoing or related aspects, the method comprises contacting the cell or the population of cells with the Cas9 endonuclease as a polypeptide, a recombinant expression vector comprising a nucleotide sequence encoding the sgRNA, the recombinant vector or AAV comprising the nucleic acid of (c); and one or more inhibitors (e.g., a 53BP1 inhibitor and/or a DNA-PK inhibitor). In some aspects, the nucleotide sequence encoding the sgRNA and the nucleic acid of (c) are provided in the same recombinant expression vector. In other aspects, the nucleotide sequence encoding the sgRNA and the nucleic acid of (c) are provided in different recombinant expression vectors. In some aspects, contacting with the Cas9 endonuclease, the recombinant expression vector(s), and the one or more inhibitors is performed either simultaneously or sequentially.

In any of the foregoing or related aspects, the method comprises contacting the cell or the population of cells with an mRNA comprising a nucleotide sequence encoding the Cas9 endonuclease; the sgRNA as an RNA; the recombinant vector or AAV comprising the nucleic acid of (c); and one or more inhibitors (e.g., a 53BP1 inhibitor and/or a DNA-PK inhibitor). In some aspects, contacting with the mRNA, the sgRNA, the recombinant vector or AAV, and the one or more inhibitors is performed either simultaneously or sequentially.

In any of the foregoing or related aspects, the method comprises contacting the cell or the population of cells with an mRNA comprising a nucleotide sequence encoding the Cas9 endonuclease; a recombinant expression vector (e.g., AAV) comprising a nucleotide sequence encoding the sgRNA; the recombinant vector or AAV comprising the nucleic acid of (c); and one or more inhibitors (e.g., a 53BP1 inhibitor and/or a DNA-PK inhibitor). In some aspects, the nucleotide sequence encoding the sgRNA and the nucleic acid of (c) are provided in the same recombinant expression vector. In other aspects, the nucleotide sequence encoding the sgRNA and the nucleic acid of (c) are provided in different recombinant expression vectors. In other aspects, contacting with the mRNA, the recombinant expression vector(s), and the one or more inhibitors is performed either simultaneously or sequentially.

In any of the foregoing or related aspects, the method comprises contacting the cell or the population of cells with a recombinant expression vector (e.g., AAV) comprising a nucleotide sequence encoding the Cas9 endonuclease; the sgRNA as an RNA; the recombinant vector or AAV comprising the nucleic acid of (c); and one or more inhibitors (e.g., a 53BP1 inhibitor and/or a DNA-PK inhibitor). In some aspects, contacting with the recombinant expression vectors, the sgRNA, and the one or more inhibitors is performed simultaneously or sequentially.

In any of the foregoing or related aspects, the method comprises contacting the cell or the population of cells with a recombinant expression vector (e.g., AAV) comprising a nucleotide sequence encoding the Cas9 endonuclease; a recombinant expression vector (e.g., AAV) comprising a nucleotide sequence encoding the sgRNA; the recombinant vector or AAV comprising the nucleic acid of (c); and one or more inhibitors (e.g., a 53BP1 inhibitor and/or a DNA-PK inhibitor). In some aspects, the nucleotide sequence encoding the Cas9 endonuclease and the nucleotide sequence encoding the sgRNA are provided in the same recombinant expression vector (e.g., AAV). In other aspects, the nucleotide sequence encoding the Cas9 endonuclease and the nucleotide sequence encoding the sgRNA are provided in different recombinant expression vectors (e.g., AAV). In some aspects, the nucleic acid of (c) and the nucleotide sequence encoding the sgRNA are provided in the same recombinant expression vector. In other aspects, the nucleic acid of (c) and the nucleotide sequence encoding the sgRNA are provided in different recombinant expression vectors. In some aspects, contacting with the recombinant expression vector(s) and the one or more inhibitors is performed simultaneously or sequentially.

In some aspects, the disclosure provides a system for correcting an E6V mutation in human beta-globin (HBB) in a cell or population of cells, the system comprising: (a) a Cas9 endonuclease as a polypeptide; (b) a single guide RNA (sgRNA) comprising a spacer sequence corresponding to a target sequence adjacent a PAM, the target sequence comprising a target site within intron 1 of HBB; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a single guide RNA (sgRNA) comprising a spacer sequence corresponding to a target sequence adjacent a PAM, the target sequence comprising a target site within intron 1 of HBB; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, thereby correcting the E6V mutation in the HBB gene in the cell or population of cells.

In some aspects, the target site is about 70 to about 200 bp downstream the E6V mutation. In some aspects, the target site is about 90, 95, 100, 105, 110, 115, 120, 125, 130, 135, 140, 145 or 150 bp downstream the E6V mutation. In some aspects, target sequence comprises a nucleotide sequence selected from SEQ ID NO: 1 or SEQ ID NO: 49. In some aspects, the target sequence consists of the nucleotide sequence of SEQ ID NO: 1. In other aspects, the target sequence consists of the nucleotide sequence of SEQ ID NO: 49.

In some aspects, the disclosure provides a system for correcting an E6V mutation in HBB in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6.

In other aspects, the disclosure provides a system for correcting an E6V mutation in HBB in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, thereby correcting the E6V mutation in the HBB gene in the cell or population of cells.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, thereby correcting the E6V mutation in the HBB gene in the cell or population of cells.

In any of the foregoing or related aspects, the codon encoding E6 is selected from GAA and GAG. In some aspects, the nucleotide sequence of (c) comprises one or more silent mutations relative to the HBB gene.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence a nucleotide sequence having at least 90% sequence identity to the nucleotide sequence of SEQ ID NO: 6, thereby correcting the E6V mutation in the HBB gene in the cell or population of cells.

In any of the foregoing or related aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 6. In some aspects, the nucleotide sequence of (c) comprises the nucleotide sequence of SEQ ID NO: 6.

In further aspects, the disclosure provides a system for correcting an E6V mutation in HBB in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence having at least 90% sequence identity to the nucleotide sequence of SEQ ID NO: 56.

In other aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence a nucleotide sequence having at least 90% sequence identity to the nucleotide sequence of SEQ ID NO: 56, thereby correcting the E6V mutation in the HBB gene in the cell or population of cells.

In any of the foregoing or related aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 56. In some aspects, the nucleotide sequence of (c) comprises the nucleotide sequence of SEQ ID NO: 56.

In other aspects, the disclosure provides a system for correcting an E6V mutation in HBB in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence having at least 90% sequence identity to the nucleotide sequence of SEQ ID NO: 19.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence having at least 90% sequence identity to the nucleotide sequence of SEQ ID NO: 19, thereby correcting the E6V mutation in the HBB gene in the cell or population of cells.

In any of the foregoing or related aspects, the nucleotide sequence of (c) comprises a nucleotide sequence having 91%, 92%, 93%, 94%, 95%, 96%, 97%, 98%, or 99% sequence identity to the nucleotide sequence of SEQ ID NO: 19. In some aspects, the nucleotide sequence of (c) comprises the nucleotide sequence of SEQ ID NO: 19.

In any of the foregoing or related aspects, the nucleic acid of (c) comprises a nucleotide sequence of about 0.5 kb to about 5.5 kb in length, about 1 kb to about 5 kb, about 1.5 kb to about 4.6 kb, about 2 kb to about 4.6 kb, about 2.5 kb to about 4.6 kb, about 3 kb to about 4.6 kb, or about 3.5 kb to about 4.6 kb. In other aspects, the nucleic acid of (c) comprises a nucleotide sequence of about 4 k to about 4.6 kb. In yet other aspects, the nucleic acid of (c) comprises a nucleotide sequence of less than about 5 kb.

In some aspects, the nucleotide sequence of (c) comprises a mutation to delete the PAM.

In some aspects, the disclosure provides a system for correcting an E6V mutation in HBB in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence with at least 90% sequence identity to the nucleotide sequence of SEQ ID NO: 8.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence with at least 90% sequence identity to the nucleotide sequence of SEQ ID NO: 8, thereby correcting the E6V mutation in the HBB gene in the cell or population of cells In some aspects, the nucleotide sequence of (c) is 91%, 92%, 93%, 94%, 95%, 96%, 97%, 98%, 99%, or 100% identical to SEQ ID NO: 8.

In some aspects, the disclosure provides a system for correcting an E6V mutation in HBB in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence with at least 90% sequence identity to the nucleotide sequence of SEQ ID NO: 57.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) a recombinant vector comprising a nucleic acid for correcting the E6V mutation, the nucleic acid comprising a nucleotide sequence with at least 90% sequence identity to the nucleotide sequence of SEQ ID NO: 57, thereby correcting the E6V mutation in the HBB gene in the cell or population of cells In some aspects, the nucleotide sequence of (c) is 91%, 92%, 93%, 94%, 95%, 96%, 97%, 98%, 99%, or 100% identical to SEQ ID NO: 57.

In other aspects, the disclosure provides a system for correcting an E6V mutation in HBB in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence with at least 90% sequence identity to the nucleotide sequence of SEQ ID NO: 20.

In some aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) a recombinant vector comprising a nucleic acid for correcting the E6V mutation, the nucleic acid comprising a nucleotide sequence with at least 90% sequence identity to the nucleotide sequence of SEQ ID NO: 20, thereby correcting the E6V mutation in the HBB gene in the cell or population of cells.

In some aspects, the nucleotide sequence of (c) is 91%, 92%, 93%, 94%, 95%, 96%, 97%, 98%, 99%, or 100% identical to SEQ ID NO: 20.

In other aspects, the disclosure provides a system for correcting an E6V mutation in human beta-globin (HBB) in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide of SEQ ID NO: 1; and (c) an AAV vector comprising a nucleotide sequence having at least 90% sequence identity to the nucleotide sequence of SEQ ID NO: 9.

In other aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) an AAV vector comprising a nucleotide sequence having at least 90% sequence identity to the nucleotide sequence of SEQ ID NO: 9, thereby correcting the E6V mutation in the HBB gene in the cell or population of cells.

In some aspects, the nucleotide sequence of (c) is 91%, 92%, 93%, 94%, 95%, 96%, 97%, 98%, 99%, or 100% identical to the sequence of SEQ ID NO: 9.

In other aspects, the disclosure provides a system for correcting an E6V mutation in human beta-globin (HBB) in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide of SEQ ID NO: 1; and (c) an AAV vector comprising a nucleotide sequence having at least 90% sequence identity to the nucleotide sequence of SEQ ID NO: 58.

In other aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 1; and (c) an AAV vector comprising a nucleotide sequence having at least 90% sequence identity to the nucleotide sequence of SEQ ID NO: 58, thereby correcting the E6V mutation in the HBB gene in the cell or population of cells.

In some aspects, the nucleotide sequence of (c) is 91%, 92%, 93%, 94%, 95%, 96%, 97%, 98%, 99%, or 100% identical to the sequence of SEQ ID NO: 58.

In yet other aspects, the disclosure provides a system for correcting an E6V mutation in human beta-globin (HBB) in a cell or population of cells, the system comprising: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide of SEQ ID NO: 49; and (c) an AAV vector comprising a nucleotide sequence having at least 90% sequence identity to the nucleotide sequence of SEQ ID NO: 21.

In further aspects, the disclosure provides a method for correcting an E6V mutation in HBB in a cell or population of cells, the method comprising contacting the cell or population of cells comprising an HBB gene encoding the E6V mutation with: (a) a Cas9 endonuclease as a polypeptide; (b) a sgRNA targeting a target site in intron 1 of HBB, the sgRNA comprising a spacer sequence corresponding to a target sequence adjacent a PAM, the target sequence comprising the nucleotide sequence of SEQ ID NO: 49; and (c) an AAV vector comprising a nucleotide sequence having at least 90% sequence identity to the nucleotide sequence of SEQ ID NO: 21, thereby correcting the E6V mutation in the HBB gene in the cell or population of cells.

In some aspects, the nucleotide sequence of (c) is 91%, 92%, 93%, 94%, 95%, 96%, 97%, 98%, 99%, or 100% identical to the sequence of SEQ ID NO: 21.

In any of the foregoing or related aspects, the Cas9 endonuclease is a *S. pyogenes* Cas9 (SpCas9) endonuclease. In some aspects, the SpCas9 endonuclease is a high fidelity SpCas9 endonuclease. In some aspects, the high fidelity SpCas9 endonuclease comprises a R691A mutation. In some aspects, the high fidelity SpCas9 endonuclease comprises at least one NLS. In some aspects, the at least one NLS is an sv40 NLS.

In any of the foregoing or related aspects, the system comprises a ribonucleoprotein complex of the sgRNA and the Cas9 endonuclease. In some aspects, the Cas9 endonuclease and the sgRNA are introduced by electroporation of the cell or the population of cells. In some aspects, the recombinant expression vector or the AAV comprising the nucleic acid is introduced before or after the electroporation. In some aspects, the Cas9 endonuclease and the sgRNA are contacted with the cell or the population of cells by electroporation. In some aspects, the recombinant expression vector or the AAV comprising the nucleic acid for correcting the E6V mutation is contacted with the cell or the population of cells before or after the electroporation.

In other aspects, the disclosure provides a pharmaceutical composition comprising a system described herein, and a pharmaceutically acceptable carrier.

In yet other aspects, the disclosure provides a kit comprising a system or pharmaceutical composition described herein, and instructions for correcting an E6V mutation in human beta-globin (HBB) in a population of cells by contacting the population with the system or pharmaceutical composition. In some aspects, the kit further comprises instructions for use with at least one inhibitor. In some aspects, the at least one inhibitor is a 53BP1 inhibitor, a DNA-PK inhibitor, or a combination thereof. In some aspects, the 53BP1 inhibitor comprises:

(i) a 53BP1 binding polypeptide that inhibits 53BP1 recruitment to the DSB in the cell;

(ii) a 53BP1 binding polypeptide comprising an amino acid sequence selected from: SEQ ID NOs: 11, 30, 33, 36, 39 and 42;

(iii) a nucleic acid comprising a nucleotide sequence encoding a 53BP1 binding polypeptide that inhibits 53BP1 recruitment to the DSB site in the cell;
(iv) a nucleic acid comprising a nucleotide sequence selected from: SEQ ID NOs: 10, 29, 32, 35, 38, 41 and 43;
(v) a recombinant vector comprising the nucleotide sequence encoding a 53BP1 binding polypeptide that inhibits 53BP1 recruitment to the DSB site in the cell; or
(vi) a recombinant vector comprising a nucleotide sequence selected from: SEQ ID NOs: 28, 31, 34, 37 and 40. In some aspects, the DNA-PK inhibitor targets the DNA-PK catalytic subunit (DNA-PKcs). In some aspects, the DNA-PK inhibitor is selected from: Nu7441, Compound 284, or Compound 987. In some aspects, the instructions comprise contacting the population of cells ex vivo. In some aspects, instructions comprise obtaining a cell or population of cells from a patient having a hemoglobinopathy associated with a mutation (e.g., SCD mutation) in exon 1 of HBB and contacting the cell or population of cells ex vivo with the system or pharmaceutical composition to introduce a gene edit that corrects the mutation. In some aspects, the instructions further comprise administering the cell or population of cells to the patient to ameliorate or treat the hemoglobinopathy. In other aspects, the instructions comprise contacting the population of cells in vivo.

In other aspects, the disclosure provides a cell or population of cells generated by any of the methods described herein.

In some aspects, the disclosure provides an isolated cell or population of isolated cells, comprising at least one chromosomal copy of an HBB gene comprising the nucleotide sequence of SEQ ID NO: 6. In other aspects, the disclosure provides an isolated cell or population of isolated cells, comprising at least one chromosomal copy of an HBB gene comprising the nucleotide sequence of SEQ ID NO: 19. In yet other aspects, the disclosure provides an isolated cell or population of isolated cells, comprising at least one chromosomal copy of an HBB gene comprising the nucleotide sequence of SEQ ID NO: 8. In further aspects, the disclosure provides an isolated cell or population of isolated cells, comprising at least one chromosomal copy of an HBB gene comprising the nucleotide sequence of SEQ ID NO: 20.

In some aspects, the disclosure provides a method for treating a patient having a disease or disorder, comprising administering a cell or population of cells described herein, thereby treating the disease or disorder. In some aspects, the disease or disorder is sickle cell disease.

In some aspects, the disclosure provides use of a cell or population of cells described herein for treating a disease or disorder in a subject. In some aspects, the disclosure provides use of a cell or population of cells described herein in the manufacture of a medicament for treating a disease or disorder in a subject.

In any of the foregoing or related aspects, the disease or disorder is a hemoglobinopathy associated with a mutation (e.g., E6V) in exon 1 of HBB. In some aspects, the disease or disorder is a beta-hemoglobinopathy associated with a mutation (e.g., E6V) in exon 1 of HBB. In some aspects, the hemoglobinopathy is sickle cell disease.

In some aspects, the disclosure provides an ex vivo method for treating or ameliorating a hemoglobinopathy associated with a mutation (e.g., E6V) in exon 1 of HBB in a patient, the method comprising isolating a cell or population of cells from the patient, contacting the cell or the population of cells with a system or pharmaceutical composition described herein to introduce a gene edit that corrects the mutation (e.g., E6V) in exon 1 of the HBB gene, and administering the cell or population of cells to the patient, thereby treating or ameliorating the hemoglobinopathy.

In some aspects, the disclosure provides an ex vivo method for treating or ameliorating a hemoglobinopathy associated with a mutation (e.g., E6V) in exon 1 of HBB in a patient, the method comprising isolating a cell or population of cells from the patient, contacting the cell or the population of cells with a system or pharmaceutical composition described herein and one or more inhibitors selected from a 53BP1 inhibitor and a DNA-PK inhibitor to introduce a gene edit that corrects the mutation (e.g., E6V) in exon 1 of the HBB gene, and administering the cell or population of cells to the patient, thereby treating or ameliorating the hemoglobinopathy.

In some aspects, the disclosure provides an ex vivo method for treating or ameliorating a hemoglobinopathy associated with a mutation (e.g., E6V) in exon 1 of HBB in a patient, the method comprising isolating a cell or population of cells from the patient, introducing a gene edit to correct the mutation (e.g., E6V) in exon 1 of the HBB gene according to a method described herein, and administering the cell or population of cells to the patient, thereby treating or ameliorating the hemoglobinopathy.

In any of the foregoing or related aspects, the cell is an HSPC or the population of cells comprises HSPCs. In some aspects, the HSPC(s) express CD34. In some aspects, the cell or population of cells is isolated from a tissue sample obtained from the patient. In some aspects, the tissue sample is a peripheral blood sample. In some aspects, the patient is administered one or more HSPC mobilizing agent(s) prior to obtaining the tissue sample. In some aspects, the one or more HSPC mobilizing agent(s) are selected from Plurexifor and granulocyte colony stimulating factor (GCSF). In some aspects, the cell or population of cells is obtained by isolating CD34-expressing cells from the tissue sample.

In some aspects, the disclosure provides an ex vivo method for treating or ameliorating a hemoglobinopathy associated with a mutation (e.g., E6V) in exon 1 of HBB in a patient, the method comprising contacting a population of iPSCs derived from the patient with a system or pharmaceutical composition described herein to introduce a gene edit that corrects the mutation (e.g., E6V) in exon 1 of the HBB gene, differentiating the population of iPSCs into a population of HSPCs, and administering the population of HSPCs to the patient, thereby treating or ameliorating the hemoglobinopathy.

In some aspects, the disclosure provides an ex vivo method for treating or ameliorating a hemoglobinopathy associated with a mutation (e.g., E6V) in exon 1 of HBB in a patient, the method comprising contacting a population of iPSCs derived from the patient with a system or pharmaceutical composition described herein and one or more inhibitors selected from a 53BP1 inhibitor and a DNA-PK inhibitor to introduce a gene edit that corrects the mutation (e.g., E6V) in exon 1 of the HBB gene, differentiating the population of iPSCs into a population of HSPCs, and administering the population of HSPCs to the patient, thereby treating or ameliorating the hemoglobinopathy.

In some aspects, the disclosure provides an ex vivo method for treating or ameliorating a hemoglobinopathy associated with a mutation (e.g., E6V) in exon 1 of HBB in a patient, the method comprising introducing a gene edit to correct the mutation (e.g., E6V) in exon 1 of the HBB gene according to a method described herein in a population of iPSCs derived from the patient, differentiating the population of iPSCs into a population of HSPCs, and administering the population of HSPCs to the patient, thereby treating or ameliorating the hemoglobinopathy.

In any of the foregoing or related aspects, the method for generating the population of iPSCs comprises isolating a population of somatic cells from the patient; and introducing one or more pluripotency-associated genes into the population to induce the somatic cells to become iPSCs. In some aspects, the somatic cells comprise fibroblasts. In some aspects, the one or more pluripotency-associated genes is selected from OCT4, SOX2, KLF4, Lin28, NANOG and cMYC. In some aspects, the differentiating comprises contacting with a combination of one or more small molecules and/or one or more transcription factors (e.g., one or more transcription factors provided as polypeptides or encoded by one or more nucleic acids (e.g., mRNA)).

In some aspects, the disclosure provides an ex vivo method for treating or ameliorating a hemoglobinopathy associated with a mutation (e.g., E6V) in exon 1 of HBB in a patient, the method comprising contacting a population of mesenchymal stem cells obtained from the patient with a system or pharmaceutical composition described herein to introduce a gene edit for correcting the mutation (e.g., E6V) in exon 1 of the HBB gene, differentiating the population of mesenchymal stem cells to a population of HSPCs, and administering the population of HSPCs to the patient, thereby treating or ameliorating the hemoglobinopathy.

In some aspects, the disclosure provides an ex vivo method for treating or ameliorating a hemoglobinopathy associated with a mutation (e.g., E6V) in exon 1 of HBB in a patient, the method comprising contacting a population of mesenchymal stem cells obtained from the patient with a system or pharmaceutical composition described herein and one or more inhibitors selected from a 53BP1 inhibitor and a DNA-PK inhibitor to introduce a gene edit that corrects the mutation (e.g., E6V) in exon 1 of the HBB gene, differentiating the population of mesenchymal stem cells to a population of HSPCs, and administering the population of HSPCs to the patient, thereby treating or ameliorating the hemoglobinopathy.

In some aspects, the disclosure provides an ex vivo method for treating or ameliorating a hemoglobinopathy associated with a mutation (e.g., E6V) in exon 1 of HBB in a patient, the method comprising introducing a gene edit to correct the mutation (e.g., E6V) in exon 1 of the HBB gene according to a method described herein in a population of mesenchymal stem cells obtained from the patient, differentiating the population of mesenchymal stem cells to a population of HSPCs, and administering the population of HSPCs to the patient, thereby treating or ameliorating the hemoglobinopathy.

In any of the foregoing or related aspects, the mesenchymal stem cells are isolated from a tissue sample obtained from the patient. In some aspects, the tissue sample is peripheral blood sample or a bone marrow sample. In some aspects, the isolating comprises aspiration of the bone marrow sample and selecting mesenchymal stem cells using density gradient centrifugation. In some aspects, the differentiation of mesenchymal stem cells to HSPCs comprises contacting with a combination of one or more small molecules and/or one or more transcription factors (e.g., one or more transcription factors provided as polypeptides or encoded by one or more nucleic acids (e.g., mRNA)).

In any of the foregoing or related aspects, lymphodepletion is performed prior to the administering of the cell or population of cells comprising a correction to the mutation (e.g., E6V) in exon 1 of the HBB gene. In some aspects, the lymphodepletion comprises chemotherapy and/or radiation to deplete or eliminate cells of hematopoietic origin in the patient's bone marrow. In some aspects, the administering of the cell or population of cells is performed by transplantation, local injection, systemic infusion, or a combination thereof. In some aspects, the administering results in an increase in the level of HbA that is sufficient to treat or ameliorate one or more clinical symptoms of the hemoglobinopathy. In some aspects, the administering results in the patient's bone marrow comprising the gene-edit for a duration of 16 weeks or longer.

In some aspects, the disclosure provides an in vivo method for treating or ameliorating a hemoglobinopathy associated with a mutation (e.g., E6V) in exon 1 of HBB in a patient comprising introducing a gene edit to correct the mutation according to a method described herein in a cell of the patient, thereby treating or ameliorating the patient's hemoglobinopathy.

In some aspects, the disclosure provides an in vivo method for treating or ameliorating a hemoglobinopathy associated with a mutation (e.g., E6V) in exon 1 of HBB in a patient comprising administering a system or pharmaceutical composition described herein to a patient, wherein the system or pharmaceutical composition introduces a gene edit to correct the mutation in a cell of the patient, thereby treating or ameliorating the patient's hemoglobinopathy.

In further aspects, the disclosure provides an in vivo method for treating or ameliorating a hemoglobinopathy associated with an E6V mutation in exon 1 of HBB in a patient comprising administering (i) a Cas9 endonuclease, an mRNA encoding the Cas9 endonuclease, or a recombinant expression vector comprising a nucleotide sequence encoding the Cas9 endonuclease; (ii) a sgRNA comprising a spacer sequence corresponding to a target sequence adjacent a PAM, the target sequence comprising a target site within intron 1 of HBB; (iii) a recombinant vector comprising a nucleic acid for correcting the E6V mutation, the nucleic acid comprising a nucleotide sequence homologous with a region of the HBB gene encoding the E6V mutation, and optionally (iv) a 53BP1 inhibitor and a DNA-PK inhibitor, wherein the nucleotide sequence comprises a codon encoding E6, wherein the sgRNA combines with the Cas9 endonuclease to induce a DSB at the target site in the HBB gene and HDR of the DSB results in exchange of the region of the HBB gene encoding the E6V mutation with the nucleic acid to correct the mutation in a cell of the patient, thereby treating or ameliorating the patient's hemoglobinopathy. In some aspects, (i)-(iii) are delivered in one or more viral vectors (e.g., AAV). In some aspects, (i)-(iii) are delivered in one or more non-viral vectors (e.g., a lipid nanoparticle (LNP)). In some aspects, (iv) is delivered in one or more non-viral vectors (e.g., an LNP). In some aspects, the method employs a combination of viral and non-viral delivery, e.g., (i)-(ii), and optionally (iv), are delivered in a non-viral vector (e.g., an LNP) and (iii) is delivered in a viral vector (e.g., AAV).

DETAILED DESCRIPTION

Figure 1:
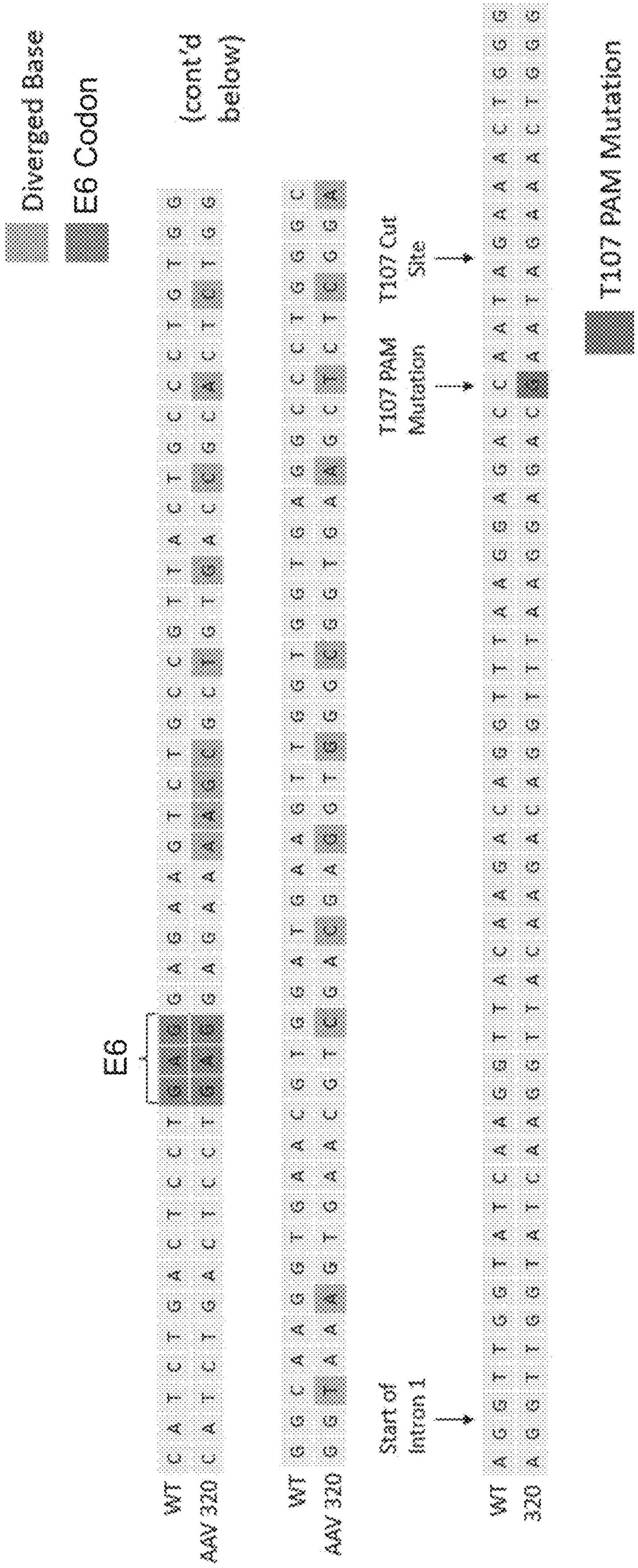
FIG. 1 provides a schematic showing a region of the wild-type (WT) HBB gene that contains the 3' end of exon 1 and 5' end of intron 1 (corresponding to nucleotides 1-136 of SEQ ID NO: 53). The cut site for the intron-targeting T107 gRNA is depicted. Also shown is an alignment to a region of AAV.320 (corresponding to nucleotides 2332-2467 of SEQ ID NO: 9), an AAV-encoded homology donor template for use with the T107 gRNA. As shown, the homology donor includes a single nucleotide substitution within the T107 PAM, a codon at position 6 downstream of the HBB start codon that encodes glutamate, and several diverged nucleotides relative to exon 1 of HBB.

The present disclosure is based, at least in part, on the discovery that an intron-targeting gRNA complexed with a Cas9 endonuclease (e.g., Cas9 nuclease from *S. pyogenes* (SpCas9)), yields efficient homology directed repair (HDR) for correcting a Glu6Val (E6V) mutation in exon 1 of HBB when combined with a donor nucleic acid encoding a correction to the mutation. In some aspects, the intron-targeting gRNA comprises a spacer sequence corresponding to a target sequence adjacent a protospacer adjacent motif (PAM) that is present within intron 1 of HBB, wherein a CRISPR/Cas complex comprising the intron-targeting gRNA induces a DNA double-stranded break (DSB) at a target site proximal the PAM. In some aspects, the donor nucleic acid encodes a correction to the E6V mutation and optionally, one or more additional gene-edits selected from (i) a silent mutation within exon 1 of the HBB gene, (ii) a mutation to the PAM, or (iii) both (i) and (ii). Without being bound by theory, incorporation of a mutation to the PAM prevents re-cutting of the HBB gene by the CRISPR/Cas complex following HDR of the DSB.

Without being bound by theory, the intron targeting gRNA/system described herein for correcting a mutation in an HBB gene does not result in the risk of generating INDELs that would disrupt the HBB gene and increase the risk of developing beta-thalassemia in a subject, which may potentially result by use of gRNA/systems targeting exon 1 of HBB.

Surprisingly, despite the CRISPR/Cas complex inducing a DSB substantially downstream of the E6V mutation (e.g., at least about 60 bp or more downstream of the E6V mutation), it was discovered that the donor nucleic acid provided an effective template for HDR of the DSB to incorporate a correction to the E6V mutation, for example, resulting in an average on-target editing frequency of about 20%, 30%, 40%, or higher. In some aspects, the donor nucleic acid is provided as a recombinant vector (e.g., AAV). In some aspects, the donor nucleic acid is 4.4-4.6 kb in length.

The present disclosure is also based, at least in part, on the discovery that a population of human-derived CD34+ hematopoietic stem/progenitor cells (HSPCs) was effectively edited using a CRISPR/Cas system comprising an intron-targeting gRNA described herein. Indeed, it was demonstrated edited CD34+ HSPCs incorporate a correction of the E6V mutation in the HBB gene, and further express mRNA encoding a corrected beta-globin polypeptide. It has also been shown that HDR of a DSB generated by a CRISPR/Cas system comprising the intron-targeting gRNA was increased when editing was performed with a 53BP1 inhibitor and/or DNA-PK inhibitor. It has been further demonstrated that off-target activity of the CRISPR/Cas system is reduced by using a Cas9 endonuclease engineered for high-fidelity. Moreover, the edited population of CD34+ HSPCs were found to effectively engraft following transplantation in a pre-clinical mouse model, resulting in a substantial portion of the bone marrow (e.g., >90%) comprising the edited cells and their progenitors. Additionally, the engrafted cells maintain the gene-edits introduced prior to transplantation and differentiate into red blood cells having substantially equivalent characteristics (e.g., enucleation) to unedited cells.

Accordingly, in some aspects, the disclosure provides methods for treating a hemoglobinopathy (e.g., sickle cell disease) associated with a mutation in the HBB gene (e.g., a mutation in exon 1 of the HBB gene) in a subject in need thereof, the method comprising: (i) introducing a correction to a hemoglobinopathy-associated mutation in HBB (e.g., E6V) in a population of HSPCs according to a method described herein; and (ii) implanting the edited population of cells into the patient. In some aspects, the method further comprises isolating the population of HSPCs from the patient prior to introducing the correction. In some aspects, the population of HSCPs are isolated from the patient following administration of Plerixafor (1,1'-(1,4-phenylenebismethylene)bis(1,4,8,11,-tetraazacyclotetradecane)), granulocyte colony stimulating factor (GCSF), or a combination thereof. In some aspects, the isolating further comprises enrichment of CD34+ cells.

I. Gene Editing to Correct a Mutation in the Human Beta-Globin Gene

Beta-thalassemia and SCD are caused by mutations in the HBB gene encoding the postnatal form of the beta subunit of hemoglobin. The beta-subunit of hemoglobin is generated from genes found in the human β-globin locus, which is composed of five β-like genes and one pseudo-β gene located on a short region of chromosome 11 (approximately 45 kb). Expression of these genes is controlled by a single locus control region (LCR), and the genes are differentially expressed throughout development. The order of the LCR and genes in the β-globin cluster is as follows: 5'-[LCR]-ε (epsilon, HBE1)-Gγ (G-gamma,HBG1)-Aγ (A-gamma, HBG2)-[ψβ (psi-beta pseudogene)]-δ (delta, HBD)-β (beta, HBB)-3'. The arrangement of the five β-like genes reflects the temporal differentiation of their expression during development, with the early embryonic stage version HbE (encoded by the epsilon gene) being located closest to the LCR, followed by the fetal version Hbf (encoded by the γ genes), the delta version, which begins shortly prior to birth and is expressed at low levels in adults as HbA-2 (constituting approximately 3% of adult hemoglobin in normal adults), and finally the beta gene, which encodes the predominant adult version HbA-1 (constituting the remaining 97% of HbA in normal adults).

Over 200 different types of mutations in the HBB gene have been identified in patients with beta-thalassemia, including mutations within the three coding exons, splicing sites, and other regulatory elements of HBB (see, e.g., Weatheral (2001) *NAT REV GENET* 2:245). A point mutation in the sixth codon downstream of the start codon (E6V) in HBB causes the SCD trait. As used herein, “E6V” refers to a point mutation in the sixth codon in the HBB open reading frame downstream of the AUG start codon, wherein the point mutation is GAG to GTG, and results in expression of a beta-globin polypeptide with valine at residue 6. Patients encoding an E6V mutation in both alleles of HBB, or a heterozygous SCD mutation in one allele combined with a beta-thalassemia mutation in the other allele, will produce dysfunctional beta-globin polypeptide that impedes hemoglobin function.

Accordingly, the disclosure provides methods, systems, and compositions for gene editing in a cell or a population of cells (e.g., HSPCs) to correct a mutation in human beta-globin (HBB). Methods for treating a patient by performing the gene-editing are further described herein. For example, in some embodiments, the gene editing is performed in a cell or population of cells (e.g., HSPCs) isolated from a patient having a disease associated with a mutation (e.g., E6V) within the HBB gene (e.g., within exon 1 of the HBB gene), wherein the cell or population of cells is administered to the patient subsequent to the gene-editing, thereby treating or ameliorating the patient’s disease. In some embodiments, the gene editing is performed by administering the systems and/or compositions described herein to the patient having the disease associated with a mutation (e.g., E6V) within the HBB gene (e.g., within exon 1 of the HBB gene), wherein the gene editing in a cell or population of cells (e.g., HSPCs) to correct the mutation occurs in vivo, thereby treating or ameliorating the patient’s disease.

Gene editing generally refers to the process of editing or changing the nucleotide sequence of a gene in a genomic DNA molecule in a cell or a population of cells, preferably in a precise, desirable and/or pre-determined manner. In some aspects, the compositions, systems, and methods of genome editing described herein use a site-directed nuclease to cleave a genomic DNA molecule at a precise target site in a gene, thereby creating a double-strand break (DSB) in the genomic DNA molecule. Several site-directed endonucleases with capability to edit eukaryotic genomes are known in the art, for example, zinc finger nucleases, transcription activator-like effector nucleases (TALENs), Mega-Tal, and CRISPR-Cas systems. The CRISPR-Cas system comprises an RNA molecule referred to as a guide RNA (gRNA) that forms a ribonucleoprotein complex with a Cas nuclease (e.g., a Cas9 nuclease) and functions to target the complex to a target sequence in the genomic DNA molecule. Once bound at the target sequence, the Cas nuclease cleaves both strands of the genomic DNA molecule at a target site within the target sequence to create a DSB. DNA breaks induced by CRISPR/Cas complex are repaired by endogenous cellular mechanisms, including non-homologous end joining (NHEJ) and/or homology directed repair (HDR). In some embodiments, the error-prone NHEJ pathway introduces small insertions or deletions (indels) at the target site. In contrast, the high-fidelity HDR pathway allows for incorporation of a precise gene edit proximal the target site that is encoded by, for example, a donor nucleic acid homologous to the gene administered to the cell or the population of cells.

In some embodiments, the disclosure provides methods, systems, and compositions for gene editing in a cell or a population of cells that results in correction of a mutation in exon 1 of the HBB gene by HDR of a DSB induced at a target site proximal the mutation (e.g., a target site up to about 200, 180, 160, 140, or 120 bp downstream of the mutation). In some embodiments, the gene editing results in correction of an E6V mutation. As used herein, a "correction of the E6V mutation" refers to incorporation of a gene-edit in an HBB gene that encodes the E6V mutation, wherein the gene-edit is incorporated by HDR of a DSB that is induced proximal the mutation, and wherein the gene-edit converts the GTG codon encoding Val at the sixth codon downstream of the start codon to a codon encoding Glu (i.e., E6V to E6), thereby providing an HBB gene that encodes a beta-globin polypeptide having glutamate at position 6. In some embodiments, the gene-edit converts the GTG codon to GAG. In some embodiments, the gene-edit converts the GTG codon to GAA.

In some embodiments, the methods, systems, and compositions for gene editing disclosed herein use a Cas endonuclease (e.g., Cas9, e.g., SpCas9), an intron-targeting gRNA, and a donor nucleic acid or a recombinant vector encoding the donor nucleic acid, wherein the donor nucleic acid comprises a nucleotide sequence homologous with a region of the HBB gene encoding the mutation, and corrects the mutation (e.g., E6V mutation), to edit an HBB gene within a cell or a population of cells (e.g., correction of the E6V mutation in an HBB gene).

In some embodiments, the method disclosed herein use a Cas endonuclease (e.g., Cas9, e.g., SpCas9), an intron-targeting gRNA, a donor nucleic acid or a recombinant vector encoding the donor nucleic acid, and a 53BP1 inhibitor and/or DNA-PK inhibitor, to improve gene editing of an HBB gene within a cell or a population of cells (e.g., correction of an E6V mutation encoded by the HBB gene). In some embodiments, the 53BP1 inhibitor comprises a polypeptide comprising an amino acid sequence set forth in SEQ ID NO: 11 or a nucleic acid (e.g., mRNA) encoding the polypeptide. In some embodiments, the nucleic acid (e.g., mRNA) comprises a nucleotide sequence set forth in SEQ ID NO: 10 or SEQ ID NO: 43. In some embodiments, the DNA-PK inhibitor is a small molecule set forth in Table 2.

II. Systems for Gene Editing

In some aspects, the disclosure provides systems for correcting a hemoglobinopathy-associated mutation in the HBB gene of a genomic DNA molecule. In some embodiments, the mutation is in exon 1 of the HBB gene. In some embodiments, the mutation is an E6V mutation. In some embodiments, the system comprises a site-directed nuclease, such as a CRISPR/Cas system, a gRNA (e.g., an intron-targeting gRNA), and a donor nucleic acid encoding a correction to the mutation, such as those described herein. In some embodiments, the site-directed nuclease is an engineered nuclease. In some embodiments, the site-directed nuclease is a Cas nuclease. In some embodiments, the Cas nuclease is Cas9. In some embodiments, the gRNA is a sgRNA, (e.g., an intron-targeting sgRNA). In some embodiments, the donor nucleic acid is encoded by a recombinant vector (e.g., an AAV).

In some embodiments, the Cas nuclease is directed to cleave (e.g., introduce a DSB) at target site in HBB. In some embodiments, the Cas nuclease is directed by a gRNA described herein to a target sequence in HBB, whereupon the Cas nuclease introduces a DSB at a target site in the target sequence. As is understood by one of skill in the art, the target sequence is adjacent to a PAM at its 3' terminus, and the gRNA spacer sequence hybridizes to the non-PAM strand that is complementary to the target sequence. Moreover, the Cas nuclease introduces the DSB at a target site that is upstream of the PAM sequence (e.g., 3 bp upstream of the PAM sequence) (see, e.g., Jiang, et al (2017) *ANNU REV BIOPHYS* 46:505).

In some embodiments, the disclosure provides an engineered CRISPR/Cas system comprising an intron-targeting gRNA. As used herein, an "intron-targeting gRNA" refers to a gRNA comprising a spacer sequence corresponding to a target sequence within intron 1 of the HBB gene. In some embodiments, the target sequence is adjacent a PAM recognized by the Cas9 endonuclease. In some embodiments, the target sequence is adjacent a PAM recognized by a Cas9 endonuclease that is SpCas9, wherein the PAM is NGG (wherein N=A,C,G,T). In some embodiments, the gRNA complexed with a Cas9 endonuclease described herein induces a DSB at a target site within the target sequence (e.g., 3 bp upstream of the PAM).

In some embodiments, the target site is within intron 1 of the HBB gene. As used herein, the "HBB gene" refers to the human gene located on chromosome 11 that encodes beta-hemoglobin. As is understood by the skilled artisan, the HBB gene contains 3 exons and is located at 11p15.4 (complement is located at 5,225,464-5,227,071 according to reference genome GRCh38.p13). The complement of exon 1 of the HBB gene is located at positions 5,226,931-5,227,021 and the complement of intron 1 of the HBB gene is located at positions 5,226,800-5,226,930, each according to reference genome GRCh38.p13. Gene information for HBB is provided in the NCBI database under Gene ID 3043.

In some embodiments, the target site is at least about 60, 70, 80, 90, 100, 110, 120, 130, 140, 150, 160, 170, 180, 190, or 200 bp downstream of the E6V mutation in the HBB gene. In some embodiments, the target site is no more than about 300, 290, 280, 270, 260, 250, 240, 230, 220, 210, or 200 bp downstream of the E6V mutation in the HBB gene.

A. Guide RNA (gRNA)

Engineered CRISPR/Cas systems comprise at least two components: 1) a guide RNA (gRNA) molecule and 2) a Cas nuclease, which interact to form a Cas nuclease/gRNA complex. In an engineered CRISPR/Cas system, a Cas nuclease/gRNA complex is targeted to a specific target sequence within a target nucleic acid (e.g., a genomic DNA molecule) by generating a gRNA comprising a spacer sequence that binds to the specific target sequence in a complementary fashion (see, e.g., Jinek et al., Science, 337, 816-821 (2012) and Deltcheva et al., Nature, 471, 602-607 (2011). Thus, the spacer sequence provides the targeting function of the Cas nuclease/gRNA complex.

The spacer sequence is a sequence that defines the target sequence in a target nucleic acid (e.g., genomic DNA molecule comprising the HBB gene). The target nucleic acid is a double-stranded molecule: one strand comprises the target sequence comprising a protospacer sequence adjacent to a PAM sequence and is referred to as the "PAM strand," and the second strand is referred to as the "non-PAM strand" and is complementary to the PAM strand. Both the gRNA spacer sequence and the target sequence are complementary to the non-PAM strand of the target nucleic acid.

In some embodiments, the disclosure provides gRNA molecules comprising a spacer sequence that corresponds to a target sequence in a genomic DNA molecule. As used herein, the term "corresponding to a target sequence" is used to reference any gRNA spacer sequence that hybridizes to the non-PAM strand of the given target sequence by Watson-Crick base-pairing, wherein the spacer sequence has sufficient complementary to the non-PAM strand of the target sequence, as to (i) enable targeting of a Cas nuclease described herein to the target sequence in the genomic DNA molecule, and/or (ii) facilitate a cleavage at a target site in the target sequence, for example, with a cleavage efficiency that is at least 10%, at least 15%, at least 20%, at least 25%, at least 30%, at least 35%, at least 40%, at least 45%, at least 50%, or higher as measured by INDELs introduced at the target site.

(i) Target Sequences

In some embodiments, a CRISPR/Cas system described herein is directed to and cleaves (e.g., introduces a DSB) at a target site in a target sequence in an HBB gene. In some embodiments, the Cas nuclease is directed by a gRNA to a target sequence with an HBB gene in a genomic DNA molecule, wherein gRNA spacer sequence hybridizes with the complementary strand of the target sequence, and wherein the Cas nuclease introduces a DSB at the target site in the target sequence.

In some embodiments, the target sequence is downstream a mutation in exon 1 of the HBB gene described herein. In some embodiments, the target sequence is downstream of the E6V mutation. In some embodiments, the target sequence is partially or fully within intron 1 of the HBB gene.

In some embodiments, the rate of HDR is a function of the distance between the mutation and the DSB. Thus, in some embodiments, the target sequence is substantially downstream of the mutation (at least about 50, 55, 60, 65, 70, 75, 80, 85, 90, 95, 100, 110, 120, 130, 140, 150, 160, 170, 180, 190, 200, or no more than 200 bp downstream of the mutation).

In some embodiments, the target sequence is in the coding strand of the HBB gene, wherein the 5' end of the target sequence is about 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 bp downstream of the 3' end of exon 1 of the HBB gene. In some embodiments, the target sequence is in the non-coding strand of the HBB gene, wherein the 3' end of the target sequence is about 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 bp downstream of the 3' end of exon 1 of the HBB gene.

In some embodiments, the Cas nuclease is directed by a gRNA to a target sequence comprising the nucleotide sequence of SEQ ID NO: 1. In some embodiments, the Cas nuclease is directed by a gRNA to a target sequence consisting of the nucleotide sequence of SEQ ID NO: 1. In some embodiments, the Cas nuclease is directed by a gRNA to a target sequence comprising the nucleotide sequence of SEQ ID NO: 49. In some embodiments, the Cas nuclease is directed by a gRNA to a target sequence consisting of the nucleotide sequence of SEQ ID NO: 49.

The length of the target sequence may depend on the nuclease system used. For example, the target sequence for a CRISPR/Cas system comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the target sequence comprises 18-24 nucleotides in length. In some embodiments, the target sequence comprises 19-21 nucleotides in length. In some embodiments, the target sequence comprises 20 nucleotides in length.

(ii) gRNA Components

In naturally-occurring type II-CRISPR/Cas systems, the gRNA is comprised of two RNA strands: 1) a CRISPR RNA (crRNA) comprising the spacer sequence and a CRISPR repeat sequence, and 2) a trans-activating CRISPR RNA (tracrRNA). In Type II-CRISPR/Cas systems, the portion of the crRNA comprising the CRISPR repeat sequence and a portion of the tracrRNA hybridize to form a crRNA: tracrRNA duplex, which interacts with a Cas nuclease (e.g., Cas9). As used herein, the terms "split gRNA" or "modular gRNA" refer to a gRNA molecule comprising two RNA strands, wherein the first RNA strand incorporates the crRNA function(s) and/or structure and the second RNA strand incorporates the tracrRNA function(s) and/or structure, and wherein the first and second RNA strands partially hybridize.

Accordingly, in some embodiments, a gRNA provided by the disclosure comprises two RNA molecules. In some embodiments, the gRNA comprises a crRNA and a tracrRNA. In some embodiments, the gRNA is a split gRNA. In some embodiments, the gRNA is a modular gRNA. In some embodiments, the split gRNA comprises a first strand comprising, from 5' to 3', a spacer sequence, and a first region of complementarity; and a second strand comprising, from 5' to 3', a second region of complementarity; and optionally a tail domain. In some embodiments, the nucleotide at the 5' end of the gRNA corresponds to the nucleotide at the 5' end the spacer sequence. In some embodiments, the spacer sequence is located at the 5' end of the crRNA. In some embodiments, the spacer sequence is located at the 5' end of the gRNA.

In some embodiments, the crRNA comprises a spacer sequence comprising a nucleotide sequence that is complementary to and hybridizes with a sequence that is complementary to the target sequence on a target nucleic acid (e.g., a genomic DNA molecule). In some embodiments, the crRNA comprises a repeat sequence that hybridizes with an anti-repeat sequence of the tracrRNA.

In some embodiments, the tracrRNA comprises all or a portion of a wild-type tracrRNA sequence from a naturally-occurring CRISPR/Cas system (e.g. *S. pyogenes* CRISPR/Cas system). In some embodiments, the tracrRNA comprises a truncated or modified variant of the wild-type tracr RNA. The length of the tracr RNA may depend on the CRISPR/Cas system used. In some embodiments, the tracrRNA comprises 5, 6, 7, 8, 9, 10, 11, 12, 13, 14, 15, 16, 17, 18, 19, 20, 25, 30, 40, 50, 60, 70, 80, 90, 100, or more than 100 nucleotides in length. In some embodiments, the tracrRNA is at least 26 nucleotides in length. In some embodiments, the tracrRNA is at least 40 nucleotides in length. In some embodiments, the tracrRNA comprises certain secondary structures, such as, e.g., one or more hairpins or stem-loop structures, or one or more bulge structures.

(iii) Methods of Spacer Sequence Selection

In some embodiments, the disclosure provides gRNA spacer sequences that target specific regions of the genome (e.g., intron 1 of the HBB gene), that are designed in silico by locating targets sequences (e.g., a 19, 20, 21, 22 bp sequence) adjacent to a PAM sequence described herein (e.g., an SpCas9 PAM, e.g., NGG) in the genomic region of interest (e.g., intron 1 of the HBB gene).

In some embodiments, the target sequence is adjacent to a PAM recognized by a Cas nuclease described herein (e.g., SpCas9). In some embodiments, the 3' end of the target sequence is adjacent to or proximal (e.g., within 1, 2, or 3 nucleotides) of the PAM. In some embodiments, the target sequence is within intron 1 of the HBB gene.

In some embodiments, the nucleotide sequence of the target sequence and the PAM comprises the formula 5' $N_{19-30}$-N-G-G 3', wherein N is any nucleotide, and wherein the four 3' terminal nucleic acids, N-G-G represent the PAM sequence. In some embodiments, the nucleotide sequence is found within intron 1 of the HBB gene.

In some embodiments, a target sequence that perfectly hybridizes with the gRNA spacer sequence occurs only once in a given eukaryotic genome. In some embodiments, the genome comprises additional sequences that imperfectly hybridize with the gRNA spacer sequence, for example, sequences having one or more mismatches (e.g., 1, 2, 3, 4, or 5 mismatches) and/or bulges, relative to the gRNA spacer sequence. In some embodiments, the genome comprises sequences that hybridize to the gRNA spacer sequence that are adjacent to a PAM sequence having at least one mismatch relative to the canonical PAM sequence. Such genomic sequences (e.g., target sequences that imperfectly hybridize to the gRNA spacer sequence or target sequences adjacent to non-canonical PAM sequence) are referred to herein as off-target sites.

In some embodiments, a method of in silico screening is used to predict cleavage efficiency of a gRNA spacer sequence at both on-target and off-target sites, thereby allowing selection of a gRNA with high cleavage efficiency at a target sequence in the genome comprising a target gene, with low or minimal cutting efficiency at off-target sites in the genome (i.e., low or minimal frequency of DNA DSBs occurring at sites other than the selected target sequence).

As described herein, selection of gRNAs with a favorable off-target profile is important for use in a therapeutic method of the disclosure, for example, to eliminate or reduce the risk of undesirable chromosomal rearrangements or off-target mutations. In some embodiments, a favorable off-target profile is one that minimizes or eliminates the number of off-target sites and/or the frequency of cutting at these sites. In some embodiments, a favorable off-target profile is one that minimizes or eliminates off-target sites in specific regions of the genome, for example within or proximal to an oncogene.

As is known in the art, the occurrence of off-target activity can be influenced by a number of factors including similarities and dissimilarities between the target site and various off-target sites, as well as the particular endonuclease used. For example, the ability of a given gRNA to promote cleavage at a target sequence in a genomic DNA molecule relates to, for example, the accessibility of the target sequence, which depends on one or more factors that include the chromatin structure of the genomic DNA molecule and/or proximity to transcription factor binding sites. For example, target sequences located within a region of the genomic DNA molecule having a high condensed chromatin structure are less accessible than target sequences located within a region of the genomic DNA molecule having an open chromatin structure. As a further example, target sequences proximal to a region of the genomic DNA molecule bound by a transcription factor or other regulatory protein may be less accessible than target sequences proximal a region of the genomic DNA molecule that is unbound by regulatory proteins. Moreover, the cell state and type of cell may influence the accessibility of target sequences, for example, by influencing the chromatin structure of genomic DNA.

In some embodiments, the nucleotide sequence of the spacer is designed or chosen using an algorithm or method known in the art. In some embodiments, the algorithm uses variables to screen for suitable gRNA spacer sequences and corresponding target sequences. Non-limiting examples of such variables include predicted melting temperature of the gRNA sequence, secondary structure formation of the gRNA sequence, predicted annealing temperature of the gRNA sequence, sequence identity, genomic context of the target sequence, chromatin accessibility of the target sequence, % GC, frequency of genomic occurrence of the target sequence (e.g., of sequences that are identical or are similar but vary in one or more spots as a result of mismatch, insertion or deletion), methylation status of the target sequence, and/or presence of SNPs within the target sequence.

In some embodiments, one or more bioinformatics tools known in the art are used to predict the off-target activity of a gRNA spacer sequence and/or identify the most likely sites of off-target activity. Non-limiting examples of bioinformatics tools for use in the present disclosure include CCTop, CRISPOR, and COSMID.

In some embodiments, identification of gRNA target sequences is best achieved through a combination of in silico selection and experimental evaluation. Experimental methods to evaluate, for example, gRNA on-target and off-target cleavage efficiency are known in the art and further described herein.

In some embodiments, cleavage efficiency is measured as frequency of INDELs proximal to the target site targeted by the gRNA spacer sequence. Methods to measure frequency of INDELs at a particular target site in a genome are known in the art. An exemplary method to measure frequency of INDELs at a predicted target site in a given target sequence comprises, (i) isolation of genomic DNA from the edited cell population and/or tissue, (ii) amplification of the DNA region comprising the target sequence (e.g., by PCR), (iii) sequencing of the amplified DNA region (e.g., by Sanger sequencing), and (iv) determining frequency of INDELs at the predicted cut site by Tracking of Indels decomposition (TIDE) assay, for example, as described by Brinkman, et al (2014) *NUCLEIC ACIDS RESEARCH* 42:e168. A further exemplary method comprises sequencing of the amplified DNA region by next-generation sequencing (NGS) and analysis of INDEL frequency at the predicted target site in the target sequence, for example, as described by Bell et al (2014) *BMC Genomics* 15:1002.

In some embodiments, cleavage efficiency is measured as the frequency of total sequence reads having an INDEL of at least ±1 nt (e.g, ±1 nt, ±2 nt, ±3 nt, ±4 nt, ±5 nt, ±6 nt, ±7 nt, ±8 nt, or ±9 nt). In some embodiments, a gRNA is selected that targets a target site either adjacent to or about 1 bp to about 200 bp downstream of the 3' end of exon 1 of the HBB gene, wherein a CRISPR/Cas system comprising the gRNA has a cleavage efficiency at the target site of at least 10%, 15%, 20%, 25%, 30%, 35%, 40%, 45%, 50% or higher. In some embodiments, a gRNA is selected that targets a target site in intron 1 of the HBB gene, wherein a CRISPR/Cas system comprising the gRNA has cleavage efficiency at the target site of at least 10%, 15%, 20%, 25%, 30%, 35%, 40%, 45%, 50% or higher. In some embodiments, cleavage efficiency is measured using TIDE analysis. In some embodiments, cleavage efficiency is measured by NGS and analysis of INDEL frequency.

(iv) Spacer Sequences

In some embodiments, the gRNAs provided by the disclosure (e.g., intron-targeting gRNAs) comprise a spacer sequence. A spacer sequence is a sequence that defines the target site in a target nucleic acid (e.g., genomic DNA molecule) for cleavage by a CRISPR/Cas complex. The target nucleic acid is a double-stranded molecule: one strand comprises the target sequence adjacent a PAM sequence and is referred to as the "PAM strand," and the second strand is referred to as the "non-PAM strand" and is complementary to the PAM strand and target sequence. Both the gRNA spacer sequence and the target sequence are complementary to the non-PAM strand of the target nucleic acid. A spacer sequence corresponding to a target sequence adjacent to a PAM sequence is complementary to the non-PAM strand of the target nucleic acid. In a sense, a spacer sequence is the RNA version of the target sequence, wherein the spacer sequence hybridizes to the non-PAM strand. In some embodiments, the spacer is sufficiently complementary to the non-PAM strand, as to target a Cas nuclease to the target nucleic acid.

In some embodiments, the spacer sequence is about 15-50, about 20-45, about 25-40 or about 30-35 nucleotides in length. In some embodiments, the spacer sequence is about 19-22 nucleotides in length. In some embodiments the spacer sequence is about 15, 16, 17, 18, 19, 20, 21, 22, 23, 24, 25, 26, 27, 28, 29 or 30 nucleotides in length. In some embodiments the spacer sequence is 19 nucleotides in length. In some embodiments, the spacer sequence is 20 nucleotides in length, in some embodiments, the spacer sequence is 21 nucleotides in length.

In some embodiments, the spacer sequence comprises a nucleotide sequence with up to 1, 2, or 3 nucleotides that are not complementary to the non-PAM strand of the target sequence, wherein the spacer sequence has sufficient complementary to the non-PAM strand of the target sequence to target a Cas nuclease to the target sequence in the target nucleic acid and/or to facilitate a DNA break proximal the target sequence. In some embodiments, the spacer comprises 1 nucleotide that is not complementary with the non-PAM strand of the target sequence in the target nucleic acid. In some embodiments, the spacer sequence comprises 2 nucleotides that are not complementary with the non-PAM strand of the target sequence in the target nucleic acid. In some embodiments, the spacer sequence comprises 3 nucleotides that are not complementary with the non-PAM strand of the target sequence in the target nucleic acid.

In some embodiments, the spacer sequence comprises a nucleotide sequence having up to 1, 2, or 3 nucleotide deletions or substitutions relative to nucleotides located 5' to 3' at positions 1, 2, or 3 of the target sequence (e.g., positions 16, 17, 18, 19, 20, 21, 22, 23, 24 or 25 upstream of the PAM).

In some embodiments, the spacer sequence corresponds to a target sequence in intron 1 of the HBB gene, the target sequence comprising the sequence 5' $N_{19-30}$-N-G-G 3'.

In some embodiments, the spacer sequence corresponds to a target sequence comprising SEQ ID NO: 1. In some embodiments, the spacer sequence corresponds to a target sequence comprising SEQ ID NO: 1, and comprises 1, 2, 3, 4, 5, 6 or more nucleotides that are not complementary with the non-PAM strand of the target nucleic acid.

In some embodiments, the spacer sequence comprises SEQ ID NO: 3. In some embodiments, the spacer sequence comprises a sequence at least 90%, 91%, 92%, 93%, 94%, 95%, 96%, 97%, 98% or 99% identical to SEQ ID NO: 3. In some embodiments, the spacer sequence consists of SEQ ID NO: 3.

In some embodiments, the spacer sequence corresponds to a target sequence comprising SEQ ID NO: 49. In some embodiments, the spacer sequence corresponds to a target sequence comprising SEQ ID NO: 49, and comprises 1, 2, 3, 4, 5, 6 or more nucleotides that are not complementary with the non-PAM strand of the target nucleic acid.

In some embodiments, the spacer sequence comprises SEQ ID NO: 51. In some embodiments, the spacer sequence comprises a sequence at least 90%, 91%, 92%, 93%, 94%, 95%, 96%, 97%, 98% or 99% identical to SEQ ID NO: 51. In some embodiments, the spacer sequence consists of SEQ ID NO: 51.

In some embodiments, the spacer sequence comprises at least one or more modified nucleotide(s) such as one or more 2'-O-methyl phosphorothioate nucleotides. In some embodiments, the disclosure provides gRNA molecules comprising a spacer sequence which comprise the nucleobase uracil (U), while any DNA encoding a gRNA comprising a spacer comprising the nucleobase uracil (U) comprises the nucleobase thymine (T) in the corresponding position(s).

(v) Single Guide RNA (sgRNA)

Engineered CRISPR/Cas nuclease systems often combine a crRNA and a tracrRNA into a single RNA molecule, referred to herein as a "single guide RNA" (sgRNA), by adding a linker between these components. Without being bound by theory, similar to a duplexed crRNA and tracrRNA, a sgRNA will form a complex with a Cas nuclease described herein (e.g., SpCas9), and guide the Cas nuclease to a target sequence and activate the Cas nuclease for cleavage of the target nucleic acid (e.g., genomic DNA).

Accordingly, in some embodiments, the gRNA comprises a crRNA and a tracrRNA described herein that are operably linked. In some embodiments, the sgRNA comprises a crRNA covalently linked to a tracrRNA. In some embodiments, the crRNA and the tracrRNA are covalently linked via a linker. In some embodiments, the sgRNA comprises a stem-loop structure via base pairing between the crRNA and the tracrRNA. In some embodiments, a sgRNA comprises, from 5' to 3', a spacer sequence, a first region of complementarity, a linking domain, a second region of complementarity, and, optionally, a tail domain.

In some embodiments, the linking domain is a tetraloop. For example, a suitable tetraloop for use in the present disclosure is any one described by Sheehy, J. P., et al RNA 16, 417-429 (2010) or Jinek, M. et al. Science 337, 816-821 (2012). In some embodiments, the linking domain comprises the nucleotide sequence GAAA or UUCG. In some embodiments, the nucleotide adjacent the 5' end of the linking domain and the nucleotide adjacent the 3' end of the linking domain form G-C base pair. In some embodiments, the sgRNA comprises 5'-C-GAAA-G-3', 5'-G-GAAA-C-3', 5'-C-UUCG-G-3', or 5'-G-UUCG-C-3'.

In some embodiments, the sgRNA comprises a 20 nucleotide spacer sequence at the 5' end of the sgRNA sequence. In some embodiments, the sgRNA comprises a less than 20 nucleotide spacer sequence at the 5' end of the sgRNA sequence. In some embodiments, the sgRNA comprises a more than 20 nucleotide spacer sequence at the 5' end of the sgRNA sequence.

In some embodiments, the sgRNA comprises no uracil at the 3' end of the sgRNA sequence. In some embodiments, the sgRNA comprises one or more uracil(s) at the 3' end of the sgRNA sequence. For example, in some embodiments, the sgRNA comprises 1 uracil (U) at the 3' end of the sgRNA sequence. In some embodiments, the sgRNA comprises 2 uracil (UU) at the 3' end of the sgRNA sequence. In some embodiments, the sgRNA comprises 3 uracil (UUU) at the 3' end of the sgRNA sequence. In some embodiments, the sgRNA comprises 4 uracil (UUUU) at the 3' end of the sgRNA sequence. In some embodiments, the sgRNA comprises 5 uracil (UUUUU) at the 3' end of the sgRNA sequence. In some embodiments, the sgRNA comprises 6 uracil (UUUUUU) at the 3' end of the sgRNA sequence. In some embodiments, the sgRNA comprises 7 uracil (UUUUUUU) at the 3' end of the sgRNA sequence. In some embodiments, the sgRNA comprises 8 uracil (UUUUUUUU) at the 3' end of the sgRNA sequence.

In some embodiments, the sgRNA comprises a spacer sequence targeting a target site in intron 1 of the HBB gene. In some embodiments, the sgRNA comprises a spacer sequence targeting a target site adjacent to the 3' end of exon 1 of the HBB gene. In some embodiments, the sgRNA comprises a spacer sequence targeting a target site proximal (e.g., ±1 bp, ±2 bp, ±3 bp, ±4 bp, ±5 bp, ±6 bp, ±7 bp, ±8 bp, or ±9 bp) to the 3' end of exon 1 of the HBB gene. In some embodiments, the sgRNA comprises a spacer sequence targeting a target site at least 10, 15, 20, 25, 30, 35, 40, 45, 50, 55, 60, 65, 70, 75, 80, 85, 90, 95, 100, 110, 120, 130, 140, 150, 160, 170, 180, 190, or 200 bp downstream of the 3' end of exon 1 of the HBB gene. In some embodiments, the sgRNA comprises a spacer sequence targeting a target site that is about 10 to about 200 bp downstream of the 3' end of exon 1 of the HBB gene.

In some embodiments, the sgRNA comprises a spacer sequence comprising SEQ ID NO: 3. In some embodiments, the sgRNA comprises SEQ ID NO: 3. In some embodiments, the sgRNA comprises a nucleotide sequence at least 90%, 91%, 92%, 93%, 94%, 95%, 96%, 97%, 98% or 99% identical to SEQ ID NO: 3.

In some embodiments, the sgRNA comprises a spacer sequence comprising SEQ ID NO: 51. In some embodiments, the sgRNA comprises SEQ ID NO: 51. In some embodiments, the sgRNA comprises a nucleotide sequence at least 90%, 91%, 92%, 93%, 94%, 95%, 96%, 97%, 98% or 99% identical to SEQ ID NO: 51.

In some embodiments, the sgRNA comprises unmodified or modified nucleotides. For example, in some embodiments, the sgRNA comprises one or more 2'-O-methyl phosphorothioate nucleotides.

In some embodiments, the sgRNA comprises the nucleotide sequence of SEQ ID NO: 4. In some embodiments, the sgRNA comprise a nucleotide sequence having at least 80%, 85%, 90%, 91%, 92%, 93%, 94%, 95%, 96%, 97%, 98%, or 99% identity to the nucleotide sequence set forth in SEQ ID NO: 4, or a nucleotide sequence having up to 1, 2, 3, 4, 5, 6, 7, 8, 9, or 10 nucleotide deletions or substitutions relative to the nucleotide sequence set forth in SEQ ID NO: 4.

In some embodiments, the sgRNA comprises the nucleotide sequence of SEQ ID NO: 52. In some embodiments, the sgRNA comprise a nucleotide sequence having at least 80%, 85%, 90%, 91%, 92%, 93%, 94%, 95%, 96%, 97%, 98%, or 99% identity to the nucleotide sequence set forth in SEQ ID NO: 52, or a nucleotide sequence having up to 1, 2, 3, 4, 5, 6, 7, 8, 9, or 10 nucleotide deletions or substitutions relative to the nucleotide sequence set forth in SEQ ID NO: 52.

(vi) Methods of Making Guide RNAs

The gRNAs of the present disclosure are produced by a suitable means available in the art, including but not limited to in vitro transcription (IVT), synthetic and/or chemical synthesis methods, or a combination thereof. Enzymatic (IVT), solid-phase, liquid-phase, combined synthetic methods, small region synthesis, and ligation methods are utilized. In one embodiment, the gRNAs are made using IVT enzymatic synthesis methods. Methods of making polynucleotides by IVT are known in the art and are described in International Application PCT/US2013/30062. Accordingly, the present disclosure also includes polynucleotides, e.g., DNA, constructs and vectors are used to in vitro transcribe a gRNA described herein.

In some aspects, non-natural modified nucleobases are introduced into polynucleotides, e.g., gRNA, during synthesis or post-synthesis. In certain embodiments, modifications are on internucleoside linkages, purine or pyrimidine bases, or sugar. In particular embodiments, the modification is introduced at the terminal of a polynucleotide; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

In some aspects, enzymatic or chemical ligation methods are used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

Certain embodiments of the invention also provide nucleic acids, e.g., vectors, encoding gRNAs described herein. In some embodiments, the nucleic acid is a DNA molecule. In other embodiments, the nucleic acid is an RNA molecule. In some embodiments, the nucleic acid comprises a nucleotide sequence encoding a crRNA. In some embodiments, the nucleotide sequence encoding the crRNA comprises a spacer flanked by all or a portion of a repeat sequence from a naturally-occurring CRISPR/Cas system. In some embodiments, the nucleic acid comprises a nucleotide sequence encoding a tracrRNA. In some embodiments, the crRNA and the tracrRNA is encoded by two separate nucleic acids. In other embodiments, the crRNA and the tracrRNA is encoded by a single nucleic acid. In some embodiments, the crRNA and the tracrRNA is encoded by opposite strands of a single nucleic acid. In other embodiments, the crRNA and the tracrRNA is encoded by the same strand of a single nucleic acid.

In some embodiments, the gRNAs provided by the disclosure are chemically synthesized by any means described in the art (see e.g., WO/2005/01248). While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together.

In some embodiments, the gRNAs provided by the disclosure are synthesized by enzymatic methods (e.g., in vitro transcription, IVT).

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

B. Site-Directed Nucleases

In some embodiments, the disclosure provides compositions and systems (e.g., an engineered CRISPR/Cas system) comprising a site-directed nuclease.

(i) Cas Nucleases

In some embodiments, the disclosure provides compositions and systems (e.g., an engineered CRISPR/Cas system) comprising a site-directed nuclease, wherein the site-directed nuclease is a Cas nuclease. As used herein, the term "Cas nuclease" refers to a nuclease that combines with an appropriate gRNA to form an RNA-guided endonuclease, wherein the RNA-guided endonuclease recognizes a specific target sequence in a DNA molecule (e.g., a genomic DNA molecule), or its complimentary sequence, having a protospacer sequence corresponding to the gRNA spacer sequence, and that is adjacent a protospacer adjacent motif (PAM) recognized by the Cas nuclease, whereupon the RNA-guided endonuclease generates a DNA break within the DNA molecule at a target site in the target sequence (e.g., 3 bp upstream of the 5' end of the PAM). Subsequently, the DNA break is subject to repair by the cellular DNA repair machinery, such as machinery for homology directed repair (HDR) and/or non-homologous end-joining (NHEJ) repair.

In some embodiments, the Cas nuclease is derived from a CRISPR/Cas Type-I, Type-II, or Type-III system. Updated classification schemes for CRISPR/Cas loci define Class 1 and Class 2 CRISPR/Cas systems, having Types I to V or VI (Makarova et al., (2015) Nat Rev Microbiol, 13(11):722-36; Shmakov et al., (2015) Mol Cell, 60:385-397). Class 2 CRISPR/Cas systems have single protein effectors. Cas proteins of Types II, V, and VI are single-protein, RNA-guided endonucleases, herein called "Class 2 Cas nucleases." Class 2 Cas nucleases include, for example, Cas9, Cpf1, C2c1, C2c2, and C2c3 proteins. The Cpf1 nuclease (Zetsche et al., (2015) Cell 163:1-13) is homologous to Cas9, and contains a RuvC-like nuclease domain.

In some embodiments, the Cas nuclease is from a Type-II CRISPR/Cas system (e.g., a Cas9 protein from a CRISPR/Cas9 system). In some embodiments, the Cas nuclease is from a Class 2 CRISPR/Cas system (a single-protein Cas nuclease such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, as described further herein.

In alternative embodiments, the Cas nuclease is from a Type-I CRISPR/Cas system. In some embodiments, the Cas nuclease is a component of the Cascade complex of a Type-I CRISPR/Cas system. For example, the Cas nuclease is a Cas3 nuclease. In some embodiments, the Cas nuclease is derived from a Type-III CRISPR/Cas system. In some embodiments, the Cas nuclease is derived from Type-IV CRISPR/Cas system. In some embodiments, the Cas nuclease is derived from a Type-V CRISPR/Cas system. In some embodiments, the Cas nuclease is derived from a Type-VI CRISPR/Cas system.

In some embodiments, the Cas nuclease from a Type-II CRISPR/Cas system is from a Type-IIA, Type-IIB, or Type-IIC system. Cas9 and its orthologs are encompassed. Non-limiting exemplary species that the Cas9 nuclease or other components are from include *Streptococcus pyogenes, Streptoccoccus lugdunensis, Streptococcus thermophilus, Streptococcus* sp., *Staphylococcus aureus, Listeria innocua, Lactobacillus gasseri, Francisella novicida, Wolinella succinogenes, Sutterella wadsworthensis, Gamma proteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria*, or *Acaryochloris marina*. In some embodiments, the Cas9 protein are from *Streptococcus pyogenes* (SpCas9). In some embodiments, the Cas9 protein is from *S. lugdunensis* (SluCas9). In some embodiments, the Cas9 protein are from *Staphylococcus aureus* (SaCas9). In some embodiments, a suitable Cas9 protein for use in the present disclosure is any disclosed in WO2019/183150 and WO2019/118935, each of which is incorporate herein by reference.

In some embodiments, a Cas nuclease comprises more than one nuclease domain. For example, in some embodiments, the Cas9 nuclease comprises at least one RuvC-like nuclease domain (e.g., Cpf1) and at least one HNH-like nuclease domain (e.g., Cas9). In some embodiments, the Cas9 nuclease introduces a DSB in the target sequence. In some embodiments, the Cas9 nuclease is modified to contain only one functional nuclease domain. For example, the Cas9 nuclease is modified such that one of the nuclease domains is mutated or fully or partially deleted to reduce its nucleic acid cleavage activity. In some embodiments, the Cas9 nuclease is modified to contain no functional RuvC-like nuclease domain. In other embodiments, the Cas9 nuclease is modified to contain no functional HNH-like nuclease domain. In some embodiments in which only one of the nuclease domains is functional, the Cas9 nuclease is a nickase that is capable of introducing a single-stranded break (a "nick") into the target sequence. In some embodiments, a conserved amino acid within a Cas9 nuclease nuclease domain is substituted to reduce or alter a nuclease activity. In some embodiments, the Cas nuclease nickase comprises an amino acid substitution in the RuvC-like nuclease domain. Exemplary amino acid substitutions in the RuvC-like nuclease domain include D10A (based on the *S. pyogenes* Cas9 nuclease). In some embodiments, the nickase comprises an amino acid substitution in the HNH-like nuclease domain. Exemplary amino acid substitutions in the HNH-like nuclease domain include E762A, H840A, N863A, H983A, and D986A (based on the *S. pyogenes* Cas9 nuclease). In some embodiments, the nuclease system described herein comprises a nickase and a pair of guide RNAs that are complementary to the sense and antisense strands of the target sequence, respectively. The guide RNAs directs the nickase to target and introduce a DSB by generating a nick on opposite strands of the target sequence (i.e., double nicking). Chimeric Cas9 nucleases are used, where one domain or region of the protein is replaced by a portion of a different protein. For example, a Cas9 nuclease domain is replaced with a domain from a different nuclease such as Fok1. A Cas9 nuclease is a modified nuclease.

In some embodiments, the Cas nuclease is a Cas9 polypeptide encoded by a CRISPR/Cas locus found in the *Staphylococcus genus*. In some embodiments, the Cas nuclease is a SpCas9 polypeptide. As used herein, "SpCas9", "SpCas9 polypeptide", and "SpCas9 nuclease" are interchangeable terms referring to wild-type Cas9 derived from *Streptococcus pyogenes*, e.g., a polypeptide having the amino acid sequence of SEQ ID NO: 48. SpCas9 forms an active CRISPR/Cas system when combined with a suitable gRNA molecule, wherein the system cleaves a genomic DNA molecule at a target site in a target sequence adjacent an SpCas9 PAM sequence (e.g., NGG).

In some embodiments, a suitable Cas9 nuclease for use in the present disclosure is a functional derivative of SpCas9 nuclease. In some embodiments, a functional derivative of SpCas9 nuclease for use in the present disclosure is any variant of wild-type SpCas9 nuclease having equivalent or similar functional properties. For example, a functional derivative of SpCas9 is any variant of wild-type SpCas9 that combines with a suitable gRNA molecule in a cell to cleave a genomic DNA molecule proximal a target sequence adjacent an SpCas9 PAM sequence (e.g., NGG) that is targeted by the gRNA molecule. In some embodiments, the functional derivative of SpCas9 nuclease has substantial sequence homology with wild-type SpCas9 (e.g., at least about 80%, about 85%, about 90%, about 95%, about 96%, about 97%, about 98%, or about 99%). In some embodiments, the functional derivative of SpCas9 nuclease has substantially equivalent cleavage efficiency (e.g., as measured by frequency of INDELs at a target site directed by the gRNA) relative to wild-type SpCas9. In some embodiments, a functional derivative of SpCas9 nuclease comprises one or more mutations relative to wild-type SpCas9 that result in increased cleavage efficiency (e.g., as measured by frequency of INDELs at a target site directed by the gRNA) relative to wild-type SpCas9. In some embodiments, a functional derivative of SpCas9 nuclease comprises one or more mutations relative to wild-type SpCas9 that result in increased fidelity, as further described herein. In some embodiments, a functional derivative of SpCas9 nuclease comprises one or more mutations relative to wild-type SpCas9 that result in improved specificity for a canonical SpCas9 PAM sequence (i.e., NGG). In some embodiments, a functional derivative of SpCas9 nuclease has one or more nuclease domains replaced with a nuclease domain from another site-directed endonuclease (e.g., Cas9 nuclease) relative to wild-type SpCas9. In some embodiments, a functional derivative of SpCas9 is a modified nuclease (e.g., a modified nuclease comprising a nuclear localization domain) relative to wild-type SpCas9, as further described herein.

(ii) High Fidelity Cas Nucleases

In some embodiments, the disclosure provides a CRISPR/Cas system comprising a Cas nuclease engineered for increased fidelity. As used herein, the term "fidelity" when used in reference to a CRISPR/Cas system comprising a Cas nuclease and gRNA refers to the specificity of the system for a target site in a DNA molecule (e.g., genomic DNA molecule) that is homologous (e.g., perfect match) to the gRNA spacer sequence. In some embodiments, a CRISPR/Cas system with increased fidelity has reduced activity at off-target sites in the DNA molecule, i.e., sites that are an imperfect match to the gRNA spacer sequence.

In some embodiments, a CRISPR/Cas system of the disclosure comprises a Cas variant comprising one or more mutations for increased fidelity. In some embodiments, the one or more mutations result in reduced activity of the CRISPR/Cas system at off-target sites in the DNA molecule, for example, compared to a system comprising an unmodified version of the Cas nuclease (e.g., wild-type Cas nuclease). In some embodiments, the CRISPR/Cas system has substantially equivalent activity for inducing cleavage at an on-target site in the DNA molecule, for example, as compared to the system comprising an unmodified version of the Cas nuclease.

Methods of making Cas variants with increased fidelity are known in the art. For example, in some embodiments, a method of structure-guided engineering is used to make a Cas variant with increased fidelity.

In some embodiments, a CRISPR/Cas system described herein comprises a Cas9 nuclease comprising one or more mutations for increased fidelity. In some embodiments, the Cas9 nuclease is derived from *S. pyogenes*, wherein the Cas nuclease comprises one or more mutations relative to wild-type SpCas9 for increased fidelity. In some embodiments, the Cas nuclease comprises a mutation of R691 relative to wild-type SpCas9 for increased fidelity. In some embodiments, the mutation of R691 is to alanine (R691A).

A suitable Cas9 nuclease with increased fidelity for use in the present disclosure includes any one described US2019/0010471; US2018/0142222; U.S. Pat. No. 9,944,912; WO2020/057481; US2019/0177710; US2018/0100148; U.S. Pat. No. 10,526,591; and US20200149020; each of which is incorporated herein by reference in their entirety.

In some embodiments, the Cas nuclease engineered for increased fidelity comprises one or more (e.g., 1, 2, 3, 4, 5, 6, 7, 8, 9, or 10) nuclear localization signals (NLSs). In some embodiments, Cas nuclease comprises one or more NLSs at the N-terminus, the C-terminus, or both. In some embodiments, the Cas nuclease comprises 1, 2, 3, 4, or 5 NLSs at the N-terminus. In some embodiments, the Cas nuclease comprises 1, 2, 3, 4, or 5 NLSs at the C-terminus. In some embodiments, the Cas nuclease comprises 1, 2, 3, 4, or 5 NLSs at the N-terminus; and 1, 2, 3, 4, or 5 NLSs at the C-terminus. In some embodiments, the NLS is a SV40 NLS, PKKKRKV (SEQ ID NO: 25) or PKKKRRV (SEQ ID NO: 26). In some embodiments, the NLS is a bipartite sequence, such as, e.g., the NLS of nucleoplasmin, KRPAATKKAGQAKKKK (SEQ ID NO: 27).

In some embodiments, the Cas nuclease engineered for increased fidelity is SpCas9 comprising an R691A mutation relative to SEQ ID NO: 48. In some embodiments, the SpCas9 comprising an R691A mutation comprises one or more (e.g., 1, 2, 3, 4, 5, 6, 7, 8, 9, or 10) nuclear localization signals (NLSs). In some embodiments, the SpCas9 comprising an R691A mutation comprises 1, 2, 3, 4, or 5 NLSs at the N-terminus; 1, 2, 3, 4, or 5 NLSs at the N-terminus; or both. In some embodiments, the NLS at the N-terminus is an SV40 NLS or a nucleoplasmin NLS. In some embodiments, the NLS at the C-terminus is an SV40 NLS or a nucleoplasmin NLS. In some embodiments, the SpCas9 comprising an R691A mutation comprises an N-terminal NLS that is an SV40 NLS, and a C-terminal NLS that is an SV40 NLS.

In some embodiments, a Cas nuclease engineered for increased fidelity reduces cleavage of one or more predicted off-target sites by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 115%, at least about 120%, at least about 125%, at least about 30%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, or at least about 200%, relative to a Cas nuclease not engineered for increased fidelity (e.g. wild-type Cas nuclease). In some embodiments, a Cas nuclease engineered for increased fidelity reduces cleavage of one or more predicted off-target sites by about 10% to about 200%, about 20% to about 190%, about 30% to about 180%, about 40% to about 170%, about 50% to about 160%, about 60% to about 150%, about 70% to about 140%, about 80% to about 130%, about 90% to about 120%, about 100% to about 110%, relative to a Cas nuclease not engineered for increased fidelity (e.g. wild-type Cas nuclease).

In some embodiments, cleavage of an off-target or on-target site is determined based on the percentage of INDELs. In some embodiments, the percentage of INDELs generated at one or more off-target sites by a Cas nuclease engineered for increased fidelity is decreased relative to the percentage of INDELs generated by a Cas nuclease not engineered for increased fidelity (e.g., wild-type Cas nuclease).

In some embodiments, a Cas nuclease engineered for increased fidelity maintains the same level of cleavage of the on-target site, and reduces the cleavage of one or more predicted off-target sites compared to a Cas nuclease not engineered for increased fidelity (e.g., wild-type Cas nuclease).

(iii) Modified Nucleases

In certain embodiments, the nuclease is optionally modified from its wild-type counterpart. In some embodiments, the nuclease is fused with at least one heterologous protein domain. At least one protein domain is located at the N-terminus, the C-terminus, or in an internal location of the nuclease. In some embodiments, two or more heterologous protein domains are at one or more locations on the nuclease.

In some embodiments, the protein domain may facilitate transport of the nuclease into the nucleus of a cell. For example, the protein domain is a nuclear localization signal (NLS). In some embodiments, the nuclease is fused with 1-10 NLS(s). In some embodiments, the nuclease is fused with 1-5 NLS(s). In some embodiments, the nuclease is fused with one NLS. In other embodiments, the nuclease is fused with more than one NLS. In some embodiments, the nuclease is fused with 2, 3, 4, or 5 NLSs. In some embodiments, the nuclease is fused with 2 NLSs. In some embodiments, the nuclease is fused with 3 NLSs. In some embodiments, the nuclease is fused with no NLS. In some embodiments, the NLS may be a monopartite sequence, such as, e.g., the SV40 NLS, PKKKRKV (SEQ ID NO: 25) or PKKKRRV (SEQ ID NO: 26). In some embodiments, the NLS is a bipartite sequence, such as, e.g., the NLS of nucleoplasmin, KRPAATKKAGQAKKKK (SEQ ID NO: 27). In some embodiments, the NLS is genetically modified from its wild-type counterpart.

In some embodiments, the protein domain is capable of modifying the intracellular half-life of the nuclease. In some embodiments, the half-life of the nuclease may be increased. In some embodiments, the half-life of the nuclease is reduced. In some embodiments, the entity is capable of increasing the stability of the nuclease. In some embodiments, the entity is capable of reducing the stability of the nuclease. In some embodiments, the protein domain act as a signal peptide for protein degradation. In some embodiments, the protein degradation is mediated by proteolytic enzymes, such as, e.g., proteasomes, lysosomal proteases, or calpain proteases. In some embodiments, the protein domain comprises a PEST sequence. In some embodiments, the nuclease is modified by addition of ubiquitin or a polyubiquitin chain. In some embodiments, the ubiquitin is a ubiquitin-like protein (UBL). Non-limiting examples of ubiquitin-like proteins include small ubiquitin-like modifier (SUMO), ubiquitin cross-reactive protein (UCRP, also known as interferon-stimulated gene-15 (ISG15)), ubiquitin-related modifier-1 (URM1), neuronal-precursor-cell-expressed developmentally downregulated protein-8 (NEDD8, also called Rub 1 in *S. cerevisiae*), human leukocyte antigen F-associated (FAT10), autophagy-8 (ATG8) and -12 (ATG12), Fau ubiquitin-like protein (FUB1), membrane-anchored UBL (MUB), ubiquitin fold-modifier-1 (UFM1), and ubiquitin-like protein-5 (UBLS).

In some embodiments, the protein domain is a marker domain. Non-limiting examples of marker domains include fluorescent proteins, purification tags, epitope tags, and reporter gene sequences. In some embodiments, the marker domain is a fluorescent protein. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreenl), yellow fluorescent proteins (e.g., YFP, EYFP, Citrine, Venus, YPet, PhiYFP, ZsYellowl), blue fluorescent proteins (e.g., EBFP, EBFP2, Azurite, mKalamal, GFPuv, Sapphire, T-sapphire,), cyan fluorescent proteins (e.g., ECFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain is a purification tag and/or an epitope tag. Non-limiting exemplary tags include glutathione-S-transferase (GST), chitin binding protein (CBP), maltose binding protein (MBP), thioredoxin (TRX), poly (NANP), tandem affinity purification (TAP) tag, myc, AcV5, AU1, AUS, E, ECS, E2, FLAG (SEQ ID NO: 95), HA, nus, Softag 1, Softag 3, Strep, SBP, Glu-Glu, HSV, KT3, S, S1, T7, V5, VSV-G, 6× His (SEQ ID NO: 94), biotin carboxyl carrier protein (BCCP), and calmodulin. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the protein domain may target the nuclease to a specific organelle, cell type, tissue, or organ.

In further embodiments, the protein domain is an effector domain. When the nuclease is directed to its target nucleic acid, e.g., when a Cas9 protein is directed to a target nucleic acid by a guide RNA, the effector domain may modify or affect the target nucleic acid. In some embodiments, the effector domain is chosen from a nucleic acid binding domain, a nuclease domain, an epigenetic modification domain, a transcriptional activation domain, or a transcriptional repressor domain. In some embodiments, the effector domain can be a nucleobase deaminase domain.

Certain embodiments of the invention also provide nucleic acids encoding the nucleases (e.g., a Cas9 protein) described herein provided on a vector. In some embodiments, the nucleic acid is a DNA molecule. In other embodiments, the nucleic acid is an RNA molecule. In some embodiments, the nucleic acid encoding the nuclease is an mRNA molecule. In certain embodiments, the nucleic acid is an mRNA encoding a Cas9 protein.

In some embodiments, the nucleic acid encoding the nuclease is codon optimized for efficient expression in one or more eukaryotic cell types. In some embodiments, the nucleic acid encoding the nuclease is codon optimized for efficient expression in one or more mammalian cells. In some embodiments, the nucleic acid encoding the nuclease is codon optimized for efficient expression in human cells. Methods of codon optimization including codon usage tables and codon optimization algorithms are available in the art.

(iv) Messenger RNA Encoding Cas Nuclease

In some aspects, the disclosure provides an mRNA encoding a Cas nuclease described herein or functional derivative thereof (e.g., high fidelity Cas nuclease), for use in methods of gene editing using a CRISPR/Cas system described herein. In some embodiments, the mRNA comprises a 5' UTR, an open reading frame (ORF) comprising a nucleotide sequence encoding the Cas nuclease, and a 3' UTR.

In some embodiments, the mRNA comprises one or more modification to improve mRNA stability, increase mRNA translation efficiency, and/or reduce mRNA immunogenicity. In some embodiments, the one or more modification is sequence optimization of the mRNA and/or chemical modification of at least one nucleotide of the mRNA.

In some embodiments, the mRNA comprises a sequence-optimized nucleotide sequence. In some embodiments, the mRNA comprises a nucleotide sequence that is sequence optimized for expression in a target cell. In some embodiments, the target cell is a mammalian cell. In some embodiments, the target cell is a human cell, a murine cell, or a non-human primate (NHP) cell. Methods of sequence optimization are known in the art, and include known sequence optimization tools, algorithms and services. Non-limiting examples include services from GeneArt (Life Technologies), DNA2.0 (Menlo Park CA), Geneious®, GeneGPS® (Atum, Newark, CA), and/or proprietary methods. In some embodiments, the nucleotide sequence is (i) sequence-optimized based on codon usage bias in a host cell (e.g., mammalian cell, e.g., human cell, murine cell, non-human primate cell) relative to a reference sequence, (ii) uridine-depleted relative to a reference sequence, or (iii) a combination of (i) and (ii), using a method of sequence optimization (e.g., GeneGPS®, e.g., Geneious®).

In some embodiments, the mRNA has chemistries suitable for delivery, tolerability, and stability within cells, e.g., following in vivo or in vitro administration. In some embodiments, the mRNA is modified, e.g., comprises a modified sugar moiety, a modified internucleoside linkage, a modified nucleoside, a modified nucleotide and/or combinations thereof. In some embodiments, the modified mRNA exhibits one or more of the following properties: is not immune stimulatory; is nuclease resistant; has improved cell uptake; has increased half-life; has increased translation efficiency; and/or is not toxic to cells or mammals, e.g., following contact with cells in vivo or ex vivo or in vitro.

Messenger RNA Components

In some embodiments, the disclosure provides an mRNA comprising an open-reading frame (ORF), wherein the ORF comprises a nucleotide sequence that encodes a Cas nuclease described herein.

In some embodiments, an mRNA of the disclosure comprises a 5' untranslated region (5' UTR), a 3' untranslated region (3' UTR), and the ORF. In some embodiments, the mRNA further comprises a 5' cap structure, a Kozak or Kozak-like sequence (also known as a Kozak consensus sequence), a polyA sequence (also known as a polyadenylation signal), a nucleotide sequence encoding a nuclear localization signal (NLS), a nucleotide sequence encoding a linker peptide, a nucleotide sequence encoding a tag peptide, or any combination thereof. In some embodiments, the consensus Kozak consensus sequence facilitates the initial binding of mRNA to ribosomes, thereby enhances its translation into a polypeptide product.

In some embodiments, an mRNA of the disclosure comprises any suitable number of base pairs sufficient to encode a Cas nuclease of the disclosure, e.g., thousands (e.g., 2000, 3000, 4000, 5000 or 6000, 7000, 8000, 9000, or 10,000) of base pairs. In some embodiments, the mRNA is about 2.5 kb, about 2.6 kb, about 2.7 kb, about 2.8 kb, about 2.9 kb, about 3 kb, about 3.1 kb, about 3.2 kb, about 3.3 kb, about 3.4 kb, about 3.5 kb, about 3.6 kb, about 3.7 kb, about 3.8 kb, about 3.9 kb, about 4 kb, about 4.1 kb, 4.2 kb, about 4.3 kb, about 4.4 kb, about 4.5 kb, about 4.6 kb, about 4.7 kb, about 4.8 kb, about 4.9 kb, about 5.0 kb, about 5.1 kb, about 5.2 kb, about 5.3 kb, about 5.4 kb, about 5.5 kb, or more in length.

In some embodiments, the 5' UTR or 3' UTR is derived from a human gene sequence. Non-limiting exemplary 5' UTR and 3' UTR include those derived from genes encoding a- and β-globin, albumin, HSD17B4, and eukaryotic elongation factor 1a. In addition, viral-derived 5' UTR and 3' UTRs can also be used and include orthopoxvirus and cytomegalovirus UTR sequences.

In some embodiments, an mRNA of the disclosure comprises a 5' cap structure. A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., $m^7G(5')ppp(5')G$, commonly written as $m^7GpppG$. This cap is a cap-0 where nucleotide N does not contain 2'OMe, or cap-1 where nucleotide N contains 2'OMe, or cap-2 where nucleotides N and N+1 contain 2'OMe. This cap may also be of the structure m2 7'3 "G(5')N as incorporated by the anti-reverse-cap analog (ARCA), and may also include similar cap-0, cap-1, and cap-2, etc., structures.

In some embodiments, an mRNA of the disclosure comprises a poly(A) tail (i.e., polyA sequence, i.e., polyadenylation signal). In some embodiments, the polyA sequence comprises entirely or mostly of adenine nucleotides or analogs or derivatives thereof. In some embodiments, the polyA sequence is a tail located adjacent (e.g., towards the 3' end) of a 3' UTR of an mRNA. In some embodiments, the polyA sequence promotes or increases the nuclear export, translation, and/or stability of the mRNA.

In some embodiments, the poly(A) tail comprises a 3' "cap" comprising modified or non-natural nucleobases or other synthetic moieties.

(v) Engineered Nucleases

In additional embodiments, the site-directed nuclease is an engineered nuclease. Exemplary engineered nucleases are meganuclease (e.g., homing endonucleases), ZFN, TALEN, and megaTAL.

Naturally-occurring meganucleases may recognize and cleave double-stranded DNA sequences of about 12 to 40 base pairs and are commonly grouped into five families. In some embodiments, the meganuclease are chosen from the LAGLIDADG family, the GIY-YIG family, the HNH family, the His-Cys box family, and the PD-(D/E)XK family. In some embodiments, the DNA binding domain of the meganuclease are engineered to recognize and bind to a sequence other than its cognate target sequence. In some embodiments, the DNA binding domain of the meganuclease are fused to a heterologous nuclease domain. In some embodiments, the meganuclease, such as a homing endonuclease, are fused to TAL modules to create a hybrid protein, such as a "megaTAL" protein. The megaTAL protein have improved DNA targeting specificity by recognizing the target sequences of both the DNA binding domain of the meganuclease and the TAL modules.

ZFNs are fusion proteins comprising a zinc-finger DNA binding domain ("zinc fingers" or "ZFs") and a nuclease domain. Each naturally-occurring ZF may bind to three consecutive base pairs (a DNA triplet), and ZF repeats are combined to recognize a DNA target sequence and provide sufficient affinity. Thus, engineered ZF repeats are combined to recognize longer DNA sequences, such as, e.g., 9-, 12-, 15-, or 18-bp, etc. In some embodiments, the ZFN comprise ZFs fused to a nuclease domain from a restriction endonuclease. For example, the restriction endonuclease is FokI. In some embodiments, the nuclease domain comprises a dimerization domain, such as when the nuclease dimerizes to be active, and a pair of ZFNs comprising the ZF repeats and the nuclease domain is designed for targeting a target sequence, which comprises two half target sequences recognized by each ZF repeats on opposite strands of the DNA molecule, with an interconnecting sequence in between (which is sometimes called a spacer in the literature). For example, the interconnecting sequence is 5 to 7 bp in length. When both ZFNs of the pair bind, the nuclease domain may dimerize and introduce a DSB within the interconnecting sequence. In some embodiments, the dimerization domain of the nuclease domain comprises a knob-into-hole motif to promote dimerization. For example, the ZFN comprises a knob-into-hole motif in the dimerization domain of FokI.

The DNA binding domain of TALENs usually comprises a variable number of 34 or 35 amino acid repeats ("modules" or "TAL modules"), with each module binding to a single DNA base pair, A, T, G, or C. Adjacent residues at positions 12 and 13 (the "repeat-variable di-residue" or RVD) of each module specify the single DNA base pair that the module binds to. Though modules used to recognize G may also have affinity for A, TALENs benefit from a simple code of recognition—one module for each of the 4 bases—which greatly simplifies the customization of a DNA-binding domain recognizing a specific target sequence. In some embodiments, the TALEN may comprise a nuclease domain from a restriction endonuclease. For example, the restriction endonuclease is FokI. In some embodiments, the nuclease domain may dimerize to be active, and a pair of TALENS is designed for targeting a target sequence, which comprises two half target sequences recognized by each DNA binding domain on opposite strands of the DNA molecule, with an interconnecting sequence in between. For example, each half target sequence is in the range of 10 to 20 bp, and the interconnecting sequence is 12 to 19 bp in length. When both TALENs of the pair bind, the nuclease domain may dimerize and introduce a DSB within the interconnecting sequence. In some embodiments, the dimerization domain of the nuclease domain may comprise a knob-into-hole motif to promote dimerization. For example, the TALEN may comprise a knob-into-hole motif in the dimerization domain of FokI.

C. Donor Nucleic Acids Encoding a Correction

The disclosure provides donor nucleic acids for correcting a mutation in a target region of the HBB gene. In some embodiments, the mutation is in exon 1 of the HBB gene. In some embodiments, the mutation is E6V.

As used herein, the "donor nucleic acid" or "donor polynucleotide" refers to an exogenous nucleic acid molecule that functions as a template for HDR of a DSB induced at a target site in a genomic DNA molecule by a gene-editing system described herein, wherein the nucleic acid comprises a nucleotide sequences homologous to a target region the genomic DNA molecule. In some embodiments, a donor nucleic acid comprises regions of homology (e.g., an AAV vector where these regions are also known as left homology arm (LHA) and right homology arm (RHA), wherein a target region of interest (e.g., target mutation) is located in or spanning the region(s) of homology to allow for efficient HDR. In some embodiments, the donor nucleic acid comprises a nucleotide sequence encoding one or more gene-edits intended for incorporation in the genomic DNA molecule, e.g., a correction to a mutation in the genomic DNA molecule, a silent mutation, a mutation to a PAM. In some embodiments, the donor nucleic acid is recognized and used by the HDR machinery to repair a DSB induced at the target site in the genomic DNA molecule by a gene-editing system described herein, wherein HDR results in repair of the DSB and exchange of a mutation in the genomic DNA molecule with the donor nucleic acid encoding a correction to the mutation.

In some embodiments, a donor nucleic acid of the disclosure functions as a template for HDR of a DSB induced at a target site in an HBB gene by a gene-editing system described herein (e.g., CRISPR/Cas system).

In some embodiments, the donor nucleic acid encodes a correction to a mutation in the HBB gene, a mutation to the HBB gene, or both. In some embodiments, the donor nucleic acid encodes a correction to a mutation in exon 1 of the HBB gene. In some embodiments, the donor nucleic acid encodes a correction to the E6V mutation. In some embodiments, the donor nucleic acid encodes one or more silent mutations to the HBB gene. In some embodiments, the donor nucleic acid encodes a mutation to a PAM.

In some embodiments, the donor nucleic acid is of a suitable length to correct or induce a mutation in the HBB gene. In some embodiments, the donor nucleic acid is about 10, 15, 20, 25, 50, 75, 100, 125, 150, 175, 200, 225, 250, 275, 300 bp or longer in length. In some embodiments, the donor nucleic acid is about 10 bp to about 50 bp in length. In some embodiments, the donor nucleic acid is about 10 bp to about 100 bp in length. In some embodiments, the donor nucleic acid is about 10 bp to about 150 bp in length. In some embodiments, the donor nucleic acid is about 100 bp to about 130 bp in length.

In some embodiments, a donor nucleic acid provided by the disclosure comprises an exonic sequence (e.g., exon 1 of HBB) which corrects the mutation (e.g., E6V). In some embodiments, the donor nucleic acid comprises exonic and intronic sequence (e.g., intronic sequence upstream or proximal a target site in intron 1 of the HBB gene).

In some embodiments, the donor nucleic acid molecule is homologous to the HBB gene to enable integration of the donor nucleic acid into the HBB gene by HDR repair of a DSB at a target site in the HBB gene. In some embodiments, the target site occurs substantially downstream of the mutation in the target gene, e.g., at least about 50, 55, 60, 65, 70, 75, 80, 85, 90, 95, 100, 110, 120, 130, 140, 150, 160, 170, 180, 190, 200, or no more than 200 bp downstream of the mutation In some embodiments, the donor nucleic acid has a length of about 400 to about 5000, about 500 to about 4500, about 1000 to about 4400 nucleotides. In some embodiments, the donor nucleic acid has a length of about 4400 nucleotides.

In some embodiments, the length of the donor nucleic acid is sufficient to be homologous to the DSB and the mutation.

In some embodiments, the disclosure provides a donor nucleic acid comprising a nucleotide sequence homologous with a region of the HBB gene encoding the E6V mutation, wherein the nucleotide sequence corrects the E6V mutation. In some embodiments the donor comprises a codon encoding an amino acid residue other than valine at a position corresponding to the E6V mutation. In some embodiments, the donor nucleic acid comprises a codon encoding E6. In some embodiments, the donor nucleic acid comprises GAG or GAA to correct the GTG codon that leads to the E6V mutation. In some embodiments, the donor nucleic acid comprises one or more silent mutations to exon 1 of the HBB gene. In some embodiments, the donor nucleic acid comprises a mutation to a PAM.

In some embodiments, the donor nucleic acid comprises a nucleotide sequence having at least about 90% identity to the nucleotide sequence set forth in SEQ ID NO: 6, or a complement thereof. In some embodiments, the donor nucleic acid comprises a nucleotide sequence having about 90%, about 91%, about 92%, about 93%, about 94%, about 95%, about 96%, about 97%, about 98%, about 99%, or about 100% identity to the nucleotide sequence set forth in SEQ ID NO: 6, or a complement thereof. In some embodiments, the donor nucleic acid comprises a nucleotide sequence having at least about 90% identify to the nucleotide sequence set forth in SEQ ID NO: 56, or a complement thereof. In some embodiments, the donor nucleic acid comprises a nucleotide sequence having about 90%, about 91%, about 92%, about 93%, about 94%, about 95%, about 96%, about 97%, about 98%, about 99%, or about 100% identity to the nucleotide sequence set forth in SEQ ID NO: 56, or a complement thereof. In some embodiments, the donor nucleic acid comprises a nucleotide sequence having at least about 90% identify to the nucleotide sequence set forth in SEQ ID NO: 19, or a complement thereof. In some embodiments, the donor nucleic acid comprises a nucleotide sequence having about 90%, about 91%, about 92%, about 93%, about 94%, about 95%, about 96%, about 97%, about 98%, about 99%, or about 100% identity to the nucleotide sequence set forth in SEQ ID NO: 19, or a complement thereof.

In some embodiments, the donor nucleic acid spans a region of HBB comprising the E6V mutation. In some embodiments, the 5' end of the donor nucleic acid aligns with a region of HBB that is about 80, 75, 70, 65, 60, 65, 50, 55, 50, 45, 40, 35, 30, 25, 20, 15, 10, 5, 4, 3, 2, or 1 bp upstream of the 5'-G-T-G-3' codon of the E6V mutation, and the 3' end of the donor nucleic acid aligns with a region of HBB that is about 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 bp downstream of the E6V mutation. In some embodiments, the 3' end of the donor nucleic acid aligns with the target site in the HBB gene or proximal to the target site in the HBB gene (e.g., ±1, ±2, ±3, ±4, ±5, ±6, ±7, ±8, ±9, ±10, ±15, ±20, ±25, ±30, ±35, ±40, ±45, or ±50 bp of the target site).

In some embodiments, the donor nucleic acid is codon optimized to improve HDR. In some embodiments, the donor nucleic acid comprises up to about 1, 2, 3, 4, 5, 6, 7, 8, 9, 10, 15, 20, 25, 30, 35, or 40 silent mutations relative to the HBB gene, wherein the silent mutations are a result of codon optimization. In some embodiments, the one or more silent mutations selected for codon optimization do not introduce a single nucleotide polymorphism (SNP) associated with β-thalassemia. In some embodiments, the donor nucleic acid comprises a nucleotide sequence that is homologous with a region of the HBB gene that comprises a PAM recognition site, or complement thereof, that is recognized by a Cas nuclease described herein, and wherein the donor nucleic acid encodes a mutation to the PAM. In some embodiments, the donor nucleic acid comprises the nucleotide sequence 5' $N_{19-30}$-N-G-G 3', or complement thereof, wherein $N_{19-30}$ corresponds to the target sequence, N-G-G corresponds to the PAM, and wherein the PAM is mutated. In some embodiments, the target sequence is set forth by SEQ ID NO: 1, wherein the PAM is mutated to N-C-G. In some embodiments, the target sequence is set forth by SEQ ID NO: 49, wherein the PAM is mutated to N-C-G.

In some embodiments, disrupting the PAM sequence improves the efficiency of productive edits; without being bound by theory, it is believed that disrupting the PAM sequence reduces or eliminates re-cutting after HDR. In some embodiments, the PAM recognition site is mutated to a polynucleotide sequence without introducing a single nucleotide polymorphism (SNP) associated with β-thalassemia.

In some embodiments, the length of the donor nucleic acid is determined based on the capacity of the delivery system (e.g., AAV) used to provide the donor nucleic acid. In some embodiments, the length of the donor nucleic acid is determined to substantially fill the sequence capacity of the delivery system (e.g., AAV) used to provide the donor nucleic acid.

In some embodiments, the disclosure provides a donor nucleic acid about 400 bases, about 500 bases, about 600 bases, about 700 bases, about 800 bases, about 900 bases, about 1 kb, about 1.5 kb, about 2 kb, about 2.5 kb, about 3 kb, about 3.5 kb, about 4 kb, or about 4.5 kb in length. In some embodiments, the donor nucleic acid is about 2.5 kb, about 2.6 kb, about 2.7 kb, about 2.8 kb, about 2.9 kb, about 3 kb, about 3.1 kb, about 3.2 kb, about 3.3 kb, about 3.4 kb, about 3.5 kb, about 3.6 kb, about 3.7 kb, about 3.8 kb, about 3.9 kb, about 4 kb, about 4.1 kb, about 4.2 kb, about 4.3 kb, about 4.4 kb or about 4.5 kb in length. In some embodiments, the donor nucleotide sequence is about 4.2 kb in length.

In some embodiments, the donor nucleic acid comprises the nucleotide sequence set forth by SEQ ID NO: 8. In some embodiments, the donor nucleic acid comprises a nucleotide sequence having at least 80%, 85%, 90%, 95%, 96%, 97%, 98% or 99% identity to SEQ ID NO: 8. In some embodiments, the donor nucleic acid consists of the nucleotide sequence set forth by SEQ ID NO: 8.

In some embodiments, the donor nucleic acid comprises the nucleotide sequence set forth by SEQ ID NO: 57. In some embodiments, the donor nucleic acid comprises a nucleotide sequence having at least 80%, 85%, 90%, 95%, 96%, 97%, 98% or 99% identity to SEQ ID NO: 57. In some embodiments, the donor nucleic acid consists of the nucleotide sequence set forth by SEQ ID NO: 57.

In some embodiments, the donor nucleic acid comprises the nucleotide sequence set forth by SEQ ID NO: 20. In some embodiments, the donor nucleic acid nucleic acid comprises the nucleotide sequence having at least 80%, 85%, 90%, 95%, 96%, 97%, 98% or 99% identity to SEQ ID NO: 20. In some embodiments, the donor nucleic acid consists of the nucleotide sequence set forth by SEQ ID NO: 20.

(i) Methods of Making Donor Nucleic Acids

In some embodiments, a donor nucleic acid described herein is introduced into a cell or a population of cells as part of a recombinant expression vector having additional sequences such as, for example, replication origins, promoters and genes encoding antibiotic resistance. In some embodiments, the donor nucleic acid is introduced as naked nucleic acid or as nucleic acid complexed with an agent such as a liposome or poloxamer. In some embodiments, the donor nucleic acid is delivered by a virus (e.g., adenovirus, AAV, herpesvirus, retrovirus, lentivirus and integrase defective lentivirus (IDLV)).

In some embodiments, the donor nucleic acid is DNA or RNA. In some embodiments, the donor nucleic acid is single-stranded or double-stranded. In some embodiments, the donor nucleic acid is introduced into a cell or a population of cells in linear or circular form. In some embodiments, wherein the donor nucleic acid is introduced in linear form, the ends of the nucleic acid are protected (e.g., from exonucleolytic degradation) by methods known to those of skill in the art. For example, one or more dideoxynucleotide residues are added to the 3' terminus of the donor nucleic acid and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In some embodiments, the donor nucleic acid is produced by suitable DNA synthesis method or means known in the art. Recombinant vectors encoding the donor nucleic acid are also readily produced by said methods. DNA synthesis is the natural or artificial creation of deoxyribonucleic acid (DNA) molecules. The term DNA synthesis refers to DNA replication, DNA biosynthesis (e.g., in vivo DNA amplification), enzymatic DNA synthesis (e.g., polymerase chain reaction (PCR); in vitro DNA amplification) or chemical DNA synthesis.

In some embodiments, each strand of the donor nucleic acid is produced by oligonucleotide synthesis. Oligonucleotide synthesis is the chemical synthesis of relatively short fragments or strands of single-stranded nucleic acids with a defined chemical structure (sequence). Methods of oligonucleotide synthesis are known in the art (see e.g., Reese (2005) Organic & Biomolecular Chemistry 3(21):3851). The two strands can then be annealed together or duplexed to form the donor nucleic acid.

In some embodiments, the nucleic acid is incorporated in a genomic DNA molecule so that expression of the donor nucleic acid is driven by the endogenous promoter at the integration site, namely the promoter that drives expression of the endogenous gene into which the donor is inserted (e.g., HBB). However, in some embodiments, the donor template comprises an exogenous promoter and/or enhancer, for example a constitutive promoter, an inducible promoter, or tissue-specific promoter. In some embodiments, the exogenous promoter is an EF1α promoter comprising a sequence of SEQ ID NO: 55. Other promoters known to those of skill in the art may also be used.

In some embodiments, exogenous sequences may also include transcriptional and/or translational regulatory sequences, for example, promoters, enhancers, insulators, internal ribosome entry sites, sequences encoding 2A peptides and/or polyadenylation signals.

D. Nucleic Acid Modifications

In some embodiments, a nucleic acid of the disclosure (e.g., gRNA, donor nucleic acid, and/or mRNA encoding a Cas nuclease) comprises chemistries suitable for delivery and stability within a cell or a population of cells. In some embodiments, the chemistries are useful for controlling the pharmacokinetics, biodistribution, bioavailability and/or efficacy of the nucleic acids described herein following in vivo administration. Accordingly, in some embodiments, the nucleic acids described herein are modified, e.g., comprise a modified sugar moiety, a modified internucleoside linkage, a modified nucleoside, a modified nucleotide, and/or combinations thereof.

In some embodiments, modified nucleic acids disclosure (e.g., gRNA, donor nucleic acid, and/or mRNA encoding a Cas nuclease) have useful properties, including enhanced stability, intracellular retention, enhanced translation, and/or the lack of a substantial induction of the innate immune response of a cell into which the nucleic acid is introduced, as compared to a reference unmodified nucleic acid. Therefore, use of modified nucleic acids may enhance the efficiency of protein production (e.g., expression of a Cas nuclease, a donor nucleic acid, and/or a gRNA), intracellular retention of the nucleic acids, efficiency of a genome editing system comprising the nucleic acid, as well as possess reduced immunogenicity.

In some embodiments, a nucleic acid of the disclosure comprises one or more (e.g., 1, 2, 3, 4, 5, 6, 7, 8, 9, 10, 20, 30, 40, 50, 60, 70, 80, 90, 100, or more) different modified nucleobases, nucleosides, nucleotides or internucleoside linkages. In some embodiments, the modified nucleic acid has reduced degradation in a cell into which the nucleic acid is introduced, relative to a corresponding unmodified nucleic acid.

In some embodiments, the modified nucleobase is a modified uracil, such as any modified uracil known in the art. In some embodiments, the modified nucleobase is a modified cytosine, such as any modified cytosine known in the art. In some embodiments, the modified nucleobase is modified adenine, such as any modified adenine known in the art. In some embodiments, the modified nucleobase is modified guanine, such as any modified guanine known in the art. In some embodiments, a nucleic acid of the disclosure includes a combination of one or more of the modified nucleobases.

In certain embodiments, a nucleic acid of the disclosure (e.g., mRNA, donor nucleic acid, recombinant vector, and/or gRNA) is uniformly modified (i.e., fully modified, modified through-out the entire sequence) for a particular modification. For example, in some embodiments, the mRNA is uniformly modified with N1-methylpseudouridine ($m^1\psi$) or 5-methyl-cytidine ($m^5C$), such that all uridines or all cytosine nucleosides in the mRNA sequence are replaced with N1-methylpseudouridine ($m^1\psi$) or 5-methyl-cytidine ($m^5C$). In some embodiments, the donor nucleic acid is uniformly modified for any type of nucleoside residue present in the sequence by replacement with a modified residue.

E. Delivery of System Components

In some embodiments, delivery of gene editing systems components described herein (e.g., gRNA, donor nucleic acid, and/or Cas nuclease) is performed by one or more methods described herein. In some embodiments, the system components, for example, gRNA (e.g., intron-targeting gRNA), donor nucleic acid, and/or a Cas nuclease described herein, are delivered by viral vectors, lipid nanoparticles (LNPs), synthetic polymers, or a combination thereof. In some embodiments, the methods of delivery described herein are suitable for administering a gene editing system of the disclosure to a target cell population or target tissue for the purpose of cellular, ex vivo, and/or in vivo gene editing.

In some embodiments, the delivery comprises administering the Cas nuclease encoded by a nucleic acid described herein (RNA or DNA). In some embodiments, the Cas nuclease is delivered as an mRNA or a recombinant expression vector (e.g., plasmid, viral vector) comprising a nucleic acid encoding the Cas nuclease. In some embodiments, the delivery comprises administering the Cas nuclease as a polypeptide. In some embodiments, the delivery comprises administering the gRNA or a nucleic acid encoding the gRNA. In some embodiments, the delivery comprises administering a sgRNA described herein or a nucleic acid encoding the sgRNA. In some embodiments, the delivery comprises administering a recombinant expression vector comprising a nucleic acid encoding the gRNA (e.g., plasmid, viral vector). In some embodiments, the delivery comprises administering a recombinant expression vector comprising a nucleic acid encoding a sgRNA described herein. In some embodiments, the delivery comprises administering a donor nucleic acid. In some embodiments, the delivery comprises administering a recombinant expression vector (e.g., plasmid, viral vector) encoding the donor nucleic acid.

In some embodiments, the delivery comprises administering the Cas nuclease as an mRNA. In some embodiments, the delivery comprises administering the mRNA, wherein the mRNA is formulated by LNP or another delivery vehicle, such as a polymeric nanoparticle. In some embodiments, the delivery comprises administering the mRNA separately formulated or co-formulated with the gRNA and/or the donor nucleic acid. In some embodiments, the mRNA, the gRNA, and/or the donor nucleic acid are each separately formulated as an LNP or polymeric nanoparticle. In some embodiments, the mRNA, the gRNA, and/or the donor nucleic acid are co-formulated as an LNP or polymeric nanoparticle.

In some embodiments, the delivery comprises administering a recombinant expression vector encoding the Cas nuclease described herein. In some embodiments, the delivery comprises administering a recombinant expression vector encoding a gRNA described herein. In some embodiments, the delivery comprises administering a recombinant expression vector encoding a sgRNA described herein. In some embodiments, the delivery comprises administering a recombinant expression vector encoding a donor nucleic acid described herein. In some embodiments, the delivery comprises administering a recombinant expression vector encoding the Cas nuclease, the gRNA, and/or the donor nucleic acid, for example, on the same recombinant expression vector. In some embodiments, the delivery comprises administering a recombinant expression vector encoding the Cas nuclease, the sgRNA, and/or the donor nucleic acid. In some embodiments, the nucleic acid encoding the Cas nuclease and the nucleic acid encoding the gRNA (e.g., sgRNA) are provided in the same recombinant expression vector. In some embodiments, the nucleic acid encoding the Cas nuclease and the nucleic acid encoding the gRNA (e.g., sgRNA) are provided in different recombinant expression vectors. In some embodiments, the nucleic acid encoding the gRNA (e.g., sgRNA) and the donor nucleic acid are provided in the same recombinant expression vector. In some embodiments, the nucleic acid encoding the gRNA (e.g., sgRNA) and the donor nucleic acid are provided in different recombinant expression vectors. In some embodiments, the delivery comprises administering the nucleic acid encoding the Cas nuclease, the gRNA, and/or the donor nucleic acid on different recombinant expression vectors, for example, up to 2, 3, or 4 recombinant expression vectors. In some embodiments, the recombinant expression vector is a non-viral vector (e.g., a plasmid). In some embodiments, the recombinant expression vector is a viral vector (e.g., an AAV). In some embodiments, the delivery comprises formulation of the one or more recombinant expression vectors using LNPs or polymeric nanoparticles.

In some embodiments, the delivery comprises administering the Cas nuclease as a polypeptide, optionally complexed with the gRNA, and the donor nucleic acid as a recombinant expression vector. In some embodiments, the delivery comprises administering the Cas nuclease as an mRNA, and administering the gRNA and/or the donor nucleic acid as a recombinant expression vector. In some embodiments, the delivery comprises administering the mRNA encoding the Cas nuclease formulated as an LNP or polymeric nanoparticle. In some embodiments, the delivery comprises administering the recombinant expression vector encoding the gRNA and/or donor nucleic acid formulated as an LNP or polymeric nanoparticle. In some embodiments, the mRNA and the recombinant expression vector are separately formulated or co-formulated.

(i) Ribonucleoprotein Complexes

In some embodiments, the Cas nuclease is delivered as a polypeptide. In some embodiments, the Cas nuclease is delivered to a cell or population of cells ex vivo or in vivo as a polypeptide either alone or in combination with gRNA described herein (e.g., intron-targeting gRNA). In some embodiments, the gRNA is a sgRNA described herein (e.g., an intron-targeting sgRNA). In some embodiments, the Cas nuclease is delivered to a cell or population of cells ex vivo or in vivo as a polypeptide that is pre-complexed with the gRNA. Such pre-complexed material is referred to herein as a "ribonucleoprotein particle" or "RNP".

In some embodiments, the Cas nuclease is pre-complexed with the gRNA, or a sgRNA described herein (e.g., intron-targeting sgRNA). In some embodiments, the gene editing system comprises an RNP. In some embodiments, the gene editing system comprises a Cas9 RNP comprising a purified Cas9 protein described herein (e.g., SpCas9) or functional derivate thereof (e.g., high fidelity Cas9 or high-fidelity SpCas9) in complex with the gRNA or sgRNA. The Cas9 protein can be expressed and purified by any means known in the art. In some embodiments, the ribonucleoprotein is assembled in vitro and delivered directly to cells using standard electroporation or transfection techniques known in the art. One benefit of the RNP is protection of the RNA from degradation.

In some embodiments, the Cas nuclease in the RNP is modified or unmodified. In some embodiments, the gRNA (e.g., crRNA, tracrRNA, or sgRNA) is modified or unmodified. Numerous modifications are known in the art and are suitable for use in the present disclosure.

In some embodiments, the Cas nuclease and the gRNA (e.g., sgRNA) are combined in an approximately 1:1 molar ratio. However, a range of molar ratios can be used to produce a RNP for use in the present disclosure.

In some embodiments, the RNP is delivered alone or using a delivery vehicle known in the art, for example, a lipid particle (e.g., LNP) or a synthetic nanoparticle (e.g., polymeric nanoparticle) or combined with one or more cell penetrating peptides (CPPs).

In some embodiments, ribonucleoprotein complexes comprising a Cas9 polypeptide described herein (e.g., SpCas9) or functional derivative thereof (e.g., high fidelity Cas9 or high-fidelity SpCas9) and a gRNA described herein are prepared for administration to a cell or population of cells (e.g, CD34+ HSPCs), e.g., by electroporation.

In some embodiments, ribonucleoprotein complexes comprising a Cas9 polypeptide described herein (e.g., SpCas9) or functional derivative thereof (e.g., high fidelity Cas9 or high-fidelity SpCas9) and the gRNA are prepared for administration directly to a target tissue. In some embodiments, the RNP complex further comprises one or more cell penetrating peptides. Cell penetrating peptides for use in promoting RNP complex uptake by cells in a target tissue are known in the art. Non-limiting examples of CPPs for promoting cellular uptake of protein complexes include penetratin, R8, TAT, Transportan, Xentry, endo-porter, synthetic CPPs and cyclic derivatives thereof.

(ii) Recombinant Vectors

The present disclosure provides a vector (e.g., recombinant expression vector) comprising a nucleotide sequence encoding a gRNA molecule of the disclosure, a site-directed nuclease of the disclosure (e.g., Cas nuclease), and/or a donor nucleic acid of the disclosure. In some embodiments, the gRNA is a sgRNA described herein (e.g., an intron-targeting sgRNA).

In some embodiments, the site-directed nuclease, gRNA, and/or the donor nucleic acid are provided by one or more vectors. As used herein, the term "vector" refers to a nucleic acid molecule capable of transporting another nucleic acid to which it has been linked. In some embodiments, the vector is a DNA vector. In some embodiments, the vector is circular. In some embodiments, the vector is linear. Non-limiting exemplary vectors include plasmids, phagemids, cosmids, artificial chromosomes, minichromosomes, transposons, viral vectors, and expression vectors.

In some embodiments, the vector is an expression vector, wherein the expression vector is capable of directing the expression of nucleic acids to which it is operably linked. As used herein, an "expression vector" or "recombinant expression vector" refers to a replicon, such as plasmid, phage, virus, or cosmid, to which another DNA segment, i.e. an "insert", is attached so as to bring about the replication of the attached segment in a cell.

In some embodiments, the vector or expression vector is a plasmid. As used herein, a "plasmid" refers to a circular double-stranded DNA loop into which additional nucleic acid segments are ligated.

In some embodiments, the vector or expression vector is a viral vector, wherein additional nucleic acid segments are ligated into the viral genome. Non-limiting exemplary viral vectors include viral vectors based on vaccinia virus; poliovirus; adenovirus; adeno-associated virus; SV40; herpes simplex virus; human immunodeficiency virus; picornaviruses. Non-limiting exemplary viral vectors also include viral vectors based on a retrovirus such as a Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus. In some embodiments, the vectors is for use in eukaryotic target cells and includes, but is not limited to, pXT1, pSG5, pSVK3, pBPV, pMSG, and pSVLSV40 (Pharmacia).

In some embodiments, a recombinant adeno-associated virus (rAAV) vector is used for delivery. Techniques to produce rAAV particles, in which an AAV genome to be packaged that includes the polynucleotide to be delivered (e.g., nucleic acid encoding one or more gRNAs and/or a site-directed endonuclease), rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 AAV rh.74 and tropism modified AAV vectors. Production of pseudotyped rAAV is disclosed in, for example, international patent application publication number WO 01/83692.

In some embodiments, a method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others (see Table 1).

TABLE 1

| Tissue/Cell Type | Serotype |
|---|---|
| Liver | AAV3, AAV5, AAV8, AAV9 |
| Skeletal muscle | AAV1, AAV7, AAV6, AAV8, AAV9 |
| Central nervous system | AAV5, AAV1, AAV4, AAV8, AAV9 |
| RPE | AAV5, AAV4, AAV2, AAV8, AAV9, AAVrh8R |
| Photoreceptor cells | AAV5, AAV8, AAV9, AAVrh8R |
| Lung | AAV9, AAV5 |
| Heart | AAV9 |
| Pancreas | AAV8 |
| Kidney | AAV2, AAV8 |

In addition to adeno-associated viral vectors, other viral vectors can be used. Such viral vectors include, but are not limited to, adenovirus, lentivirus, alphavirus, enterovirus, pestivirus, baculovirus, herpesvirus, Epstein Barr virus, papovavirus, poxvirus, vaccinia virus, and herpes simplex virus.

In some embodiments, the vector comprises one or more transcription and/or translation control elements. In some embodiments, the more transcription and/or translation control elements used depends on the target cell population and the vector system. In some embodiments, any number of suitable transcription and translation control elements, including constitutive and inducible promoters, transcription enhancer elements, transcription terminators, etc. are used in the expression vector, such as those further described below.

In some embodiments, a vector comprising a nucleic acid encoding a gRNA molecule of the disclosure, a donor nucleic acid of the disclosure, and/or a site directed endonuclease of the disclosure is operably linked to a control element, e.g., a transcriptional control element, such as a promoter. In some embodiments, the transcriptional control element is functional in a eukaryotic cell, e.g., a mammalian cell, e.g., a human cell. In some embodiments, the nucleotide sequence encoding the gRNA molecule, the donor nucleic acid, and/or the site directed endonuclease is operably linked to one or more control elements that enable expression of the nucleotide sequence encoding the gRNA, donor nucleic acid, and/or a site directed endonuclease in eukaryotic cells, e.g., mammalian cells, e.g., human cells.

In some embodiments, the promoter is a constitutively active promoter (i.e., a promoter that is constitutively in an active/"ON" state). In some embodiments, the promoter is an inducible promoter (i.e., a promoter whose state, active/"ON" or inactive/"OFF", is controlled by an external stimulus, e.g., the presence of a particular temperature, compound, or protein). In some embodiments, the promoter is a spatially restricted promoter (i.e., transcriptional control element, enhancer, etc.) (e.g., tissue specific promoter, cell type specific promoter, etc.). In some embodiments, the promoter is temporally restricted promoter (i.e., the promoter is in the "ON" state or "OFF" state during specific stages of embryonic development or during specific stages of a biological process).

Suitable promoters for use in the present disclosure include those derived from viruses and are referred to herein as viral promoters, or they include those derived from an organism, including prokaryotic or eukaryotic organisms.

Exemplary promoters include, but are not limited to, the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Exemplary eukaryotic promoters (i.e., promoters functional in a eukaryotic cell) include, but are not limited to, those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

In some embodiments, a suitable promoter for use in the present disclosure include any promoter that drives expression by an RNA polymerase (e.g., pol I, pol II, pol III). In some embodiments, a gRNA molecule of the disclosure is encoded by vector comprising a RNA polymerase III promoter (e.g., U6 and H1). Descriptions of and parameters for enhancing the use of such promoters are known in art, and additional information and approaches are regularly being described; see, e.g., Ma, H. et al., *Molecular Therapy—Nucleic Acids* 3, e161 (2014) doi:10.1038/mtna.2014.12.

In some embodiments, the expression vector comprises a ribosome binding site for translation initiation and a transcription terminator. In some embodiments, the expression vector comprises appropriate sequences for amplifying expression. In some embodiments, the expression vector comprises nucleotide sequences encoding non-native tags (e.g., histidine tag, hemagglutinin tag, green fluorescent protein, etc.), for example, that are operably-linked to a site-directed endonuclease, thereby providing a fusion protein of the site-directed endonuclease.

Methods of introducing a nucleic acid to a host cell or a population of host cells are known in the art, and any known method can be used to introduce a nucleic acid (e.g., an expression construct) into a cell. In some embodiments, a nucleotide sequence encoding a gRNA, a site directed endonuclease, and/or a donor nucleic acid, introduced either as DNA or RNA, are provided to a population of cells using known transfection techniques; see, e.g. Angel and Yanik (2010) PLoS ONE 5(7): e 11756, and the commercially available TransMessenger® reagents from Qiagen, Stemfect™ RNA Transfection Kit from Stemgent, and TransIT®-mRNA Transfection Kit from Mims Bio LLC (See, also Beumer et al. (2008). PNAS 105(50):19821-19826). In some embodiments, the nucleic acids are provided as a DNA vectors, e.g. plasmids, cosmids, minicircles, phage, viruses, etc. In some embodiments, the vectors comprising the nucleic acid(s) are maintained episomally, e.g. as plasmids, minicircle DNAs, viruses such cytomegalovirus, adenovirus, etc. In some embodiments, the vectors integrated into the host cell genome, through homologous recombination or random integration, e.g. retrovirus-derived vectors such as MMLV, HIV-1, ALV, etc.

(iii) Nanoparticle Compositions

In some embodiments, the gene editing system components described herein, including (i) a site-directed endonuclease of the disclosure (e.g., Cas nuclease); (ii) one or more nucleic acids of the disclosure, e.g., gRNA, donor nucleic acid, recombinant expression vector, and/or mRNA; or (iii)

a combination of (i)-(ii), are delivered to a cell or a population of cells, ex vivo or in vivo, by a lipid nanoparticle (LNP) or other delivery vehicle (e.g., polymeric nanoparticles) to facilitate cellular uptake and/or to protect them from degradation when delivered to a subject. In some embodiments, the system components are formulated, individually or combined together in nanoparticle compositions described herein.

In some embodiments, the nanoparticle composition comprises a lipid. LNPs include, but are not limited to, liposomes and micelles. Any number of lipids may be present, including cationic and/or ionizable lipids, anionic lipids, neutral lipids, amphipathic lipids, conjugated lipids (e.g., PEGylated lipids), and/or structural lipids. Such lipids can be used alone or in combination.

Nanoparticles are ultrafine particles typically ranging between 1 and 100 to 500 nanometers (nm) in size with a surrounding interfacial layer and often exhibiting a size-related or size-dependent property. Nanoparticle compositions are myriad and encompass lipid nanoparticles (LNPs), liposomes (e.g., lipid vesicles), and lipoplexes. For example, a nanoparticle composition can be a liposome having a lipid bilayer with a diameter of 500 nm or less. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle composition comprises an mRNA, one or more gRNAs, a donor nucleic acid, one or more recombinant expression vectors, and/or an RNP complex described herein.

In some embodiments, the nanoparticle composition comprises an mRNA encoding a Cas nuclease described herein (e.g., SpCas9) or functional derivative thereof (e.g., high fidelity Cas9 or SpCas9), a gRNA described herein, and/or a donor nucleic acid described herein. In some embodiments, the mRNA, gRNA, and/or donor nucleic acid are each separately formulated for delivery, e.g., in lipid nanoparticles. In some embodiments, the mRNA, gRNA, and/or donor nucleic acid are co-formulated for delivery, e.g., in a lipid nanoparticle.

In some embodiments, the nanoparticle composition comprises a recombinant expression vector encoding the Cas nuclease (e.g., SpCas9) or the functional derivative thereof (e.g., high fidelity Cas9 or SpCas9), the gRNA, and/or the donor nucleic acid, e.g., by the same or separate recombinant expression vector(s). In some embodiments, the recombinant expression vector(s) are co-formulated for delivery, e.g., in lipid nanoparticles. In some embodiments, a recombinant expression vector encoding the Cas nuclease and a recombinant expression vector encoding the gRNA, and/or donor nucleic acid are separately formulated for delivery, e.g., in lipid nanoparticles.

In some embodiments, the disclosure provides LNP compositions comprising: (a) one or more nucleic acid molecules described herein (e.g., mRNA, gRNA, donor nucleic acid, and/or recombinant expression vector) and/or a RNP complex described herein; and (b) one or more lipid moieties selected from the group consisting of amino lipids, helper lipids, structural lipids, phospholipids, ionizable lipids, PEG lipids, lipoid, and cholesterol or cholesterol derivatives. In some embodiments, the disclosure provides LNP compositions comprising: (a) one or more nucleic acid molecules described herein (e.g., mRNA, gRNA, donor nucleic acid, and/or recombinant expression vector) and/or a RNP complex described herein; and (b) one or more lipid moieties selected from the group consisting of ionizable lipids, amino lipids, anionic lipids, neutral lipids, amphipathic lipids, helper lipids, structural lipids, PEG lipids, and lipoids, and optionally (c) targeting moieties.

In some embodiments, the LNPs of the present disclosure are formed by any method known in the art including, but not limited to, a continuous mixing method, a direct dilution process, and an in-line dilution process. Additional techniques and methods suitable for the preparation of the LNPs described herein include coacervation, microemulsions, supercritical fluid technologies, phase-inversion temperature (PIT) techniques.

F. Exemplary Systems

In some embodiments, the disclosure provides a gene-editing system, wherein the system is for correcting a mutation in exon 1 of a HBB gene in a cell or population of cells (e.g., CD34+ HSPCs), the system comprising: (a) a site-directed endonuclease, an mRNA encoding the site-directed endonuclease, or a recombinant expression vector comprising a nucleotide sequence encoding the site-directed endonuclease; (b) a gRNA or a sgRNA comprising a spacer sequence corresponding to a target sequence adjacent a PAM, the target sequence comprising a target site within intron 1 of HBB; and (c) a recombinant vector comprising a donor nucleic acid for correcting the mutation, the donor nucleic acid comprising a nucleotide sequence homologous with a region of the HBB gene encoding the mutation, wherein the nucleotide sequence corrects the mutation. In some embodiments, the gRNA or the sgRNA combines with the site-directed endonuclease (e.g., Cas9) to induce a DSB at the target site in the HBB gene. In some embodiments, the site-directed endonuclease is a Cas nuclease. In some embodiments, the Cas nuclease is a Cas9 polypeptide. In some embodiments, the Cas9 polypeptide is a SpCas9 polypeptide. In some embodiments, the SpCas9 polypeptide is engineered to be a high fidelity SpCas9.

In some embodiments, the target site is at least about 60, 65, 70, 75, 80, 85, 90, 95, 100, 105, 110, 115, 120, 125, 130, 135, 140, 145, 150, 155, 160, 165, 170, 175, or 180 bp downstream of the mutation. In some embodiments, the target site is about 60 to about 200 bp downstream of the mutation. In some embodiments, the target site is about 70 to about 190 bp downstream of the mutation. In some embodiments, the target site is about 70 to about 180 bp downstream of the mutation. In some embodiments, the target site is about 70 to about 170 bp downstream of the mutation. In some embodiments, the target site is about 80 to about 160 bp downstream of the mutation. In some embodiments, the target site is about 80 to about 150 bp downstream of the mutation. In some embodiments, the target site is about 90 to about 140 bp downstream of the mutation. In some embodiments, the target site is about 100 to about 140 bp downstream of the mutation. In some embodiments, the target site is about 100 to about 130 bp downstream of the mutation. In some embodiments, the target site is about 110 to about 130 bp downstream of the mutation. In some embodiments, the target site is about 105, 110, 115, 120, 125, or 130 bp downstream of the mutation. In some embodiments, the mutation is the E6V mutation.

In some embodiments, the gRNA or the sgRNA combines with the site-directed endonuclease (e.g., Cas9) to induce a DSB at the target site in intron 1 of the HBB gene, wherein the cleavage efficiency, as measured by an average frequency of INDELs induced at the target site (e.g., as measured by NGS analysis), is at least 10%, 15%, 20%, 25%, 30%, 35%, 40%, 45%, or 50%. In some embodiments, the cleavage efficiency, as measured by an average frequency of INDELs induced at the target site (e.g., as measured by NGS analysis), is about 10%, 15%, 20%, 25%, 30%, 35%, 40%, 45%, 50%, 55%, 60%, 65%, 70%, 75%, 80%, 85%, 90%, 95%, or higher.

In some embodiments, the target site is about 80 to about 180 bp downstream of the mutation in the HBB gene (e.g., E6V), and the cleavage efficiency, as measured by an average frequency of INDELs induced at the target site (e.g., as measured by NGS analysis), is about 10%, 15%, 20%, 25%, 30%, 35%, 40%, 45%, 50%, 55%, 60%, 65%, 70%, 75%, 80%, 85%, 90%, 95%, or higher. In some embodiments, the target site is about 90 to about 140 bp downstream of the mutation in the HBB gene (e.g., E6V), and the cleavage efficiency, as measured by an average frequency of INDELs induced at the target site (e.g., as measured by NGS analysis), is about 10%, 15%, 20%, 25%, 30%, 35%, 40%, 45%, 50%, 55%, 60%, 65%, 70%, 75%, 80% or higher. In some embodiments, the target site is about 100 to about 130 bp downstream of the mutation in the HBB gene (e.g., E6V), and the cleavage efficiency, as measured by an average frequency of INDELs induced at the target site (e.g., as measured by NGS analysis), is about 10%, 15%, 20%, 25%, 30%, 35%, 40%, 45%, 50%, 55%, 60%, 65%, 70%, 75%, 80% or higher.

In some embodiments, HDR of the DSB results in exchange of the region of the HBB gene encoding the mutation (e.g., E6V) with the donor nucleic acid encoding a correction of the mutation. In some embodiments, the average allelic editing frequency resulting from HDR, e.g., as measured by NGS analysis, is at least about 15%, 20%, 25%, 30%, 35%, 40%, 45%, 50%, 55%, 60% or higher. In some embodiments, the target site is about 80 to about 180 bp downstream of the mutation in the HBB gene (e.g., E6V), and the average allelic editing frequency resulting from HDR, e.g., as measured by NGS analysis, is about 15%, 20%, 25%, 30%, 35%, 40%, 45%, 50%, 55%, 60%, or higher. In some embodiments, the target site is about 90 to about 140 bp downstream of the mutation in the HBB gene (e.g., E6V), and the average allelic editing frequency resulting from HDR, e.g., as measured by NGS analysis, is about 15%, 20%, 25%, 30%, 35%, 40%, 45%, 50%, 55%, 60%, or higher. In some embodiments, the target site is about 100 to about 130 bp downstream of the mutation in the HBB gene (e.g., E6V), and the average allelic editing frequency resulting from HDR, e.g., as measured by NGS analysis, is about 15%, 20%, 25%, 30%, 35%, 40%, 45%, 50%, 55%, 60%, or higher.

In some embodiments, the disclosure provides a gene-editing system, wherein the system is for correcting an E6V mutation in exon 1 of a HBB gene in a cell or population of cells (e.g., CD34+ HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA comprising a spacer sequence corresponding to a target sequence adjacent a PAM, the target sequence comprising a target site within intron 1 of HBB; and (c) a recombinant vector comprising a donor nucleic acid for correcting the E6V mutation, the donor nucleic acid comprising a nucleotide sequence homologous with a region of the HBB gene encoding the E6V mutation, wherein the nucleotide sequence corrects the E6V mutation.

In some embodiments, the disclosure provides a gene-editing system, wherein the system is for correcting an E6V mutation in exon 1 of a HBB gene in a cell or population of cells (e.g., CD34+ HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA comprising a spacer sequence corresponding to a target sequence adjacent a PAM, the target sequence comprising a target site within intron 1 of HBB; and (c) a recombinant vector comprising a donor nucleic acid for correcting the E6V mutation, the donor nucleic acid comprising a nucleotide sequence homologous with a region of the HBB gene encoding the E6V mutation, wherein the nucleotide sequence comprises a codon encoding E6.

In some embodiments, the disclosure provides a gene-editing system, wherein the system is for correcting an E6V mutation in exon 1 of a HBB gene in a cell or population of cells (e.g., CD34+ HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA comprising a spacer sequence corresponding to a target sequence adjacent a PAM, the target sequence comprising a target site within intron 1 of HBB; and (c) a recombinant vector comprising a donor nucleic acid for correcting the E6V mutation, the donor nucleic acid comprising a nucleotide sequence homologous with a region of the HBB gene encoding the E6V mutation, wherein the nucleotide sequence comprises a codon encoding an amino acid residue other than valine at a position corresponding to the E6V mutation.

In some embodiments, the target site is at least about 60, 65, 70, 75, 80, 85, 90, 95, 100, 105, 110, 115, 120, 125, 130, 135, 140, 145, 150, 155, 160, 165, 170, 175, or 180 bp downstream of the E6V mutation. In some embodiments, the target site is about 60 to about 200 bp downstream of the E6V mutation. In some embodiments, the target site is about 70 to about 190 bp downstream of the E6V mutation. In some embodiments, the target site is about 70 to about 180 bp downstream of the E6V mutation. In some embodiments, the target site is about 70 to about 170 bp downstream of the E6V mutation. In some embodiments, the target site is about 80 to about 160 bp downstream of the E6V mutation. In some embodiments, the target site is about 80 to about 150 bp downstream of the E6V mutation. In some embodiments, the target site is about 90 to about 140 bp downstream of the E6V mutation. In some embodiments, the target site is about 100 to about 140 bp downstream of the E6V mutation. In some embodiments, the target site is about 100 to about 130 bp downstream of the E6V mutation. In some embodiments, the target site is about 110 to about 130 bp downstream of the E6V mutation. In some embodiments, the target site is about 105, 110, 115, 120, 125, or 130 bp downstream of the E6V mutation.

In some embodiments, the disclosure provides a gene-editing system, wherein the system is for correcting an E6V mutation in HBB in a cell or population of cells (e.g., CD34+HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of a nucleotide sequence selected from SEQ ID NO: 1 or SEQ ID NO: 49; and (c) a recombinant vector comprising a donor nucleic acid for correcting the E6V mutation, the donor nucleic acid comprising a nucleotide sequence homologous with a region of the HBB gene encoding the E6V mutation, wherein the nucleotide sequence corrects the E6V mutation.

In some embodiments, the disclosure provides a gene-editing system, wherein the system is for correcting an E6V mutation in HBB in a cell or population of cells (e.g., CD34+ HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of a nucleotide sequence selected from SEQ ID NO: 1 or SEQ ID NO: 49; and (c) a recombinant vector comprising a donor nucleic acid for correcting the E6V mutation, the donor nucleic acid comprising a nucleotide sequence homologous with a region of the HBB gene encoding the E6V mutation, wherein the nucleotide sequence comprises a codon encoding E6.

In some embodiments, the disclosure provides a gene-editing system, wherein the system is for correcting an E6V mutation in HBB in a cell or population of cells (e.g., CD34+ HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of a nucleotide sequence selected from SEQ ID NO: 1 or SEQ ID NO: 49; and (c) a recombinant vector comprising a donor nucleic acid for correcting the E6V mutation, the donor nucleic acid comprising a nucleotide sequence homologous with a region of the HBB gene encoding the E6V mutation, wherein the nucleotide sequence comprises a codon encoding an amino acid residue other than valine at a position corresponding to the E6V mutation.

In some embodiments, the donor nucleic acid comprises a nucleotide sequence which corrects the E6V mutation, wherein the correction is GAA or GAG. In some embodiments, the codon that corrects the mutation is GAA or GAG.

In some embodiments, the sgRNA combines with the Cas9 endonuclease to induce a DSB at the target site in the HBB gene, wherein the cleavage efficiency, as measured by frequency of INDELs induced at the target site (e.g., as measured by NGS analysis), is at least 10%, 15%, 20%, 25%, 30%, 35%, 40%, 45%, or 50%. In some embodiments, the target site is about 80 to about 180 bp downstream of the E6V mutation, and the cleavage efficiency, as measured by an average frequency of INDELs induced at the target site (e.g., as measured by NGS analysis), is about 20%, 25%, 30%, 35%, 40%, 45%, 50%, 55%, 60%, 65%, 70%, 75%, 80% or higher. In some embodiments, the target site is about 90 to about 140 bp downstream of the E6V mutation, and the cleavage efficiency, as measured by an average frequency of INDELs induced at the target site (e.g., as measured by NGS analysis), is about 20%, 25%, 30%, 35%, 40%, 45%, 50%, 55%, 60%, 65%, 70%, 75%, 80% or higher. In some embodiments, the target site is about 100 to about 130 bp downstream of the E6V mutation, and the cleavage efficiency, as measured by an average frequency of INDELs induced at the target site (e.g., as measured by NGS analysis), is about 20%, 25%, 30%, 35%, 40%, 45%, 50%, 55%, 60%, 65%, 70%, 75%, 80% or higher.

In some embodiments, HDR of the DSB results in exchange of the region of the HBB gene encoding the E6V mutation with the donor nucleic acid encoding a correction to the mutation. In some embodiments, the average allelic editing frequency resulting from HDR, e.g., as measured by NGS analysis, is at least about 15%, 20%, 25%, 30%, 35%, 40%, 45%, 50%, 55%, 60% or higher. In some embodiments, the target site is about 80 to about 180 bp downstream of the E6V mutation in the HBB gene, and the average allelic editing frequency resulting from HDR, e.g., as measured by NGS analysis, is about 15%, 20%, 25%, 30%, 35%, 40%, 45%, 50%, 55%, 60%, or higher. In some embodiments, the target site is about 90 to about 140 bp downstream of the E6V mutation in the HBB gene, and the average allelic editing frequency resulting from HDR, e.g., as measured by NGS analysis, is about 15%, 20%, 25%, 30%, 35%, 40%, 45%, 50%, 55%, 60%, or higher. In some embodiments, the target site is about 100 to about 130 bp downstream of the E6V mutation in the HBB gene, and the average allelic editing frequency resulting from HDR, e.g., as measured by NGS analysis, is about 15%, 20%, 25%, 30%, 35%, 40%, 45%, 50%, 55%, 60%, or higher.

In some embodiments, the target sequence consists of the nucleotide sequence SEQ ID NO: 1 and the donor nucleic acid comprises a nucleotide sequence having at least 85%, 86%, 87%, 88%, 89%, 90%, 91%, 92%, 93%, 94%, 95%, 96%, 97%, 98%, or 99% sequence identity to the nucleotide sequence set forth in SEQ ID NO: 6. In some embodiments, the target sequence consists of the nucleotide sequence SEQ ID NO: 1 and the donor nucleic acid comprises the nucleotide sequence set forth in SEQ ID NO: 6.

In some embodiments, the target sequence consists of the nucleotide sequence SEQ ID NO: 1 and the donor nucleic acid comprises a nucleotide sequence having at least 85%, 86%, 87%, 88%, 89%, 90%, 91%, 92%, 93%, 94%, 95%, 96%, 97%, 98%, or 99% sequence identity to the nucleotide sequence set forth in SEQ ID NO: 56. In some embodiments, the target sequence consists of the nucleotide sequence SEQ ID NO: 1 and the donor nucleic acid comprises the nucleotide sequence set forth in SEQ ID NO: 56.

In some embodiments, the target sequence consists of the nucleotide sequence SEQ ID NO: 49 and the donor nucleic acid comprises a nucleotide sequence having at least 85%, 86%, 87%, 88%, 89%, 90%, 91%, 92%, 93%, 94%, 95%, 96%, 97%, 98%, or 99% sequence identity to the nucleotide sequence set forth in SEQ ID NO: 19. In some embodiments, the target sequence consists of the nucleotide sequence SEQ ID NO: 49 and the donor nucleic acid comprises the nucleotide sequence set forth in SEQ ID NO: 19.

In some embodiments, the disclosure provides a gene-editing system, wherein the system is for correcting an E6V mutation in HBB in a cell or population of cells (e.g., CD34+ HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA comprising a spacer sequence corresponding to a target sequence adjacent a PAM, the target sequence comprising a target site within intron 1 of HBB; and (c) a recombinant vector comprising a donor nucleic acid for correcting the E6V mutation, the donor nucleic acid comprising a nucleotide sequence having at least 85%, 86%, 87%, 88%, 89%, 90%, 91%, 92%, 93%, 94%, 95%, 96%, 97%, 98%, or 99% sequence identity to the nucleotide sequence selected from: SEQ ID NO: 6 or SEQ ID NO: 19. In some embodiments, the disclosure provides a gene-editing system, wherein the system is for correcting an E6V mutation in HBB in a cell or population of cells (e.g., CD34+ HSPCs), the system comprising: (a) a Cas9 endonuclease, an mRNA encoding the Cas9 endonuclease, or a recombinant expression vector comprising a nucleotide sequence encoding the Cas9 endonuclease; (b) a sgRNA comprising a spacer sequence corresponding to a target sequence adjacent a PAM, the target sequence comprising a target site within intron 1 of HBB; and (c) a recombinant vector comprising a donor nucleic acid for correcting the E6V mutation, the donor nucleic acid comprising a nucleotide sequence having at least 85%, 86%, 87%, 88%, 89%, 90%, 91%, 92%, 93%, 94%, 95%, 96%, 97%, 98%, or 99% sequence identity to the nucleotide sequence selected from: SEQ ID NO: 6, SEQ ID NO: 19 and SEQ ID NO: 56.

In some embodiments, the disclosure provides a gene-editing system, wherein the system is for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence set forth by SEQ ID NO: 1; and (c) a recombinant vector comprising a donor nucleic acid for correcting the E6V mutation, the donor nucleic acid comprising a nucleotide sequence having at least 85%, 86%, 87%, 88%, 89%, 90%, 91%, 92%, 93%, 94%, 95%, 96%, 97%, 98%, or 99% sequence identity to the nucleotide sequence set forth by SEQ ID NO: 6. In some embodiments, the donor nucleic acid comprises the nucleotide sequence set forth by SEQ ID NO: 6. In some embodiments, the spacer sequence comprises a nucleotide sequence that is at least about 90%, 91%, 92%, 93%, 94%, 95%, 96%, 97%, 98% or 99% identical to SEQ ID NO: 3. In some embodiments, the spacer sequence comprises the nucleotide sequence set forth by SEQ ID NO: 3.

In some embodiments, the disclosure provides a gene-editing system, wherein the system is for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence set forth by SEQ ID NO: 1; and (c) a recombinant vector comprising a donor nucleic acid for correcting the E6V mutation, the donor nucleic acid comprising a nucleotide sequence having at least 85%, 86%, 87%, 88%, 89%, 90%, 91%, 92%, 93%, 94%, 95%, 96%, 97%, 98%, or 99% sequence identity to the nucleotide sequence set forth by SEQ ID NO: 56. In some embodiments, the donor nucleic acid comprises the nucleotide sequence set forth by SEQ ID NO: 56. In some embodiments, the spacer sequence comprises a nucleotide sequence that is at least about 90%, 91%, 92%, 93%, 94%, 95%, 96%, 97%, 98% or 99% identical to SEQ ID NO: 3. In some embodiments, the spacer sequence comprises the nucleotide sequence set forth by SEQ ID NO: 3.

In some embodiments, the disclosure provides a gene-editing system, wherein the system is for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence set forth by SEQ ID NO: 49; and (c) a recombinant vector comprising a donor nucleic acid for correcting the E6V mutation, the donor nucleic acid comprising a nucleotide sequence having at least 85%, 86%, 87%, 88%, 89%, 90%, 91%, 92%, 93%, 94%, 95%, 96%, 97%, 98%, or 99% sequence identity to the nucleotide sequence set forth by SEQ ID NO: 19. In some embodiments, the donor nucleic acid comprises the nucleotide sequence set forth by SEQ ID NO: 19. In some embodiments, the spacer sequence comprises a nucleotide sequence that is at least about 90%, 91%, 92%, 93%, 94%, 95%, 96%, 97%, 98% or 99% identical to SEQ ID NO: 51. In some embodiments, the spacer sequence comprises the nucleotide sequence set forth by SEQ ID NO: 51.

In some embodiments, the disclosure provides a gene-editing system for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence of SEQ ID NO: 1; and (c) a recombinant vector encoding a donor nucleic acid for correcting the E6V mutation, the donor nucleic acid comprising a nucleotide sequence with at least 80%, 85%, 90%, 95%, 96%, 97%, 98% or 99% sequence identity to the nucleotide sequence of SEQ ID NO: 8. In some embodiments, the donor nucleic acid of (c) comprises the nucleotide sequence of SEQ ID NO: 8. In some embodiments, the spacer sequence comprises a nucleotide sequence at least 90%, 91%, 92%, 93%, 94%, 95%, 96%, 97%, 98% or 99% identical to SEQ ID NO: 3. In some embodiments, the spacer sequence comprises the nucleotide sequence set forth by SEQ ID NO: 3.

In some embodiments, the disclosure provides a gene-editing system for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence of SEQ ID NO: 1; and (c) a recombinant vector encoding a donor nucleic acid for correcting the E6V mutation, the donor nucleic acid comprising a nucleotide sequence with at least 80%, 85%, 90%, 95%, 96%, 97%, 98% or 99% sequence identity to the nucleotide sequence of SEQ ID NO: 57. In some embodiments, the donor nucleic acid of (c) comprises the nucleotide sequence of SEQ ID NO: 57. In some embodiments, the spacer sequence comprises a nucleotide sequence at least 90%, 91%, 92%, 93%, 94%, 95%, 96%, 97%, 98% or 99% identical to SEQ ID NO: 3. In some embodiments, the spacer sequence comprises the nucleotide sequence set forth by SEQ ID NO: 3.

In some embodiments, the disclosure provides a gene-editing system for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence of SEQ ID NO: 49; and (c) a recombinant vector encoding a donor nucleic acid for correcting the E6V mutation, the donor nucleic acid comprising a nucleotide sequence with at least 80%, 85%, 90%, 95%, 96%, 97%, 98% or 99% sequence identity to the nucleotide sequence of SEQ ID NO: 20. In some embodiments, the donor nucleic acid of (c) comprises the nucleotide sequence of SEQ ID NO: 20. In some embodiments, the spacer sequence comprises a nucleotide sequence at least 90%, 91%, 92%, 93%, 94%, 95%, 96%, 97%, 98% or 99% identical to SEQ ID NO: 51. In some embodiments, the spacer sequence comprises the nucleotide sequence set forth by SEQ ID NO: 51.

In some embodiments, the recombinant vector encoding the donor nucleic acid is an AAV vector. In some embodiments, the AAV vector is about 2.5 kb-4.6 kb in length. In some embodiments, the AAV vector is an AAV type 6 (AAV6). In some embodiments, the AAV vector comprises 5' and 3' inverted terminal repeats (ITRs) derived from AAV type 2 (AAV2). In some embodiments, the 5' ITR comprises a nucleotide sequence having at least 80% 80%, 85%, 86%, 87%, 88%, 89%, 90%, 91%, 92%, 93%, 94%, 95%, 96%, 97%, 98%, or 99% sequence identity to SEQ ID NO: 5. In some embodiments, the 5' ITR comprises a nucleotide sequence set forth by SEQ ID NO: 5. In some embodiments, the 3' ITR comprises a nucleotide sequence having at least 80% 80%, 85%, 86%, 87%, 88%, 89%, 90%, 91%, 92%, 93%, 94%, 95%, 96%, 97%, 98%, or 99% sequence identity to SEQ ID NO: 7. In some embodiments, the 3' ITR comprises a nucleotide sequence set forth by SEQ ID NO: 7.

In some embodiments, the disclosure provides a gene-editing system, wherein the system is for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence of SEQ ID NO: 1; and (c) an AAV comprising a nucleotide sequence having at least at least 80% 80%, 85%, 86%, 87%, 88%, 89%, 90%, 91%, 92%, 93%, 94%, 95%, 96%, 97%, 98%, or 99% sequence identity to SEQ ID NO: 9. In some embodiments, the AAV vector of (c) comprises the nucleotide sequence of SEQ ID NO: 9. In some embodiments, the spacer sequence comprises a nucleotide sequence at least 90%, 91%, 92%, 93%, 94%, 95%, 96%, 97%, 98% or 99% identical to SEQ ID NO: 3. In some embodiments, the spacer sequence comprises the nucleotide sequence set forth by SEQ ID NO: 3.

In some embodiments, the disclosure provides a gene-editing system, wherein the system is for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence of SEQ ID NO: 1; and (c) an AAV vector comprising a nucleotide sequence having at least at least 80% 80%, 85%, 86%, 87%, 88%, 89%, 90%, 91%, 92%, 93%, 94%, 95%, 96%, 97%, 98%, or 99% sequence identity to SEQ ID NO: 58. In some embodiments, the AAV vector of (c) comprises the nucleotide sequence of SEQ ID NO: 58. In some embodiments, the spacer sequence comprises a nucleotide sequence at least 90%, 91%, 92%, 93%, 94%, 95%, 96%, 97%, 98% or 99% identical to SEQ ID NO: 3. In some embodiments, the spacer sequence comprises the nucleotide sequence set forth by SEQ ID NO: 3.

In some embodiments, the disclosure provides a gene-editing system, wherein the system is for correcting an E6V mutation in HBB in a cell or population of cells, the system comprising: (a) a Cas9 endonuclease, an mRNA encoding the Cas9 endonuclease, or a recombinant expression vector comprising a nucleotide sequence encoding the Cas9 endonuclease; (b) a sgRNA targeting a target site in intron 1 of HBB, the sgRNA comprising a spacer sequence corresponding to a target sequence adjacent a PAM, the target sequence consisting of the nucleotide sequence of SEQ ID NO: 49; and (c) an AAV vector comprising a nucleotide sequence having at least at least 80% 80%, 85%, 86%, 87%, 88%, 89%, 90%, 91%, 92%, 93%, 94%, 95%, 96%, 97%, 98%, or 99% sequence identity to SEQ ID NO: 21. In some embodiments, the AAV vector of (c) comprises the nucleotide sequence of SEQ ID NO: 21. In some embodiments, the spacer sequence comprises a nucleotide sequence at least 90%, 91%, 92%, 93%, 94%, 95%, 96%, 97%, 98% or 99% identical to SEQ ID NO: 51. In some embodiments, the spacer sequence comprises the nucleotide sequence set forth by SEQ ID NO: 51.

In some embodiments, the Cas9 endonuclease of any one of the foregoing systems is SpCas9. In some embodiments, the SpCas9 is a high fidelity SpCas9 endonuclease. In some embodiments, the high fidelity SpCas9 endonuclease comprises a R691A mutation relative to SEQ ID NO: 48. In some embodiments, the high fidelity SpCas9 endonuclease comprises at least one NLS. In some embodiments, the at least one NLS is an sv40 NLS.

In some embodiments, the Cas9 endonuclease of any one of the foregoing systems is a polypeptide. In some embodiments, the system comprises a ribonucleoprotein complex of the sgRNA and the Cas9 endonuclease. In some embodiments, the ribonucleoprotein complex is introduced by electroporation of the cell or the population of cells. In some embodiments, the recombinant expression vector or the AAV encoding the donor nucleic acid is introduced before the electroporation. In some embodiments, the recombinant expression vector or the AAV encoding the donor nucleic acid is introduced during the electroporation. In some embodiments, the recombinant expression vector or the AAV encoding the donor nucleic acid is introduced after the electroporation.

In some embodiments, the Cas9 endonuclease of any one of the foregoing systems is an mRNA. In some embodiments, the mRNA and the sgRNA are introduced by electroporation of the cell or the population of cells. In some embodiments, the recombinant expression vector or the AAV encoding the donor nucleic acid is introduced before the electroporation. In some embodiments, the recombinant expression vector or the AAV encoding the donor nucleic acid is introduced during the electroporation. In some embodiments, the recombinant expression vector or the AAV encoding the donor nucleic acid is introduced after the electroporation.

In some embodiments, Cas9 endonuclease of any one of the foregoing systems is a recombinant expression vector comprising a nucleotide sequence encoding the Cas9 endonuclease. In some embodiments, the recombinant expression vector is an AAV. In some embodiments, the sgRNA is introduced by electroporation of the cell or the population of cells. In some embodiments, the AAV encoding the Cas9 endonuclease is added before, during, or after the electroporation. In some embodiments, the recombinant expression vector or the AAV comprising the donor nucleic acid is added before, during, or after the electroporation.

In some embodiments, any one of the foregoing systems comprises a recombinant expression vector comprising a nucleotide sequence encoding the Cas9 endonuclease and a recombinant expression vector comprising a nucleotide sequence encoding the sgRNA. In some embodiments, the nucleotide sequence encoding the Cas9 endonuclease and the nucleotide sequence encoding the sgRNA are provided in the same recombinant expression vector. In some embodiments, the nucleotide sequence encoding the Cas9 endonuclease and the nucleotide sequence encoding the sgRNA are provided in the same recombinant expression vectors. In some embodiments, the donor nucleic acid and the nucleotide sequence encoding the sgRNA are provided in the same recombinant expression vector. In some embodiments, the donor nucleic acid and the nucleotide sequence encoding the sgRNA are provided in the same recombinant expression vectors. In some embodiments, the recombinant expression vectors are AAVs. In some embodiments, the recombinant expression vectors comprising the nucleotide sequence encoding the Cas9 endonuclease, the nucleotide sequence encoding the sgRNA, and the donor nucleic acid are administered simultaneously or sequentially.

In some embodiments, the disclosure provides a cell edited with any one of the foregoing system, wherein the cell is an HSPC or an LT-HSPC. In some embodiments, the HSPC or LT-HSPC is a CD34-expressing cell. In some embodiments, the disclosure provides a population of cells edited with any one of the foregoing systems, wherein the population of cells comprises HSPCs and/or LT-HSPCs. In some embodiments, the population of cells comprises CD34-expressing HSPCs and/or CD34-expressing LT-HSPCs. In some embodiments, the cell or population of cells is isolated from a tissue sample obtained from a human donor. In some embodiments, the tissue sample is a peripheral blood sample. In some embodiments, the human donor is administered one or more HSPC mobilizing agent(s) prior to obtaining the tissue sample. In some embodiments, the one or more HSPC mobilizing agent(s) are selected from Plurexifor and granulocyte colony stimulating factor (GCSF). In some embodiments, the human donor has sickle cell disease.

In some embodiments, the disclosure provides a population of cells edited with any one of the foregoing systems, wherein when the system is introduced to the cell or population of cells, the sgRNA combines with the Cas9 endonuclease to induce a DSB at the target site in the HBB gene, and wherein HDR of the DSB results in exchange of the region of the HBB gene encoding the mutation (e.g., E6V) with the donor nucleic acid for correcting the mutation. In some embodiments, the frequency of HDR in the population of cells is at least about 15%, 20%, 25%, 30%, 35%, 40%, 45%, 50%, 55%, or 60%. In some embodiments, the frequency of INDELs induced at the target site is reduced by at least 2-10 fold relative to a population of cells introduced without the donor nucleic acid.

III. Engineered Human Cells

Provided herein are methods of gene-editing within an HBB gene by repair of a DNA DSB in the HBB gene using a donor nucleic acid encoding the gene-edit. In some embodiments, the HBB gene is edited to correct a disease-associated mutation (e.g., an E6V mutation), wherein the mutation is associated with a hemoglobinopathy or a beta-hemoglobinopathy. In some embodiments, the HBB gene, or a portion thereof, is edited by replacement with a different polynucleotide sequence, such as a polynucleotide sequence encoding a corrected version of the HBB gene.

In some embodiments, the disclosure provides a cell or population of cells comprising at least one chromosomal copy of an HBB gene comprising the nucleotide sequence set forth in SEQ ID NO: 6. In some embodiments, the disclosure provides a cell or population of cells comprising at least one chromosomal copy of an HBB gene comprising a nucleotide sequence having at least about 90%, about 91%, about 92%, about 93%, about 94%, about 95%, about 96%, about 97%, about 98%, or about 99% sequence identity to the nucleotide sequence set forth in SEQ ID NO: 6. In some embodiments, the disclosure provides a cell or population of cells comprising at least one chromosomal copy of an HBB gene comprising the nucleotide sequence set forth in SEQ ID NO: 56. In some embodiments, the disclosure provides a cell or population of cells comprising at least one chromosomal copy of an HBB gene comprising a nucleotide sequence having at least about 90%, about 91%, about 92%, about 93%, about 94%, about 95%, about 96%, about 97%, about 98%, or about 99% sequence identity to the nucleotide sequence set forth in SEQ ID NO: 56. In some embodiments, the disclosure provides a cell or population of cells comprising at least one chromosomal copy of an HBB gene comprising the nucleotide sequence set forth in SEQ ID NO: 19. In some embodiments, the disclosure provides a cell or population of cells comprising at least one chromosomal copy of an HBB gene comprising a nucleotide sequence having at least about 90%, about 91%, about 92%, about 93%, about 94%, about 95%, about 96%, about 97%, about 98%, or about 99% sequence identity to the nucleotide sequence set forth in SEQ ID NO: 19. In some embodiments, the disclosure provides a cell or population of cells comprising at least one chromosomal copy of an HBB gene comprising the nucleotide sequence set forth in SEQ ID NO: 8. In some embodiments, the disclosure provides a cell or population of cells comprising at least one chromosomal copy of an HBB gene comprising a nucleotide sequence having at least about 90%, about 91%, about 92%, about 93%, about 94%, about 95%, about 96%, about 97%, about 98%, or about 99% sequence identity to the nucleotide sequence set forth in SEQ ID NO: 8. In some embodiments, the disclosure provides a cell or population of cells comprising at least one chromosomal copy of an HBB gene comprising the nucleotide sequence set forth in SEQ ID NO: 57. In some embodiments, the disclosure provides a cell or population of cells comprising at least one chromosomal copy of an HBB gene comprising a nucleotide sequence having at least about 90%, about 91%, about 92%, about 93%, about 94%, about 95%, about 96%, about 97%, about 98%, or about 99% sequence identity to the nucleotide sequence set forth in SEQ ID NO: 57. In some embodiments, the disclosure provides a cell or population of cells comprising at least one chromosomal copy of an HBB gene comprising the nucleotide sequence set forth in SEQ ID NO: 20. In some embodiments, the disclosure provides a cell or population of cells comprising at least one chromosomal copy of an HBB gene comprising a nucleotide sequence having at least about 90%, about 91%, about 92%, about 93%, about 94%, about 95%, about 96%, about 97%, about 98%, or about 99% sequence identity to the nucleotide sequence set forth in SEQ ID NO: 20.

In some embodiments, an HBB gene is edited using methods herein to correct a disease-associated mutation that results in a hemoglobinopathy. In some embodiments, an HBB gene is edited using methods herein to correct a disease-associated mutation that results in a beta-hemoglobinopathy (e.g., sickle cell disease, e.g., beta-thalassemia). In some embodiments, an HBB gene is edited using methods herein to correct a disease-associated mutation that results in altered expression and/or functionality of beta-globin, wherein the alteration results in a hemoglobinopathy (e.g., sickle cell disease, e.g., beta-thalassemia).

In some embodiments, the hemoglobinopathy is treated by administering a population of gene-edited human cells to a patient having the hemoglobinopathy. In some embodiments, a population of cells is isolated from the patient and edited to correct a genetic mutation associated with the hemoglobinopathy prior to being reintroduced to the patient for treatment of the hemoglobinopathy. In some embodiments, the hemoglobinopathy is associated with changes in the genetically determined structure or expression of hemoglobin. These include changes to the molecular structure of the hemoglobin chain, as well as changes in which synthesis of one or more chains is reduced or absent, such as occurs with various thalassemias. In some embodiments, a population of cells is gene-edited and introduced to the patient for treatment of a β-hemoglobinopathies (e.g., β-thalassemias, e.g., sickle cell disease). In some embodiments, a population of cells is gene-edited and introduced to a patient for treatment of sickle cell disease (SCD), which includes sickle cell anemia (SCA), sickle hemoglobin C disease, sickle beta-plus-thalassemia, and sickle beta-zero-thalassemia. All forms of SCD are caused by mutations within the HBB gene. SCA is caused by the E6V mutation. The mutant protein, when incorporated into hemoglobin, results in unstable hemoglobin HbS ($\alpha 2\beta 2S$) in contrast to normal adult hemoglobin HbA ($\alpha 2\beta 2A$). When HbS is the predominant form of hemoglobin, it results in red blood cells (RBCs) with distorted sickle shape. Sickled RBCs are less flexible than normal RBCs, and tend to get stuck in small blood vessels, resulting in vaso-occlusive events. These events are associated with tissue ischemia leading to acute and chronic pain.

In some embodiments, the population of gene-edited cells reintroduced to the patient comprises gene-edited progenitor cells, such as gene-edited erythroid progenitor cells. In some embodiments, an advantage of introducing gene-edited progenitor cells previously isolated from the same patient (i.e., autologous cells) is the cells are completely matched to the patient, and thus may be administered safely without risk of inducing, for example, graft vs. host disease.

In some embodiments, the gene-edited progenitor cells give rise to a population of circulating gene-edited erythroid cells that are effective for ameliorating one or more clinical conditions associated with the patient's hemoglobinopathy. In some embodiments, the progenitor cells comprise a gene-edit within the HBB gene that corrects a mutation (e.g., E6V) associated with a β-hemoglobinopathy (e.g., SCD). In some embodiments, the progenitor cells give rise to a population of circulating erythroid cells having the gene-edit within the HBB gene (e.g., correction of E6V), wherein the circulating erythroid cells are effective for ameliorating one or more clinical conditions associated with the patient's β-hemoglobinopathy (e.g., SCD). In some embodiments, the level of normal adult hemoglobin is increased (e.g., by about 10%, 20%, 30%, 40%, 50%, 60%, 70%, 80%, or higher) relative to patients with the β-hemoglobinopathy (e.g., SCD).

In some embodiments, the population of cells taken from the patient comprises somatic cells, wherein the population of cells is reprogrammed to generate a population of cells comprising induced pluripotent stem cells (iPSCs). In some embodiments, a population of cells comprising iPSCs is gene-edited to correct the disease-associated mutation and then differentiated (e.g., to erythroid cells or erythroid progenitor cells) prior to administration to the patient.

In some embodiments, a population of cells is isolated from a patient comprises hematopoietic stem cells (HSCs) and/or hematopoietic progenitor cells (HPCs). In some embodiments, the population of cells comprises HSCs, HPCs, long-term hematopoietic stem and progenitor cells (LT-HSPC), or a combination thereof. In some embodiments, a population of cells comprising HSCs, HPCs, and/or LT-HSPCs is gene-edited to correct a mutation associated with the hemoglobinopathy, and introduced to the patient for treatment of the hemoglobinopathy.

A. Engineered Hematopoietic Stem and Progenitor Cells (HSPCs)

In some embodiments, the disclosure provides a population of cells comprising HSPCs is engineered (e.g., gene-edited) according to methods described herein. In some embodiments, the population of cells is isolated from a patient with the hemoglobinopathy, wherein the population of cells is engineered to correct a disease-associated mutation, or a mutation associated with a hemoglobinopathy (e.g., β-hemoglobinopathy). In some embodiments, the population of cells is isolated from a patient with sickle cell disease, wherein the population of cells is engineered to correct an E6V mutation in the HBB gene.

As used herein, the term "stem cell" refers to a cell with the capacity or potential, under certain conditions, to differentiate to a cell having a more specialized or differentiated phenotype, and which retains the capacity, under certain circumstances, to proliferate without substantially differentiating. For example, in some embodiments, a stem cell refers to an undifferentiated mother cell whose descendants (progeny) specialize by differentiation, often along different differentiation pathways, e.g., by acquiring specific functions and/or phenotypes. Self-renewal is an important function of the stem cell. In theory, self-renewal occurs by either of two distinct mechanisms. Stem cells divide asymmetrically, with one daughter retaining the stem state and the other daughter expressing a distinct and specific function and phenotype. Alternatively, the stem cells divide symmetrically into two cells with the stem state. In some embodiments, a population of stem cells includes stem cells dividing by both mechanisms, ultimately maintaining a portion of the population in the stem state, and a portion of the population giving rise to differentiated progeny. Generally, "progenitor cells" have a cellular phenotype that is more primitive (i.e., at an earlier step along a developmental pathway or progression than fully or terminally differentiated cell). Progenitor cells can give rise to multiple distinct differentiated cell types or to a single differentiated cell type, depending on the developmental pathway and on the environment in which the cells develop and differentiate.

A "hematopoietic stem and progenitor cells (HSPCs)" refers to cells of a stem cell lineage that give rise to all blood cell types. Blood cells are produced by proliferation and differentiation of a population of HSCs in the bone marrow. HSCs have the capability to replenish themselves by self-renewal, and generally comprise two populations: short-term HSCs and long-term HSCs. Short term HSCs are capable of self-renewal for a short period of time, while long-term HSCs are capable of indefinite self-renewal. LT-HSCs are largely in a quiescent state, dividing only once every 145 days (Wilson, A. et al. (2008) Cell 135:1118-1129). During differentiation, the progeny of HSCs, which include HPCs, progress through various intermediate maturational stages in a progression that results in lineage restricted precursor cells. In some embodiments, the progenitor cells differentiate to common myeloid progenitor cells, which include those that undergo final differentiation to myeloid cells (e.g., monocytes, macrophages, myeloid dendritic cells), thrombocytes, mast cells, erythroid cells, granulocytes (e.g., neutrophils, basophils, eosinophils). In some embodiments, the progenitor cells differentiate to common lymphoid progenitor cell, which include those that undergo final differentiation to lymphoid cells (e.g., B cells, T cells, NK cells, lymphoid dendritic cells). HSPCs differentiate along different lineage precursor pathways depending upon exposure to specific growth factors and other components of the hematopoietic microenvironment, wherein the HSPCs mature through a series of intermediate differentiation cellular types, to reach an ultimate differentiation state (e.g., erythroid cells).

In some embodiments, a population of HSPCs express one or more cell surface markers according to a phenotype that is characteristic of human hematopoietic progenitor cells. In some embodiments, the population of HSPCs has positive expression for the cell surface marker CD34. In some embodiments, the population of HSPCs has positive expression for one or more cell surface markers selected from: CD38, CD45RA, CD90, c-Kit tyrosine kinase receptor, stem cell antigen-1 (Sca-1), CD133 and CD49f. In some embodiments, the population of HSPCs has negative or low expression for one or more cell surface markers selected from: CD38, CD45RA, CD90, Thy-1.1 cell surface antigen and CD49f. In some embodiments, the population of HSPCs has negative or low expression of one or more lineage cell surface markers selected from: CD2, CD3, CD11b, CD11c, CD14, CD16, CD19, CD24, CD56, CD66b, CD235.

In some embodiments, the population of HSPCs comprises LT-HSCs.

In some embodiments, the population of HSPCs comprise cells of the erythroid lineage, wherein the cells express one or more cell surface markers according to a phenotype that is characteristic of human erythroid cells, e.g., positive expression of CD71 and Terl 19.

Methods for isolation of HSPCs are known in the art, such as those described in U.S. Pat. Nos. 5,643,741, 5,087,570, 5,677,136, 7,790,458, 10,006,004, 10,086,045, 7,939,057, 10,058,57, each of which are incorporated by reference herein. In some embodiments, a population of cells comprising HSPCs is derived from the patient (e.g., an autologous HSPC). In some embodiments, a population of cells comprising HSPCs is derived from a healthy donor (e.g., an allogenic HSPC). In some embodiments, a population of cells comprising HSPCs is derived from human cord blood. In some embodiments, a population of cells comprising HSPCs is derived from bone marrow. In some embodiments, a population of cells comprising HSPCs is derived from human peripheral blood.

HSPCs are predominantly found in the bone marrow, with only low levels found in peripheral blood under normal physiological conditions. However, the interactions of HSPCs with stromal cells in the bone marrow may be disrupted by treatment with certain compounds, resulting in rapid mobilization of large numbers of HSCPs into circulation. Accordingly, in some embodiments, a population of cells comprising HSPCs is derived following treatment of a subject (e.g., a patient, a healthy donor) with a stem cell mobilizer. In some embodiments, a stem cell mobilizer comprises a CXCR4 antagonist. The chemokine stromal cell derived factor-1 (e.g., CXCL12) is a chemokine that binds to CXCR4 on HSPCs and signals for retention in the bone marrow. By blocking this interaction with a CXCR4 antagonist, HSPCs are rapidly mobilize to the blood (Broxmeyer, et al. (2005) J. Exp Med 18:1307-1318; Devine, S. et al (2008) Blood 112:990-998). Non-limiting examples of a CXCR4 antagonist include TG-0054 (TaiGen Biotechnology, Co., Ltd. (Taipei, Taiwan)), AMD3465, AMD3100 (e.g., wherein AMD or AMD3100 is used interchangeably with plerixafor, rINN, USAN, JM3100, and its trade name, Mozobil™, see U.S. Pat. Nos. 6,835,731 and 6,825,351), and NIBR1816 (Novartis, Basil, Switzerland). In some embodiments, a stem-cell mobilizer is plerixafor.

In some embodiments, a stem cell mobilizer comprises a colony stimulating factor. Non-limiting examples of a colony stimulating factor include, but are not limited to, granulocyte colony stimulating factor (G-CSF), granulocyte-macrophage colony stimulating factor (GM-CSF), macrophage colony stimulating factor (M-CSF), stem cell factor (SCF), FLT-3 ligand, or a combination thereof. Use of G-CSF as a stem cell mobilizing factor has demonstrated increased yield of stem cells from peripheral blood (Morton, et al (2001) Blood 98:3186; Smith, T. et al. (1997) J. Clin. Oncol. 15:5-10) In some embodiments, a stem cell mobilizer is a combination of a CXCR4 antagonist and a colony stimulating factor. In some embodiments, a stem cell mobilizer is a combination of Plerixafor and G-CSF.

In some embodiments, CD34+ HSPCs are enriched following isolation from a subject (e.g., a patient, a healthy donor). In some embodiments, CD34+ HSPCs are enriched from human blood, bone marrow, or cord blood. Methods of enriching CD34+ HSPCs are known in the art. In some embodiments, CD34+ HSPCs are enriched using a magnetic cell separator. In some embodiments, CD34+ HSPCs are enriched by fluorescent activated cell sorting (FACS). In some embodiments, CD34+ HSPCs are enriched by magnetic bead sorting for cells expressing CD34.

In some embodiments, an enriched population of CD34+ HSPCs has a purity of at least 40%, at least 50%, at least 60%, at least 70%, at least 80%, at least 90%, or at least 100%. In some embodiments, an enriched population of CD34+ HSPCs has a purity of at least 90%, at least 91%, at least 92%, at least 93%, at least 94%, at least 95%, at least 96%, at least 97%, at least 98%, at least 99%, or at least 100%.

In some embodiments, an enriched population of CD34+ HSPCs comprises LT-HSCs. In some embodiments, the proportion of the population that are LT-HSCs is 0.01-0.05%, 0.01-0.1%, 0.05-0.1%, 0.05-1%, 0.1-0.5%, 0.1-0.7%, 0.1-1.0%, 0.1-1.5%, 0.1-2.0%, 0.5-1.5%, 0.5-2.0%, or 1-2%. In some embodiments, the proportion of the population that are LT-HSCs is 0.05-1%. In some embodiments, the proportion of the population that is LT-HSCs is 0.1-1%. In some embodiments, the proportion of the population that is LT-HSCs is 0.1-2%. In some embodiments, the proportion of the population that is LT-HSCs is at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, or at least about 1.0% of the population.

In some embodiments, gene-editing of human-derived HSPCs is performed prior to enrichment of CD34+ cells. In some embodiments, gene-editing of human-derived HSPCs is performed following enrichment of CD34+ cells. In some embodiments, following gene-editing, a method is used to selected for gene-edited HSPCs from a population comprising CD34+ HSPCs. In some embodiments, a method of isolating gene-edited HSPCs comprises enrichment of HSPCs expressing truncated nerve growth factor (tNGFR), such as is described by Dever et al (2016) Nature 539:384-389.

Methods of maintaining and inducing expansion of HSCPs in ex vivo culture are known in the art. In some embodiments, the method comprises culturing with one or more cytokines and/or one or more growth factors that induce ex vivo expansion and/or promotes survival. In some embodiments, the method comprises culturing (e.g. in serum free medium) with one or more cytokines is selected from: IL-3, IL-6, and thrombopoietin (TPO). In some embodiments, the method comprises culture (e.g., in serum free medium) with one or more growth factors selected from stem cell factor (SCF) and Fms-like tyrosine kinase 3 (Flt3) ligand.

For ex vivo therapy, transplantation requires clearance of bone-marrow niches for donor HSPCs to engraft. Methods are known in the art for depletion of the bone-marrow niche, including methods of treating with radiation, chemotherapy or a combination thereof.

B. Engineered Induced Pluripotent Stem Cells

In some embodiments, genetically engineered human cells of the disclosure are derived from induced pluripotent stem cells (iPSCs). iPSCs are reprogrammed from somatic cells to a pluripotent state wherein they can differentiate into all three germ layers. An advantage of using iPSCs is that the cell can be derived from the same subject to which the progenitor cells are to be administered. That is, a somatic cell can be obtained from a subject, reprogrammed to an iPSC, and then re-differentiated into a progenitor cell to be administered to the subject for treatment of a disorder (e.g., an autologous progenitor). Since the progenitors are derived from an autologous source, the risk of engraftment rejection or allergic responses is reduced compared to the use of cells from another subject or group of subjects. Thus, an iPSC can be gene-edited and reintroduced into a patient for correction of a disease resulting from a somatic genetic mutation.

Briefly, human iPSCs can be obtained by transducing somatic cells with stem cell associated transcription factors that include OCT4, SOX2, and NANOG (Budniatzky et al. (2014) Stem Cells Transl Med 3:448-457; Barret et al. Stem Cells Trans Med (2014) 3:1-6; Focosi et al. (2014) Blood Cancer Journal 4:e211). Exemplary methods for reprogramming somatic cells to generate iPSCs are known in the art as described by US 2019/0038771 which is incorporated by reference herein.

IV. Methods of Generating Gene-Edited Cells

In some embodiments, the disclosure provides improved methods for editing a cell or a population of cells (e.g., HSPCs) to correct a mutation encoded by the HBB gene (e.g., E6V). In some embodiments, the disclosure provides methods for improving HDR of a DSB in a target region in an HBB gene. In some embodiments, the methods disclosed herein utilize a donor nucleic acid for correcting the mutation or a recombinant vector encoding the donor nucleic acid, a gRNA (e.g., intron-targeting gRNA), and a site-directed endonuclease (e.g., SpCas9) to edit an HBB gene within a cell or a population of cells (e.g., correct an E6V mutation encoded by the HBB gene). In some embodiments, the method disclosed herein utilize a donor nucleic acid for correcting the mutation or a recombinant vector encoding the donor nucleic acid, a gRNA (e.g., intron-targeting gRNA), a site-directed endonuclease (e.g., SpCas9), and a 53BP1 inhibitor and/or DNA-PK inhibitor, to improve genome editing of an HBB gene within a cell or a population of cells (e.g., correction of an E6V mutation encoded by the HBB gene).

A. Methods of Increasing HDR

The repair of DNA breaks (e.g., DSBs) in cells is accomplished primarily through two DNA repair pathways, namely the non-homologous end joining (NHEJ) repair pathway and homology-directed repair (HDR) pathway.

During NHEJ, the Ku70/80 heterodimers bind to DNA ends and recruit the DNA protein kinase (DNA-PK) (Cannan & Pederson (2015) J Cell Physiol 231:3-14). Once bound, DNA-PK activates its own catalytic subunit (DNA-PKcs) and further enlists the endonuclease Artemis (also known as SNM1c). At a subset of DSBs, Artemis removes excess single-strand DNA (ssDNA) and generates a substrate that will be ligated by DNA ligase IV. DNA repair by NHEJ involves blunt-end ligation mechanism independent of sequence homology via the canonical DNA-PKcs/Ku70/80 complex.

During DNA repair by HDR, DSB ends are resected to expose 3' ssDNA tails, primarily by the MRE11-RAD50-NBS1 (MRN) complex (Heyer et al., (2010) Annu Rev Genet 44: 113-139). Under physiological conditions, the adjacent sister chromatid will be used as a repair template, providing a homologous sequence, and the ssDNA will invade the template mediated by the recombinase Rad51, displacing an intact strand to form a D-loop. D-loop extension is followed by branch migration to produce double-Holliday junctions, the resolution of which completes the repair cycle. HDR often requires error-prone polymerases yet is typically viewed as error-free (Li and Xu (2016) Acta Biochim Biophys Sin 48(7): 641-646).

The NHEJ pathway limits HDR first by being a fast-acting repair pathway that seals the broken DNA ends through a DNA ligase IV-dependent mechanism. Secondly, in NHEJ the Ku70/Ku80 heterodimer binds to the DNA ends with high affinity to block their processing by the nucleases that generate the single-stranded DNA tails that are necessary for initiation of HDR (Lieber, M. et al. (2010) Annu Rev Biochem 79:181-211; Symington, L. et al. (2011) Annu Review Genetics 45:247-271). Thirdly, 53BP1 is actively recruited to sites of damaged chromatin present at a DNA DSB where it functions to suppress the formation of 3' ssDNA tails and antagonize the action of BRCA1, a factor involved in HDR (Escribano-Diaz, C. (2013) Molecular cell 49:872-883; Feng, L. et al. (2013) J. Biol Chem. 288:11135-11143).

During the cell cycle, NHEJ occurs predominantly during G0/G1 and G2 (Chiruvella et al., (2013) Cold Spring Harb Perspect Biol 5:a012757). Current studies have shown that NHEJ is the only DSB repair pathway active during G0 and G1, while HDR functions primarily during the S and G2 phases, playing a major role in the repair of replication-associated DSBs (Karanam et al., (2012) Mol Cell 47:320-329; Li and Xu (2016) Acta Biochim Biophys Sin 48(7): 641-646). NHEJ, unlike HDR, is active in both dividing and non-dividing cells, not just dividing cells, which enables the development of therapies based on genome editing for non-dividing adult cells, such as, for example, cells of the eye, brain, pancreas, or heart.

A third repair mechanism is microhomology-mediated end joining (MMEJ), also referred to as "Alternative NHEJ", in which the genetic outcome is similar to NHEJ in that small deletions and insertions can occur at the cleavage site. MMEJ makes use of homologous sequences of a few nucleotides flanking the DNA break site to drive a more favored DNA end joining repair outcome, and recent reports have further elucidated the molecular mechanism of this process (Cho and Greenberg, (2015) Nature 518:174-176; Mateos-Gomez et al., (2015) Nature 518, 254-257; Ceccaldi et al., (2015) Nature 528, 258-262). The key mechanistic steps are resection of DSB ends, annealing of microhomologous regions, removal of heterologous flaps, fill-in synthesis and ligation. PARP1 plays a key role in binding to DNA blunt ends and initiating the MMEJ pathway by recruiting DNA polymerase theta (Polθ). Polθ) enables the formation of resected DNA ends, as well as enabling the fill-in synthesis (Wang. H. et al. (2017) Cell Biosci 7:6).

(i) Inhibition of 53BP1

In some embodiments, the disclosure provides methods for increasing HDR of a DSB mediated by a site-directed nuclease in a target gene in a cell or population of cells, e.g., CD34+ HSPCs, by inhibition of 53BP1. In some embodiments, the disclosure provides methods for increasing HDR of a DSB mediated by a site-directed nuclease in a cell or population of cells expressing an E6V mutation in HBB, by inhibition of 53BP1.

The p53-binding protein 1 (53BP1) is a key regulator of cellular response to DNA damage. The choice of repair pathway for repair of a DNA DSB is largely controlled by an antagonism between 53BP1, a pro-NHEJ factor, and BRCA1, a pro-HDR factor (Chapman, J. et al. (2012) Molecular cell 47:497-510). 53BP1 promotes NHEJ repair over HDR repair by suppressing formation of 3' single-stranded DNA tails, which is the rate-limiting step in the initiation of the HDR pathway, and by inhibiting BRCA1 recruitment to DSB sites (Escribano-Diaz, C. et al. (2013) Mol Cell. 49:872-883; Feng, L. et al (2013) J Biol Chem 288:11135-11143). Loss of 53BP1 has been shown to increase HDR efficiency, (Canny, M. et al. (2018) Nat Biotechnol. 36(1):95-102). Thus, inhibition of 53BP1 is expected to reduce DSB repair by the NHEJ pathway and favor repair by the HDR pathway.

Distinct protein domains in the 53BP1 structure are required to enable its function as a pro-NHEJ factor (Zimmermann et al (2014) Trends Cell Biol 24:108-117). Human 53BP1 is a large (e.g., 200 kDa, 1972 amino acids) multi-domain protein that enables recruitment to DSB sites and binding of protein factors involved in DNA repair. The 53BP1 N-terminus is comprised of a large subunit that is heavily phosphorylated following DNA damage and facilitates binding interactions with DNA repair machinery. The central portion of 53BP1 comprises a focus-forming region that is essential for binding to damaged chromatin, which allows recruitment to DSB sites. It comprises a nuclear localization signal (NLS), a tandem Tudor domain that binds to di-methylated histone H4 lysine 20 (e.g., H4K20Me2), and a ubiquitin-dependent recruitment (UDR) motif that recognizes histone H2A/H2AX ubquitinated on lysine 15 (e.g., H2A(X)K15Ub) (Botuyan, M. (2006) Cell 127:1361-1373; Fradet-Turcotte et al (2013) Nature 499:50-54). The focus-forming region extends from amino acids 1220-1711 of human 53BP1, with the tandem Tudor domain extending from amino acids 1484-1603 and the UDR extending from amino acids 1604-1631. The 53BP1 C-terminus is comprised of repeating BRCA1 C-terminus (BRCT) domains that are important for DNA repair in heterochromatin (Noon et al (2010) Nat Cell Biol 12:177-184) and mediate interactions with the tumor suppressor p53 that guides cellular response to DNA damage (Iwabuchi, et al (1994) PNAS 91:6098-6102).

The functionality of 53BP1 for promoting the NHEJ pathway requires recruitment to damaged chromatin through its tandem Tudor and UDR domains and binding to repair machinery through phosphorylation of the 53BP1 N-terminus.

Accordingly, the present disclosure provides 53BP1 inhibitors that inhibit NHEJ and promote HDR repair of a DSB in a target gene. In some embodiments, a 53BP1 inhibitor of the disclosure inhibits 53BP1 recruitment to DSB sites. In some embodiments, a 53BP1 inhibitor of the disclosure inhibits 53BP1 recruitment by inhibiting, reducing, disrupting or blocking an interaction of 53BP1 with damaged chromatin. In some embodiments, a 53BP1 inhibitor of the disclosure inhibits, reduces, disrupts or blocks an interaction of the 53BP1 focus forming region (amino acids 1220-1711) with DSB sites. In some embodiments, a 53BP1 inhibitor of the disclosure inhibits, reduces, disrupts or blocks an interaction of the 53BP1 focus forming region (amino acids 1220-1711) with damaged chromatin. In some embodiments, a 53BP1 inhibitor of the disclosure inhibits, reduces, disrupts or blocks an interaction of the 53BP1 tandem Tudor domain with damaged chromatin (e.g., with methylated histone, H4K20Me2). In some embodiments, a 53BP1 inhibitor of the disclosure inhibits, reduces, disrupts or blocks the interaction of the 53BP1 UDR motif with damaged chromatin (e.g., with ubquitinylated histone, H2A (X)K15Ub).

In some embodiments, a 53BP1 inhibitor of the disclosure inhibits, reduces, disrupts or blocks protein-protein interactions with the 53BP1 BRCT domain. In some embodiments, a 53BP1 inhibitor of the disclosure inhibits, reduces, disrupts or blocks the interactions of the 53BP1 BRCT domain with the tumor suppressor p53.

In some embodiments, a 53BP1 inhibitor of the disclosure inhibits, reduces, disrupts or blocks the ability of 53BP1 to bind to DNA repair factors. In some embodiments, a 53BP1 inhibitor of the disclosure inhibits, reduces, disrupts or blocks phosphorylation of the 53BP1 N-terminus, thus inhibiting, reducing or preventing binding of DNA repair factors. In some embodiments, a 53BP1 inhibitor of the disclosure binds to phosphorylated sites on the 53BP1 N-terminus, thus inhibiting, reducing or preventing DNA repair factors from recognizing and binding to phosphorylated sites on the 53BP1 N-terminus. In some embodiments, a 53BP1 inhibitor of the disclosure reduces, eliminates or removes phosphorylated sites on the 53BP1 N-terminus (e.g., by promoting or catalyzing a dephosphorylation mechanism), thus reducing, eliminating or removing sites required for binding of DNA repair factors. In some embodiments, a 53BP1 inhibitor that binds to phosphorylated sites on 53BP1 and facilitates HDR is suppressor of cancer cell invasion (SCAI) or a fragment thereof. In some embodiments, binding of SCAI or a fragment thereof prevents binding of the DNA repair factor RAP1-interacting factor homolog (RIF1). In some embodiments, blocking RIF1 binding to 53BP1 results in increased HDR repair of a DNA DSB.

In some embodiments, the 53BP1 inhibitor of the disclosure inhibits, disrupts or blocks 53BP1 recruitment to DSB sites in the cell. In some embodiments, the 53BP1 inhibitor of the disclosure inhibits, disrupts or blocks an interaction of 53BP1 with damaged chromatin in the cell. In some embodiments, the 53BP1 inhibitor of the disclosure inhibits, disrupts or blocks binding of DNA repair factors to sites of phosphorylation on the 53BP1 N-terminus. In some embodiments, the 53BP1 inhibitor of the disclosure is a small molecule. In some embodiments, the 53BP1 inhibitor of the disclosure is a polypeptide. In some embodiments, the 53BP1 inhibitor of the disclosure is a nucleic acid.

In some embodiments, recruitment of 53BP1 to a DSB site occurs via recognition of damaged chromatin. In some embodiments, recruitment of 53BP1 to damaged chromatin occurs through recognition of H4K20me2 through the 53BP1 UDR motif. In some embodiments, recognition of damaged chromatin by 53BP1 is dependent upon ubiquitination of histones. In some embodiments, inhibition of histone ubiquitination results in inhibition of 53BP1 recruitment to DSB sites.

Acetylation of 53BP1 has been shown to inhibit 53BP1 binding to damaged chromatin (Guo et al (2018) Nucleic Acids Res 46:689-703). In some embodiments, an inhibitor of 53BP1 promotes post-translational modification of 53BP1. In some embodiments, an inhibitor of 53BP1 promotes post-translation modification of 53BP1 that prevents 53BP1 binding to damaged chromatin. In some embodiments, an inhibitor of 53BP1 promotes acetylation of 53BP1. In some embodiments, an inhibitor of 53BP1 promotes acetylation of the 53BP1 UDR motif. In some embodiments, acetylation of 53BP1 prevents 53BP1 recruitment to DSB sites.

In some embodiments, a 53BP1 inhibitor is identified by binding affinity for the 53BP1 polypeptide. Methods of measuring binding affinity of an inhibitor to a protein are known in the art. Non-limiting examples include measuring inhibitor affinity by enzyme-linked immunosorbent assay (e.g., ELISA), immunoblot, immunoprecipitation-based assay, fluorescence polarization assay, fluorescence resonance energy transfer assay, fluorescence anisotropy assay, yeast surface display (Gai (2007) Curr Opin Struct Biol 17:467-473), kinetic exclusion assay, surface plasmon resonance, or isothermal titration calorimetry. In some embodiments, a method of measuring binding affinity is an ELISA wherein an inhibitor is measured for affinity to the 53BP1 polypeptide. In some embodiments, binding affinity is evaluated by a competition-based ELISA wherein binding of an inhibitor to the 53BP1 polypeptide is measured in the presence of increasing concentrations of a known 53BP1 binding partner (e.g., a histone methyl-lysine peptide with affinity for 53BP1).

In some embodiments, a 53BP1 inhibitor is identified by binding affinity for a fragment of the 53BP1 polypeptide. In some embodiments, a fragment is a domain of the 53BP1 polypeptide. In some embodiments, the domain is the Tudor domain. In some embodiments, the domain is the UDR motif. In some embodiments, the domain comprises the N-terminus of the 53BP1 polypeptide.

In some embodiments, a 53BP1 inhibitor of the disclosure binds to the 53BP1 polypeptide. Methods of determining the structural interactions that enable binding of the inhibitor with the 53BP1 polypeptide are known in the art. Non-limiting examples include X-ray crystallography, nuclear magnetic resonance (NMR) spectroscopy, electron microscopy, small-angle X-ray scattering (SAXS), and small-angle neutron scattering (SANS). In some embodiments, the structural interactions are determined by a mutagenesis experiment wherein residues of the 53BP1 polypeptide are mutated and the effect on inhibitor binding are evaluated. Such methods enable identification of key residues that contribute to binding In some embodiments, the 53BP1 inhibitor of the disclosure is a 53BP1 binding polypeptide that inhibits 53BP1 recruitment to the DSB in the cell. In some embodiments, a 53BP1 binding polypeptide of the disclosure inhibits, disrupts or blocks binding of 53BP1 to damaged chromatin in the cell. In some embodiments, a 53BP1 binding polypeptide of the disclosure inhibits, disrupts or blocks the 53BP1 tandem Tudor domain from binding to damaged chromatin in the cell. In some embodiments, a 53BP1 binding polypeptide of the disclosure inhibits, disrupts or blocks the 53BP1 UDR motif from binding to damaged chromatin in the cell.

In some embodiments, an inhibitor of 53BP1 is a polypeptide identified from a phage-display library or a variant thereof as described by US 2019/0010196A, which is incorporated by reference herein. In some embodiments, a polypeptide inhibitor of 53BP1 has binding affinity for the 53BP1 Tudor domain. The 53BP1 Tudor domain is involved in recognition of methylated residues on the histone core that facilitates recruitment of 53BP1 to a DNA DSB site. In some embodiments, a 53BP1 polypeptide inhibitor of the disclosure inhibits, reduces or prevents recruitment of 53BP1 to a DNA DSB by binding to the 53BP1 Tudor domain.

In some embodiments, a 53BP1 polypeptide inhibitor of the disclosure is modified, by, for example, substitution of one or more amino acid residues, insertion of one or more amino acid residues, or deletion of one or more amino acid residues. In some embodiments, a 53BP1 polypeptide inhibitor of the disclosure is modified by chemical modifications. Techniques for modification of one or more amino acid residues are known to one skilled in the art. In some embodiments, a modification is substitution of one or more amino acid residues. In one embodiment, a modification increases binding affinity of the 53BP1 polypeptide inhibitor for the 53BP1 polypeptide or a fragment thereof.

In some embodiments, a modified polypeptide inhibitor of 53BP1 is identified by affinity for the 53BP1 Tudor domain. Affinity for the 53BP1 Tudor domain may be assessed by suitable assays known to one skilled in the art. In some embodiments, affinity is measured by a competitive immunoprecipitation assay against an endogenous polypeptide that binds 53BP1, for example, dimethylated histone H4 Lys20. In some embodiments, affinity is measured by isothermal calorimetry using recombinant 53BP1. In some embodiments, affinity is determined by assessing 53BP1 recruitment to DSB sites. In some embodiments, a 53BP1 polypeptide inhibitor of the disclosure has a quantifiable binding affinity for the 53BP1 Tudor domain of approximately 0.5 to 15×10-9 M, 0.5 to 25×10-9, 0.5 to 50×10-9 M, 0.5 to 100×10-9 M, 0.5 to 200×10-9 M, 1 to 200×10-9 M, 1 to 300×10-9 M, 1 to 400×10-9 M, 1 to 500×10-9 M, 100 to 250×10-9 M, 100 to 500×10-9 M, or 200 to 500×10-9 M. In some embodiments, a 53BP1 polypeptide inhibitor of the disclosure has a quantifiable binding affinity for the 53BP1 Tudor domain of approximately 200 to 500×10-9 M. In some embodiments, a 53BP1 polypeptide inhibitor of the disclosure has a quantifiable binding affinity for the 53BP1 Tudor domain of approximately 250×10-9 M.

In some embodiments, a 53BP1 polypeptide inhibitor of the disclosure comprises a polypeptide sequence of SEQ ID NO: 11. In some embodiments, a 53BP1 polypeptide inhibitor of the disclosure comprises a polypeptide sequence that is at least about 50%, 60%, 70% or 80% identical to the polypeptide sequence of SEQ ID NO: 11. In some embodiments, a 53BP1 polypeptide inhibitor comprises a polypeptide sequence that is at least about 90%, 95%, 96%, 97%, 98% or 99% identical to the polypeptide sequence of SEQ ID NO: 11. In some embodiments, a 53BP1 polypeptide inhibitor of the disclosure comprises a polypeptide sequence that is at least about 95% identical to the polypeptide sequence of SEQ ID NO: 11. In some embodiments, a 53BP1 polypeptide inhibitor of the disclosure comprises a polypeptide sequence that is at least about 96% identical to the polypeptide sequence of SEQ ID NO: 11. In some embodiments, a 53BP1 polypeptide inhibitor of the disclosure comprises a polypeptide sequence that is at least about 97% identical to the polypeptide sequence of SEQ ID NO: 11. In some embodiments, a 53BP1 polypeptide inhibitor of the disclosure comprises a polypeptide sequence that is at least about 98% identical to the polypeptide sequence of SEQ ID NO: 11. In some embodiments, a 53BP1 polypeptide inhibitor of the disclosure comprises a polypeptide sequence that is at least about 99% identical to the polypeptide sequence of SEQ ID NO: 11. In some embodiments, percent identity is made by a comparison that is performed by a BLAST algorithm wherein the parameters of the algorithm are selected to encompass the largest match between the respective polypeptide sequences over the entire length of the polypeptide sequence as set forth by SEQ ID NO: 11. BLAST algorithms are often used for sequence analysis and are well known by one skilled in the art (Altschul, S., et al. (1990) J. Mol. Biol 215:403-410; Gish, W. et al. (1993) Nat. Genet. 3:266-272; Madden, T. et al. (1996) Meth. Enzymol. 266:131-141; Altschul, S. et al. (1997) Nucleic Acids Res. 25:3389-3402; Zhang, J. et al. (1997) Genome Res. 7:649-656; Wootton, J. et al., (1993) Comput. Chem. 17:149-163; Hancock, J. et al. (1994) Comput. Appl. Biosci. 10:67-70).

In some embodiments, a 53BP1 polypeptide inhibitor of the disclosure comprises a fragment of a polypeptide comprising the polypeptide sequence of SEQ ID NO: 11 that retains binding to the 53BP1 Tudor domain. In some embodiments, a fragment has at least 1-5, at least 1-10, at least 5-15, at least 10-20, at least 15-30, at least 15-40 fewer amino acid residues than a polypeptide comprising a polypeptide sequence as set forth by SEQ ID NO: 11.

In some embodiments, a 53BP1 polypeptide inhibitor of the disclosure comprises a fusion polypeptide comprising a polypeptide comprising the polypeptide sequence of SEQ ID NO: 11 that retains binding to the 53BP1 Tudor domain. In some embodiments, a fusion polypeptide is obtained by addition of amino acids or peptides or by substitutions of individual amino acids or peptides that enable by chemical coupling with suitable reagents to a fusion partner. In some embodiments, a fusion is prepared by preparation and expression of a vector comprising a gene encoding a polypeptide described herein and a gene encoding a fusion partner. In some embodiments, a fusion partner is a polypeptide, non-limiting examples include an enzyme, a fluorescent tag, a purification tag, a toxin, an antibody fragment, or an albumin fragment. In some embodiments, a fusion partner is a chemical label, non-limiting examples include a fluorescent dye, biotin, a radioactive label, a saccharide, or a phosphate.

In some embodiments, a 53BP1 polypeptide inhibitor as described herein is encoded by a polynucleotide. In some embodiments, a 53BP1 polypeptide inhibitor as described herein is provided as a nucleic acid comprising a nucleotide sequence encoding the 53BP1 polypeptide inhibitor. In some embodiments, the nucleic acid is a DNA molecule. In some embodiments, the nucleic acid is an RNA molecule. In some embodiments, the nucleic acid is a messenger RNA (mRNA). Methods of preparing mRNA or high expression of an encoded polypeptide are known in the art. In some embodiments, an mRNA comprises an open-reading frame (ORF) encoding an inhibitor of 53BP1. In some embodiments, the nucleic acid encoding a 53BP1 polypeptide inhibitor comprises an mRNA comprising an ORF encoding the amino acid sequence of SEQ ID NO: 11.

In some embodiments, a nucleic acid comprising a nucleotide sequence encoding a 53BP1 polypeptide inhibitor is delivered to a cell by a vector. Methods of delivering nucleic acids to a cell using a vector are known in the art and are described herein.

In some embodiments, a 53BP1 inhibitor of the disclosure comprises a gene-editing system for disrupting a gene encoding 53BP1. In some embodiments, the 53BP1 inhibitor comprises a CRISPR/Cas9 gene editing system. Methods of using CRISPR-Cas gene editing technology to create a genomic deletion in a cell (e.g., a knock-out in a gene of a cell) are known (e.g., Bauer (2015) Vis Exp 95:e52118). In some embodiments, a knock-out of a gene encoding 53BP1 using CRISPR-Cas gene editing comprises contacting a cell with Cas9 polypeptide and a gRNA targeting the 53BP1 gene locus. In some embodiments, gRNA sequence targeting the 53BP1 gene locus is designed using the 53BP1 gene sequence using methods known in the art (see e.g., Briner (2014) Molecular Cell 56:333-339). In some embodiments, gRNAs targeting the 53BP1 gene locus create indels in the region of the 53BP1 gene that disrupt expression of 53BP1 in the cell. In some embodiments, 50-100%, 50-90%, 50-80%, 50-70%, 50-60%, 60-100%, 60-90%, 60-80%, 60-70%, 70-100%, 70-90%, 70-80%, 80-100%, 80-90%, or 90-100% of cells in the edited population lack detectable expression of 53BP1.

In some embodiments, a 53BP1 inhibitor of the disclosure comprises a small interfering RNA (siRNA) which silences 53BP1 expression. Methods of silencing 53BP1 expression using siRNA are taught by US 2019/0010196 which is incorporated by reference herein. Methods of delivering siRNA can be performed using non-viral or viral delivery methods as described in the art (e.g., Gao (2009) Mol Pharm 6:651-658; Oliveira (2006) J Biomed Biotechnol 2006: 63675; Tatiparti (2017) Nanomaterials 7:77). In some embodiments, a cell is transfected with siRNA targeting 53BP1 mRNAs. In some embodiments, expression of 53BP1 is decreased by about 50%, by about 60%, by about 70%, by about 80%, by about 90%, or by about 100% following transfection with siRNA targeting 53BP1 mRNA.

(ii) Inhibition of DNA-PK

In some embodiments, the disclosure provides methods for increasing HDR of a DSB mediated by a site-directed nuclease in a target gene in a cell or population of cells, e.g., CD34+ HSPCs, by inhibition of DNA-PK, e.g., by inhibition of the DNA-PK catalytic subunit (DNA-PKcs). In some embodiments, the disclosure provides methods for increasing HDR of a DSB mediated by a site-directed nuclease in a cell or population of cells expressing an E6V mutation in HBB by inhibition of DNA-PK. In some embodiments, the disclosure provides methods for increasing HDR of a DSB mediated by a site-directed nuclease in a target gene in a cell or population of cells, e.g., CD34+ HSPCs, by inhibition of 53BP1 and DNA-PK. In some embodiments, the disclosure provides methods for increasing HDR of a DSB mediated by a site-directed nuclease in a cell or population of cells expressing an E6V mutation in HBB by inhibition of 53BP1 and DNA-PK.

The DNA-PKcs is a member of the phosphatidylinositol-3 (PI-3) kinase-like kinase family (PIKK) and is a key kinase involved in NHEJ repair. DNA-PKcs is directed to DSB sites by binding to the Ku70/80 heterodimer that has high-affinity for broken dsDNA ends and is first recruited to DSB sites. The complex formed at the DSB comprising DNA, Ku70/80 and DNA-PKcs is referred to as "DNA-PK" (Gottlieb (1993) Cell 72:131-142). The large DNA-PK complex is responsible for holding the two ends of a broken DNA molecule together. Additionally, binding of DNA-PKcs to the DNA-Ku70/80 complex results in activation of DNA-PKcs kinase activity (Yoo et al (1999) Nucleic Acids Res 27:4679-4686; Calsou (1999) J Biol Chem 274:7848-7856). DNA-PKcs phosphorylates numerous NHEJ repair factors, thus enabling their function in NHEJ repair.

Accordingly, the present disclosure provides DNA-PK inhibitors that inhibit NHEJ and promote HDR repair of a DSB in a target gene. In some embodiments, a DNA-PK inhibitor of the disclosure inhibits, reduces, disrupts, or blocks the ability of DNA-PK to recruit to a DSB site. In some embodiments, a DNA-PK inhibitor of the disclosure inhibits, reduces, disrupts, or blocks the ability of DNA-PKcs to bind to Ku70/80 to form a DNA-PK complex. In some embodiments, a DNA-PK inhibitor of the disclosure inhibits, reduces, disrupts, or blocks the function of the DNA-PK kinase domain. In some embodiments, a DNA-PK inhibitor of the disclosure inhibits, reduces, disrupts, or blocks phosphorylation of NHEJ factors by the DNA-PK kinase domain. In some embodiments, a DNA-PK inhibitor of the disclosure is a polypeptide. In some embodiments, a DNA-PK inhibitor is a nucleic acid. In some embodiments, a DNA-PK inhibitor is a small molecule. In some embodiments, a DNA-PK inhibitor of the disclosure is a small molecule that inhibits, disrupts or blocks the DNA-PK kinase domain.

In some embodiments, a DNA-PK inhibitor of the disclosure is identified by binding affinity for a functional domain of DNA-PK (e.g., DNA-PKcs). Methods of measuring binding affinity of an inhibitor for a protein domain are known in the art. Non-limiting examples include measuring inhibitor affinity by enzyme-linked immunosorbent assay (e.g., ELISA), immunoblot, immunoprecipitation-based assay, fluorescence polarization assay, fluorescence resonance energy transfer assay, fluorescence anisotropy assay, yeast surface display (Gai (2007) Curr Opin Struct Biol 17:467-473), kinetic exclusion assay, surface plasmon resonance, or isothermal titration calorimetry.

In some embodiments, a DNA-PK inhibitor of the disclosure binds to DNA-PKcs. Methods of determining the structural interactions that enable binding of the inhibitor with DNA-PKcs are known in the art. Non-limiting examples include X-ray crystallography, nuclear magnetic resonance (NMR) spectroscopy, electron microscopy, small-angle X-ray scattering (SAXS), and small-angle neutron scattering (SANS). In some embodiments, the structural interactions are determined by a mutagenesis experiment wherein residues of DNA-PKcs are mutated and the effect on inhibitor binding are evaluated. Such methods enable identification of key residues that contribute to binding In some embodiments, a method of inhibition of DNA-PK function in a cell comprises contacting the cell with a small molecule inhibitor of DNA-PK. In some embodiments, the DNA-PK inhibitor of the disclosure is a small molecule inhibitor Nu7441 (e.g., Leahy (2004) Bioorg Med Chem Lett 14:6083-6087). In some embodiments, the DNA-PK inhibitor of the disclosure is a PI 3-kinase inhibitor LY294002, which has been found to inhibit DNA-PKcs function in vitro (Izzard (1999) Cancer Res 59:2581-2586). In some embodiments, the DNA-PK inhibitor of the disclosure is a small molecule inhibitor capable of selectively inhibiting the activity of DNA-PKcs compared to PI 3-kinase. Non-limiting examples include 2-amino-chromen-4-ones that are described by WO 03/024949, which is incorporated by reference herein. In some embodiments, the DNA-PK inhibitor of the disclosure is a small molecule inhibitor of DNA-PKcs function, including 1 (2-hydroxy-4-morpholin-4-yl-phenyl)-ethanone (e.g., Kashishian (2003) Mol Cancer Ther 2:1257-1264). In some embodiments, the DNA-PK inhibitor of the disclosure is a small molecule inhibitor of DNA-PKcs function SU11752 (e.g., Ismail (2004) Oncogene 23:873-882). In some embodiments, the DNA-PK inhibitor of the disclosure is a small molecule inhibitor of DNA-PKcs function described in U.S. Pat. No. 9,592,232, incorporated herein by reference. In some embodiments, the DNA-PK inhibitor of the disclosure is a small molecule inhibitor of DNA-PKcs function described in U.S. Pat. No. 7,402,607, incorporated herein by reference. In some embodiments, the DNA-PK inhibitor of the disclosure is a small molecule inhibitor of DNA-PKcs function described in U.S. Pat. No. 6,893,821, incorporated herein by reference. In some embodiments, the DNA-PK inhibitor of the disclosure is a small molecule inhibitor of DNA-PKcs function described in US 2018/0194782.

In some embodiments, the DNA-PK inhibitor of the disclosure is Compound 984 or Compound 296 described in U.S. Pat. No. 9,592,232. The structures of Compound 984 and Compound 296 are provided below in Table 2:

TABLE 2

| DNA-PK Inhibitors | |
|---|---|
| 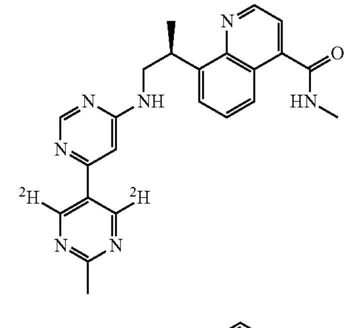 | Compound 984 |
| 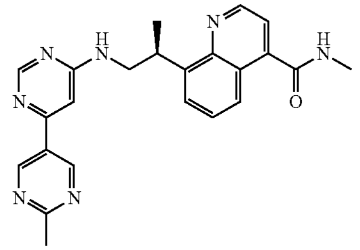 [SMILES: CNC(=O)c1ccnc2c([C@H](C)CNc3cc(-c4cnc(C)nc4)ncn3)cccc12] | Compound 296 |

(iii) Inhibition of Other Targets

In some embodiments, the disclosure provides methods for increasing HDR of a DSB mediated by a site-directed nuclease in a target gene in a cell or population of cells, e.g., CD34+ HSPCs, by inhibition of the NHEJ pathway, alone or in combination with inhibition of 53BP1 and/or DNA-PK. In some embodiments, the disclosure provides methods for increasing HDR of a DSB mediated by a site-directed nuclease in a target gene in a cell or population of cells expressing an E6V mutation in the HBB gene, by inhibition of the NHEJ pathway, alone or in combination with inhibition of 53BP1 and/or DNA-PK. In some embodiments, the disclosure provides a method of inhibiting the NHEJ pathway by inhibition of key NHEJ enzymes. For example, in some embodiments, the disclosure provides a method of inhibiting the NHEJ pathway by inhibition of Ku70/80. In some embodiments, the disclosure provides inhibitors of Ku70/80 including CYREN (e.g., Arnoult (2017) Nature 549:548-552). In some embodiments, the disclosure provides a method of inhibiting the NHEJ pathway by inhibition of DNA Ligase IV. In some embodiments, the disclosure provides inhibitors of DNA Ligase IV, including Scr7 (Maruyama (2015) Nat Biotechnol 33:538-542).

In some embodiments, the disclosure provides methods of increasing or improving repair of a DNA DSB by HDR by inhibition of the MMEJ pathway (e.g., methods of MMEJ inhibition reviewed in Sfeir (2015) 40:701-714). In some embodiments, the disclosure provides methods of inhibition of the MMEJ pathway by inhibition of DNA polymerase theta (Pol θ). In some embodiments, the disclosure provides method of inhibition of the MMEJ pathway by inhibition of PARP. In some embodiments, the disclosure provides PARP inhibitors, including molecules developed for the treatment of cancer, including Veliparib and Olaparib. In some embodiments, inhibition of the MMEJ pathway comprises inhibition of MRE11. In some embodiments, the disclosure provides MRE11 inhibitors, including Mirin and derivatives (e.g., Shibata (2014) Molec Cell 53:7-18).

In some embodiments, the disclosure provides methods for increasing HDR of a DSB mediated by a site-directed nuclease in a target gene in a cell or population of cells, e.g., CD34+ HSPCs, by treatment of a cell or population of cells with a compound that stimulates HDR efficiency. In some embodiments, the disclosure provides methods for increasing HDR of a DSB mediated by a site-directed nuclease in a target gene in a cell or population expressing an E6V mutation in the HBB gene, by treatment of a cell or population of cells with a compound that stimulates HDR efficiency. In some embodiments, the disclosure provides a stimulator of HDR, wherein the stimulator of HDR is an agonist that promotes the function of a factor in the HDR pathway. In some embodiments, the disclosure provides a stimulator of an HDR factor, wherein the HDR factor is RAD51. In some embodiments, the disclosure provides agonists of RAD51, including RS-1 (e.g., Jayathilaka (2008) PNAS 105:15848-15853).

(iv) Combination of Inhibitors

In some embodiments, the disclosure provides methods for increasing HDR of a DSB mediated by a site-directed nuclease in a target gene in a cell or population of cells, e.g., CD34+ HSPCs, by treatment with an inhibitor of 53BP1 in combination with an inhibitor of the NHEJ pathway. In some embodiments, the disclosure provides methods for increasing HDR of a DSB mediated by a site-directed nuclease in a target gene in a cell or population of cells expressing an E6V mutation in the HBB gene, by treatment with an inhibitor of 53BP1 in combination with an inhibitor of the NHEJ pathway. In some embodiments, a method of increasing HDR is treatment with an inhibitor of 53BP1 in combination with an inhibitor of DNA-PK. In some embodiments, a method of increasing HDR is treatment with a polypeptide inhibitor of 53BP1 in combination with an inhibitor of DNA-PK. In some embodiments, a method of increasing HDR is treatment with a polypeptide inhibitor of 53BP1 comprising the amino acid sequence identified by SEQ ID NO: 11 in combination with a small molecule inhibitor of DNA-PK. In some embodiments, a method of increasing HDR is treatment with a polypeptide inhibitor of 53BP1 comprising the amino acid sequence identified by SEQ ID NO: 11 in combination with Compound 984 or Compound 296.

In some embodiments, a method of increasing HDR is treatment with an inhibitor of 53BP1 in combination with an inhibitor of Ku70/80. In some embodiments, a method of increasing HDR is treatment with a polypeptide inhibitor of 53BP1 comprising the amino acid sequence identified by SEQ ID NO: 11 in combination with an inhibitor of Ku70/80. In some embodiments, a method of increasing HDR is treatment with an inhibitor of 53BP1 in combination with an inhibitor of DNA Ligase IV. In some embodiments, a method of increasing HDR is treatment with a polypeptide inhibitor of 53BP1 comprising the amino acid sequence identified by SEQ ID NO: 11 in combination with an inhibitor of DNA Ligase IV.

In some embodiments, a method of increasing HDR is treatment with an inhibitor of 53BP1 in combination an inhibitor of the MMEJ pathway. In some embodiments, a method of increasing HDR is treatment with a polypeptide inhibitor of 53BP1 comprising the amino acid sequence identified by SEQ ID NO: 11 in combination with an inhibitor of the MMEJ pathway. In some embodiments, a method of increasing HDR is treatment with a polypeptide inhibitor of 53BP1 comprising the amino acid sequence identified by SEQ ID NO: 11 in combination with an inhibitor of PARP. In some embodiments, a method of increasing HDR is treatment with a polypeptide inhibitor of 53BP1 comprising the amino acid sequence identified by SEQ ID NO: 11 in combination with an inhibitor of DNA polymerase theta.

B. Methods to Evaluate Gene-Editing

In some embodiments, the disclosure provides methods for quantifying the frequency of HDR resulting in incorporation of a donor nucleic acid at a DSB induced in the HBB gene. For example, after performing the gene-edit, the nucleotide sequence of PCR amplicons generated using PCR primer that flank the DSB site is analyzed for the presence of the nucleotide sequence comprising the donor polynucleotide. In some embodiments, next-generation sequencing (NGS) techniques are used to determine the extent of donor nucleic acid incorporation into the region proximal the DSB by analyzing PCR amplicons for the presence or absence of the donor nucleic acid sequence.

In some aspects, the incorporation of the donor nucleic acid for correcting a mutation in HBB is determined by nucleotide sequence analysis of mRNA transcribed from the HBB gene. An mRNA transcribed from genomic DNA incorporating the donor polynucleotide is analyzed by a suitable method known in the art. For example, conversion of mRNA extracted from cells treated or contacted with a gene-editing system of the disclosure is enzymatically converted into cDNA, which is further by analyzed by NGS analysis to determine the extent of mRNA transcript comprising the corrected mutation.

In other aspects, the incorporation of the donor nucleic acid and its ability to correct a mutation in HBB is determined by protein sequence analysis of a polypeptide express from the HBB gene. In some embodiments, a donor polynucleotide corrects a mutation by the incorporation of a codon into the open reading frame of the coding sequence of the HBB gene, wherein translation of an mRNA transcribed from the HBB gene provides a beta-globin polypeptide comprising an amino acid change encoded by the codon. The amino acid change in the beta-globin polypeptide is determined by protein sequence analysis using techniques including, but not limited to, liquid chromatography, mass spectrometry, or immunoblotting using an antibody reactive to the amino acid change.

C. Methods of Gene-Editing

In some embodiments, the disclosure provides a method for correcting a mutation in HBB (e.g., E6V) in a cell or a population of cells (e.g., HSPCs) by gene-editing, wherein the cell or population of cells comprise an HBB gene encoding the mutation, wherein the gene-editing comprises contacting the cell or population of cells with: (a) a Cas endonuclease described herein, an mRNA encoding the Cas endonuclease, or a recombinant expression vector comprising a nucleotide sequence encoding the Cas endonuclease; (b) a gRNA described herein (e.g. an intron-targeting gRNA); and (c) a donor nucleic acid for correcting the mutation described herein or a recombinant vector encoding the donor nucleic acid, wherein the gRNA combines with the Cas endonuclease to induce a DSB at the target site in the HBB gene, and wherein HDR of the DSB results in exchange of the region of the HBB gene encoding the mutation with the correction encoded by the donor nucleic acid, thereby correcting the mutation in the HBB gene in the cell or population of cells. In some embodiments, the method further comprises contacting the cell or population of cells with a 53BP1 inhibitor described herein. In some embodiments, the method further comprises contacting the cell or population of cells with a DNA-PK inhibitor described herein. In some embodiments, the method further comprises contacting the cell or population of cells with a 53BP1 and DNA-PK inhibitor described herein.

In some embodiments, the gene-editing results in an average allelic editing frequency of at least 15%, 20%, 25%, 30%, 35%, 40%, 45%, 50%, 55%, or 60%. In some embodiments, the gene-editing results in an average allelic editing frequency of about 15% to about 30%. In some embodiments, the gene-editing results in an average allelic editing frequency of about 15% to about 40%. %. In some embodiments, the gene-editing results in an average allelic editing frequency of about 30% to about 40%. In some embodiments, the gene-editing results in an average allelic editing frequency of about 20% to about 60%. In some embodiments, the gene-editing results in an average allelic editing frequency of about 40% to about 60%.

In some embodiments, the gene-editing results in an average on-target frequency of INDELs proximal the target site that is less than 50%, 40%, 30%, or 20%. In some embodiments, the gene-editing results in an average off-target frequency of INDELs less than 5%, or less than 1%. In some embodiments, the gene-editing results in an off-target frequency of INDELs less than 0.9%, 0.8%, 0.6%, 0.7%, 0.6%, 0.5%, 0.4%, 0.3%, 0.2%, or 0.1%.

In some embodiments, the average frequency of INDELs introduced in the beta-globin polypeptide as a result of gene-editing is less than 5%, 4%, 3%, 2%, or 1%. In some embodiments, the frequency of INDELs introduced in the beta-globin polypeptide as a result of gene-editing is not detectable.

In some embodiments, the gene-editing is performed within 12, 36, 48, or 72 hours of thawing a population of cells or obtaining a population of cells from a biological source (e.g. a human source, e.g., a human patient). In some embodiments, the population of cells is purified following editing, e.g., using FACS.

In some embodiments, the gene-editing provides a gene-edited cell or population of gene-edited cells. As used herein, the term “gene-edited cell” or “genetically engineered cell” or “genome edited cell” each interchangeably refer to a cell comprising at least one genetic modification introduced by a gene-editing method, system, or composition described herein. In some embodiments, the gene-edited cell comprises at least one genetic modification to correct a mutation in the HBB gene. In some embodiments, the mutation is in exon 1 of HBB. In some embodiments, the mutation is E6V. In some embodiments, the correction occurs by HDR of a DSB induced within intron 1 of HBB. In some embodiments, the correction is encoded by donor nucleic acid described herein.

In some embodiments, the gene-editing is performed using any cell or population of cells described herein. In some embodiments, the gene-editing is performed using a population of cells obtained from a. In some embodiments, the population of cell is obtained from patient with sickle cell disease. In some embodiments, the population of cell is obtained from a patient with an E6V mutation in at least one HBB allele. In some embodiments, the population of cell is obtained from a patient with an E6V mutation in both HBB alleles. In some embodiments, the population of cells are CD34+ HSPCs.

In some embodiments, the gene-editing is performed in a population of cells described herein, wherein the gene-editing results in a population of cells having at least 10%, 15%, 20%, 25%, 30%, 35%, 40%, 45%, 50% or higher of the total population of cells that are gene-edited cells.

In some embodiments, the gene-editing is performed in a population of cells obtained from a patient with a hemoglobinopathy (e.g., a population of CD34+ HSPCs), wherein the gene-editing results in a population of cells having at least 10%, 15%, 20%, 25%, 30%, 35%, 40%, 45%, 50% or higher of the total population of cells that are gene-edited cells, and wherein the gene-edited cells comprise a correction to a mutation associated with the hemoglobinopathy.

In some embodiments, the gene-editing is performed in a population of cells obtained from a patient with a β-hemoglobinopathy (e.g., a population of CD34+ HSPCs), wherein the gene-editing results in a population of cells having at least 10%, 15%, 20%, 25%, 30%, 35%, 40%, 45%, 50% or higher of the total population of cells that are gene-edited cells, and wherein the gene-edited cells comprise a correction to a mutation in HBB associated with the β-hemoglobinopathy.

In some embodiments, the gene-editing is performed in a population of cells obtained from a patient with sickle cell disease (e.g., a population of CD34+ HSPCs), wherein the gene-editing results in a population of cells having at least 10%, 15%, 20%, 25%, 30%, 35%, 40%, 45%, 50% or higher of the total population of cells that are gene-edited cells, and wherein the gene-edited cells comprise a correction to an E6V mutation in HBB associated with the sickle cell disease. In some embodiments, the population of cells is obtained from a patient with an E6V mutation in both HBB alleles, wherein the gene-edited cells comprise a correction the E6V mutation in one or both HBB alleles.

In some embodiments, the gene-editing results in a population of cells exhibiting increased expression of a corrected beta-globin polypeptide. In some embodiments, the level of corrected beta-globin polypeptide expressed by the population of cells is 30%, 35%, 40%, 45%, 50% or greater of the total hemoglobin.

In some embodiments, the gene-editing results in a population of cells exhibiting increased expression of normal adult hemoglobin. In some embodiments, the expression of normal adult hemoglobin (HbA) is increased by about 1.1-fold, 1.2-fold, 1.3-fold, 1.4-fold, 1.5-fold, 1.6-fold, 1.7-fold, 1.8-fold, 1.9-fold or 2-fold relative to the population of cells prior to gene-editing. In some embodiments, the gene-editing results in a population of cells exhibiting expression of HbA that is at least about 20% to about 80% of total hemoglobin expression. In some embodiments, sickle Hb is reduced to less than 60% of total hemoglobin.

In some embodiments, wherein the population of cell is derived from a patient with sickle cell disease, the gene-editing results in a population of cells with reduced expression of sickle hemoglobin (HbS). In some embodiments, the expression of HbS is reduced by about 1.1-fold, 1.2-fold, 1.3-fold, 1.4-fold, 1.5-fold, 1.6-fold, 1.7-fold, 1.8-fold, 1.9-fold or 2-fold relative to the population of cells prior to gene-editing.

V. Pharmaceutical Compositions

The present disclosure includes pharmaceutical compositions comprising a donor nucleic acid, a gRNA, and a Cas9 protein, in combination with one or more pharmaceutically acceptable excipient, carrier or diluent. In some embodiments, the disclosure provides pharmaceutical compositions comprising a donor nucleic acid or recombinant vector, a gRNA, a Cas9 protein, and a 53BP1 inhibitor and/or DNA-PK inhibitor, in combination with one or more pharmaceutically acceptable excipient, carrier or diluent. In particular embodiments, the donor nucleic acid is encapsulated in a nanoparticle, e.g., a lipid nanoparticle. In some embodiments, the gRNA is encapsulated in a nanoparticle. In some embodiments, a Cas nuclease (e.g., SpCas9) is encapsulated in a nanoparticle. In some embodiments, the 53BP1 inhibitor is encapsulated in a nanoparticle, e.g., a lipid nanoparticle. In some embodiments, the DNA-PK inhibitor is encapsulated in a nanoparticle, e.g., a lipid nanoparticle. In some embodiments, the donor nucleic acid, gRNA, Cas9 protein, 53BP1 inhibitor and/or DNA-PK inhibitor are encapsulated in the same or different nanoparticle, e.g., lipid nanoparticle. In particular embodiments, an mRNA encoding a Cas nuclease or nanoparticle encapsulating a Cas nuclease is present in a pharmaceutical composition. In various embodiments, the one or more mRNA present in the pharmaceutical composition is encapsulated in a nanoparticle, e.g., a lipid nanoparticle.

In some embodiments, the disclosure provides pharmaceutical compositions comprising a population of cells edited according to a method described herein, in combination with one or more pharmaceutically acceptable excipient, carrier, or diluent. In some embodiments, the pharmaceutical composition comprises a physiological tolerable carrier together with the cell composition. In some embodiments, the pharmaceutical composition is not substantially immunogenic when administered to a mammal or human patient for therapeutic purposes.

In some embodiments, the population of cells is administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising a population of cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with a population of cells edited according to a method described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiological tolerable carriers are well known in the art. Exemplary liquid carriers are sterile aqueous solutions that contain no materials in addition the active ingredients and water, or contain a buffer such as a sodium phosphate at physiological pH value, physiological saline, or both, such as phosphate-buffered saline. Still further, aqueous carriers can contain more than one buffer salt, as well as salts such as sodium and potassium chlorides, dextrose, polyethylene glycol, and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

VI. Kits

The present disclosure provides kits for carrying out the methods described herein. In some embodiments, the kit comprises a system or pharmaceutical composition described herein. In some embodiments, the kit comprises instructions for correcting a mutation (e.g., SCD mutation) in exon 1 of the HBB gene in a cell or population of cells by contacting the cell or population of cells with the system or pharmaceutical composition. In some embodiments, the kit further comprises instructions for contacting the cell or population of cells with at least one inhibitor. In some embodiments, the at least one inhibitor is a 53BP1 inhibitor, a DNA-PK inhibitor, or a combination thereof. In some embodiments, the instructions comprise contacting the cell or population of cells ex vivo. In some embodiments, the instructions comprise contacting the cell or population of cells in vivo.

In some embodiments, the kit includes a gRNA (e.g., intron-targeting gRNA), a nucleic acid or recombinant expression vector encoding the gRNA, a site-directed endonuclease, a nucleic acid or an mRNA encoding the site-directed endonuclease, a recombinant expression vector comprising a nucleic acid encoding the site-directed endonuclease, a donor nucleic acid, a recombinant expression vector encoding the donor nucleic acid, or a combination thereof. In some embodiments, a kit for use in the present disclosure comprises: (1) a gRNAs or sgRNA (e.g., an intron-targeting gRNA or sgRNA) described herein, and (2) reagents for reconstitution and/or dilution of (1). In some embodiments, a kit for use in the present disclosure comprises: (1) a nucleic acid encoding the gRNA or sgRNA, and (2) reagents for reconstitution and/or dilution of (1). In some embodiments, a kit for use in the present disclosure comprises: (1) a recombinant expression vector comprising a nucleotide sequence encoding the gRNA or sgRNA, and (2) reagents for reconstitution and/or dilution of (1). In some embodiments, a kit for use in the present disclosure comprises: (1) the gRNAs or sgRNA, the nucleic acid encoding the a gRNAs or sgRNA, or the recombinant expression vector encoding the gRNA or sgRNA formulated as an LNP, and (2) reagents for reconstitution and/or dilution of (1).

In some embodiments, a kit for use in the present disclosure comprises: (1) a site-directed endonuclease (e.g., Cas nuclease; e.g., Cas9) described herein that is a polypeptide, and (2) reagents for reconstitution and/or dilution of (1). In some embodiments, a kit for use in the present disclosure comprises: (1) an mRNA encoding the site-directed endonuclease, and (2) reagents for reconstitution and/or dilution of (1). In some embodiments, a kit for use in the present disclosure comprises: (1) a recombinant expression vector comprising a nucleotide sequence encoding the site-directed endonuclease, and (2) reagents for reconstitution and/or dilution of (1). In some embodiments, a kit for use in the present disclosure comprises: (1) the site-directed endonuclease, the mRNA encoding the site-directed endonuclease, or the recombinant expression vector encoding the site-directed endonuclease, formulated as an LNP, and (2) reagents for reconstitution and/or dilution of (1).

In some embodiments, a kit for use in the present disclosure comprises: (1) a donor nucleic acid described herein, and (2) reagents for reconstitution and/or dilution of (1). In some embodiments, a kit for use in the present disclosure comprises: (1) a recombinant expression vector comprising a nucleotide sequence encoding the donor nucleic acid, and (2) reagents for reconstitution and/or dilution of (1). In some embodiments, a kit for use in the present disclosure comprises: (1) the donor nucleic acid, or the recombinant expression vector encoding the donor nucleic acid, formulated as an LNP, and (2) reagents for reconstitution and/or dilution of (1).

In some embodiments, a kit for use in the present disclosure comprises: (1) (i) the gRNA or sgRNA, (ii) the mRNA comprising a nucleotide sequence encoding the site-directed endonuclease, and (2) reagents for reconstitution and/or dilution of (i) and (ii). In some embodiments, (1)(i) or (1)(ii) are formulated as an LNP. In some embodiments, (1)(i) and (1)(ii) are formulated as an LNP, either as separate LNPs or the same LNP.

In some embodiments, a kit for use in the present disclosure comprises: (1) (i) the gRNA or sgRNA, and (ii) the site-directed endonuclease as a polypeptide; and (2) reagents for reconstitution and/or dilution of (i) and (ii). In some embodiments, (1)(i) or (1)(ii) are formulated as an LNP. In some embodiments, (1)(i) and (1)(ii) are formulated as an LNP, either as separate LNPs or the same LNP. In some embodiments, the reconstitution and/or dilution provides a ribonucleoprotein complex of (1)(i) and (1)(ii). In some embodiments, the ribonucleoprotein complex is formulated as an LNP.

In some embodiments, a kit for use in the present disclosure comprises: (1) (i) the gRNA or sgRNA, and (ii) the recombinant expression vector encoding the site-directed endonuclease; and (2) reagents for reconstitution and/or dilution of (i) and (ii). In some embodiments, (1)(i) or (1)(ii) are formulated as an LNP. In some embodiments, (1)(i) and (1)(ii) are formulated as an LNP, either as separate LNPs or the same LNP.

In some embodiments, the kit further comprises (1) a donor nucleic acid described herein, optionally wherein the donor nucleic acid is formulated as an LNP, and (2) reagents for reconstitution and/or dilution of (1). In some embodiments, the kit further comprises (1) a recombinant expression vector comprising a nucleotide sequence encoding the donor nucleic acid, optionally wherein the recombinant expression vector is formulated as an LNP, and (2) reagents for reconstitution and/or dilution of (1).

In some embodiments, any one of the foregoing kits comprise instructions for correcting a mutation (e.g., E6V) in exon 1 of the HBB gene in a cell or population of cells obtained from a patient having a hemoglobinopathy associated with the mutation, wherein the instructions comprise contacting the cell or population of cells ex vivo with the gRNA, site-directed endonuclease, nucleic acid(s), donor nucleic acids, and/or recombinant expression vector(s). In some embodiments, the instructions comprise the contacting the cell or population of cells with at least one inhibitor. In some embodiments, the kit further comprises instructions for administering the corrected cell or population of cells to the patient to ameliorate or treat the hemoglobinopathy.

In some embodiments, any one of the foregoing kits comprise instructions for correcting a mutation (e.g., E6V) in exon 1 of HBB in a cell or population of cells in a patient having a hemoglobinopathy associated with the mutation, wherein the instructions comprise contacting the cell or population of cells in vivo with the gRNA, site-directed endonuclease, nucleic acid(s), donor nucleic acids, and/or recombinant expression vector(s). Any kit described above can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the site-directed endonuclease, or improve the specificity of targeting.

In addition to the above-mentioned components, a kit can further comprise instructions for using the components of the kit to practice the methods described herein (e.g., for correcting a mutation in HBB). The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

In some embodiments, the kit comprises instructions for use with at least one inhibitor, e.g., for increasing HDR to correct a mutation in HBB. In some embodiments, the at least one inhibitor is a 53BP1 inhibitor described herein. In some embodiments, the at least one inhibitor is a DNA-PK inhibitor described herein. In some embodiments, the at least one inhibitor includes a 53BP1 inhibitor and a DNA-PK inhibitor. In some embodiments, the 53BP1 inhibitor is (i) a polypeptide comprising an amino acid sequence having at least about 90%, about 91%, about 92%, about 93%, about 94%, about 95%, about 96%, about 97%, about 98%, or about 99% sequence identity to the amino acid sequence set forth in SEQ ID NO: 11; (ii) a nucleic acid (e.g., mRNA) encoding the polypeptide; or (iii) a recombinant expression vector comprising a nucleic acid encoding the polypeptide. In some embodiments, the 53BP1 inhibitor is a polypeptide comprising the amino acid sequence set forth in SEQ ID NO: 11. In some embodiments, the nucleic acid (e.g., mRNA) comprises a nucleotide sequence having at least about 90%, about 91%, about 92%, about 93%, about 94%, about 95%, about 96%, about 97%, about 98%, or about 99% sequence identity to a nucleotide sequence set forth in SEQ ID NO: 10 or SEQ ID NO: 43. In some embodiments, the nucleic acid (e.g., mRNA) comprises the nucleotide sequence of SEQ ID NO: 10 or SEQ ID NO: 43. In some embodiments, the DNA-PK inhibitor is a small molecule set forth in Table 2.

VII. Methods of Treatment

Provided herein are methods of treating a patient having a hemoglobinopathy by introducing a gene-edit in a genomic DNA molecule as described herein, such as correcting a mutation in a genomic DNA molecule. In some embodiments, the methods are for treating a patient having a beta-hemoglobinopathy by introducing a gene-edit in HBB as described herein, such as a gene-edit for correcting a mutation (e.g., E6V) in HBB.

As used herein, a "hemoglobinopathy" refers to a defect in the structure, function, or expression of hemoglobin in a patient. In some embodiments, the defect results from a mutation in the coding region of a beta-globin gene (e.g., HBB), or in a promoter or intron of the gene, wherein the mutation results in a reduction in the amount of hemoglobin produced compared to hemoglobin produced in the absence of the mutation, or a reduction in the function of hemoglobin compared to hemoglobin produced in the absence of the mutation. Beta-hemoglobinopathies include, but are not limited to, sickle cell disease (e.g., sickle cell anemia), sickle cell trait, beta-thalassemia. In some embodiments, a method of the disclosure comprises treating a beta-hemoglobinopathy by introducing a correction to a mutation in the HBB gene.

In some embodiments, the disclosure provides methods for treating a patient having sickle cell disease, wherein the method comprises introducing a gene-edit in HBB as described herein, such as a gene-edit that corrects an E6V mutation in HBB. In some embodiments, the patient has only one HBB allele comprising the E6V mutation. In some embodiments, the patient has both HBB alleles comprising the E6V mutation.

In some embodiments, the disclosure provides methods for treating a hemoglobinopathy (e.g., SCD), the method comprising (i) isolation of a population of cells (e.g., CD34+ HSPCs) from a tissue sample obtained from the patient, (ii) introducing a gene-edit in HBB in the genomic DNA of the population of cells to correct the hemoglobinopathy-causing mutation (e.g., E6V), and (iii) transplanting the edited population of cells into the patient.

In some embodiments, the disclosure provides methods for treating a hemoglobinopathy (e.g., SCD), the method comprising (i) preparation of a population of cells comprising patient-specific induced pluripotent stem cells, (ii) introducing a gene-edit in HBB in the genomic DNA of the population of cells to correct the hemoglobinopathy-causing mutation (e.g., E6V), (iii) differentiating the population of cells to HSPCs, and (iii) transplanting the population of cells into the patient.

In some embodiments, the transplantation requires clearance of bone marrow niches for the donor HSPCs to engraft. Known methods are used, including radiation and/or chemotherapy. Additionally, immunodepletion of bone marrow cells, e.g., by antibodies or antibody toxin conjugates directed against hematopoietic cell surface markers, are also encompassed by the disclosure. Success of HSC transplantation depends upon efficient homing to bone marrow, subsequent engraftment, and bone marrow repopulation. In some embodiments, the ability of the engrafted cells to repopulate the bone marrow compartment and/or the ability of the engrafted cells to differentiate to establish a multi-lineage engraftment of the bone-marrow are criteria used to evaluate the success of the engraftment.

A. Administration and Efficacy

The terms "administering," "introducing," and "transplanting," are used interchangeably in the context of the placement of cells, e.g., gene-edited CD34+ HSPCs, as into a subject, by a method or route that results in at least partial localization of the introduced cells at a desired site (e.g., bone marrow), such that a desired effect(s) is produced. The cells e.g., gene-edited CD34+ HSPCs, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the lifetime of the patient, i.e., long-term engraftment. For example, in some aspects described herein, an effective amount of CD34+ HSPCs is administered via a systemic route of administration, such as an intraperitoneal or intravenous route.

The terms "individual," "subject," "host," and "patient" are used interchangeably herein and refer to any subject for whom diagnosis, treatment, or therapy is desired. In some embodiments, the subject is a mammal. In some embodiments, the subject is a human.

When provided prophylactically, progenitor cells described herein can be administered to a subject in advance of any symptom of a hemoglobinopathy, e.g., prior to initiation of the switch from fetal γ-globin to predominantly β-globin and/or prior to the development of significant anemia or other symptom associated with the hemoglobinopathy. Accordingly, the prophylactic administration of a population of cells (e.g., CD34+ HSPCs) edited according to a method described herein serves to prevent a hemoglobinopathy, as disclosed herein.

When provided therapeutically, a population of cells (e.g., CD34+ HSPCs) edited according to a method described herein is provided at (or after) the onset of a symptom or indication of a hemoglobinopathy, e.g., upon the onset of sickle cell disease.

In some embodiments, the population of cells (e.g., CD34+ HSPCs) being administered according to the methods described herein can comprise allogeneic cells (e.g., allogeneic CD34+ HSPCs) obtained from one or more donors. "Allogeneic" refers to a population of cell obtained from one or more different donors of the same species, where the genes at one or more loci are not identical. For example, a hematopoietic progenitor cell population being administered to a subject can be derived from umbilical cord blood obtained from one more unrelated donor subjects, or from one or more non-identical siblings. In some cases, syngeneic hematopoietic progenitor cell populations can be used, such as those obtained from genetically identical animals, or from identical twins.

In some embodiments, the population of cells (e.g., CD34+ HSPCs) being administered according to the methods described herein comprise autologous cells (e.g., autologous CD34+ HSPCs); that is, the population of cells is obtained or isolated from a subject and administered to the same subject, i.e., the donor and recipient are the same.

The term "effective amount" refers to the amount of a population of cells (e.g., CD34+ HSPCs) edited according to a method described herein, or their progeny, needed to prevent or alleviate at least one or more sign or symptom of a hemoglobinopathy, and relates to a sufficient amount of a composition to provide the desired effect, e. g., to treat a subject having a hemoglobinopathy.

The term "therapeutically effective amount" therefore refers to an amount of a population of cells (e.g., CD34+ HSPCs) edited according to a method described herein, or their progeny, or a composition comprising the population of cells or their progeny, that is sufficient to promote a particular effect when administered to a typical subject, such as one who has or is at risk for a hemoglobinopathy. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of a population of cells (e.g., CD34+ HSPCs) for administration according to a method described herein, comprises at least $10^2$ cells, at least $5\times10^2$ cells, at least $10^3$ cells, at least $5\times10^3$ cells, at least $10^4$ cells, at least $5\times10^4$ cells, at least $10^5$ cells, at least $5\times10^5$ cells, at least $1\times10^6$, at least $2\times10^6$ cells, at least $3\times10^6$ cells, at least $4\times10^6$ cells, at least $6\times10^6$ cells, at least $6\times10^6$ cells, at least $7\times10^6$ cells, at least $8\times10^6$ cells, at least $9\times10^6$ cells, or at least $1\times10^7$ cells. The population of cells can be derived from one or more donors, or are obtained from an autologous source. In some embodiments, the population of cells are expanded in culture prior to administration to the subject in need thereof.

Modest increases in the levels of HbA expressed by hematopoietic cells in a patient having a hemoglobinopathy can be beneficial for ameliorating one or more symptoms of the disease and/or for increasing long-term survival. For example, upon administration of a population of cells (e.g., CD34+ HSPCs) gene-edited according to a method described herein, the presence of erythroid cells derived from the population of cells provides a increase in the level of HbA that is beneficial. in some embodiments, the administration results in a level of HbA that is at least about 20% of total Hb, at least about 30% of total Hb, at least about 40% of total Hb, at least about 50% of total Hb, at least about 60% of total Hb, at least about 70% of total Hb, or at least about 80% or higher of total Hb.

The efficacy of a treatment comprising a composition for the treatment of a hemoglobinopathy can be determined by the skilled clinician. However, a treatment is considered an "effective treatment" if any one or all of the signs or symptoms of, as but one example, levels of HbA are altered in a beneficial manner (e. g., increased by at least 10%), or other clinically accepted symptoms or markers of disease are improved or ameliorated. Efficacy can also be measured by failure of an individual to worsen as assessed by hospitalization or need for medical interventions (e. g., reduced transfusion dependence, or progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e. g., arresting, or slowing the progression of symptoms; or (2) relieving the disease, e.g., causing regression of symptoms; and (3) preventing or reducing the likelihood of the development of symptoms.

The treatment according to the present disclosure can ameliorate one or more symptoms associated with a β-hemoglobinopathy by increasing the amount of HbA in the individual. Symptoms and signs typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

VIII. Definitions

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

As used herein, the term "about" (alternatively "approximately") will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "base pair" refers to two nucleobases on opposite complementary polynucleotide strands, or regions of the same strand, that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds.

As used herein, the term "codon" refers to a sequence of three nucleotides that together form a unit of genetic code in a DNA or RNA molecule. A codon is operationally defined by the initial nucleotide from which translation starts and sets the frame for a run of successive nucleotide triplets, which is known as an "open reading frame" (ORF). For example, the string GGGAAACCC, if read from the first position, contains the codons GGG, AAA, and CCC; if read from the second position, it contains the codons GGA and AAC; and if read from the third position, GAA and ACC. Thus, every nucleic sequence read in its 5'→3' direction comprises three reading frames, each producing a possibly distinct amino acid sequence (in the given example, Gly-Lys-Pro, Gly-Asn, or Glu-Thr, respectively). DNA is double-stranded defining six possible reading frames, three in the forward orientation on one strand and three reverse on the opposite strand. Open reading frames encoding polypeptides are typically defined by a start codon, usually the first AUG codon in the sequence.

As used herein, the term "complementary" or "complementarity" refers to a relationship between the sequence of nucleotides comprising two polynucleotide strands, or regions of the same polynucleotide strand, and the formation of a duplex comprising the strands or regions, wherein the extent of consecutive base pairing between the two strands or regions is sufficient for the generation of a duplex structure. It is known that adenine (A) forms specific hydrogen bonds, or "base pairs", with thymine (T) or uracil (U). Similarly, it is known that a cytosine (C) base pairs with guanine (G). It is also known that non-canonical nucleobases (e.g., inosine) can hydrogen bond with natural bases. A sequence of nucleotides comprising a first strand of a polynucleotide, or a region, portion or fragment thereof, is said to be "sufficiently complementary" to a sequence of nucleotides comprising a second strand of the same or a different nucleic acid, or a region, portion, or fragment thereof, if, when the first and second strands are arranged in an antiparallel fashion, the extent of base pairing between the two strands maintains the duplex structure under the conditions in which the duplex structure is used (e.g., physiological conditions in a cell). It should be understood that complementary strands or regions of polynucleotides can include some base pairs that are non-complementary. Complementarity may be "partial," in which only some of the nucleobases comprising the polynucleotide are matched according to base pairing rules. Or, there may be "complete" or "total" complementarity between the nucleic acids. Although the degree of complementarity between polynucleotide strands or regions has significant effects on the efficiency and strength of hybridization between the strands or regions, it is not required for two complementary polynucleotides to base pair at every nucleotide position. In some embodiments, a first polynucleotide is 100% or "fully" complementary to a second polynucleotide and thus forms a base pair at every nucleotide position. In some embodiments, a first polynucleotide is not 100% complementary (e.g., is 90%, or 80% or 70% complementary) and contains mismatched nucleotides at one or more nucleotide positions. While perfect complementarity is often desired, some embodiments can include one or more but preferably 6, 5, 4, 3, 2, or 1 mismatches.

As used herein, the term "contacting" means establishing a physical connection between two or more entities. For example, contacting a cell with an agent (e.g., a nucleic acid molecule, a system, a lipid nanoparticle composition, or pharmaceutical composition of the disclosure) means that the cell and the agent are made to share a physical connection. Methods of contacting cells with external entities both in vivo, in vitro, and ex vivo are well known in the biological arts. In exemplary embodiments of the disclosure, the step of contacting a mammalian cell with a composition (e.g a nucleic acid molecule, a system, a lipid nanoparticle composition, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a nucleic acid molecule, a system, a lipid nanoparticle composition, or pharmaceutical composition of the disclosure) and a cell may be contacted, for example, by adding the composition to the culture medium of the cell and may involve or result in transfection. Moreover, more than one cell (e.g., a population of cells) may be contacted by an agent described herein.

As used herein, the term "culture" can be used interchangeably with the terms "culturing", "grow", "growing", "maintain", "maintaining", "expand", "expanding" when referring to a cell culture or the process of culturing. The term refers to a cell (e.g., a primary cell) that is maintained outside its normal environment (e.g., a tissue in a living organism) under controlled conditions. Cultured cells are treated in a manner that enables survival. Culturing conditions can be modified to alter cell growth, homeostasis, differentiation, division, or a combination thereof in a controlled and reproducible manner. The term does not imply that all cells in the culture survive, grow, or divide as some may die, enter a state of quiescence, or enter a state of senescence. Cells are typically cultured in media, which can be changed during the course of the culture. Components can be added to the media or environmental factors (e.g., temperature, humidity, atmospheric gas levels) to promote cell survival, growth, homeostasis, division, or a combination thereof.

As used herein the term, "double-strand break" (DSB) refers to a DNA lesion generated when the two complementary strands of a DNA molecule are broken or cleaved, resulting in two free DNA ends or termini. DSBs may occur via exposure to environmental insults (e.g., irradiation, chemical agents, or UV light) or generated deliberately (e.g., via a system comprising a site-directed endonuclease) and for a defined biological purpose (e.g., to induce a mutation in a genomic DNA molecule).

As used herein, the term "genome editing", "gene-editing" and "genomic editing" are used interchangeably, and generally refer to the process of editing or changing the nucleotide sequence of a genome, preferably in a precise or predetermined manner. Examples of methods of genome editing described herein include methods of using site-directed endonucleases to cut genomic DNA at a precise target location or sequence within a genome, thereby creating a DNA break (e.g., a DSB) within the target sequence, and repairing the DNA break such that the nucleotide sequence of the repaired genome has been changed at or near the site of the DNA break.

Double-strand DNA breaks (DSBs) can be and regularly are repaired by natural, endogenous cellular processes such as homology-directed repair (HDR) and non-homologous end-joining (NHEJ) (see e.g., Cox et al., (2015) Nature Medicine 21(2):121-131).

As used herein, an "insertion" or an "addition" refers to a change in an amino acid or nucleotide sequence resulting in the addition of one or more amino acid residues or nucleotides, respectively, to a molecule as compared to a reference sequence, for example, the sequence found in a naturally-occurring molecule (e.g., a wild-type gene allele).

As used herein, the term "intron" refers to any nucleotide sequence within a gene that is removed by RNA splicing mechanisms during maturation of the final RNA product (e.g., an mRNA). An intron refers to both the DNA sequence within a gene and the corresponding sequence in a RNA transcript (e.g., a pre-mRNA). Sequences that are joined together in the final mature RNA after RNA splicing are "exons". As used herein, the term "intronic sequence" refers to a nucleotide sequence comprising an intron or a portion of an intron. Introns are found in the genes of most eukaryotic organisms and can be located in a wide range of genes, including those that generate proteins, ribosomal RNA (rRNA), and transfer RNA (tRNA). When proteins are generated from intron-containing genes, RNA splicing takes place as part of the RNA processing pathway that follows transcription and precedes translation.

As used herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

As used herein, an "mRNA" refers to a messenger ribonucleic acid. An mRNA may be naturally or non-naturally occurring or synthetic. For example, an mRNA may include modified and/or non-naturally occurring components such as one or more nucleobases, nucleosides, nucleotides, or linkers. An mRNA may include a cap structure, a 5' transcript leader, a 5' untranslated region, an initiator codon, an open reading frame, a stop codon, a chain terminating nucleoside, a stem-loop, a hairpin, a polyA sequence, a polyadenylation signal, and/or one or more cis-regulatory elements. An mRNA may have a nucleotide sequence encoding a polypeptide. Translation of an mRNA, for example, in vivo translation of an mRNA inside a mammalian cell, may produce a polypeptide. Traditionally, the basic components of a natural mRNA molecule include at least a coding region, a 5'-untranslated region (5'-UTR), a 3'UTR, a 5' cap and a polyA sequence.

As used herein, the term "naturally occurring" as applied to an object refers to the fact that an object can be found in nature. For example, a polypeptide or polynucleotide sequence, or components thereof such as amino acids or nucleotides, that is present in an organism (including viruses) that can be isolated from a source in nature and which has not been intentionally modified by man in the laboratory is naturally occurring.

As used herein, the term "nucleic acid" refers to deoxyribonucleotides or ribonucleotides and polymers or oligomers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Polymers of nucleotides are referred to as "polynucleotides".

As used herein, the term "percent identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website. The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions.

IX. Equivalents and Scope

Those skilled in the art will recognize, or be able to ascertain using no more than routine experimentation, many equivalents to the specific embodiments, described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein.

It is also noted that the term "comprising" is intended to be open and permits but does not require the inclusion of additional elements or steps. When the term "comprising" is used herein, the term "consisting of" is thus also encompassed and disclosed Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1: In Vitro Editing of HBB in CD34+ HSPCs Using Intron Targeting T107 RNP and an AAV-Donor Template Encoding a SCD Correction The efficiency of CRISPR/Cas gene-editing using an intron-targeting gRNA was evaluated for introducing a precise gene-edit in the human HBB gene locus in CD34+ hematopoietic stem and progenitor cells (HSPCs). The sickle cell disease (SCD) mutation in HBB results from a single nucleotide substitution in the $6^{th}$ codon downstream the HBB start codon that converts the wild-type GAG codon encoding Glu to a GTG codon encoding Val (i.e., E6V mutation). A correction of the SCD mutation reverts the GUG codon to a codon encoding Glu (e.g., GAG or GAA). The gene-editing approach that was evaluated included introducing Cas9 and a gRNA directed to a target sequence adjacent to a PAM, e.g., a target sequence within intron 1 of the HBB gene. The Cas9 and gRNA form a CRISPR/Cas complex that induces a DSB at a target site that is 3 bp upstream the PAM sequence. An AAV-encoded donor template is provided (e.g., AAV6), wherein the donor template is homologous to a region of the HBB gene and includes the correction to the E6V mutation and one or more additional gene-edits to the HBB gene (e.g., a silent mutation, e.g., a mutation to the PAM).

The T107 intron targeting gRNA was used to evaluate this approach. As shown in Table 3, the T107 gRNA spacer sequence has the nucleotide sequence set forth in SEQ ID NO: 3 and the T107 target sequence has the nucleotide sequence of SEQ ID NO: 1. The T107 target sequence is located in intron 1 of the HBB gene, and is adjacent an SpCas9 PAM sequence (TGG) that is located in the non-coding strand. As shown in FIG. 1, the T107 cut site is depicted in the coding strand of the HBB gene (non-PAM strand). In the Examples section, editing with T107 refers to editing performed with T107 sgRNA set forth by SEQ ID NO: 4, unless indicated otherwise.

TABLE 3

Sequences of HBB intron-targeting T107 sgRNA

| Name/ Description | Sequence | SEQ ID NO |
|---|---|---|
| HBB Target Sequence | TCCACATGCCCAGTTTCTAT | 1 |
| HBB Target Sequence with PAM | TCCACATGCCCAGTTTCTAT **TGG** | 2 |
| Spacer Sequence | UCCACAUGCCCAGUUUCUAU | 3 |
| sgRNA (spacer in bold) | **uscscsACAUGCCCAGUUUCUAU** GUUUUAGAGCUAGAAAUAGCAAG UUAAAAUAAGGCUAGUCCGUUAU CAACUUGAAAAAGUGGCACCGAG UCGGUGCusususU | 4 |

a. c, g, u: 2' O-methyl phosphorothioate nucleotides
s: phosphorothioate nucleotides
A, C, G, U, N: canonical RNA nucleotides To introduce a correction to the sickle cell mutation in HBB, the AAV-encoded homology donor referred to as "AAV.320" and identified by sequence in Table 4 was used. As shown in FIG. 1, the AAV.320 donor template encodes a correction of the SCD mutation (E6V→E6). The codon for glutamate at position 6 downstream the HBB start codon is wild-type "GAG." Additionally, the AAV.320 donor template encodes a single nucleotide substitution that converts the T107 PAM to TCG, thereby preventing re-cutting following HDR-mediated correction of HBB with the AAV.320 donor template. The AAV.320 donor template also encodes multiple silent mutations to exon 1 of the HBB gene that resulted from codon optimization of the donor template. The silent mutation immediately downstream the E6 codon is used to enable detection of the gene-edit in HSPCs derived from either a healthy human donor or a patient with SCD.

TABLE 4

Sequence of AAV.320 Homology Donor Template Encoding a SCD Correction

| Name/Description | SEQ ID NO |
|---|---|
| 5' ITR | 5 |
| Region encoding E6V → E6 and PAM mutation | 6 |
| 3' ITR | 7 |
| AAV.320 | 8 |
| AAV.320 with ITRs (4435 nt) | 9 |

The exon-targeting R02 sgRNA was used for comparison. The R02 guide targets exon 1 of the HBB locus. The R02 target gene sequence, spacer sequence, and full-length sgRNA sequence are identified in Table 5. In the Examples section, editing with R02 refers to editing performed with R02 sgRNA set forth by SEQ ID NO: 15, unless indicated otherwise. The AAV-encoded homology donor template used for correction with the R02 sgRNA is referred to as "AAV.323" and is identified by sequence in Table 6. The AAV.323 donor template encodes glutamate with a GAA codon at position 6 downstream the HBB start codon.

TABLE 5

Sequences of exon-targeting R02 sgRNA

| Name/Description | Sequence | SEQ ID NO |
|---|---|---|
| HBB Target Sequence | CTTGCCCCACAGGGCAGTAA | 12 |
| HBB Target Sequence with PAM | CTTGCCCCACAGGGCAGTAA**CGG** | 13 |
| R02 Spacer Sequence | CUUGCCCCACAGGGCAGUAA | 14 |
| R02 sgRNA (spacer in bold) | **csusus****GCCCCACAGGGCAGUAA**G UUUUAGAGCUAGAAAUAGCAAGUU AAAAUAAGGCUAGUCCGUUAUCAA CUUGAAAAAGUGGCACCGAGUCGG UGCusususU | 15 |

a, c, g, u: 2' O-methyl phosphorothioate nucleotides
s: phosphorothioate nucleotides
A, C, G, U, N: canonical RNA nucleotides

TABLE 6

Sequence of AAV.323 Homology Donor Template Encoding a SCD Correction

| Name/Description | SEQ ID NO |
|---|---|
| 5' ITR | 5 |
| Gene-edit (E6V → E6) | 45 |
| 3' ITR | 7 |
| AAV.323 | 44 |
| AAV.323 with ITRs | 46 |

Gene-editing of HBB was evaluated in CD34+ HSPCs. Briefly, frozen CD34+ HSPCs derived from plerixafor-mobilized peripheral blood obtained from healthy human donors was purchased from a commercial vendor. HSPCs were maintained in culture media containing IL-3 and were incubated at 37° C. under atmospheric conditions containing 5% carbon dioxide and 4% oxygen. HSPCs were maintained in culture and gene-editing was performed following two days of culture. To perform gene-editing, the cells were electroporated with RNP. Specifically, $1\times10^6$ cells were electroporated using the Maxcyte HSC-3 program with RNP containing 20 μg SpCas9 and 20 μg sgRNA (T107 or R02). AAV donor template was administered to cells prior to electroporation. Specifically, the cells were incubated with AAV (AAV.320 or AAV.323 respectively) at a dose of 10,000 MOI for one hour prior to electroporation.

Given efficiency of HDR repair is poor due to competition with other repair pathways (e.g., the NHEJ pathway), particularly in non-dividing or slowly dividing cells such as HSPCs, editing was also evaluated following treatment with molecules that inhibit targets in the NHEJ pathway, including 53BP1 and DNA-PK. Specifically, editing was performed with a polypeptide inhibitor of 53BP1 (i53, amino acid sequence set forth in SEQ ID NO: 11) and small molecule inhibitor of the DNA-PK catalytic subunit (Nu7441). The 53BP1 inhibitor i53 was introduced as an mRNA-encoded protein to the cells at a dose of 1 μg during electroporation with RNP (mRNA ORF nucleotide sequence set forth in SEQ ID NO: 10). The DNA-PK inhibitor Nu7441 was introduced following electroporation at a concentration of 5 μM, and edited cells were incubated with Nu7441 for 48 hours following electroporation.

To evaluate HDR editing efficiency, genomic DNA was harvested from treated cells, and the frequency of the HBB allele encoding the expected gene edit (i.e., GAA encoding glutamate at position 6 downstream the HBB start codon ("E6") for cells transduced with AAV.323 and silent mutations for cells transduced with AAV.320) was evaluated using a PCR amplification-based assay followed by next-generating sequencing (NGS). The frequency of INDELs at the predicted gRNA cut site was evaluated by NGS analysis.

Figure 2A:
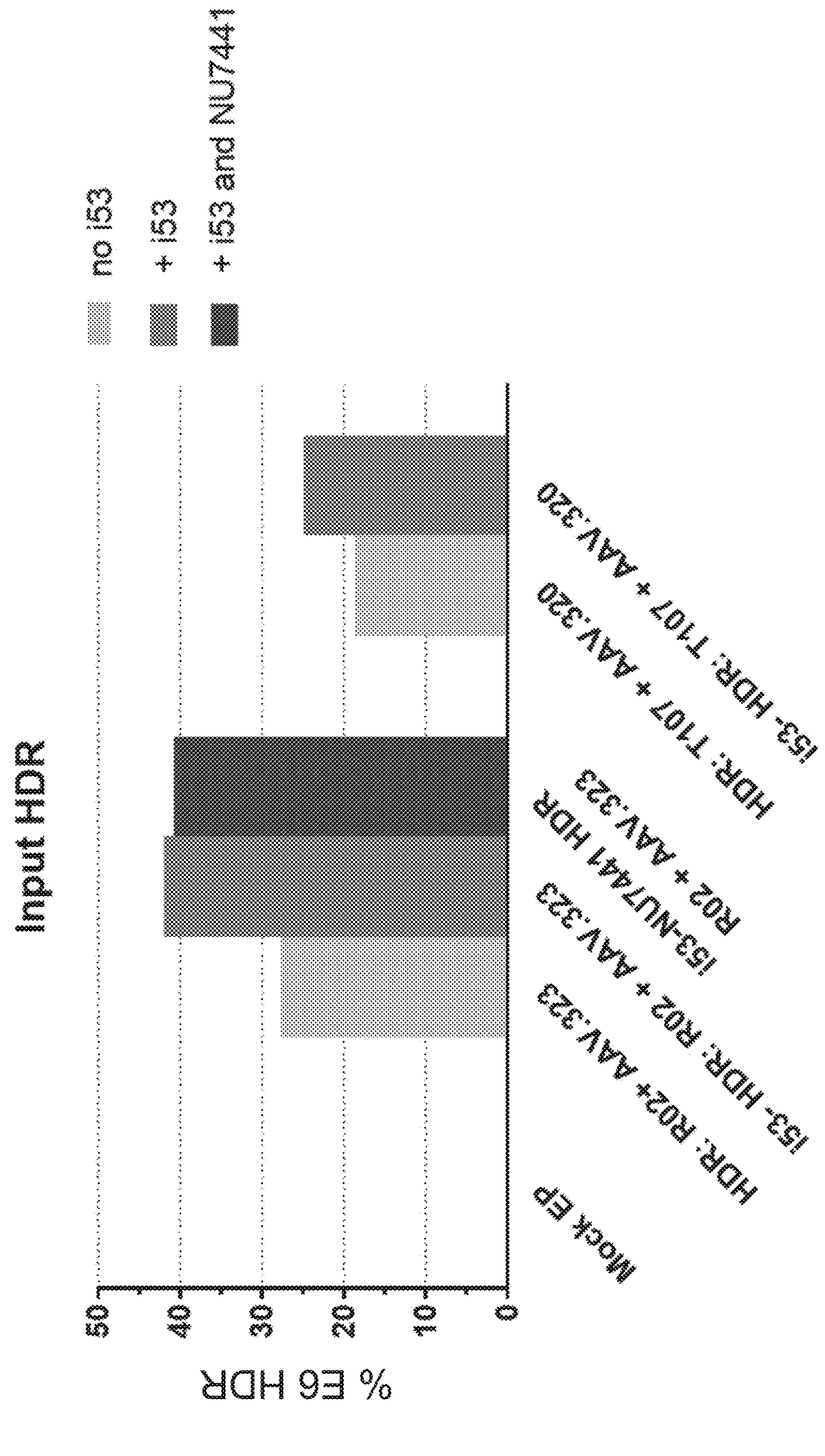
FIGS. 2A-2B provide bar graphs quantifying the frequency of incorporation of a donor-template-encoded gene-edit by HDR (FIG. 2A) and frequency of INDELs (FIG. 2B) in the HBB gene locus in CD34+ HSPCs derived from healthy donors that were edited with ribonucleoprotein (RNP) containing SpCas9 and the exon-targeting guide R02 (R02 RNP) or the intron-targeting guide T107 (T107 RNP) and a corresponding AAV-encoded homology donor (AAV.323 or AAV.320 respectively) encoding a correction to the SCD mutation. Cells were edited with RNP+AAV only or were edited in combination with inhibitors of the NHEJ repair pathway (53BP1 inhibitor i53 and DNA-PK inhibitor Nu7441). Control cells were electroporated in the absence of RNP or AAV (mock EP).
Figure 2B:
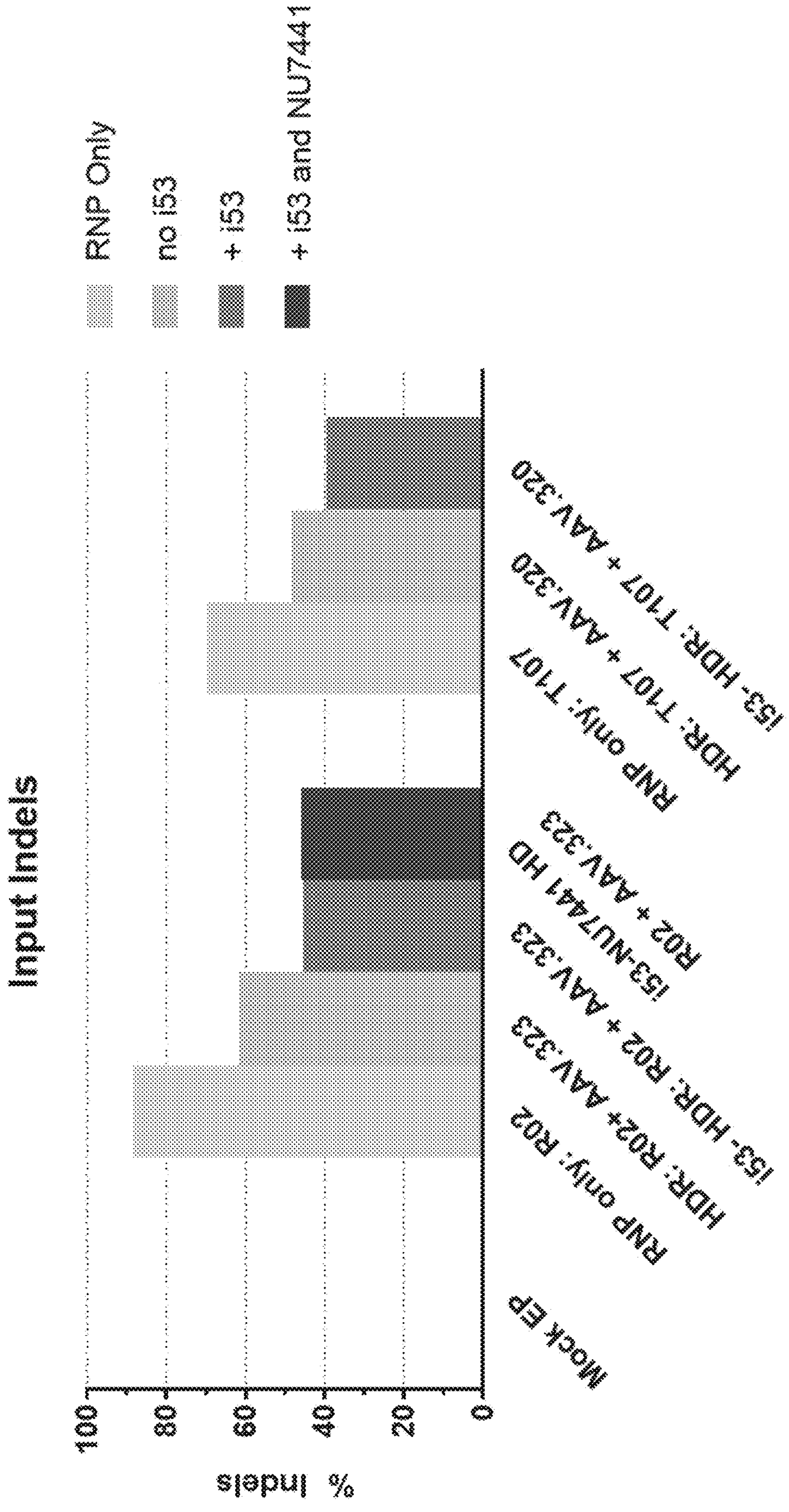

As shown in FIG. 2A, the frequency of genomic DNA incorporating a donor-template-encoded gene-edit in HBB was approximately 18% for cells edited with T107 RNP+AAV.320. An increase in HDR efficiency to approximately 25% was observed if editing included treatment with i53. Cells edited with R02 RNP+AAV.323 had HDR efficiency of approximately 28% that was increased to greater than 40% if editing included treatment with i53 or with i53 and Nu7441. FIG. 2B shows the frequency of INDELs at the predicted gRNA cut site. Treatment with NHEJ pathway inhibitors reduced frequency of INDELs.

Together, these data demonstrate effective incorporation of a donor template-encoded gene edit in the HBB locus in CD34+ HSPCs with either an intron-targeting or exon-targeting gRNA.

Example 2: In Vivo Engraftment of CD34+ HSPCs Following Editing with T107 RNP and an AAV Donor Template Human CD34+ HSPCs edited as described in Example 1 were evaluated for the ability to engraft and retain the gene-edit following administration in vivo.

Briefly, HSPCs were administered to mice following editing with R02 RNP+AAV.323 or T107 RNP+AAV.320 as described in Example 1, either alone or combined with i53 mRNA or with i53 mRNA and Nu7441. Treatment groups included HSPCs edited with:

(i) RNP and AAV (R02+AAV.323 or T107+AAV.320);
(ii) RNP only (R02 RNP only or T107 RNP only);
(iii) AAV only (AAV.323+mock EP or AAV.320+mock EP);
(iv) RNP, AAV, and i53 mRNA (R02 RNP+AAV.323+i53 or T107+AAV.320+i53); or
(v) RNP, AAV, i53 mRNA, and Nu7441 (R02 RNP+AAV.323+i53+Nu7441).

Each cohort received a dose of $0.5\times10^6$ HSPCs per mouse. Control groups received HSPCs exposed to electroporation only (mock EP) or not electroporated (culture control). The cells were administered by intravenous injection to NBSGW mice at 2 days following electroporation. Recipient mice were treated with sublethal irradiation (100 cGy) at 1 day prior to administration of HSPCs to eliminate hematopoietic cells in the bone marrow and enable engraftment of the donor cells.

Figure 3:
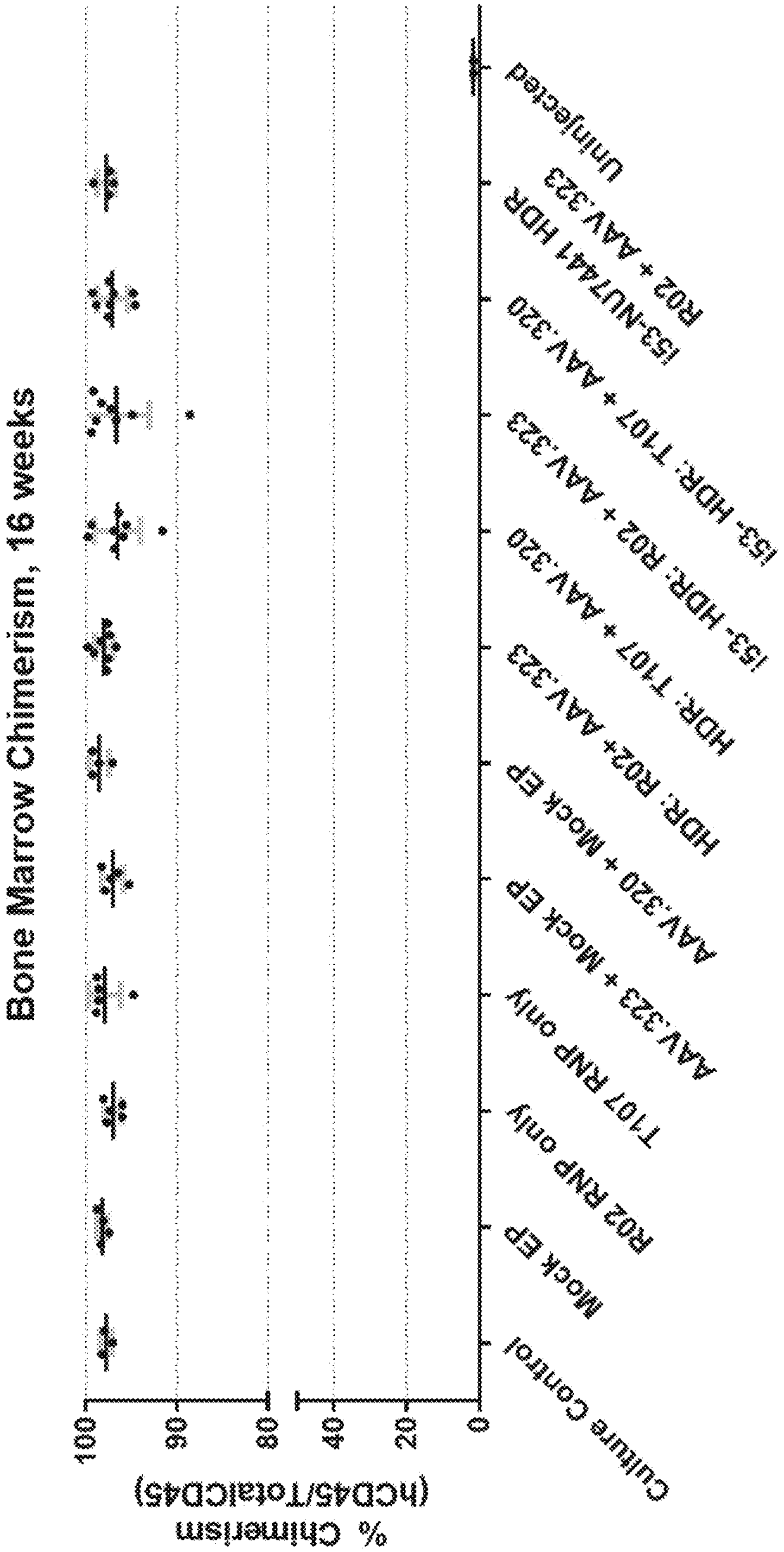
FIG. 3 provides a graph quantifying engraftment of human cells in mouse bone marrow isolated at 16 weeks following in vivo administration of HSPCs edited as in FIGS. 2A-2B. Engraftment is measured as percent human chimerism, which is the fraction or % of cells expressing human CD45 relative to total CD45 (h+m CD45)-expressing cells as quantified by flow cytometry.

Bone marrow extracted at 16 weeks following HSPC administration was evaluated for presence of human hematopoietic cells and maintenance of the HBB gene-edit. Presence of human hematopoietic cells was measured by flow cytometry in mouse bone marrow samples. The antibodies used for labeling cell-surface markers are shown in Table 7. Cells were gated on singlet, live cells. Mouse and human CD45-expressing hematopoietic cells were distinguished by antibodies targeting mouse or human CD45. Engraftment was measured as percent chimerism which was defined as the quantity of human CD45 positive cells divided by the total number of CD45 positive cells (human and mouse CD45 expressing cells combined). The lineage of human CD45 positive cells was determined using markers for CD19 (B cells), CD3 (T cells), CD33 (myeloid cells), and CD34 (HSPCs). As shown in FIG. 3, administration of HSPCs edited with any of the conditions resulted in greater than 90% chimerism in the bone marrow.

TABLE 7

Antibodies to Distinguish Human Hematopoietic Cells in Mouse Bone Marrow

| Antibody | Clone | Fluorophore | Catalog # |
|---|---|---|---|
| Anti-mouse CD45 | 30-F11 | APC | 103112 |
| Anti-human CD45 | HI30 | BV786 | 563716 |
| Anti-human CD19 | HIB19 | PE-Cy7 | 302216 |
| Anti-human CD3 | UCHT1 | APC-Cy7 | 300426 |
| Anti-human CD33 | P67.6 | PE | 366608 |
| Anti-human CD34 | 581 | BV421 | 562577 |

Figure 4A:
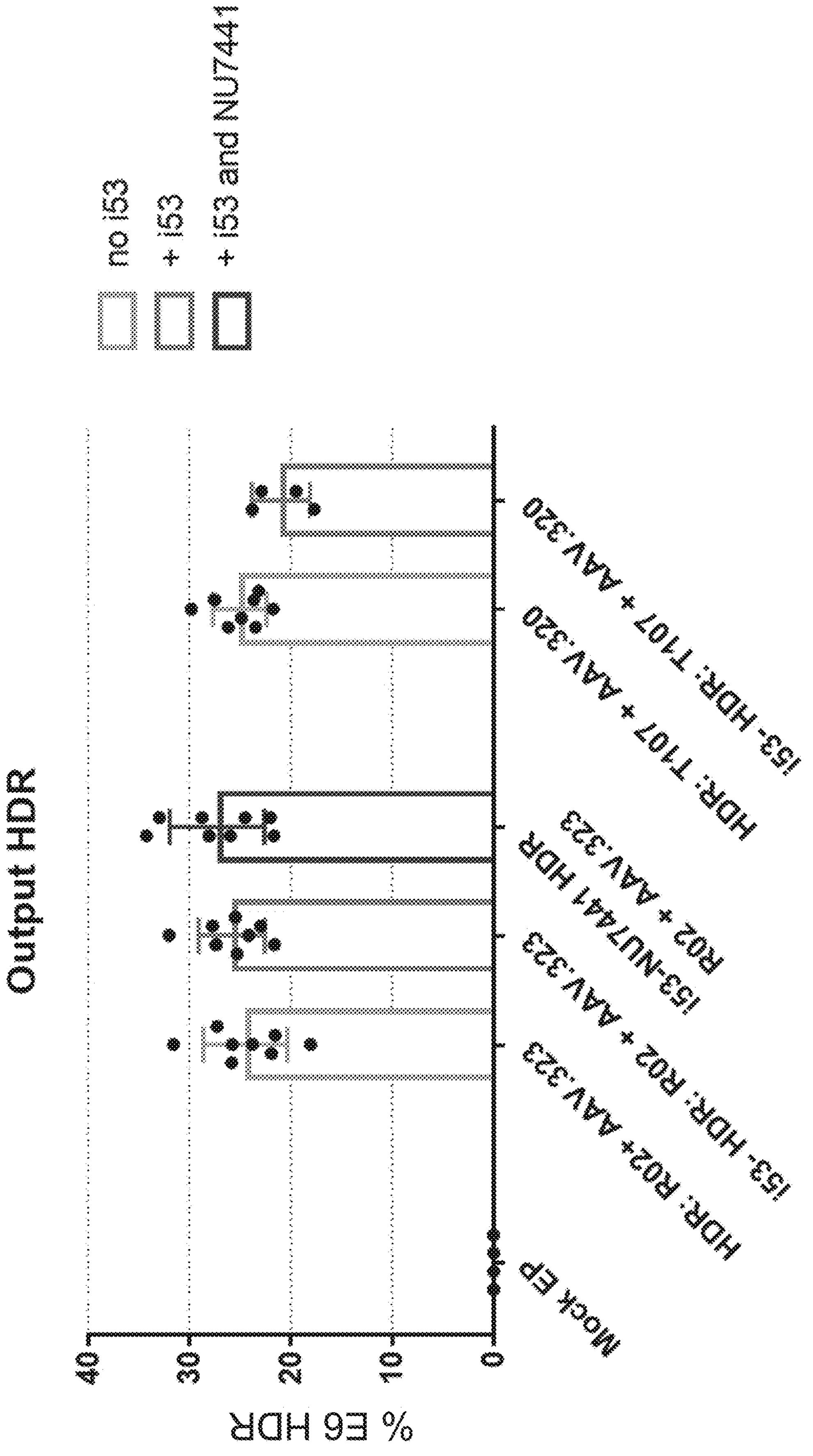
FIGS. 4A-4B provide graphs quantifying the persistence of a donor template-encoded gene-edit (HDR) (FIG. 4A) and frequency of INDELs (FIG. 4B) in the HBB gene locus in the cells that are generated from engrafted human bone marrow cells, as measured in genomic DNA harvested from mouse bone marrow at 16 weeks following in vivo administration of HSPCs as in FIG. 3. Input cell INDELs (as shown in FIG. 2B) are plotted in FIG. 4B as a comparison to the INDELs measured in genomic DNA harvested from bone marrow for each cohort of animals.
Figure 4B:
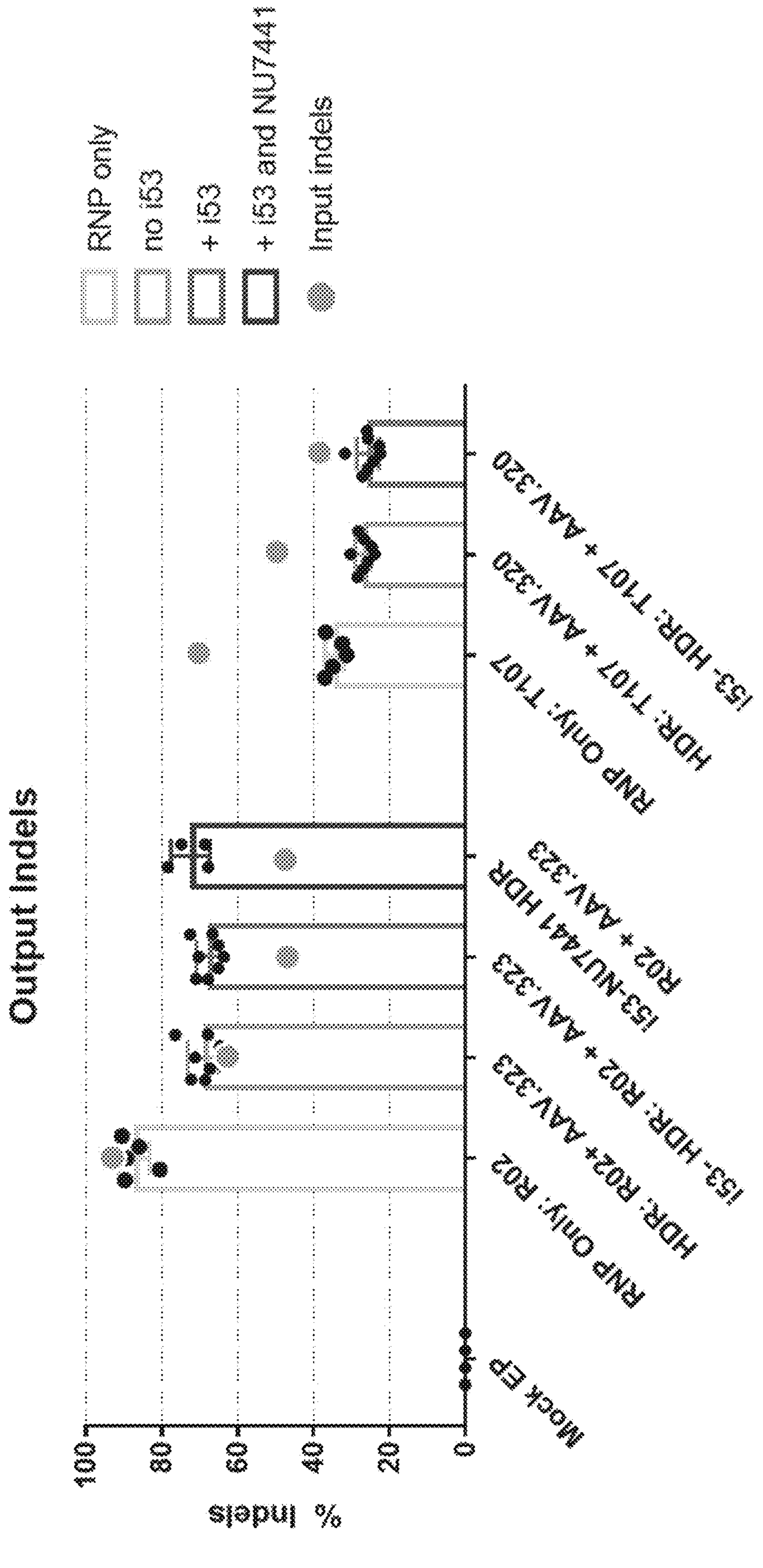

Maintenance of gene-editing was evaluated in mouse bone marrow collected at 16 weeks post-administration of HSPCs. Incorporation of the desired gene edit (i.e., GAA encoding glutamate at position 6 downstream of the HBB start codon for cells transduced with AAV.323 and silent mutations for cells transduced with AAV.320) in the HBB locus and frequency of INDELs at the HBB cut site was evaluated in genomic DNA harvested from mouse bone marrow samples at 16 weeks post-administration using NGS as described in Example 1. Shown in FIGS. 4A-4B is the frequency of genomic DNA extracted from bone marrow that encoded the desired gene-edit (FIG. 4A) and the frequency of INDELs at the HBB cut site (FIG. 4B). For mice administered HSPCs edited with T107 RNP+AAV.320, the frequency of the donor template-encoded gene-edit was comparable in bone marrow at 16 weeks post-administration to HSPCs prior to administration. Additionally, the frequency of INDELS at the T107 cut site was reduced in bone marrow compared to HSPCs prior to administration. These results demonstrate that progenitor cells derived from edited HSPCs maintain the desired gene-edit following in vivo administration.

Example 3: Analysis of Globin Monomer Expression Following Editing with T107 RNP and an AAV Donor Template The globin monomers produced by CD34+ HSPCs following editing with T107 RNP and in vitro differentiation was investigated to determine whether editing would result in a β-thalassemia phenotype (i.e., reduced beta-globin production).

Briefly, CD34+ HSPCs were isolated from plerixafor+GCSF-dual mobilized peripheral blood obtained from healthy human donors. The cells were seeded in Phase I media at a cell density of $2\times10^5$ cells/mL. Cells were cultured at 37° C. under normoxic conditions (i.e., oxygen 20%). Editing was performed following two days of in vitro culture. Briefly, $5\times10^5$ cells were electroporated with: (1) RNP containing 20 μg SpCas9 and 20 μg T107 sgRNA and 10,000 MOI AAV.320 (T107 RNP+AAV.320); or (2) RNP containing 20 μg SpCas9 and 20 μg R02 sgRNA either with or without 10,000 MOI AAV.323 (R02 RNP+AAV.323 and R02 RNP only respectively). The cells were transduced with AAV donor template by incubation for 1 hour prior to electroporation. Control cells were electroporated without RNP or AAV (mock EP).

Following editing, both edited cells and control cells were differentiated to erythrocytes. Briefly, edited cells were plated in fresh Phase I media at a density of $2\times10^5$ cells/mL, and re-plated at similar density in fresh Phase I media on days 3 and 5 post-editing. On day 7 post-editing, the cells were incubated in Phase II media at a density of $2.5\times10^5$ cells/mL. On day 10 post-editing, the cells were incubated in Phase III media at a density of $1.2\times10^6$ cells/mL.

Globin monomers produced by differentiated cells was assessed on day 18 of differentiation. Briefly, approximately $1\times10^6$ cells were harvested, centrifuged, and prepared for HPLC analysis. Globin monomers expressed by edited cells and control cells were detected using HPLC with separation by reverse phase chromatography. The chromatography enabled separation and quantification of globin molecules (e.g., beta-globin, delta-globin, alpha-globin, gamma2-globin, and gammal-globin). Beta-globin and beta-globin-like molecules were further differentiated based on elution time. These included wild-type beta globin (B), beta-globin with SCD mutation (S) and unknown beta-globin (U). Unknown beta-globin was further characterized based upon analysis by mass spectrometry.

Editing with R02 RNP alone induces a high frequency of INDELs in the HBB gene. Such INDELs can introduce frameshift mutations in HBB that disrupt gene expression. Thus, HSPCs edited with R02 RNP and differentiated to erythrocytes are expected to produce decreased levels of beta-globin monomers (i.e., B+S+U) relative to total globin. It was evaluated if editing using R02 RNP+AAV would prevent this phenotype by reducing frequency of INDELs in the HBB gene. Given the T107 RNP cut site is located in intron 1 of HBB, and INDELs introduced at the cut site are not expected to introduce frameshift mutations that would alter the HBB open reading frame, it was evaluated if editing with T107 RNP+AAV would likewise prevent this phenotype.

Figure 4C:
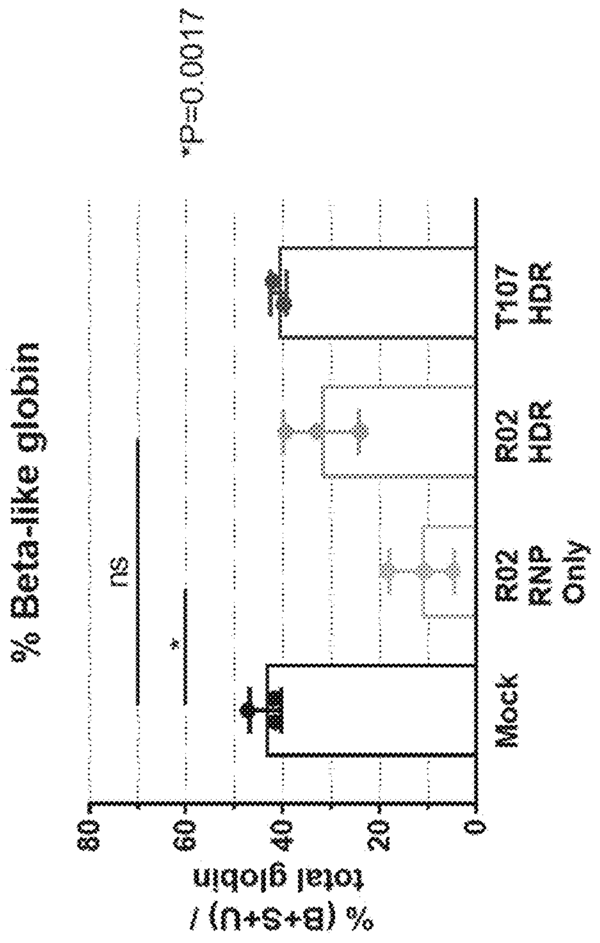
FIG. 4C provides a bar graph quantifying the ratio of beta-like globin monomers (beta-globin (B), sickle-globin which is beta-globin with SCD mutation (S), and unknown beta-globin mutants (U)) to total globin expressed following editing and in vitro differentiation. Cells were edited with R02 RNP only, R02 RNP+AAV, or T107 RNP+AAV, wherein the AAV-encoded donor-template introduces the E6V mutation. Control cells were electroporated without RNP or AAV (mock).

As shown in FIG. 4C, CD34+ HSPCs edited with R02 RNP alone had an approximately 1.8-fold decrease in beta-globin monomers (B+S+U) relative to total globin monomer compared to mock EP control cells, indicating overall reduced expression of beta-globin and beta-globin-like monomers. In contrast, no significant difference in the level of beta-globin monomers (B+S+U) relative to total globin was observed for cells edited with R02 RNP+AAV.323 or T107 RNP+AAV.320 compared to mock EP control cells.

Figure 4D:
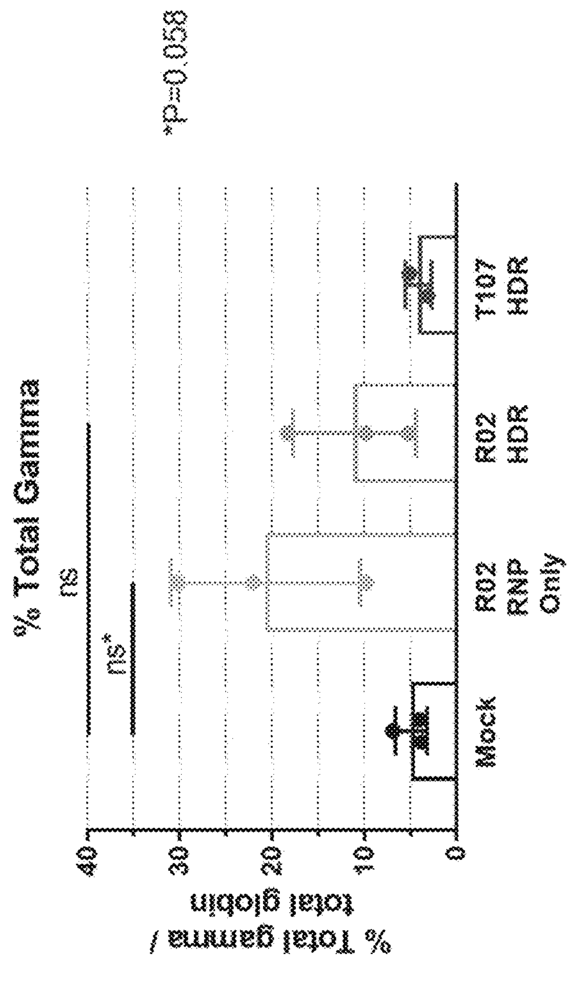
FIG. 4D provides a bar graph quantifying the ratio of total gamma-globin to total globin as expressed by cells edited as in FIG. 4C.

Furthermore, the level of gamma globin expressed by edited cells following in vitro differentiation was also assessed using the HPLC assay. As shown in FIG. 4D, the level of total gamma-globin relative to total globin was increased in cells edited with either R02 RNP alone or R02+AAV.323 relative to mock EP control cells. The level for cells edited with T107 RNP+AAV.320 was comparable to mock EP control cells.

Example 4: HDR Efficiency with DNA-PK Inhibitors for Editing the HBB Gene in CD34+HSPCs Potent inhibitors of the DNA-PK enzyme complex that functions in the NHEJ repair machinery were evaluated for blocking NHEJ repair and improving HDR efficiency when used with CRISPR/Cas components for editing the HBB gene locus. Specifically, Compounds 984 and 296 have been reported as reversible inhibitors of the DNA-PK catalytic subunit (DNA-PKcs), with high affinity and selectivity. The compounds are described in U.S. Pat. No. 9,592,232, which is herein incorporated by reference. The chemical structures of Compounds 984 and 296 are provided in Table 2. As described in this Example, the effect of DNA-PK inhibition using Compound 296 or Compound 984 was compared to the effect of 53BP1 inhibition using i53 for increased HDR repair at the HBB gene locus in CD34+ HSPCs.

Specifically, frozen CD34+ HSPCs isolated from dual-mobilized (plerixafor+GCSF) peripheral blood obtained from healthy human donors was thawed and seeded in media with components as described in Example 1. The cells were maintained in culture, and gene-editing was performed following two days of culture.

For editing, $5\times10^5$ CD34+ HSPCs were electroporated with RNP containing 20 μg SpCas9 and 20 μg T107 sgRNA. Electroporation was performed using the CA-137 program of the Lonza Amaza™ 4D-Nucleofector™. The cells were transduced with AAV donor template for 1 hour at 37° C. prior to electroporation. AAV-encoded homology donor template referred to as "AAV.310", which is identified by sequence in Table 8. The AAV.310 donor template encodes a SCD mutation, specifically valine at the $6^{th}$ codon downstream the HBB start codon (E6V). The cells were treated with AAV at a dose of 10,000 MOI. The cells were electroporated and immediately plated in medium containing Compound 296 or Compound 984 for 48 hours at various concentration, from 0.014 μM to 10 μM. For comparison, control cells were electroporated with T107 RNP+AAV.310 in the absence of either inhibitor. Additionally, comparison was made to HSPCs electroporated with T107 RNP+AAV.310 and treated with 1 μg i53 mRNA.

TABLE 8

Sequence of AAV.310 Homology Donor Template Encoding a SCD Mutation

| Name/Description | SEQ ID NO |
|---|---|
| 5' ITR | 5 |
| Region encoding E6 → E6V and PAM mutation | 22 |
| 3' ITR | 7 |
| AAV.310 | 23 |
| AAV.310 with ITRs | 24 |

Edited cells were evaluated for viability using trypan blue, and for incorporation of gene-edits at 2 days post-electroporation. The efficiency of HDR repair for introducing an E6V mutation in the HBB gene was quantified by NGS assay as described in Example 1, and the frequency of INDELs induced at the T107 cut site was also evaluated by NGS analysis.

Figure 5A:
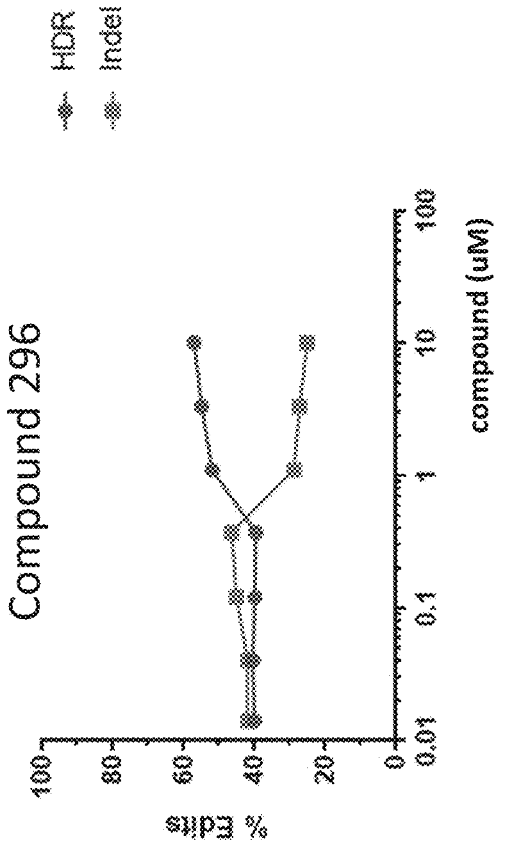
FIGS. 5A-5B provide graphs quantifying frequency of incorporation of a donor template-encoded gene-edit by HDR and frequency of INDELs in the HBB gene locus in healthy donor CD34+ HSPCs edited with T107 RNP and AAV encoding a homology donor with a SCD mutation (AAV.310) either alone or in combination with DNA-PK inhibitor Compound 296 (FIG. 5A) or Compound 984 (FIG. 5B) at the concentrations indicated.
Figure 5B:
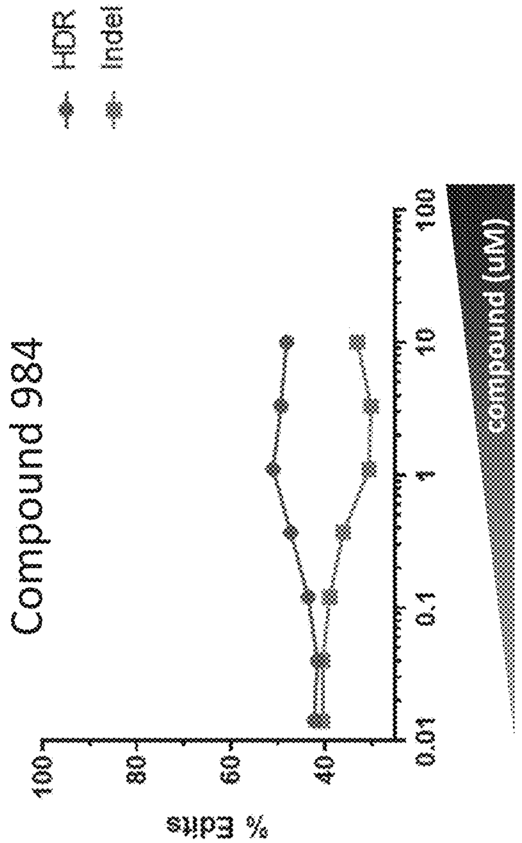

As shown in FIGS. 5A-5B, the level of HDR repair was increased by approximately 1.3-fold for HSPCs edited with 1.1 μM of Compound 296 or Compound 984 compared to control cells edited with T107 RNP+AAV.310 only. Additionally, as shown in Table 9, the frequency of INDELs at the T107 cut site was reduced with treatment of either DNA-PK inhibitor by approximately 1.6-fold compared to control cells.

TABLE 9

Editing Efficiency for T107 RNP Combined with DNA-PK Inhibitor Compound 296 or 984

| Group | Compound 296 % INDELs | Compound 296 % HDR | Compound 984 % INDELs | Compound 984 % HDR |
|---|---|---|---|---|
| T107 RNP only | 83 | 0 | 83 | 0 |
| T107 RNP + AAV.310 + 0 μM Compound # | 40 | 39 | 44 | 39 |
| T107 RNP + AAV.310 + 0.014 μM Compound # | 41 | 41 | 40 | 40 |
| T107 RNP + AAV.310 + 0.04 μM Compound # | 42 | 40 | 40 | 42 |
| T107 RNP + AAV.310 + 0.012 μM Compound # | 45 | 40 | 39 | 44 |
| T107 RNP + AAV.310 + 0.037 μM Compound # | 46 | 39 | 36 | 51 |
| T107 RNP + AAV.310 + 1.1 μM Compound # | 29 | 52 | 31 | 51 |
| T107 RNP + AAV.310 + 3.3 μM Compound # | 27 | 55 | 30 | 49 |
| T107 RNP + AAV.310 + 10 μM Compound # | 25 | 57 | 33 | 48 |
| T107 RNP + AAV.310 + i53 | 42 | 35 | 42 | 35 |

Figure 6:
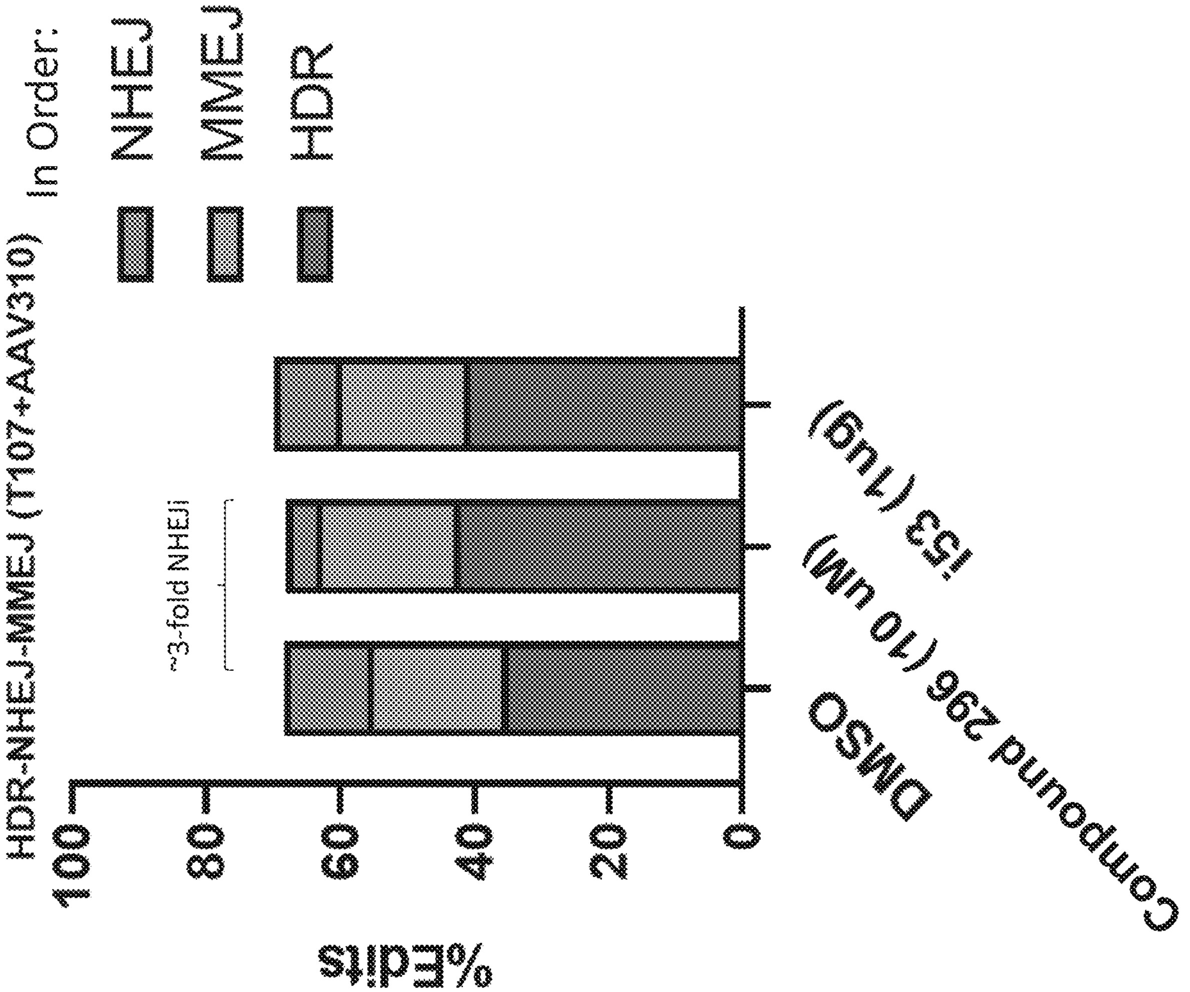
FIG. 6 provides a bar graph quantifying the percentage of total sequence reads having a deletion in HBB of 9 nt (corresponding to repair by the MMEJ pathway), an INDEL in HBB of ±1 nt (corresponding to repair by NHEJ), or incorporation of a donor-template-encoded gene-edit by HDR following editing of healthy donor CD34+ HSPCs with T107 RNP and AAV.310 alone (DMSO) or in combination with Compound 296 at 10 μM or 1 μg mRNA encoding i53.

The INDELs species identified in edited cells were further evaluated to determine frequency of repair by NHEJ or MMEJ repair pathways. An INDEL of ±1 nt was considered due to NHEJ repair; a deletion of −9 nt was considered due to MMEJ repair based on the microhomology present on either side of the T107 cut site. Based on percentage of total reads corresponding to these INDEL species, the ratio of gene edits due to NHEJ and MMEJ repair was evaluated. As shown in FIG. 6, cells edited in the presence of 10 μM Compound 296 had up to a 3-fold decrease in INDELs due to NHEJ repair, with no substantial reduction in INDEL species due to MMEJ repair. Treatment with i53 also modestly reduced INDELs due to NHEJ repair (1.3-fold reduction) and did not affect INDEL species due to MMEJ repair. Thus, reduced frequency of INDELs with treatment of compound 296 or i53 is largely due to suppression of the NHEJ repair pathway.

Together these data demonstrate a substantial improvement in HDR editing efficiency and decreased frequency of INDELs in the HBB gene locus when DNA-PK inhibitors Compound 296 or 984 are combined with RNP containing T107 sgRNA.

Example 5: In Vitro Evaluation of CD34+ HSCPs Following Editing with T107 RNP, an AAV Donor Template, and DNA-PK Inhibitors The presence of gene-edits in the HBB gene locus and mRNA transcribed from HBB was evaluated following editing of HSPCs with T107 RNP and AAV.310 either alone or with the DNA-PK inhibitors described in Example 4.

Briefly, frozen CD34+ HSPCs isolated from Plerixafor mobilized peripheral blood, obtained from healthy human donors were thawed. The cells were seeded in CD34 cell media at a cell density of $2\times10^5$ cells/mL. Cells were cultured at 37° C. under normoxic conditions (i.e., oxygen 20%). Gene-editing was performed following two days of in vitro culture. For editing, $5\times10^5$ CD34+ HSPCs were electroporated with RNP containing 200 μg/ml Cas9 and 200 μg/ml T107 sgRNA. The Cas9 used was either wild-type SpCas9 or an SpCas9 variant having a R691A mutation that has been reported to have increased fidelity by reducing Cas9 nuclease activity at sites with gRNA mismatches, while maintaining cutting efficiency at on-target sites (see, e.g., Vakulskas, et al (2018) *NAT MED* 24:1216). The SpCas9 R691A variants has an N-terminal and C-terminal sv40 NLS and is referred to herein as HF SpCas9_1. The cells were transduced with AAV.310, 1 hour prior to electroporation, at a dose of 10,000 MOI. The cells were plated in CD34 cell medium containing Compound 296 or Compound 984 immediately following the electroporation, at a concentration of 1 μM or 3 μM for 48 hours. For comparison, control cells were electroporated with T107 RNP, and no DNA-PK inhibitor was added to this group. Additionally, comparison was made to HSPCs edited with T107 RNP+AAV.310 and treated with 1 μg i53 mRNA during electroporation (T107 RNP+AAV.310+i53). Post electroporation cells were resuspended in CD34 cell medium at a density of $2\text{-}5\times10^5$ cells/ml and incubated at 37° C. for 48 hours.

Following editing, cells were differentiated to erythrocytes. Briefly, cells were plated in fresh CD34 media at a density of $2\times10^5$ cells/mL, and re-plated at similar density in fresh CD34 media on days 3 and 5 post-editing. On day 7 and 10 post-editing, the cells were incubated in Phase II media at a density of $2.5\times10^5$ and $1\times10^6$ cells/mL respectively. On day 12 post-editing, the cells were incubated in Phase III media at a density of $1\times10^6$ cells/mL. On day 14 cells were plated at a density of $2\times10^6$ cells/ml in Phase III media and maintained till day 18 at 37° C. Cell growth was measured at various time points between day 0 and day 18 post-editing, and the percentage of viable cells was measured by staining with tryphan blue. No difference in cell growth over time or percent viability was observed between T107 RNP+AAV.310 edited cells and edited cells treated with Compound 296, Compound 984, or i53 (data not shown).

Editing Efficiency in DNA and RNA

At 48 hours post electroporation genomic DNA was isolated from the edited cells and HDR to introduce the sickle mutation and INDEL frequencies were evaluated using next gene sequencing and computational analysis. On day 10 of differentiation, incorporation of the SCD mutation and frequency of INDELs present in mRNA transcribed from the HBB gene locus of edited cells was determined using RNA amplicon sequencing.

Figure 7A:
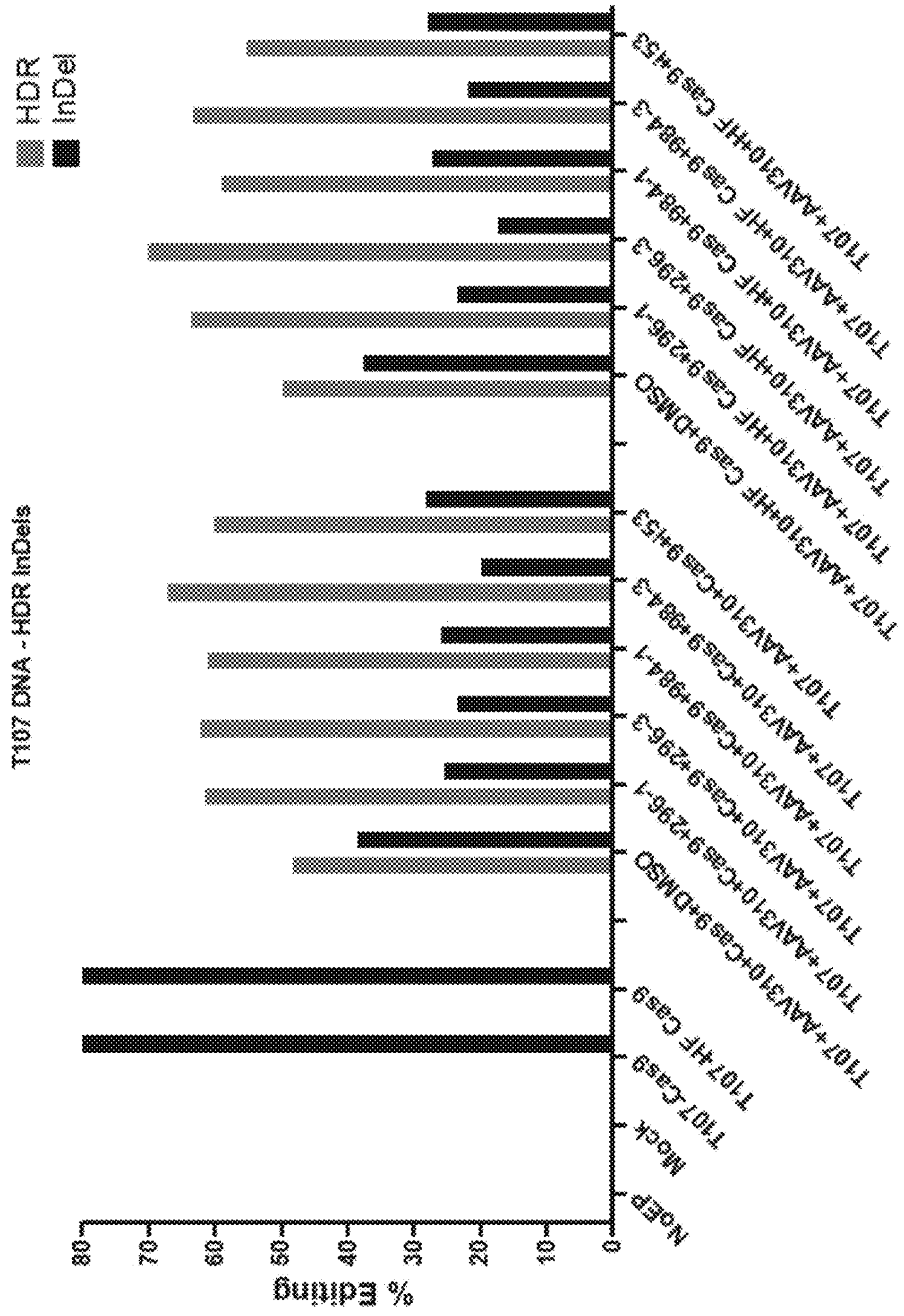
FIGS. 7A-7B provide graphs quantifying the frequency of a donor template-encoded gene edit incorporated by HDR and frequency of INDELs in HBB as measured in genomic DNA 2 days following electroporation (FIG. 7A) or in mRNA transcribed from the HBB gene (FIG. 7B) on day 10 of in vitro differentiation of edited cells into erythroid progenitors. Editing was performed with T107 RNP containing wild-type SpCas9 or high fidelity SpCas9 (HF SpCas9_1) and AAV.310. Editing was performed with RNP and AAV only (T107+AAV.310+Cas9+DMSO or T107+AAV.310+ HF SpCas9_1+DMSO), or performed in combination with Compound 296 at 1 μM or 3 μM (+296-1 or +296-3 respectively), Compound 984 at 1 μM or 3 μM (+984-1 or +984-3 respectively), or mRNA encoding i53 (+i53). Control cells were unedited (no EP), electroporated in the absence of RNP and AV (mock EP), or electroporated with T107 RNP only.

As shown in FIG. 7A, the level of HDR repair was increased for edited cells that were treated with Compound 296 or Compound 984 compared to cells edited with T107 RNP+AAV.310 only. Additionally, the frequency of INDELs at the T107 cut site was decreased for cells edited in the presence Compound 296 or Compound 984. No substantial difference in editing was observed using wild-type SpCas9 or HF SpCas9_1.

Figure 7B:
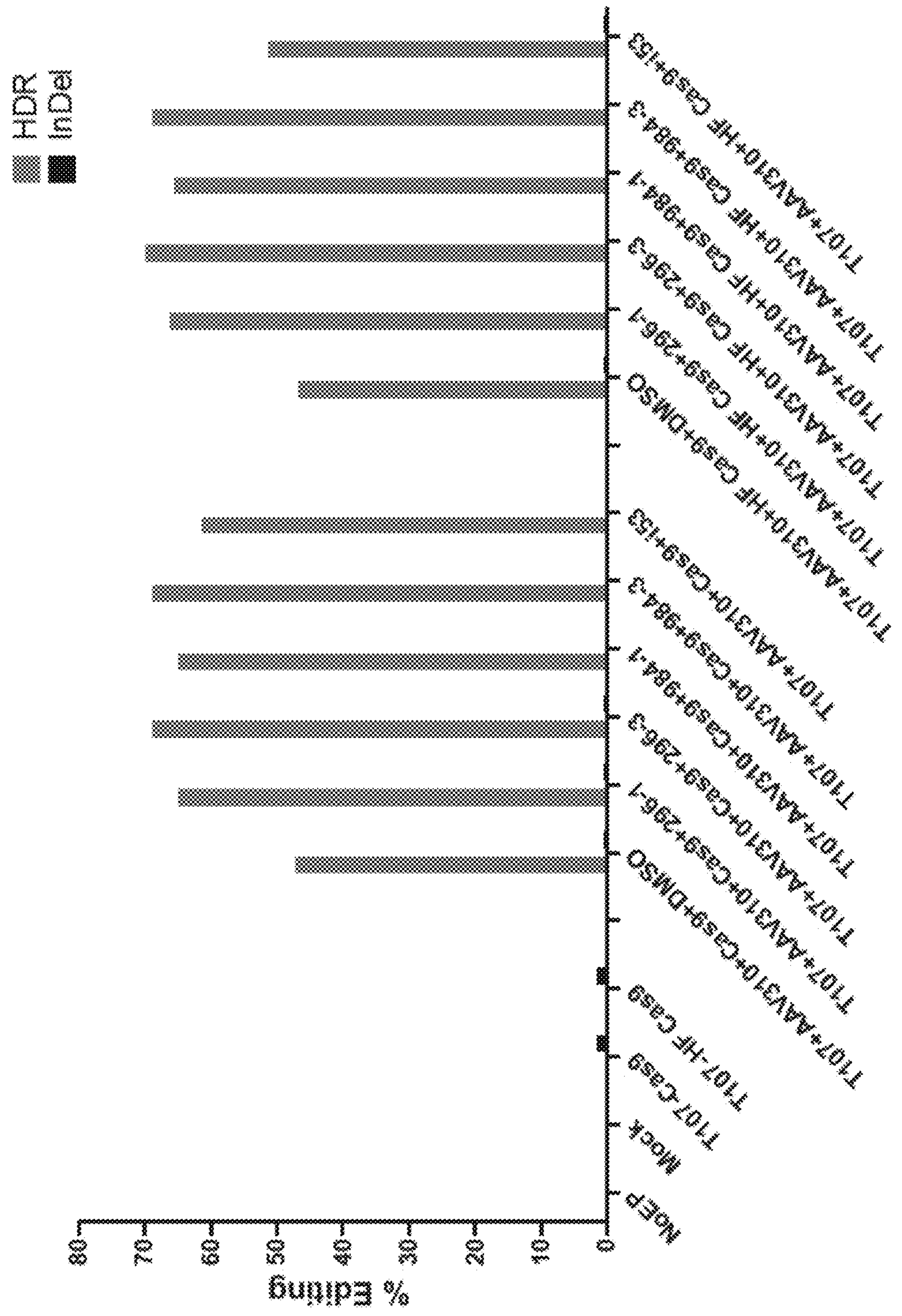

As shown in FIG. 7B, the frequency of INDELs measured in HBB mRNA transcripts in cells edited with T107 RNP+AAV.310 was negligible, indicating use of an intron-targeting gRNA is an effective strategy to prevent INDEL formation that could result in a defective mRNA transcript, for example, INDEL formation in the coding sequence of HBB.

Globin and Hemoglobin Analysis

Figure 7C:
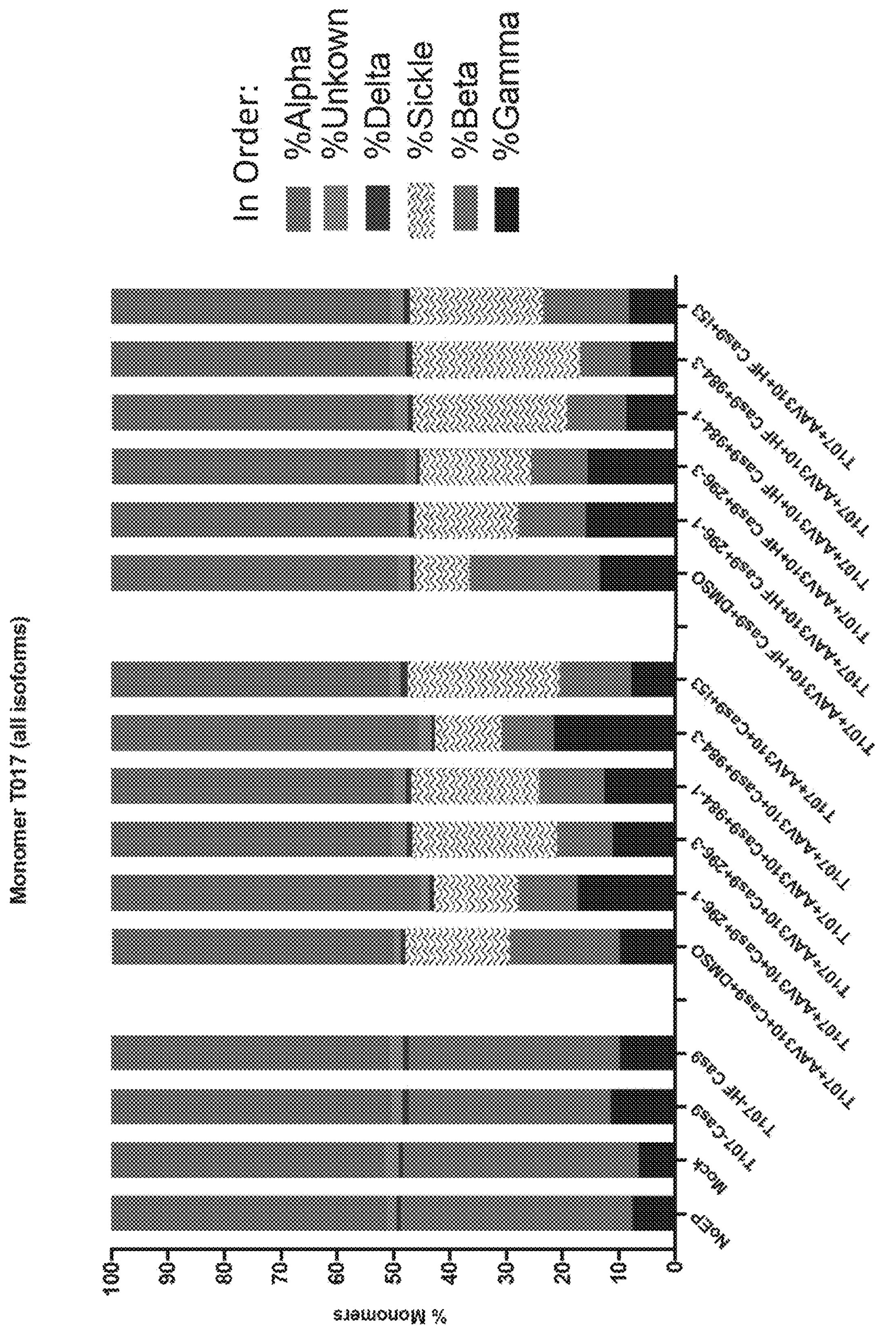
FIG. 7C provides a graph quantifying the percentage of total globin monomers that were gamma-globin, beta-globin, sickle beta-globin, unknown beta-globin, delta-globin, and alpha-globin produced by edited cells differentiated into erythroid progenitors as in FIGS. 7A-7B and evaluated on day 18 of differentiation.

Additionally, on day 18 post-editing, expression of globin monomers was assessed in differentiated cells by HPLC as described in Example 3. As shown in FIG. 7C, the percentage of alpha-globin was consistent between edited cells and control cells. However, cells edited with T107 RNP+AAV.310 either alone or combined with Compound 296, Compound 984, or i53 had increased expression of sickle-globin compared to control cells. Accordingly, the editing was sufficient to both introduce the SCD mutation in HBB and result in expression of sickle globin.

Figure 7D:
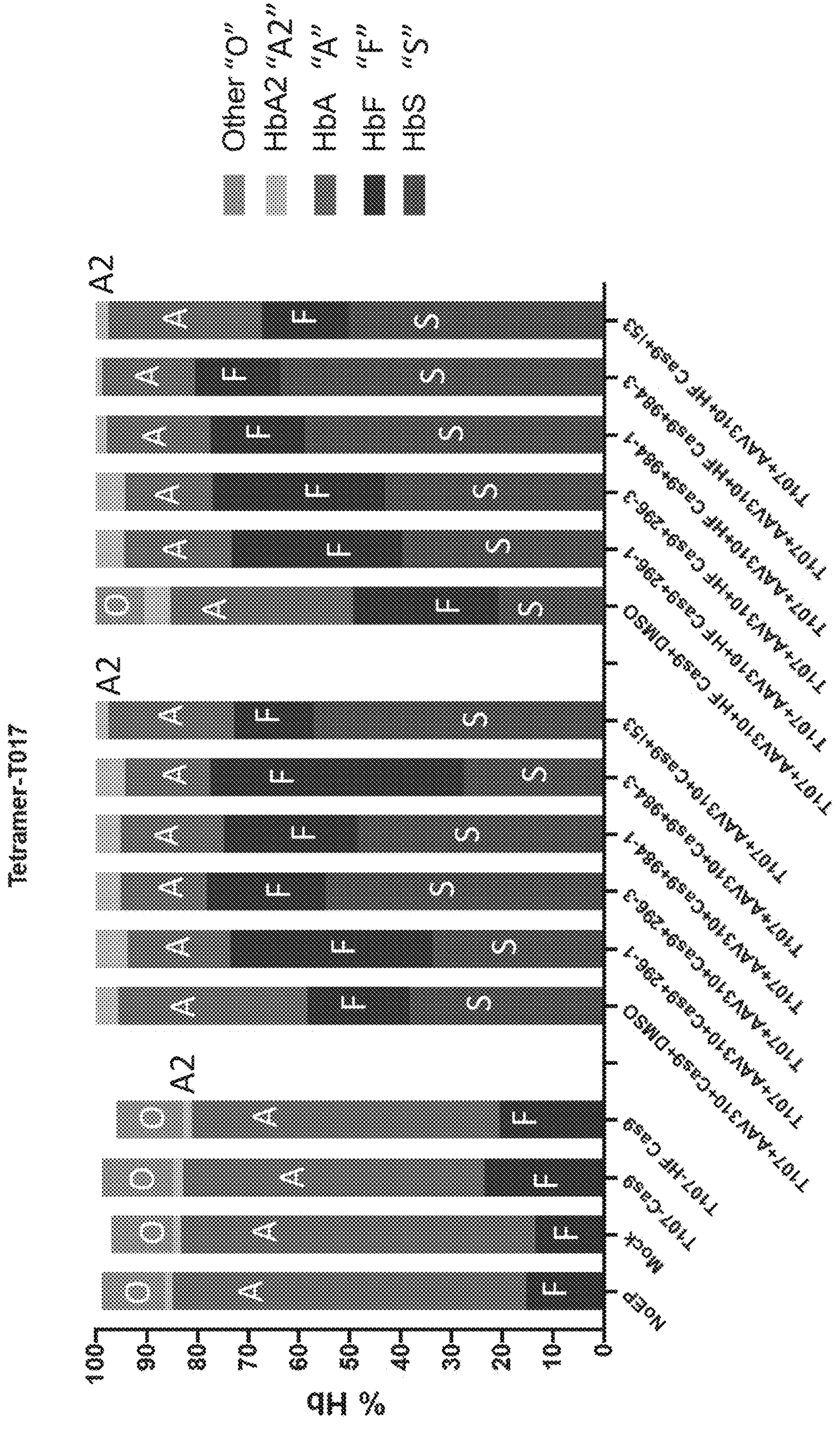
FIG. 7D provides a graph quantifying the percentage of total hemoglobin (Hb) tetramer that was sickle hemoglobin (HbS), fetal hemoglobin (HbF), healthy adult hemoglobin (HbA), hemoglobin A2 (HbA2), and other hemoglobins as produced by edited cells differentiated into erythroid progenitors as in FIGS. 7A-7B and evaluated on day 18 of differentiation.

Furthermore, production of hemoglobin tetramers was also evaluated by HPLC. The analysis included quantification of HbS tetramer containing sickle-globin ($\alpha2\beta$(E6V)2), HbF tetramer ($\alpha2\gamma2$), HbA ($\alpha2\beta2$), and HbA2 ($\alpha2\delta2$) produced by edited cells. As shown in FIG. 7D, increased HbS production and decreased HbA production was seen in differentiated cells following editing with T107 RNP+AAV.310 either alone or combined with treatment with Compound 296, Compound 984, or i53 as compared to control cells. Thus, the editing was also sufficient to alter hemoglobin output following in vitro differentiation.

Erythrocyte Functionality

Figure 7E:
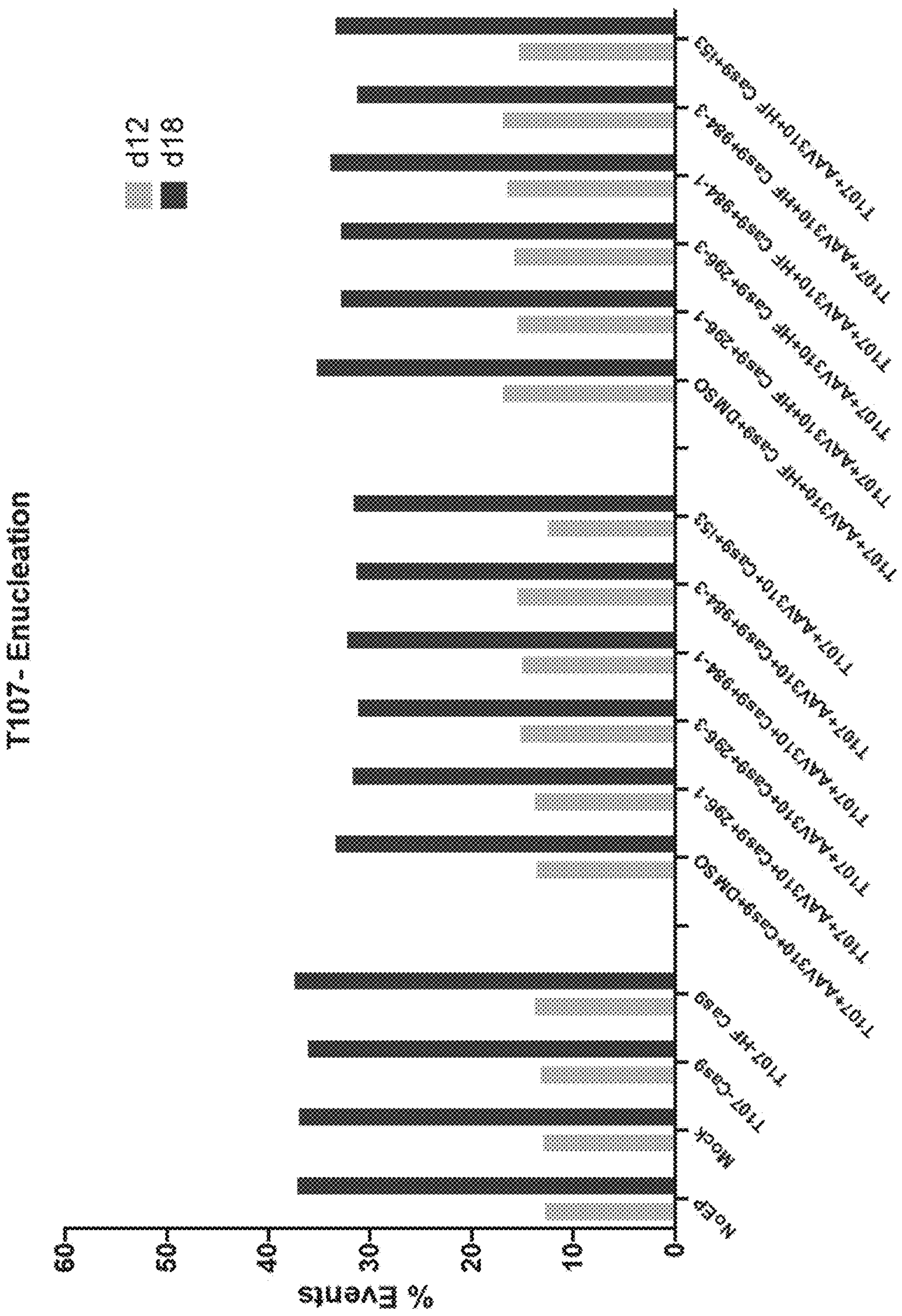
FIG. 7E provides a graph quantifying the percentage of enucleated cells as measured by flow cytometry from edited cells differentiated into erythroid progenitors as in FIGS. 7A-7B and evaluated on day 12 and day 18 of differentiation.

The ability of edited cells to differentiate to functional erythrocytes was assessed by determining expression of erythrocyte-associated cell surface markers and enucleation using flow cytometry on day 12 and 18 post editing. Briefly, $4\times10^5$ cells were obtained, and half were stained for erythrocyte cell-surface markers and half were used for detection of enucleation. For staining cell-surface markers, the cells were incubated in PBS containing 1% human serum albumin (PBS-A) and an antibody cocktail of anti-CD233(BRIC6-Band3)-FITC, anti-CD71-PE, anti-CD235a(GlyA)-PE/Cy7, and anti-CD49d ($\alpha$4)-VioBlue. For detection of enucleation, 2 drops of NucRed nuclear staining reagent was added to 1 mL PBS-A, and 100 μL was added to plated cells. Following incubation, both cell samples were labeled with Sytox Blue solution (1:1000 dilution in PBS-A) for live/dead analysis. Samples were then assessed by flow cytometry As shown in FIG. 7E, cells edited with T107 RNP+AAV.310 alone or combined with Compound 296, Compound 984, or i53 demonstrated levels of enucleation comparable to control cells (>30% of cell population having enucleation on day 18 post-editing).

Additionally, the proportion of the population that was CD71+CD235a+ erythrocytes was similar for cells edited with T107 RNP+AAV.310 alone or combined with inhibitors as compared to control cells when evaluated on day 12 and day 18 post-editing (data not shown).

Example 6: In Vivo Engraftment of CD34+ HSPCs Following Editing with T107 RNP, an AAV Donor Template, and DNA-PK Inhibitors The ability of CD34+ HSPCs edited with T107 RNP and an AAV-donor template encoding either a SCD mutation (AAV.310) or SCD correction (AAV.320) were evaluated for the ability to engraft and retain the SCD gene-edit following administration in vivo. Healthy donor CD34+ HSPCs were edited with T107 RNP+AAV only or combined with DNA-PK inhibitors (Compound 984) or i53.

Briefly, frozen CD34+ HSPCs isolated from plerixafor-mobilized peripheral blood obtained from two healthy human donors were thawed and seeded in media with components as described in Example 1. The cells were maintained in culture, and gene-editing was performed following two days of culture. For editing, $5\times10^5$ CD34+ HSPCs were electroporated with RNP containing 20 μg SpCas9 and 20 μg T107 sgRNA. Electroporation was performed using the CA-137 program of the Lonza Amaxa™ 4D-Nucleofector™. The cells were transduced with AAV.310 or AAV.320 for 1 hour at 37° C. prior to electroporation at a dose of 10,000 MOI. The cells were electroporated and immediately plated in medium containing Compound 984 at 1 μM or 3 μM. For comparison, control cells were electroporated with T107 RNP and an AAV-donor template (AAV.310 or AAV.320) in the absence of the inhibitor. Additionally, comparison was made to HSPCs electroporated with T107 RNP and an AAV-donor template (AAV.310 or AAV.320) and treated with 1 μg i53 mRNA during electroporation. Control cells included CD34+ HSPCs electroporated with T107 RNP only and CD34+ HSPCs electroporated in the absence of RNP, AAV, and inhibitor (mock EP).

Cells were maintained in culture for two days following electroporation. Fold change in cell-growth between day 0 and day 2 post-electroporation was quantified. CD34+ HSPCs edited with T107 RNP+AAV.310 or T107 RNP+AAV.320 demonstrated similar levels of cell-growth, and no substantial change in cell growth was observed if the cells were edited with i53 or Compound 984 (data not shown).

Figure 7F:
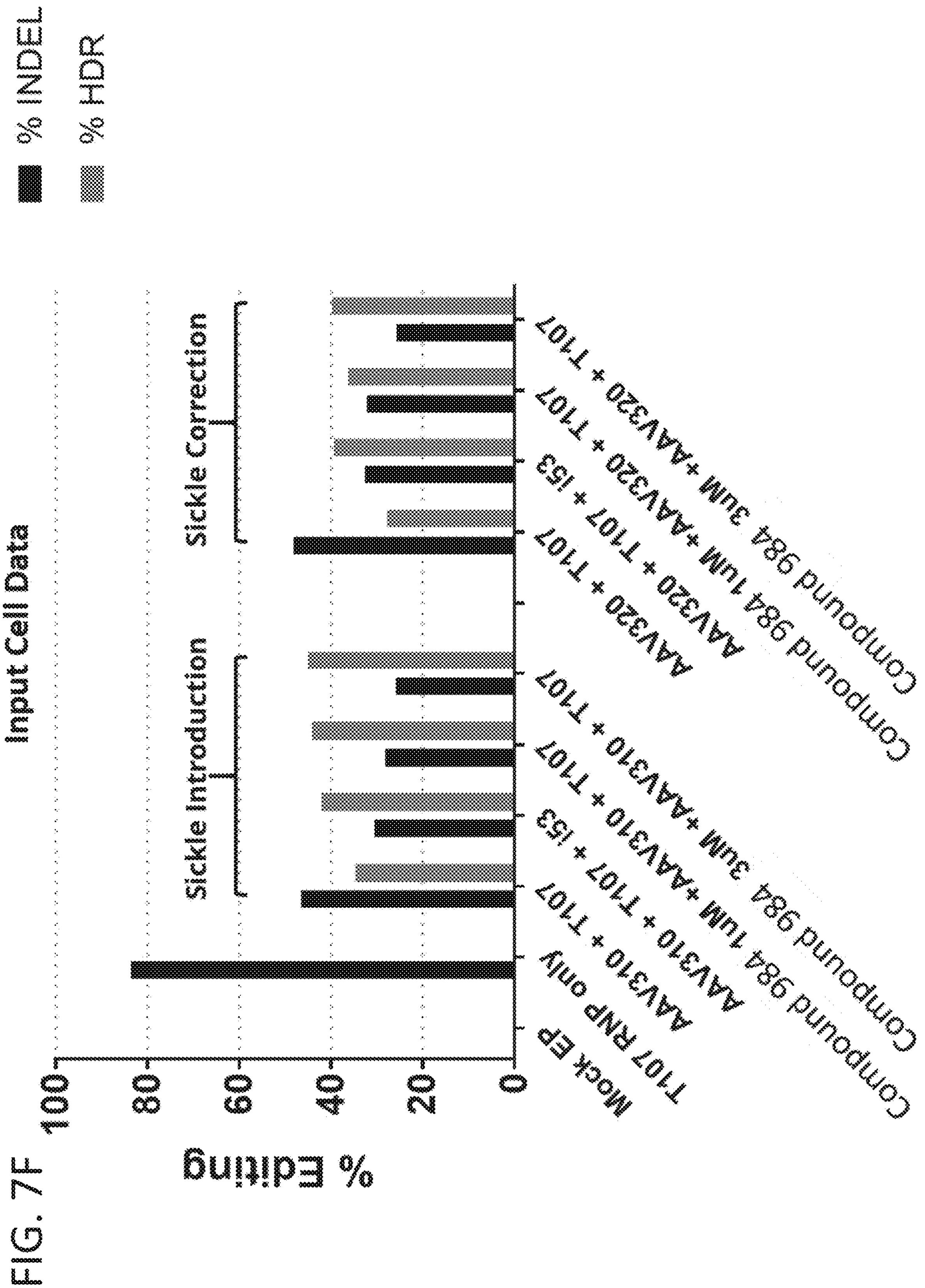
FIG. 7F provides a graph quantifying the frequency of incorporation of a donor template-encoded gene edit by HDR and frequency of INDELs in HBB as measured in healthy donor CD34+ HSPCs edited with T107 RNP and either an AAV.310 donor template encoding a SCD mutation or an AAV.320 donor template encoding a SCD correction. Editing was performed with T107 RNP+AAV only; T107 RNP+AAV combined with Compound 984 at 1 μM or 3 μM; or T107 RNP+AAV combined with mRNA encoding i53. Control cells were edited with T107 RNP only (no AAV or inhibitor) or electroporated without RNP, AAV, or inhibitor (mock EP).

Additionally, gene-edits in HBB were evaluated in CD34+ HSPCs following two days of in vitro culture. The efficiency of HDR for incorporating HBB gene-edits encoded by AAV.310 or AAV.320 and the frequency of INDELs at the T107 cut site were quantified by NGS as described in Example 1, and is shown in FIG. 7F. Editing with T107 RNP only resulted in a frequency of 83% INDELs at the T107 cut site that was reduced if editing was performed in combination with either AAV.310 or AAV.320. Additionally, editing that included treatment with i53 or Compound 984 resulted in decreased frequency of INDELs and increased frequency of HDR relative to editing performed with T107 RNP and AAV only.

Following two days of in vitro culture, HSPCs were administered by intravenous injection to NBSGW mice at a dose of $0.5\times10^6$ cells per mouse. Recipient mice were treated with sublethal irradiation (100 cGy) at 1 day prior to administration of HSPCs. The study groups included administration of HSPCs edited as follows:

(i) mock EP;
(ii) T107 RNP only;
(iii) T107 RNP+AAV.310;
(iv) T107 RNP+AAV.310+i53;
(v) T107 RNP+AAV.310+Compound 984 1 μM;
(vi) T107 RNP+AAV.310+Compound 984 3 μM;
(vii) T107 RNP+AAV.320;
(viii) T107 RNP+AAV.320+i53;
(ix) T107 RNP+AAV.320+Compound 984 1 μM; and
(x) T107 RNP+AAV.320+Compound 984 3 μM.

Figure 7G:
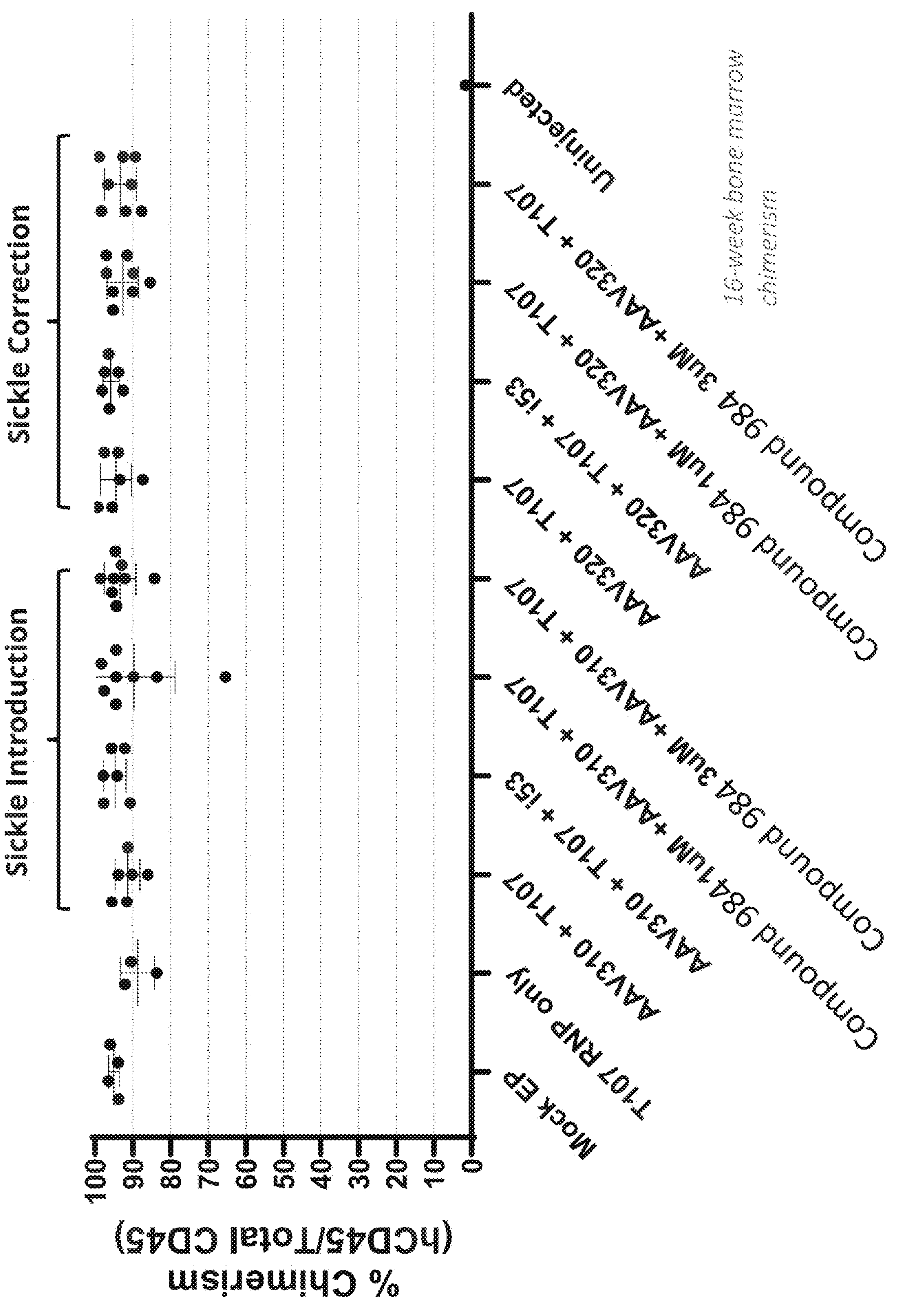
FIGS. 7G-7H provide graphs quantifying engraftment of human cells as measured in mouse bone marrow (FIG. 7G) or mouse blood (FIG. 7H) isolated at 16 weeks following in vivo administration of CD34+ HSPCs edited as in FIG. 7F. Engraftment is measured as percent human chimerism, which is the fraction or % of cells expressing human CD45 relative to total CD45 (h+m CD45)-expressing cells as quantified by flow cytometry.
Figure 7H:
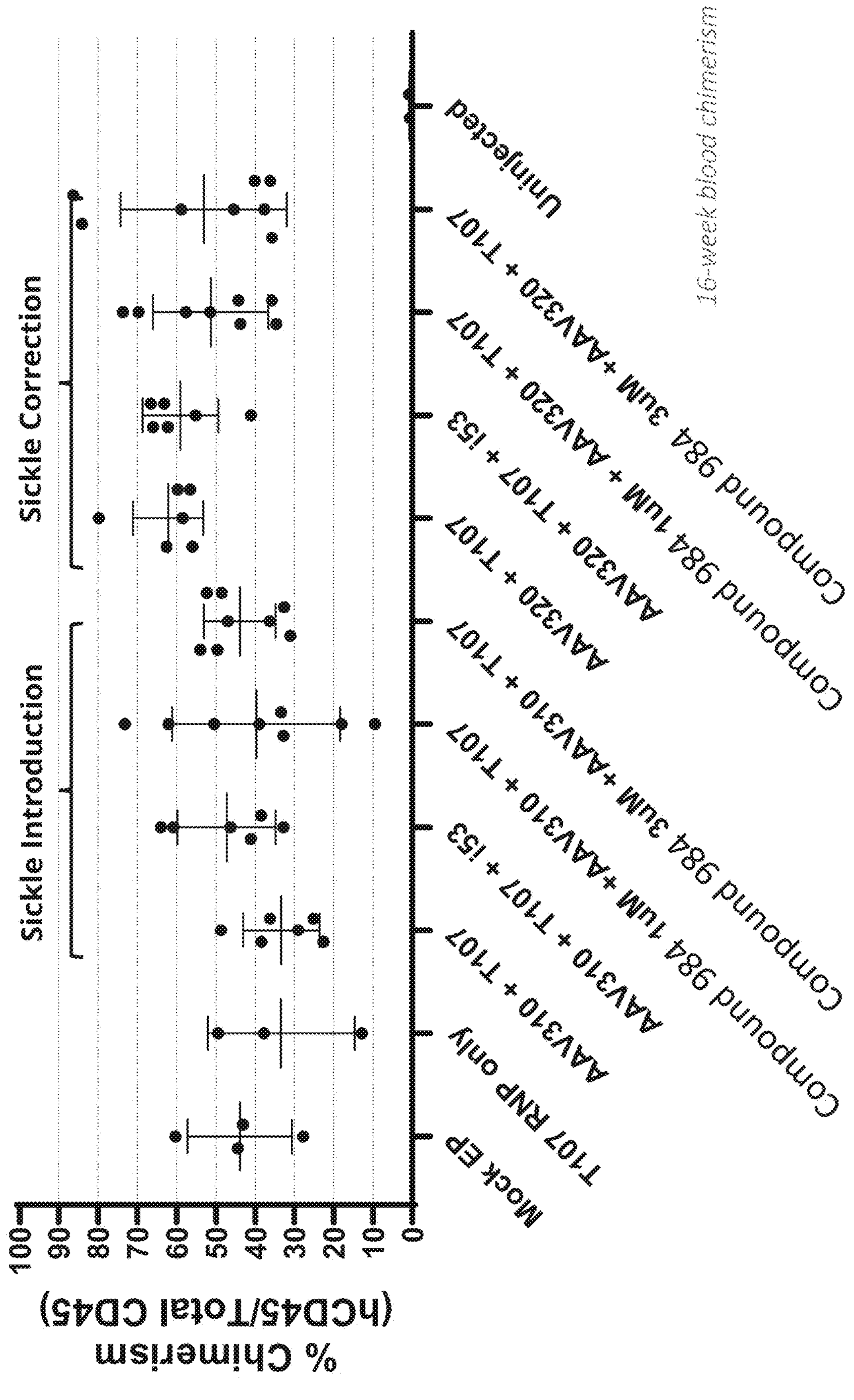

Blood and bone marrow were extracted at 16 weeks following HSPC administration and were evaluated for presence of human hematopoietic cells using flow cytometry as described in Example 2. Additionally, the lineage of human CD45+ cells was determined using markers for human B cells, T cells, myeloid cells, and HSPCs as described in Example 2. As shown in FIGS. 7G-7H, the percent chimerism (percentage of human CD45+ cells relative total cells expressing human CD45 or mouse CD45) in mouse bone marrow and blood was comparable for mice that were administered cells edited with T107 RNP and either AAV.310 or AAV.320. Similarly, the percent chimerism was comparable in mice that were administered HSPCs edited with i53 or Compound 984. Moreover, the lineage distribution evaluated in each mouse treatment group was comparable (data not shown).

Figure 7I:
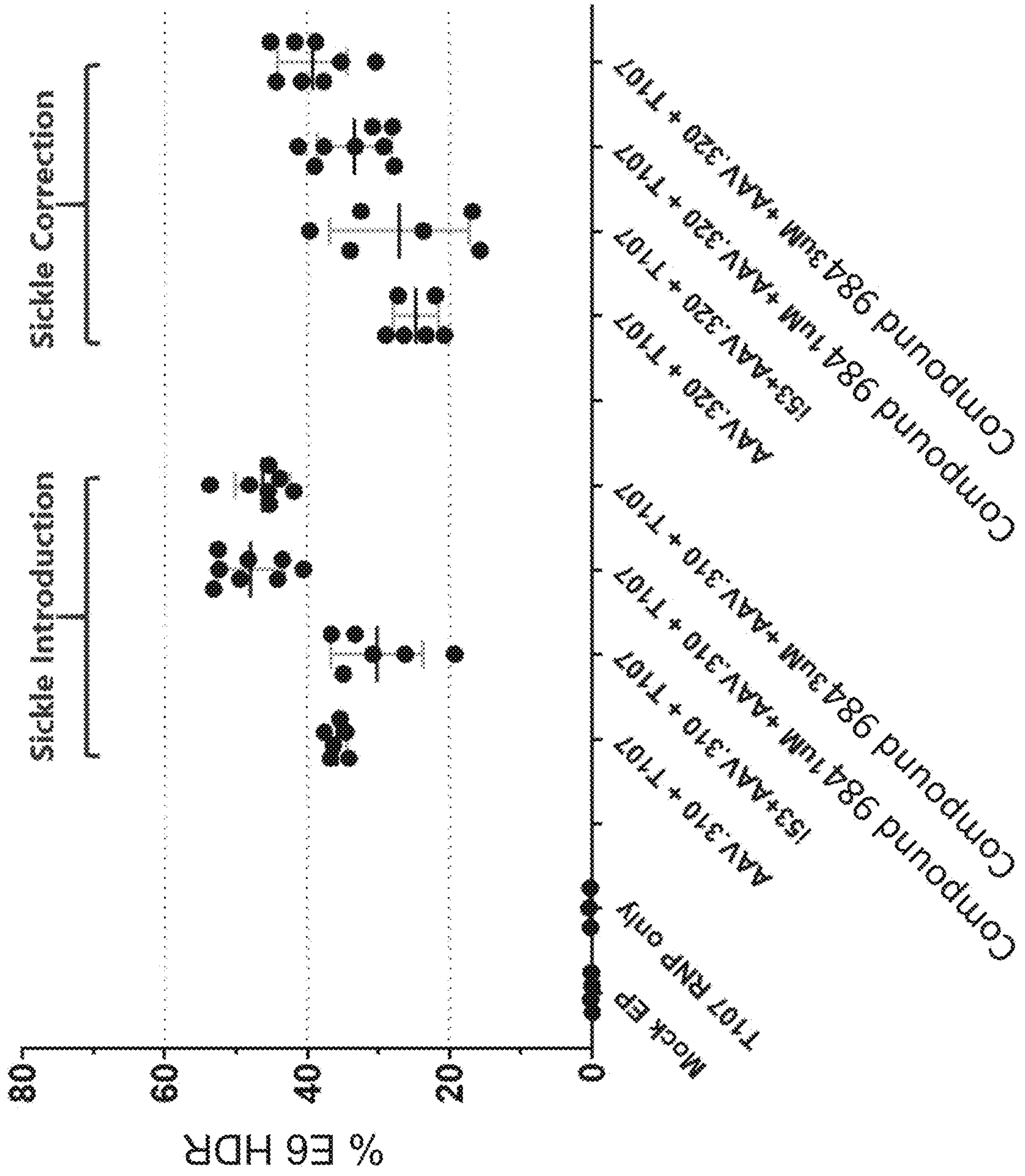
FIGS. 7I-7J provide graphs quantifying the long term persistence of gene edited cells in the BM of mice engrafted with edited HSPCs as measured by the frequency of a donor template-encoded gene edit (which is the E6 HDR) (FIG. 7I) and frequency of INDELs (FIG. 7J) in HBB as measured in genomic DNA harvested from mouse bone marrow isolated 16 weeks following in vivo administration of CD34+ HSPCs edited as in FIG. 7F.
Figure 7J:
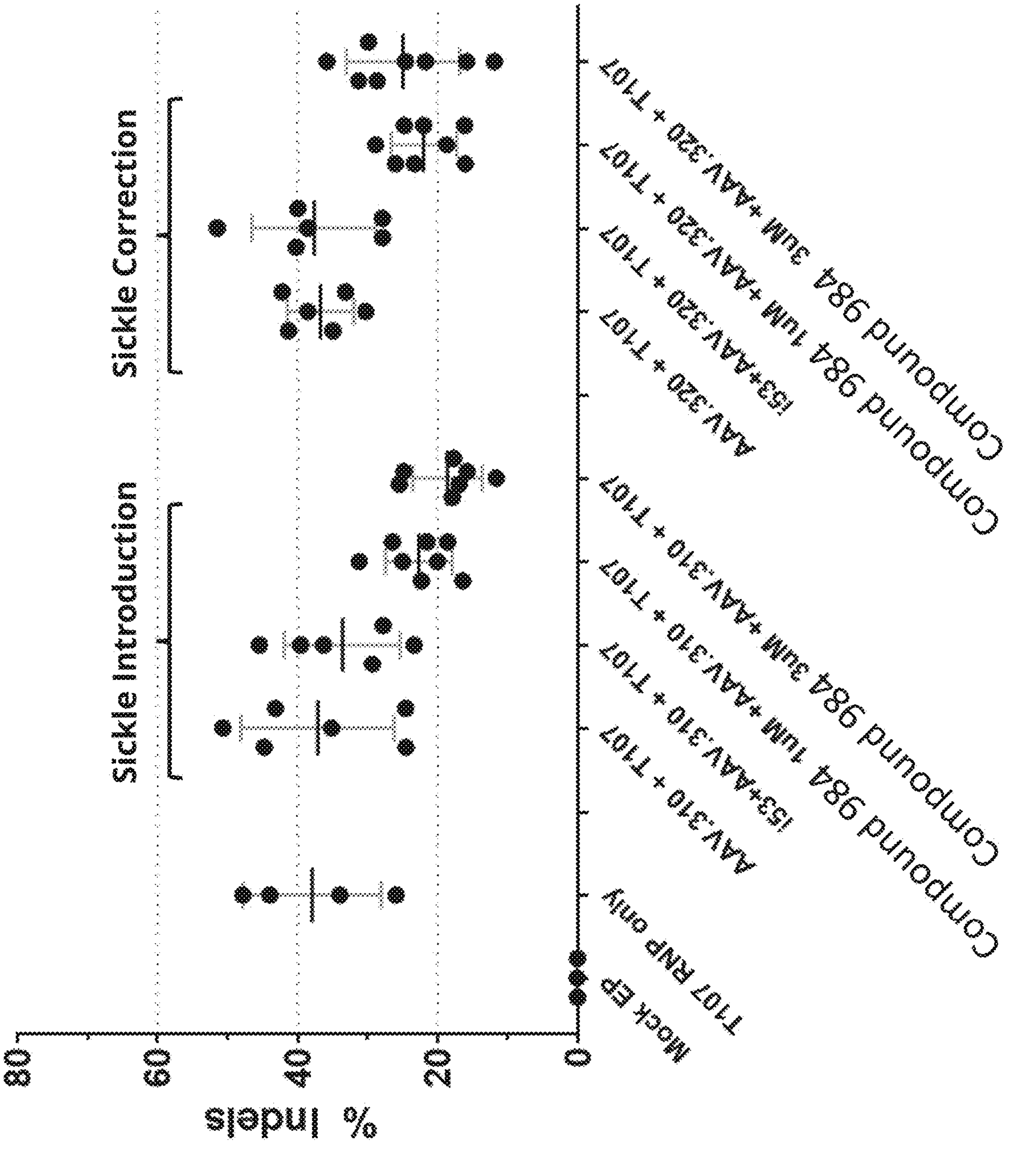

The long term persistence of gene-edited (in HBB gene) HSPCs was evaluated in genomic DNA extracted from mouse bone marrow collected at 16 weeks. The frequency of donor template-encoded gene-edits incorporated in HBB by HDR and the frequency of INDELs at the T107 cut site were quantified by NGS, and are shown in FIG. 7I and FIG. 7J respectively. The frequency of gene-edits as measured in mouse bone marrow was comparable to the frequency of gene-edits in input CD34+ HSPCs prior to transplantation (see FIG. 7F). Thus, long term hematopoietic cells derived from edited CD34+ HSPCs engrafted and maintained the desired gene-edit following in vivo administration and transplantation. This suggests grafts will be maintained throughout life of the animal and provides rational for therapeutic use of this technique in human disease (SCD) treatment.

Example 7: In Vitro Editing of CD34+HSPCs with T107 RNP and ssODN

Efficiency of HDR was evaluated using T107 RNP or R02 RNP combined with a corresponding single-stranded donor oligonucleotide (ssODN). Specifically, a 200 mer ssODN was used having a donor template encoding a SCD mutation flanked by a left and right homology arms. The sequence of the ssODN used with T107 RNP is set forth by SEQ ID NO: 17; the sequence of the ssODN used with R02 RNP is set forth by SEQ ID NO: 16.

Editing was performed using healthy donor CD34+ HSPCs derived from plerixafor-mobilized peripheral blood that were cultured as described in Example 1. Following two days of culture, $0.5\times10^6$ cells CD34+ HSPCs were electroporated with RNP containing 20 μg SpCas9 and 20 μg T107 sgRNA or 20 μg R02 sgRNA. Electroporation was performed using the CA-137 program of the Lonza Amaza™ 4D-Nucleofector™. ssODN donor template (1 μM) was added to the electroporation in samples where indicated. Additionally, following electroporation, the cells were immediately plated in medium containing the DNA-PK inhibitor Compound 984 at 3 μM. Control cells were electroporated with T107 RNP only; R02 RNP only; electroporated in the absence of RNP, ssODN, and inhibitor (mock); or not electroporated.

Figure 7K:
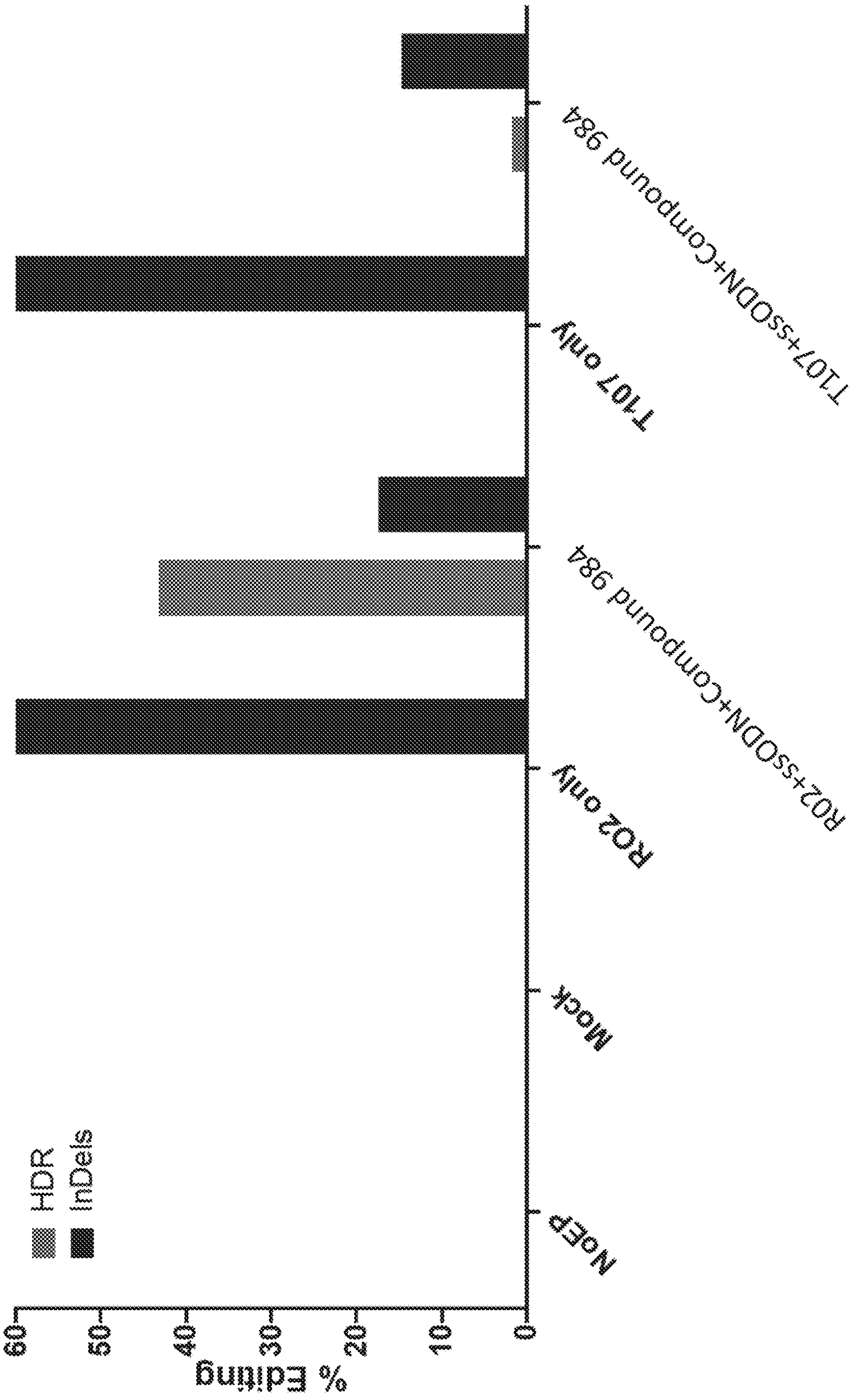
FIG. 7K provides a graph quantifying the frequency of a E6V HDR using single-stranded oligo DNA nucleotide (ssODN) as donor templates in healthy donor-derived CD34+ HSPCs following editing with (i) T107 RNP, ssODN, and Compound 984; or (ii) R02 RNP, ssODN, and Compound 984. Control groups were edited with T107 RNP only; R02 RNP only; electroporation in the absence of RNP, ssODN, or Compound 984 (Mock); or no electroporation.

On day 2 post-editing, the efficiency of HDR repair for inducing a SCD mutation in the HBB gene was quantified by NGS assay as described in Example 1, and the frequency of INDELs induced at the guide cut site was also evaluated by NGS analysis. As shown in FIG. 7K, the efficiency of HDR for introducing the ssODN-encoded gene-edit was approximately 40% if R02 RNP was combined with ssODN and Compound 984 to perform editing. Additionally, INDELs induced at the R02 cut site were reduced compared to editing with R02 RNP only. However, efficiency of HDR was low if T107 RNP was combined with ssODN and Compound 984 to perform editing.

Example 8: Comparison of Guides Targeting Intron 1 of HBB

The T223 intron targeting gRNA was evaluated for introducing a gene-edit in human HBB in CD34+ HSPCs. As shown in Table 10, the T223 gRNA spacer sequence is the nucleotide sequence set forth in SEQ ID NO: 51; and the T223 target sequence has the nucleotide sequence of SEQ ID NO: 49. The T223 target sequence is located in intron 1, and is adjacent an SpCas9 PAM sequence (GGG). The T223 PAM is located 10 nt upstream the T107 PAM. Additionally, the T223 cut site is 116 bp downstream the E6V mutation. In the Examples section, editing with T223 refers to editing performed with T223 sgRNA set forth by SEQ ID NO: 52, unless indicated otherwise.

TABLE 10

Sequences of intron-targeting T223 sgRNA

| Name/ Description | Sequence | SEQ ID NO |
|---|---|---|
| HBB Target Sequence | TAAGGAGACCAATAGAAACT | 49 |
| HBB Target Sequence with PAM | TAAGGAGACCAATAGAAACT GGG | 50 |
| T223 Spacer Sequence | UAAGGAGACCAAUAGAAACU | 51 |
| T223 sgRNA (spacer in bold) | **usasasGGAGACCAAUAGAAACU** GUUUUAGAGCUAGAAAUAGCAAG UUAAAAUAAGGCUAGUCCGUUAU CAACUUGAAAAAGUGGCACCGAG UCGGUGCusUsUsU | 52 |

a, c, g, u: 2' O-methyl phosphorothioate nucleotides
s: phosphorothioate nucleotides
A, C, G, U, N: canonical RNA nucleotides Healthy donor CD34+ HSPCs derived from plerixafor-mobilized peripheral blood were cultured as described in Example 1 for two days prior to editing. Editing was performed using $1\times10^6$ CD34+ HSPCs per treatment group. The cells were electroporated with RNP containing the following 20 μg SpCas9 and 20 μg T107 sgRNA, 20 μg T223 sgRNA, or 20 μg R02 sgRNA. Electroporation was performed using the CA-137 program of the Lonza Amaza™ 4D-Nucleofector™. The cells were transduced with AAV6 donor templates encoding a SCD mutation (AAV.309; AAV.310; AAV.311) by incubating the cells with AAV at a dose of 10,000 MOI for one hour prior to electroporation. Control cells were transduced with AAV only and electroporated in the absence of RNP.

Figure 8A:
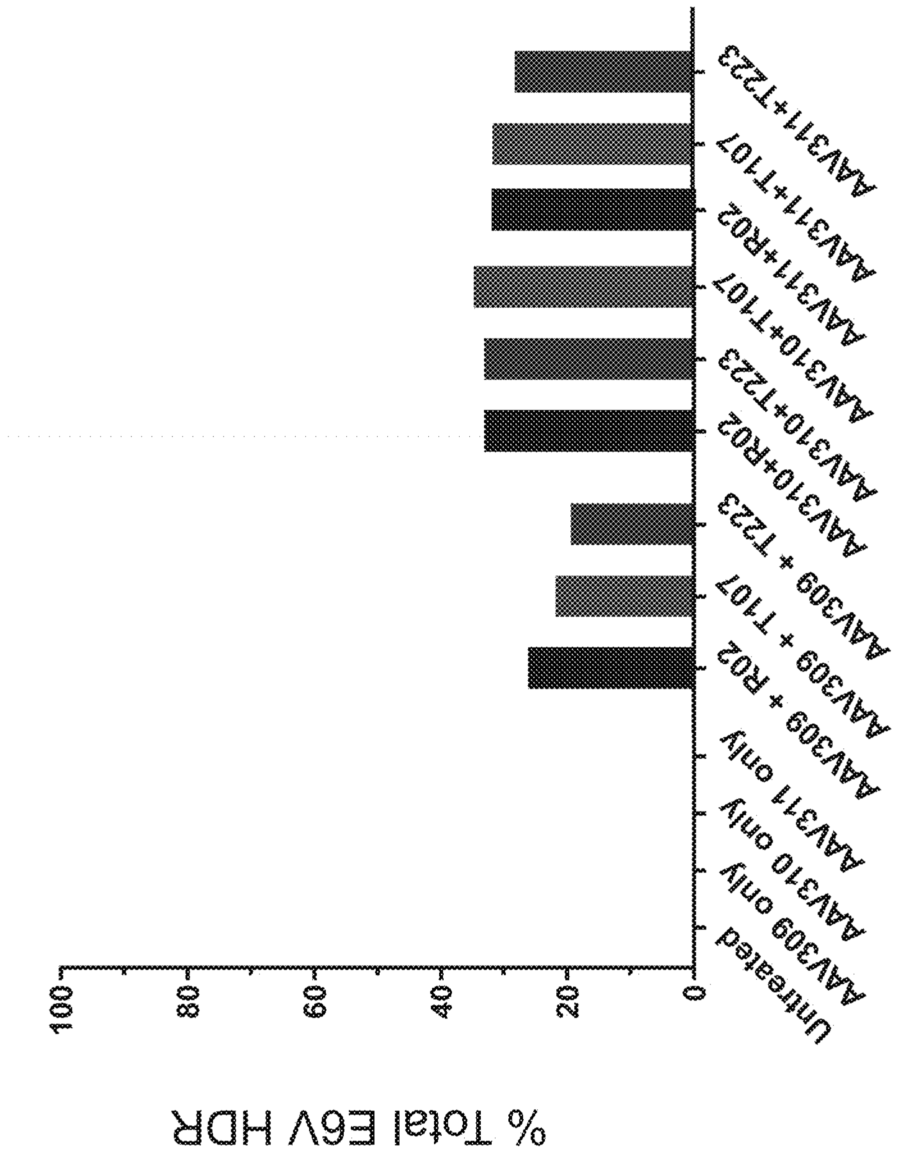
FIG. 8A provides a bar graph quantifying the frequency of incorporation of a donor template-encoded gene-edit by HDR repair in the HBB gene locus in CD34+ HSPCs derived from a healthy donor that were edited with R02 RNP, T107 RNP, or RNP containing the intron-targeting T223 gRNA when combined with AAV-donor templates AAV.309, AAV.310, or AAV.311. Control cells were edited with AAV donor template only.

On day 2 post-editing, the efficiency of HDR repair for inducing a SCD mutation in the HBB gene was quantified by NGS assay as described in Example 1. As shown in FIG. 8A, editing performed with intron-targeting guides T107 and T223 resulted in similar levels of HDR for introducing the SCD mutation with each of the AAV donor templates evaluated.

Figure 8B:
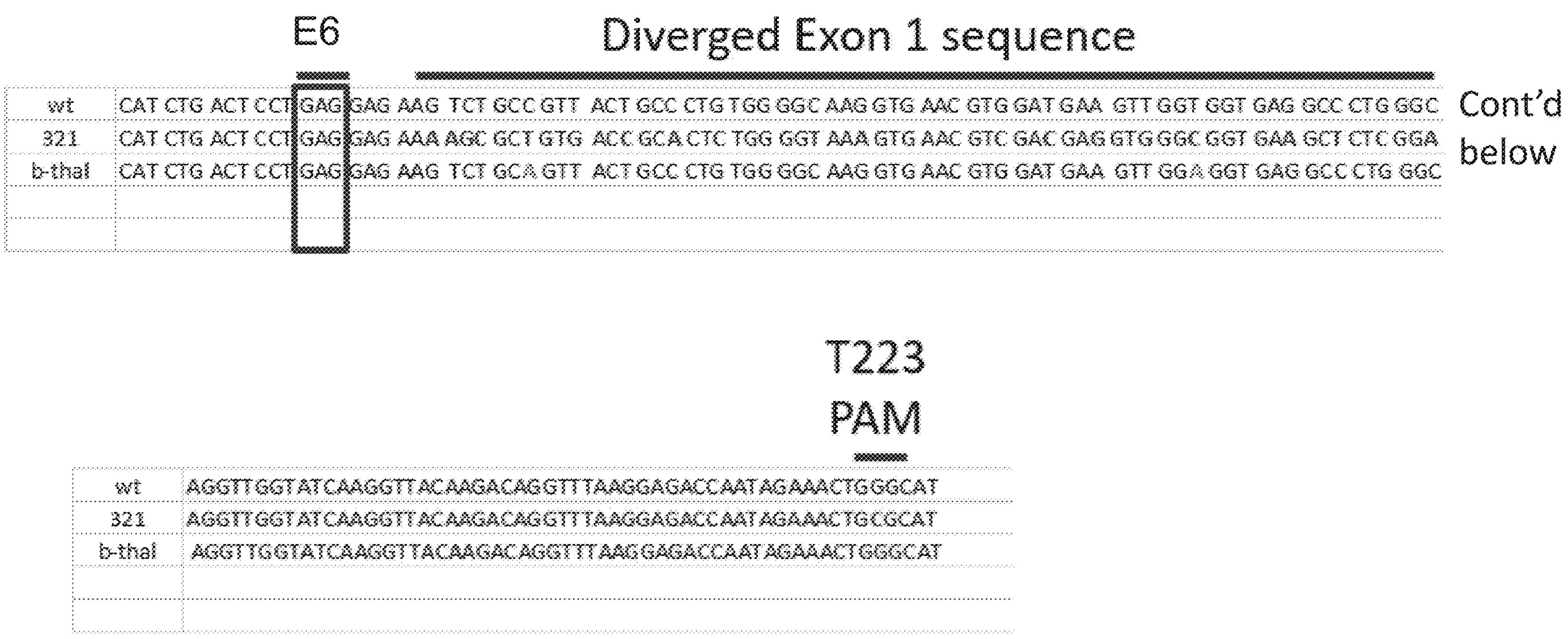
FIG. 8B provides a schematic showing the region of wild-type (WT) HBB or HBB with a beta-thalassemia mutation that contains the 3' end of exon 1 and 5' end of intron 1 (SEQ ID NO: 53 or SEQ ID NO: 54, respectively). The PAM sequence for the intron-targeting T223 gRNA (T223 RNP) is depicted. Also shown is an alignment to a region of AAV.321 (corresponding to nucleotides 2343-2481 of SEQ ID NO: 21), an AAV-encoded homology donor for use with T223. As shown, the homology donor contains a single nucleotide substitution within the T223 PAM, a codon at position 6 downstream the HBB start codon that encodes glutamate, and several diverged nucleotides relative to exon 1 of HBB.

Example 9: In Vitro Editing of HBB in CD34+ HSPCs Using Intron Targeting T223 RNP and an AAV Donor Template Encoding a SCD Correction The T223 intron targeting guide was further evaluated with an AAV-donor template encoding a correction to the SCD mutation. Specifically, the AAV-encoded homology donor referred to as "AAV.321" and identified by sequences in Table 11 was used in combination with the T223 guide for introducing a gene-edit in HBB. As shown in FIG. 8B, the AAV.321 donor template encodes a correction to the E6V mutation in HBB exon 1 with glutamate encoded at codon 6 downstream the HBB start codon as wild-type codon "GAG". Additionally, the AAV.321 donor template encodes a single nucleotide mutation that converts the T223 PAM sequence from GGG to GCG, thereby preventing re-cutting by SpCas9/T223 sgRNA following correction of HBB with the AAV.321 donor template.

TABLE 11

Sequence of the AAV.321 Homology Donor Template Encoding SCD Correction

| Name/Description | SEQ ID NO |
|---|---|
| 5' ITR | 18 |
| Region encoding E6V → E6 and PAM mutation | 19 |
| 3' ITR | 7 |
| AAV.321 | 20 |
| AAV.321 with ITRs | 21 |

Gene-editing of HBB was evaluated using CD34+ HSPCs that were derived and maintained in culture as described in Example 1. HSPCs were subjected to gene-editing following two days of culture. To perform gene-editing, the cells were electroporated with RNP. Specifically, $5\times10^6$ cells were electroporated using the Maxcyte Buffer/HSC-3 program with RNP containing 20 μg SpCas9 and 20 μg sgRNA (T223 or R02). Cells were transfected with corresponding AAV donor template at a dose of 10,000 MOI (AAV.321 or AAV.323 respectively). The effect of 53BP1 inhibition and DNA-PK inhibitions on editing with RNP+AAV was also evaluated by treating cells with 1 μM i53 mRNA or 1 μg i53 mRNA+1 μM Nu7441. Nu7441 was added post electroporation for 48 hours in culture.

(i) T223 RNP+AAV.321; and (ii) T223 RNP+AAV.321+i53.

Cell samples treated with exon-targeting R02 included:

(i) R02 RNP+AAV.323;

(ii) R02 RNP+AAV.323+i53; and (iii) R02 RNP+AAV.323+i53+Nu7441. For the cell samples of (i) and (ii), electroporation was performed using the CA-137 program of the Lonza Amaza™ 4D-Nucleofector™.

Control samples included:

(i) cells that were not edited (culture control);

(ii) cells electroporated in the absence of RNP or AAV (mock EP);

(iii) cells electroporated with T223 RNP only; and (iv) cells electroporated in the absence of RNP and treated with AAV (AAV.321+mock EP).

The cells were cultured for two days following electroporation and prior to evaluation of editing efficiency. To evaluate editing efficiency, genomic DNA was harvested from edited cells, and frequency of HDR and frequency of INDELs at the predicted gRNA cut site was evaluated as described in Example 1.

Figure 9A:
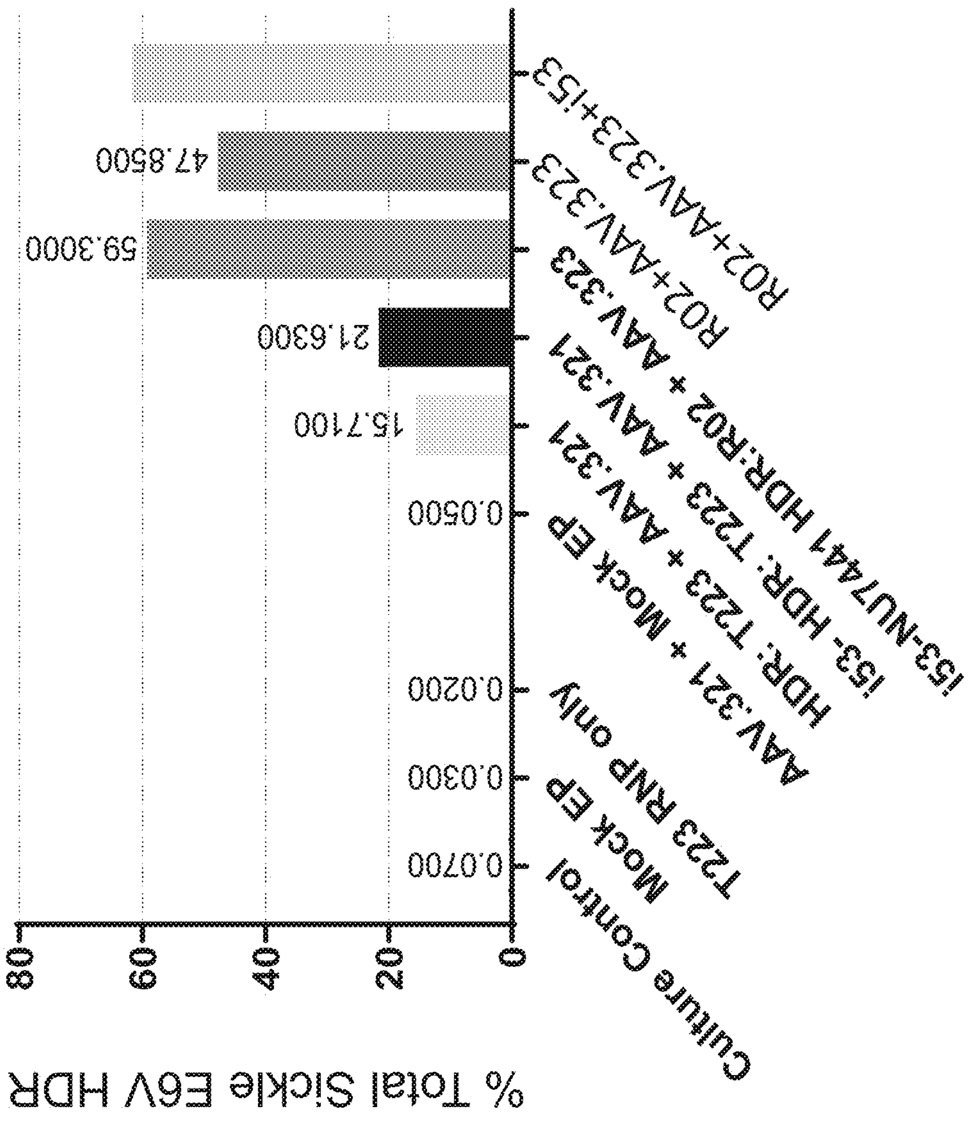
FIGS. 9A-9B provide bar graphs quantifying the frequency of incorporation of a donor-template-encoded gene edit by HDR repair (FIG. 9A) and frequency of INDELs (FIG. 9B) in the HBB gene locus in CD34+HSPCs derived from healthy donors that were edited with T223 RNP and AAV.321. Editing was performed with T223 RNP+AAV.321 only or in combination with mRNA encoding i53. Comparison is shown to CD34+HSPCs edited with R02 RNP+AAV.323 alone, R02 RNP+AAV.323 combined with i53 mRNA, or R02 RNP+AAV.323 combined with i53 mRNA and Nu7441. Control cells were untreated (culture control), electroporated in the absence of RNP or AAV (mock EP), electroporated and treated with AAV.321 (AAV.321+mock EP), or electroporated with T223 RNP only.
Figure 9B:
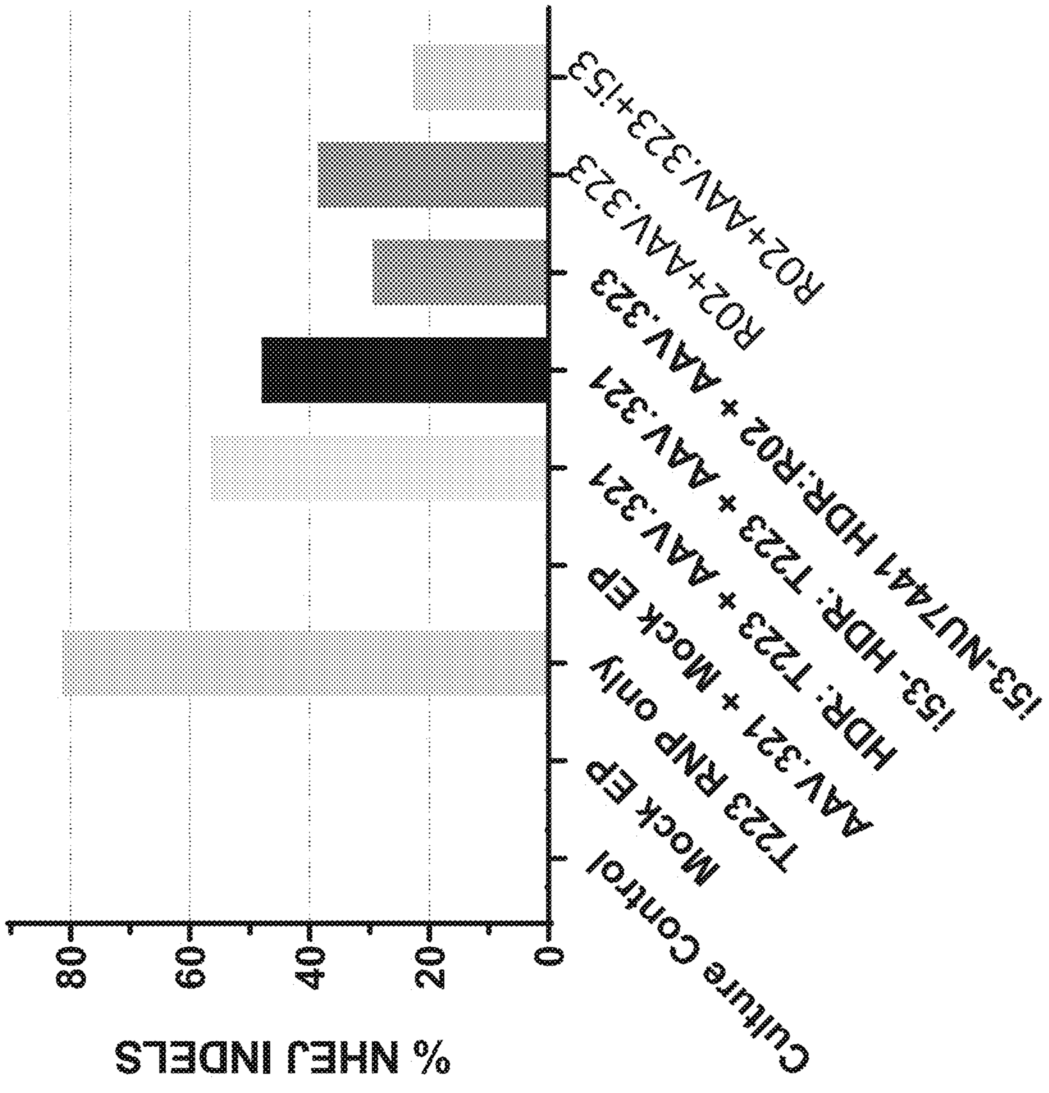

As shown in FIG. 9A, the frequency of genomic DNA incorporating the E6V gene-edit was improved if T223 RNP+AAV.321-edited cells were treated with i53. Additionally, the frequency of INDELs at the T223 cut site was reduced in edited cells that were treated with i53 (FIG. 9B). Together, these data demonstrate effective correction of the HBB locus in CD34+ HSPCs with T223 intron-targeting gRNA.

Example 10: Evaluation of HSPCs Edited Using T223 gRNA Following Administration In Vivo Human CD34+ HSPCs edited as described in Example 9 were evaluated for the ability to engraft and retain the gene-edit following administration in vivo.

Briefly, NBSGW mice received a dose of $0.5\times10^6$ HSPCs, edited as described in Example 9. Control animals received the same dose of HSPCs that were unedited (culture), mock EP cells, RNP-only edited cells, or AAV-only cells. The cells were administered by intravenous injection to the mice at 2 days following electroporation. Recipient mice were treated with sublethal irradiation (100 cGy) at 1 day prior to administration of HSPCs to eliminate hematopoietic cells in the bone marrow and enable engraftment of the donor cells.

Blood samples were extracted at 8 weeks following HSPC administration and both blood and bone marrow samples were extracted at 16 weeks following HSPC administration. The samples were evaluated for presence of human hematopoietic cells by flow cytometry using labeling with the cell-surface markers shown in Table 6. Cells were gated on singlet, live cells. Mouse and human CD45-expressing hematopoietic cells were distinguished as described in Example 2, with engraftment (percent chimerism) measured as the quantity of human CD45 positive cells divided by the total number of CD45 positive cells (human and mouse CD45 expressing cells combined). Moreover, the percentage of erythroid cells that were of human origin (hGlyA+) was measured in bone marrow at 16 weeks. The lineage of human CD45 positive cells was also determined as described in Example 2.

Figure 10A:
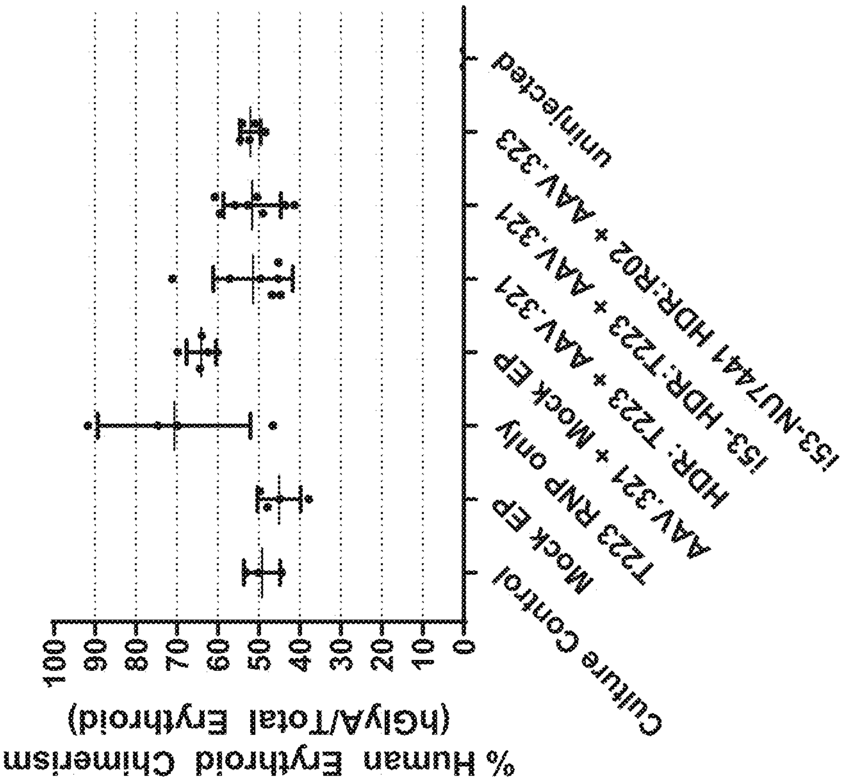
FIGS. 10A-10B provide graphs quantifying the percent of human erythroid lineage cells (gGlyA+) within all the erythroid (human+mouse) lineage cells in the mouse bone marrow (FIG. 10A) or % of human CD45+ chimerism in the mouse bone marrow (FIG. 10B) isolated at 16 weeks following in vivo administration of HSPCs edited as in FIGS. 9A-9B. Engraftment is measured as percent chimerism, which is the % or fraction of cells expressing human CD45 relative to total (human+mouse) CD45-expressing cells as quantified by flow cytometry.
Figure 10B:
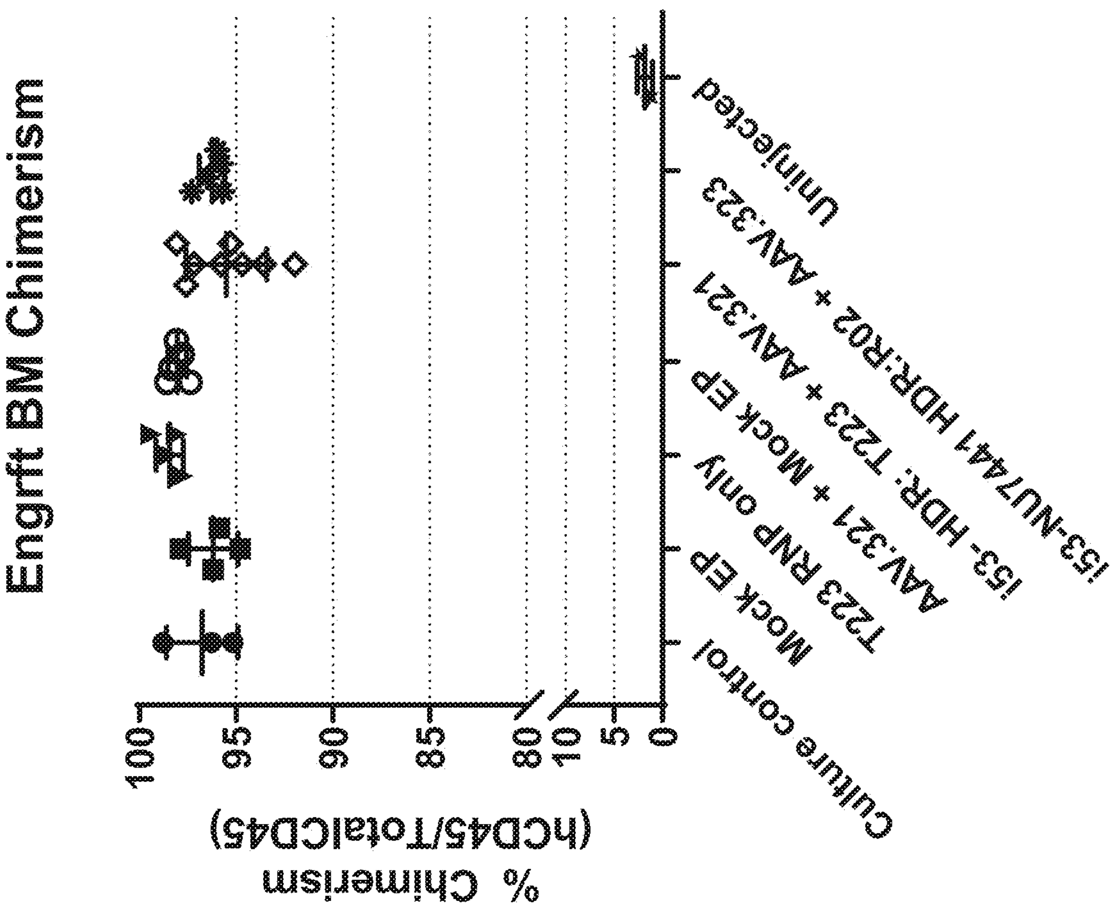

As shown in FIGS. 10A-10B, administration of HSPCs edited with any of the conditions resulted in high levels of chimerism in bone marrow isolated at 16 weeks. FIG. 10A provides analysis of the percentage of total (human+mouse) erythroid cells that were human origin when evaluated in bone marrow at 16 weeks. FIG. 10B provides analysis of the percentage of total (human+mouse) CD45+ cells that were human origin when measured in bone marrow at 16 weeks.

Lineage distribution (CD34+, myeloid, T cells, B cells) was also similar between the groups (data not shown) when measured at 16 weeks.

Figure 11A:
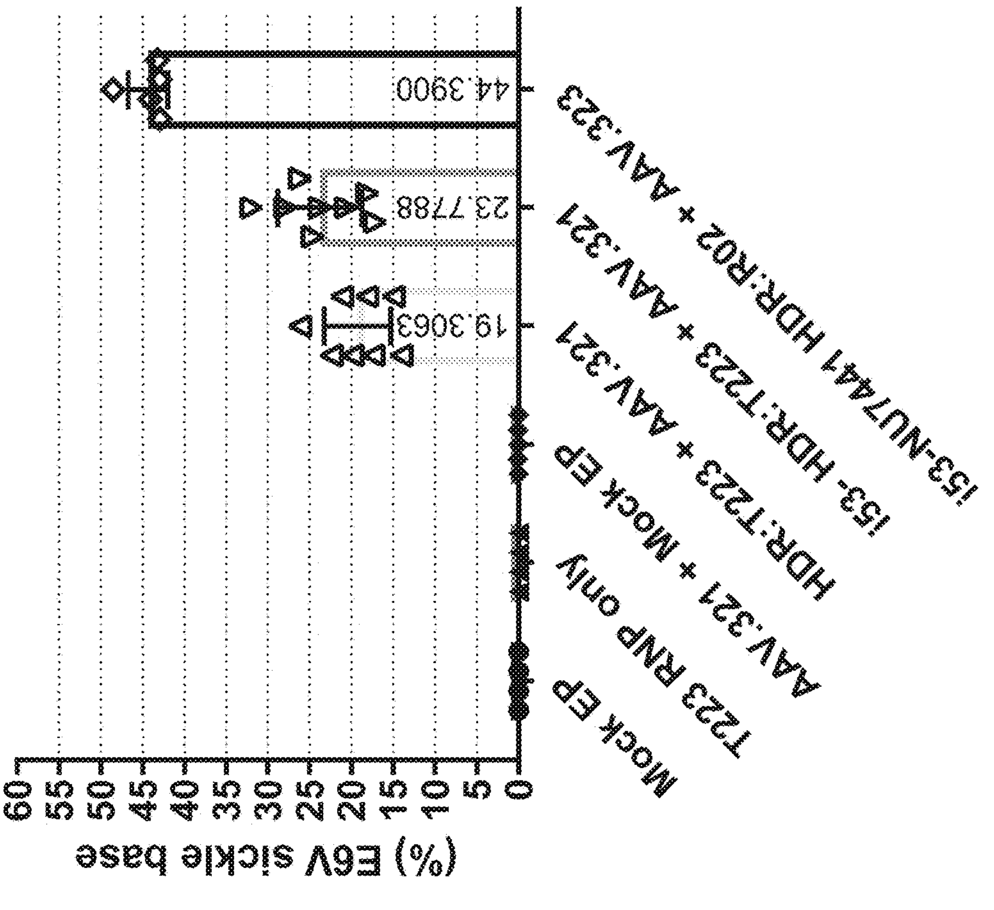
FIGS. 11A-11B provide graphs quantifying the frequency of incorporation of a HDR gene-edit (FIG. 11A) and frequency of INDELs (FIG. 11B) in the HBB gene locus as measured in genomic DNA harvested from mouse bone marrow at 16 weeks following in vivo administration of HSPCs as in FIGS. 10A-10B.
Figure 11B:
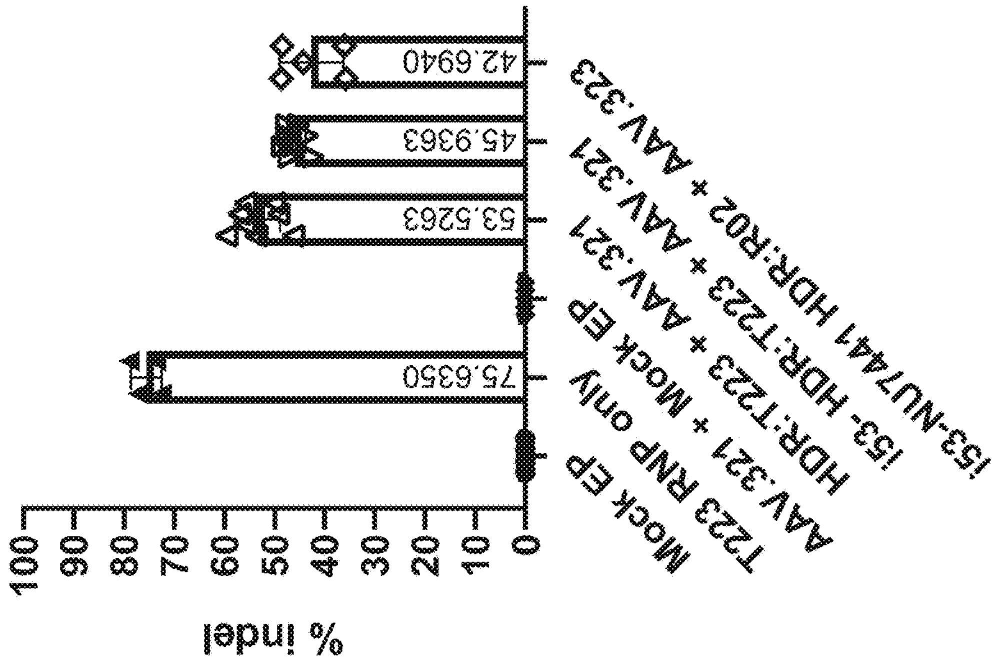

Long term persistence of gene-edited cells (HSPCs) was evaluated in mouse bone marrow collected at 16 weeks post-administration of HSPCs. Incorporation of the desired gene edit in the HBB locus and frequency of INDELs at the HBB cut site was evaluated in genomic DNA harvested from mouse bone marrow samples at 16 weeks post-administration using NGS as described in Example 1. Shown in FIGS. 11A-11B is the frequency of genomic DNA extracted from bone marrow that encoded the desired gene-edit (FIG. 11A) and the frequency of INDELs at the HBB cut site (FIG. 11B). For HSPCs edited with T223 intron guide and AAV (i.e., T223 RNP+AAV.321), the frequency of editing by HDR to incorporate the donor template-encoded gene-edit was comparable in bone marrow at 16 weeks post-administration relative to that measured in the input transplanted cell population (19.3% vs. 15.7%). Additionally, frequency of INDELs at the T223 cut site was comparable post-administration relative to the input transplanted cell population (see FIG. 9B). Together, these data indicate that the input CD34+ HSPC population that had been modified with the desired edits, persisted long term in the animals (16 weeks) and were able to generate edited human lineage cells in the mouse BM.

Example 11: Analysis of Off-Target Genomic Editing with HBB Intron-Targeting gRNAs Off-target sites were investigated that hybridize and are edited by the intron-targeting gRNA (T107 and T223) when provided as an RNP complex with wild-type SpCas9 polypeptide. A comparison was made to off-target sites identified for exon-targeting R02 gRNA provided as RNP.

Briefly, an analysis to identify putative off-target sites was performed using two approaches. The first approach was to computationally screen the human genome to identify genomic sequences complementary to the gRNA spacer sequence with i) up to 3 mismatches, or ii) 2 mismatches and 1 gap. The homology computation off-target prediction was performed using CCTOP, CRISPOR, and COSMID algorithms. Using this approach, the following were identified:

(i) 179 off-target sequences were predicted to have homology to the R02 spacer sequence;
(ii) 173 off-target sequences were predicted to have homology to the T107 spacer sequence; and
(iii) 260 were predicted to have homology to the T223 spacer sequence.

The second approach was to screen candidate off-target sites using GUIDE-Seq (see, e.g., Tsai et al (2015) *NAT. BIOTECHNOL.* 33:187). Based on this approach, the following number of genomic sites were identified as undergoing off-target cleavage per each gRNA:

(i) 36 GUIDE-Seq off-target sites for R02 gRNA;
(ii) 12 GUIDE-Seq off-target sites for T07 gRNA; and
(iii) 43 GUIDE-Seq off-target sites for T223 gRNA.

Candidate off-target sequences were screened using a quantitative hybrid capture assay. Briefly, $5\times10^5$ CD34+ HSPCs were isolated from plerixafor-mobilized peripheral blood obtained from healthy human donors was thawed and seeded in media with components as described in Example 1. The HSPCs cultured for two days, then electroporated with RNP containing 15 μg SpCas9 polypeptide and 15 μg sgRNA, either R02, T107, or T223 sgRNA. The SpCas9 polypeptide used for editing was obtained from two separate commercial vendors, and is referred to as WT SpCas9_1 and WT SpCas9_2 herein. Control cells were electroporated without RNP.

Edited and control cells were harvested, and genomic DNA was extracted using a DNeasy kit (Qiagen). The genomic DNA samples were hybridized with short probes that were prepared to overlay the region of the genomic DNA that included the putative off-target sequences (computational prediction+guide seq). Bound genomic DNA was then enriched using a pull-down purification targeting the hybridization probe. The genomic DNA was then sequenced for frequency of INDELs by NGS analysis. The ratio of total number of reads with INDELs to the total number of reads was quantified for each putative target site for genomic DNA isolated from edited cells and control cells. For putative off-target sites with a frequency of INDELs exceeding 0.2% in edited cells compared to donor-matched control cells, the target site was evaluated by statistical testing. A paired, one-sided T test was used to identify sites with a statistically significant difference in frequency of INDELs between edited and control cells ($p<0.05$).

Based on this analysis, the following number of sites were identified as having a statistically significant level of off-target editing per each RNP complex:

(i) 2 sites for R02 RNP containing either WT SpCas9_1 or WT SpCas9_2 (sites identified in Table 12);
(ii) 1 site for T107 RNP containing WT SpCas9_1 (sites as identified in Table 13) and 0 sites using WT SpCas9_2; and
(iii) 3 sites for T223 RNP containing WT SpCas9_1 (sites as identified in Table 14).

It was evaluated whether gene-editing at off-target sites would be reduced using a SpCas9 variant engineered for increased fidelity (i.e., SpCas9 with R691A mutation), while retaining on-target cutting efficiency. Accordingly, RNP complex containing R02 sgRNA or T107 sgRNA and a SpCas9 R691A high fidelity (HiFi) variant with a R691A mutant were evaluated for frequency of edits at on-target and off-target sites in CD34+ HSPCs. Two SpCas9 R691A HiFi variants were evaluated, HF SpCas9_1 as described in Example 5, and a second variant having three N-terminal NLS sequences (referred to as HF SpCas9_2). For editing, $5\times10^5$ CD34+ HSPCs were electroporated with RNP containing 15 μg of sgRNA (R02 or T107) and 15 μg of either HF_SpCas9_1 or HF_SpCas9_2.

The presence of off-target cut-sites for cells edited with RNP containing SpCas9 R691A HiFi variant was evaluated as described above for RNP containing wild-type SpCas9. Based on the analysis, the number of off-target sites were reduced for each gRNA evaluated with the high fidelity SpCas9 variant.

Specifically, editing with R02 RNP containing wild-type SpCas9 and high fidelity SpCas9 is compared in Table 12. The frequency of INDELs at the OT1 off-target site was statistically significant using R02 RNP with either HF_SpCas9_1 or HF_SpCas9_2, however it was substantially reduced relative to that induced using wild-type SpCas9. Additionally, OT2 did not have a statistically significant level of INDEL formation when editing was performed with R02 RNP containing either HF_SpCas9_1 or HF_SpCas9_2. No off-target sites were identified that were statistically significant using T107 RNP containing either HF SpCas9 variant (Table 13).

Together these data indicate editing performed with a SpCas9 R691A variant reduces risk of introducing a DNA break at an off-target site. Moreover, as the analysis indicated editing with T107 RNP had minimal off-target sites, the T107 intron-targeting guide has a high safety profile.

TABLE 12

On-Target and Off-Target Editing using RNP containing SpCas9 and R02 gRNA

| SpCas9 | OT1 % INDEL | OT2 % INDEL |
|---|---|---|
| WT SpCas9_1 | 48.7 | 0.7 |
| WT SpCas9_2 | 28.8 | 0.3 |
| HF SpCas9_1 | 1.6 | 0.1 |
| HF SpCas9_2 | 1.2 | 0.1 |

OT1 = chr9: 101,833,575-101,833,624
OT2 = chr12: 124,319,275-124,319,308

TABLE 13

On-Target and Off-Target Editing using RNP containing SpCas9 and T107 gRNA

| SpCas9 | Average INDEL Frequency % Site 1 |
|---|---|
| WT SpCas9_1 | 0.14 |
| WT SpCas9_2 | NS |
| HF SpCas9_1 | NS |
| HF SpCas9_2 | NS |

Site 1 = chr11: 104427718-104427739
NS = not significant

TABLE 14

| On-Target and Off-Target Editing using RNP containing SpCas9 and T223 gRNA | | | |
|---|---|---|---|
| | Average INDEL Frequency % | | |
| SpCas9 | Site 1 | Site 2 | Site 3 |
| WT SpCas9_1 | 0.51 | 0.31 | 0.11 |

Site 1 = chr12: 49473115-49473144
Site 2 = chr10: 14091788-14091821
Site 3 = chr10: 58481374-58481395
NS = not significant

Example 12: Analysis of Off-target Genomic Editing with T107 RNP Alone or in Combination with a DNA-PK Inhibitor This example describes experiments performed to measure the frequency of INDELs at the genome site identified as a putative T107 off-target site as described in Example 11. The effect of editing performed with a DNA-PK inhibitor on frequency of INDELs at this site was also evaluated.

Editing at the putative off-target site was evaluated for cells electroporated with (i) T107 RNP only, (ii) T107 RNP+AAV.310, or (iii) T107 RNP+AAV.310 followed by incubation with Compound 296 at a concentration of 1 μM or 3 μM. Control cells were electroporated without RNP, AAV donor template, or the DNA-PK inhibitor. Briefly, $5\times10^5$ CD34+ HSPCs were isolated from plerixafor-mobilized peripheral blood obtained from healthy human donors, thawed, and seeded in media with components as described in Example 1. The HSPCs were cultured for two days, then electroporated with RNP containing 200 μg/ml SpCas9 polypeptide and 200 μg/ml T107 sgRNA. The SpCas9 polypeptide used for editing was WT SpCas9_1. Electroporation was performed using the CA-137 program of the Lonza Amaxa™ 4D-Nucleofector™. The cells were transduced with AAV donor (10,000 MOI) for 1 hour at 37° C. prior to electroporation. The cells were electroporated and immediately plated in medium containing Compound 296 for 48 hours. Genomic DNA was harvested from the cells and the frequency of INDELs at the putative off-target site were evaluated by NGS.

Figure 12:
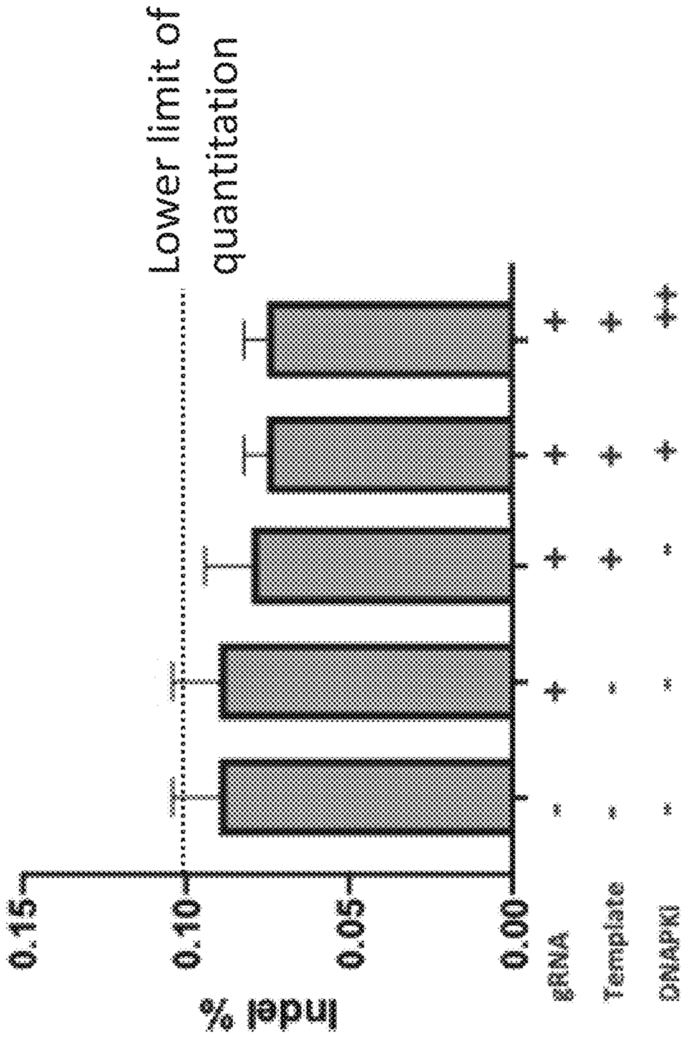
FIG. 12 provides a graph quantifying frequency of INDELs at a non-HBB gene site in the genome evaluated for off-target cleavage by T107 RNP. The analysis was performed in CD34+ HSPCs edited with T107 RNP only, T107 RNP+AAV.310, or T107 RNP+AAV.310 combined with a DNA-PK inhibitor (Compound 296) at a concentration of 1 μM ("+") or 3 μM ("++"). Control cells were electroporated in the absence of RNP, AAV, or DNA-PK inhibitor.

As shown in FIG. 12, the frequency of INDELs determined by NGS was below the threshold of detection for cells edited with T107 RNP alone, T107 RNP+AAV, or T107 RNP+AAV in combination with the DNA-PK inhibitor. These data support the finding that editing of HBB using T107 RNP has a low risk of off-target editing.

Example 13: Editing of Healthy Donor or SCD CD34+ HSPCs with T107 RNP and an AAV Donor Template Encoding a SCD Correction in the Presence of a DNA-PK Inhibitor Gene-editing was evaluated in CD34+ HSPCs derived from healthy human donors and patients with a SCD mutation following electroporation with T107 RNP and an AAV.320 donor template encoding a correction to the SCD mutation and incubation with or without the DNA-PK inhibitor Compound 984.

Editing in healthy donor CD34+ HSPCs was performed as follows. Frozen CD34+ HSPCs isolated from dual mobilized (plerixafor+GCSF) peripheral blood obtained from healthy human donors were thawed. The cells were seeded in CD34 cell media at a cell density of $2\times10^5$ cells/mL. Cells were cultured at 37° C. under normoxic conditions (i.e., oxygen 20%). Gene-editing was performed following two days of in vitro culture. For editing, $5\times10^5$ CD34+ HSPCs were electroporated with RNP containing 200 μg/ml wild-type SpCas9 and 200 μg/ml T107 sgRNA. The cells were transduced with AAV.320, 1 hour prior to electroporation, at a dose of 10,000 MOI. The cells were plated in CD34 cell media containing Compound 984 immediately following the electroporation, at a concentration of 3 μM for 48 hours. Following editing, cells were differentiated to erythrocytes as described in Example 5.

Editing in SCD CD34+ HSPCs was performed as follows. Frozen CD34+ HSPCs (n=1) isolated from plerixafor mobilized peripheral blood cells obtained from patients with SCD were thawed. For n=2 SCD patients PBMCs were used as source of CD34+ cells. PBMCs isolated form SCD patient whole blood were also thawed similar to CD34+ cells. The cells (CD34+ cells and PBMCs) were seeded in CD34 cell media at a cell density of $2\times10^5$ cells/mL. Cells were cultured at 37° C. under normoxic conditions (i.e., oxygen 20%). Gene-editing was performed following two days of in vitro culture. For editing, $5\times10^5$ CD34+ HSPCs or PBMCs were electroporated with RNP containing 200 μg/ml μg SpCas9 and 200 μg/ml T107 sgRNA. The cells were transduced with AAV.320, 1 hour prior to electroporation, at a dose of 10,000 MOI. The cells were plated CD34 cell media containing Compound 984 immediately following the electroporation, at a concentration of 3 μM for 48 hours. Control cells were electroporated with T107 RNP and AAV.320, and no DNA-PK inhibitor was added to this group. Following editing, cells were differentiated to erythrocytes as described in Example 5.

Figure 13B:
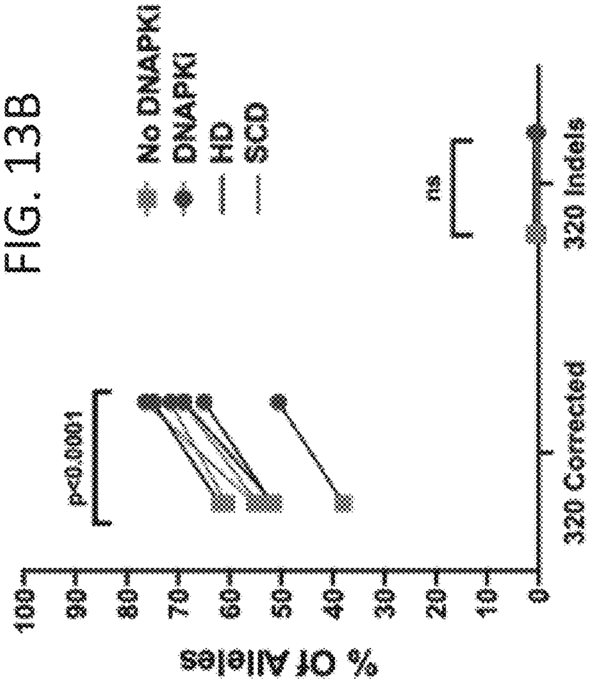
FIGS. 13A-13B provide graphs quantifying frequency of HDR for incorporation of a donor template-encoded gene-edit (includes SCD correction) and frequency of INDELs at the T107 cut site in the HBB gene (FIG. 13A) or mRNA transcribed from the HBB gene (FIG. 13B) in CD34+ HSPCs from healthy donors or patients with SCD that were edited with T107 RNP+AAV.320 in the presence or absence of a DNA-PK inhibitor (Compound 984).
Figure 13A:
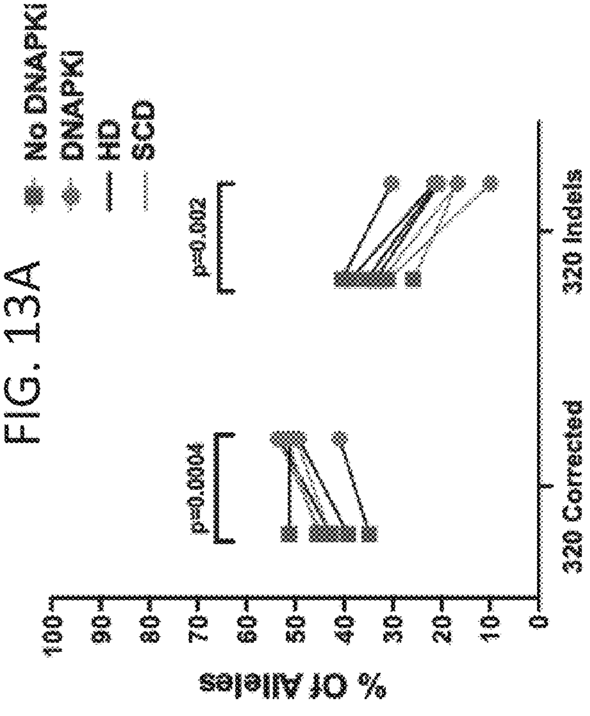

For healthy donor cells genomic DNA was isolated from unedited and edited cells at 2 days post electroporation for NGS to determine the HDR editing frequency. While in SCD patient derived cells editing rate was evaluated from cells at day 10 of in-vitro differentiation. As shown in FIG. 13A, the efficiency of HDR for incorporation of the donor template-encoded HBB gene correction was significantly increased in the presence of the DNA-PK inhibitor in CD34+ HSPCs derived from both healthy donors and patients with SCD. Additionally, the frequency of INDELs at the T107 gRNA cut site was significantly reduced for editing performed in the presence of the DNA-PK inhibitor.

At 10 days following in-vitro differentiation incorporation of the SCD mutation and frequency of INDELs present in mRNA transcribed from the HBB gene locus of edited cells was determined using RNA amplicon sequencing. As shown in FIG. 13B, INDELs in HBB mRNA transcripts were not detectable in edited CD34+ HSPCs derived from either healthy donors or patients with SCD. Additionally, the incorporation of gene-edits encoded by the donor template was significantly increased in the presence of the DNA-PK inhibitor.

Figure 13C:
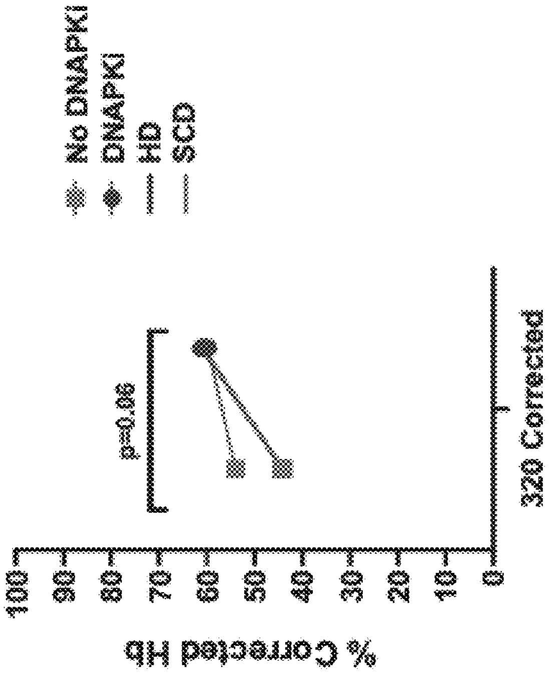
FIG. 13C provides a graph quantifying the percentage of wild-type adult hemoglobin expressed by CD34+ HSPCs obtained from SCD patients following editing with T107 RNP+AAV.320 in the presence or absence of a DNA-PK inhibitor (Compound 984) and differentiation into erythroid progenitor cells.

At 18 days following in-vitro differentiation, expression of hemoglobin tetramers was assessed by HPLC as described in Example 5 in cells differentiated from patient-derived CD34+ HSPCs. As shown in FIG. 13C, the percentage of hemoglobin tetramer incorporating corrected beta-globin was increased for cells edited in the presence of the DNA-PK inhibitor.

Example 14: Engraftment and Persistence of Gene-Editing Following In Vivo Administration of CD34+ HSPCs Edited with T107 RNP and an AAV Donor Template in the Presence of a DNA-PK Inhibitor Additional experiments were performed to support the findings described in Example 6. Specifically, CD34+

HSPCs were edited using T107 RNP and an AAV.310 donor template encoding a SCD mutation alone or in the presence of a DNA-PK inhibitor (Compound 984).

Frozen CD34+ HSPCs isolated from plerixafor-mobilized peripheral blood obtained from healthy human donors were thawed and seeded in media with components as described in Example 1. The cells were maintained in culture, and gene-editing was performed following two days of culture. For editing, $5\times10^5$ CD34+ HSPCs were electroporated with RNP containing 200 μg/ml μg wild-type SpCas9 and 200 μg/ml T107 sgRNA. Electroporation was performed using the CA-137 program of the Lonza Amaxa™ 4D-Nucleofector™. The cells were transduced with AAV.310 for 1 hour at 37° C. prior to electroporation at a dose of 10,000 MOI. The cells were electroporated and immediately plated in medium only or medium containing Compound 984 at 3 μM. Control cells were electroporated with T107 RNP only or in the absence of RNP, AAV, and inhibitor. Cells were maintained in culture for two days following electroporation. Genomic DNA was harvested from edited cells and used to evaluate HDR efficiency by NSG as described in Example 1.

Following two days of in vitro culture, HSPCs were administered by intravenous injection to NBSGW mice at a dose of $0.5\times10^6$ cells per mouse. Recipient mice were treated with sublethal irradiation (100 cGy) at 1 day prior to administration of HSPCs. The study groups included administration of HSPCs edited as follows: (i) mock EP; (ii) T107 RNP only; (iii) T107 RNP+AAV; and (iv) T107 RNP+AAV+ Compound 984. In total three independent replicates of the study were performed.

Figure 14A:
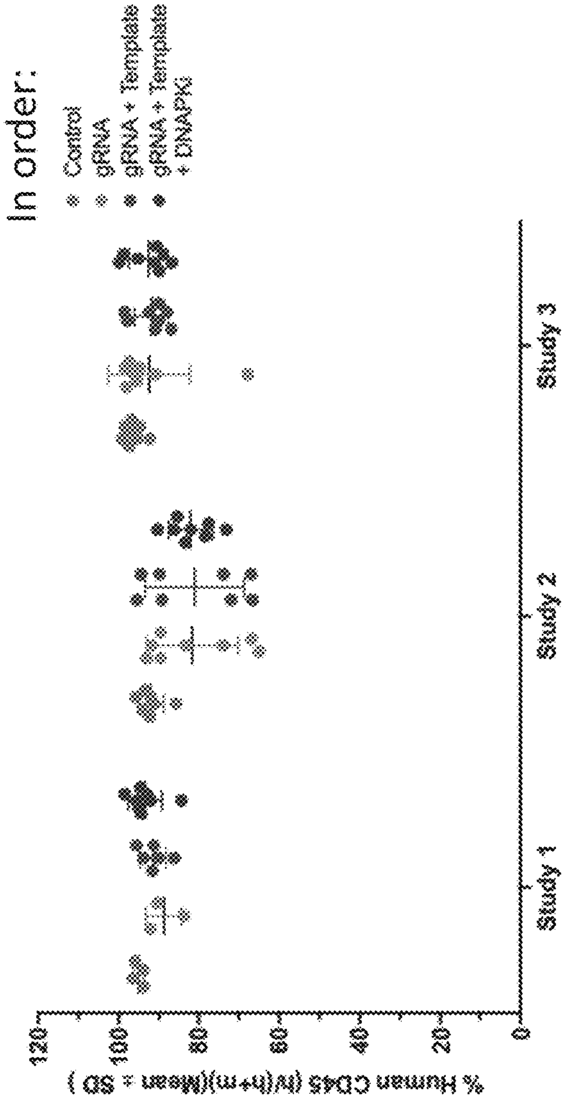
FIGS. 14A-14B provide graphs quantifying engraftment of human cells as measured in mouse bone marrow (FIG. 14A) or peripheral blood (FIG. 14B) isolated at 16 weeks following in vivo administration of healthy donor-derived CD34+ HSPCs edited with T107 RNP only, T107 RNP+AAV.310, or T107 RNP+AAV.310 in the presence of a DNA-PK inhibitor (Compound 984). Control cells were electroporated in the absence of RNP, AAV, or DNA-PK inhibitor. Data is provided for three independent replicates of the study (note study 1 in FIGS. 14A-14B provide the data as presented in FIGS. 7G-7H for animal cohorts administered control CD34+ HSPCs or CD34+ HSPCs edited with T107 RNP only, T107 RNP+AAV.310, or T107 RNP+AAV.310+Compound 984 3 μM).
Figure 14B:
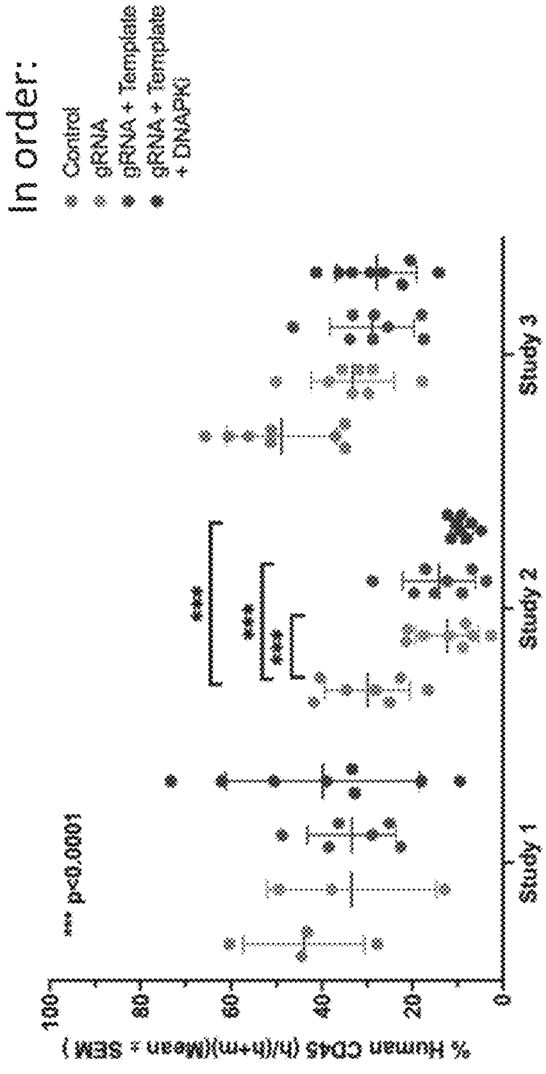

Bone marrow and peripheral blood was extracted at 16 weeks following HSPC administration and evaluated for presence of human hematopoietic cells using flow cytometry as described in Example 2. The percent chimerism (percentage of human CD45+ cells relative total cells expressing human CD45 or mouse CD45) in mouse bone marrow and peripheral blood is respectively shown in FIGS. 14A-14B. Chimerism in bone marrow was comparable between the treatment groups.

Figure 14C:
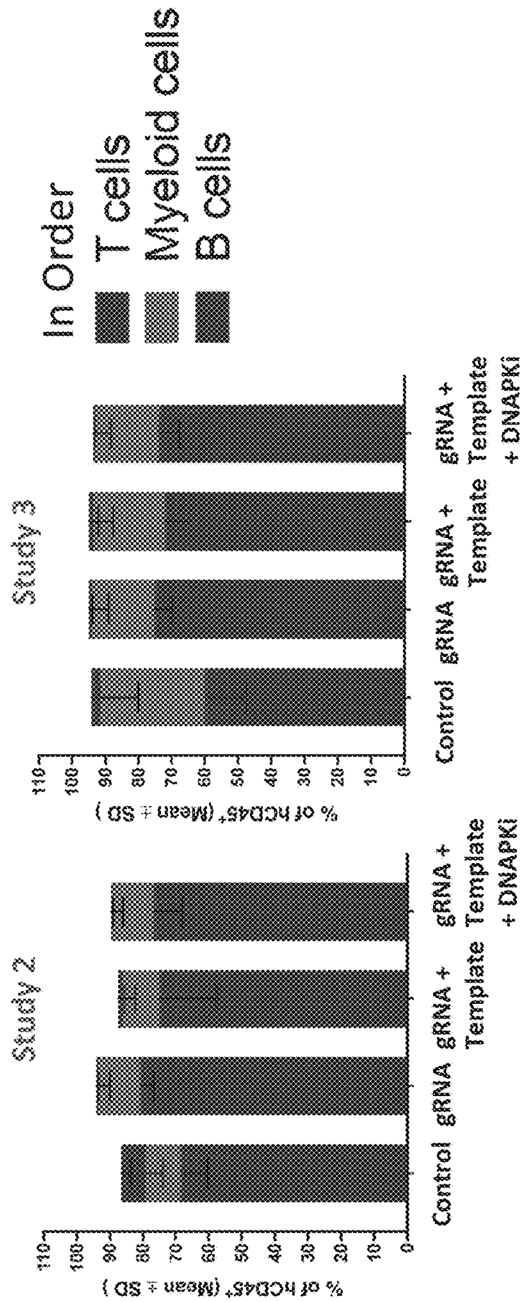
FIG. 14C provides a graph quantifying the multi-lineage composition measured in mouse peripheral blood obtained from mice described in FIGS. 14A-14B.

Additionally, the lineage of human CD45+ cells was determined using markers for human B cells, T cells, myeloid cells, and HSPCs as described in Example 2. Lineage distribution evaluated in each mouse treatment group is shown in FIG. 14C. Multi-lineage composition of human cells in peripheral blood was comparable between the treatment groups.

Figure 14D:
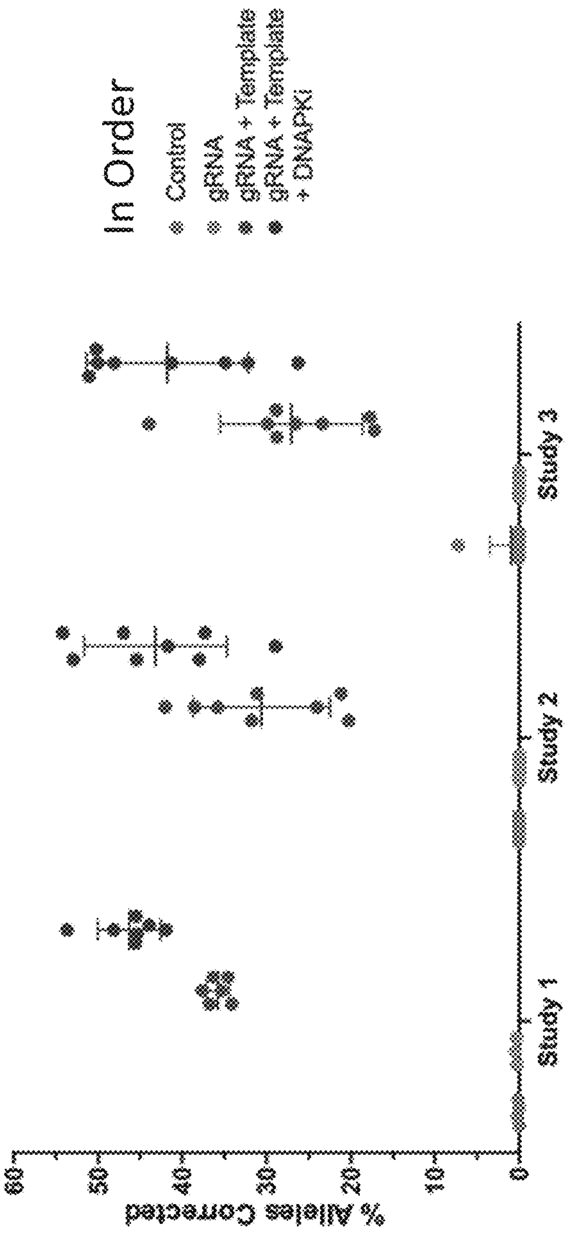
FIG. 14D provides a graph quantifying long term persistence of gene-editing as measured in genomic DNA harvested at 16 weeks from the bone marrow of mice described in FIGS. 14A-14B. Shown is the frequency of the donor template-encoded gene edit in the HBB gene and frequency of INDELs at the T107 gRNA cut site. Data is provided for three independent replicates of the study (note study 1 in FIG. 14D provide the data as presented in FIG. 7I for animal cohorts administered control CD34+ HSPCs or CD34+ HSPCs edited with T107 RNP only, T107 RNP+AAV.310, or T107 RNP+AAV.310+Compound 984 3 μM).

The long term persistence of edits in the HBB gene present in HSPCs administered to each mouse cohorts was evaluated in genomic DNA extracted from bone marrow collected at 16 weeks. The frequency of donor template-encoded gene-edits in the HBB gene incorporated by HDR was quantified by NGS and is shown in FIG. 14D. The frequency of gene-edits as measured in mouse bone marrow was comparable to the frequency of gene-edits in CD34+ HSPCs prior to transplantation, which was approximately 45% for cells edited with T107 RNP+AAV.310 in the presence of Compound 984. Thus, desired gene-edits persist for an extended period following in vivo administration of edited CD34+ HSPCs.

SEQUENCE LISTING

| Name/Identifier | Sequence | SEQ ID NO |
|---|---|---|
| T107 Target Sequence | TCCACATGCCCAGTTTCTAT | 1 |
| T107 Target Sequence + PAM in bold | TCCACATGCCCAGTTTCTAT<br>**TGG** | 2 |
| T107 Spacer Sequence | UCCACAUGCCCAGUUUCUAU | 3 |
| T107 sgRNA | **uscscsACAUGCCCAGUUUCUAU**<br>GUUUUAGAGCUAGAAAUAGCAAG<br>UUAAAAUAAGGCUAGUCCGUUAU<br>CAACUUGAAAAAGUGGCACCGAG<br>UCGGUGCusususU<br>a, c, g, u: 2' O-methyl phosphorothioate nucleotides<br>s: phosphorothioate nucleotides<br>A, C, G, U, N: canonical RNA nucleotides | 4 |
| AAV.320 5' ITR | CCTGCAGGCAGCTGCGCGCTCGCTCGCTCACTGAGGCCGCCCGGGCGTCGGGCGA<br>CCTTTGGTCGCCCGGCCTCAGTGAGCGAGCGAGCGCGCAGAGAGGGAGTGGCCAA<br>CTCCATCACTAGGGGTTCCT | 5 |
| AAV. 320 sequence with correction to GAG<br>E6V correction in bold<br>PAM mutation in underline | **GAG**GAGAAAAGCGCTGTGACCGCACTCTGGGGTAAAGTGAACGTCGACGAGGTGG<br>GCGGTGAAGCTCTCGGAAGgttggtatcaaggttacaagacaggtttaaggaga<br>cGa | 6 |
| 3' ITR | AGGAACCCCTAGTGATGGAGTTGGCCACTCCCTCTCTGCGCGCTCGCTCGCTCAC<br>TGAGGCCGGGCGACCAAAGGTCGCCCGACGCCCGGGCTTTGCCCGGGCGGCCTCA<br>GTGAGCGAGCGAGCGCGCAGCTGCCTGCAGG | 7 |

-continued

SEQUENCE LISTING

| Name/Identifier | Sequence | SEQ ID NO |
|---|---|---|
| AAV.320 with correction to GAG | CTTGCTTTGACAATTTTGGTCTTTCAGAATACTATAAATATAACCTATATTATAA<br>TTTCATAAAGTCTGTGCATTTTCTTTGACCCAGGATATTTGCAAAAGACATATTC<br>AAACTTCCGCAGAACACTTTATTTCACATATACATGCCTCTTATATCAGGGATGT<br>GAAACAGGGTCTTGAAAACTGTCTAAATCTAAAACAATGCTAATGCAGGTTTAAA<br>TTTAATAAAATAAAATCCAAAATCTAACAGCCAAGTCAAATCTGCATGTTTTAAC<br>ATTTAAAATATTTTAAAGACGTCTTTTCCCAGGATTCAACATGTGAAATCTTTTC<br>TCAGGGATACACGTGTGCCTAGATCCTCATTGCTTTAGTTTTTTACAGAGGAATG<br>AATATAAAAAGAAAATACTTAAATTTTATCCCTCTTACCTCTATAATCATACATA<br>GGCATAATTTTTTAACCTAGGCTCCAGATAGCCATAGAAGAACCAAACACTTTCT<br>GCGTGTGTGAGAATAATCAGAGTGAGATTTTTTCACAAGTACCTGATGAGGGTTG<br>AGACAGGTAGAAAAAGTGAGAGATCTCTATTTATTTAGCAATAATAGAGAAAGCA<br>TTTAAGAGAATAAAGCAATGGAAATAAGAAATTTGTAAATTTCCTTCTGATAACT<br>AGAAATAGAGGATCCAGTTTCTTTTGGTTAACCTAAATTTTATTTCATTTTATTG<br>TTTTATTTTATTTTATTTTATTTTATTTTGTGTAATCGTAGTTTCAGAGTGTTAG<br>AGCTGAAAGGAAGAAGTAGGAGAAACATGCAAAGTAAAAGTATAACACTTTCCTT<br>ACTAAACCGACATGGGTTTCCAGGTAGGGGCAGGATTCAGGATGACTGACAGGGC<br>CCTTAGGGAACACTGAGACCCTACGCTGACCTCATAAATGCTTGCTACCTTTGCT<br>GTTTTAATTACATCTTTTAATAGCAGGAAGCAGAACTCTGCACTTCAAAAGTTTT<br>TCCTCACCTGAGGAGTTAATTTAGTACAAGGGGAAAAAGTACAGGGGGATGGGAG<br>AAAGGCGATCACGTTGGGAAGCTATAGAGAAAGAAGAGTAAATTTTAGTAAAGGA<br>GGTTTAAACAAACAAAATATAAAGAGAAATAGGAACTTGAATCAAGGAAATGATT<br>TTAAAACGCAGTATTCTTAGTGGACTAGAGGAAAAAAATAATCTGAGCCAAGTAG<br>AAGACCTTTTCCCCTCCTACCCCTACTTTCTAAGTCACAGAGGCTTTTTGTTCCC<br>CCAGACACTCTTGCAGATTAGTCCAGGCAGAAACAGTTAGATGTCCCCAGTTAAC<br>CTCCTATTTGACACCACTGATTACCCCATTGATAGTCACACTTTGGGTTGTAAGT<br>GACTTTTTATTTATTTGTATTTTTGACTGCATTAAGAGGTCTCTAGTTTTTTATC<br>TCTTGTTTCCCAAAACCTAATAAGTAACTAATGCACAGAGCACATTGATTTGTAT<br>TTATTCTATTTTTAGACATAATTTATTAGCATGCATGAGCAAATTAAGAAAAACA<br>ACAACAAATGAATGCATATATATGTATATGTATGTGTGTATATATACACACATAT<br>ATATATATATTTTTTCTTTTCTTACCAGAAGGTTTTAATCCAAATAAGGAGAAGA<br>TATGCTTAGAACCGAGGTAGAGTTTTCATCCATTCTGTCCTGTAAGTATTTTGCA<br>TATTCTGGAGACGCAGGAAGAGATCCATCTACATATCCCAAAGCTGAATTATGGT<br>AGACAAAACTCTTCCACTTTTAGTGCATCAACTTCTTATTTGTGTAATAAGAAAA<br>TTGGGAAAACGATCTTCAATATGCTTACCAAGCTGTGATTCCAAATATTACGTAA<br>ATACACTTGCAAAGGAGGATGTTTTTAGTAGCAATTTGTACTGATGGTATGGGGC<br>CAAGAGATATATCTTAGAGGGAGGGCTGAGGGTTTGAAGTCCAACTCCTAAGCCA<br>GTGCCAGAAGAGCCAAGGACAGGTACGGCTGTCATCACTTAGACCTCACCCTGTG<br>GAGCCACACCCTAGGGTTGGCCAATCTACTCCCAGGAGCAGGGAGGGCAGGAGCC<br>AGGGCTGGGCATAAAAGTCAGGGCAGAGCCATCTATTGCTTACATTTGCTTCTGA<br>CACAACTGTGTTCACTAGCAACCTCAAACAGACACCATGGTGCATCTGACTCCTG<br>AGGAGAAAAGCGCTGTGACCGCACTCTGGGGTAAAGTGAACGTCGACGAGGTGGG<br>CGGTGAAGCTCTCGGAAGgttggtatcaaggttacaagacaggtttaaggagacG<br>aatagaaactgggCATGTGGAGACAGAGAAGACTCTTGGGTTTCTGATAGGCACT<br>GACTCTCTCTGCCTATTGGTCTATTTTCCCACCCTTAGGCTGCTGGTGGTCTACC<br>CTTGGACCCAGAGGTTCTTTGAGTCCTTTGGGGATCTGTCCACTCCTGATGCTGT<br>TATGGGCAACCCTAAGGTGAAGGCTCATGGCAAGAAAGTGCTCGGTGCCTTTAGT<br>GATGGCCTGGCTCACCTGGACAACCTCAAGGGCACCTTTGCCACACTGAGTGAGC<br>TGCACTGTGACAAGCTGCACGTGGATCCTGAGAACTTCAGGGTGAGTCTATGGGA<br>CGCTTGATGTTTTCTTTCCCCTTCTTTTCTATGGTTAAGTTCATGTCATAGGAAG<br>GGGATAAGTAACAGGGTACAGTTTAGAATGGGAAACAGACGAATGATTGCATCAG<br>TGTGGAAGTCTCAGGATCGTTTAGTTTCTTTTATTTGCTGTTCATAACAATTGT<br>TTTCTTTTGTTTAATTCTTGCTTTCTTTTTTTTTCTTCTCCGCAATTTTTACTAT<br>TATACTTAATGCCTTAACATTGTGTATAACAAAAGGAAATATCTCTGAGATACAT<br>TAAGTAACTTAAAAAAAAACTTTACACAGTCTGCCTAGTACATTACTATTTGGAA<br>TATATGTGTGCTTATTTGCATATTCATAATCTCCCTACTTTATTTTCTTTTATTT<br>TTAATTGATACATAATCATTATACATATTTATGGGTTAAAGTGTAATGTTTTAAT<br>ATGTGTACACATATTGACCAAATCAGGGTAATTTTGCATTTGTAATTTTAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCATT<br>CTAAAGAATAACAGTGATAATTTCTGGGTTAAGGCAATAGCAATATCTCTGCATA<br>TAAATATTTCTGCATATAAATTGTAACTGATGTAAGAGGTTTCATATTGCTAATA<br>GCAGCTACAATCCAGCTACCATTCTGCTTTTATTTTATGGTTGGGATAAGGCTGG<br>ATTATTCTGAGTCCAAGCTAGGCCCTTTTGCTAATCATGTTCATACCTCTTATCT<br>TCCTCCCACAGCTCCTGGGCAACGTGCTGGTCTGTGTGCTGGCCCATCACTTTGG<br>CAAAGAATTCACCCCACCAGTGCAGGCTGCCTATCAGAAAGTGGTGGCTGGTGTG<br>GCTAATGCCCTGGCCCACAAGTATCACTAAGCTCGCTTTCTTGCTGTCCAATTTC<br>TATTAAAGGTTCCTTTGTTCCCTAAGTCCAACTACTAAACTGGGGGATATTATGA<br>AGGGCCTTGAGCATCTGGATTCTGCCTAATAAAAAACATTTATTTTCATTGCAAT<br>GATGTATTTAAATTATTTCTGAATATTTTACTAAAAAGGGAATGTGGGAGGTCAG<br>TGCATTTAAAACATAAAGAAATGAAGAGCTAGTTCAAACCTTGGGAAAATACACT<br>ATATCTTAAACTCCATGAAAGAAGGTGAGGCTGCAAACAGCTAATGCACATTGGC<br>AACAGCCCCTGATGCATATGCCTTATTCATCCCTCAGAAAAGGATTCAAGTAGAG<br>GCTTGATTTGGAGGTTAAAGTTTTGCTATGCTGTATTTTACATTACTTATTGTTT | 8 |

-continued

SEQUENCE LISTING

| Name/Identifier | Sequence | SEQ ID NO |
|---|---|---|
| | TAGCTGTCCTCATGAATGTCTTTTCACTACCCATTTGCTTATCCTGCATCTCTCA<br>GCCTTGACTCCACTCAGTTCTCTTGCTTAGAGATACCACCTTTCCCCTGAAGTGT<br>TCCTTCCATGTTTTACGGCGAGATGGTTTCTCCTCGCCTGGCCACTCAGCCTTAG<br>TTGTCTCTGTTGTCTTATAGAGGTCTACTTGAAGAAGGAAAAACAGGGGTCATGG<br>TTTGACTGTCCTGTGAGCCCTTCTTCCCTGCCTCCCCCACTCACAGTGACCCGGA<br>ATCTGCAGTGCTAGTCTCCCGGAACTATCACTCTTTCACAGTCTGCTTTGGAAGG<br>ACTGGGCTTAGTATGAAAAGTTAGGACTGAGAAGAATTTGAAAGGCGGCTTTTTG<br>TAGCTTGATATTCACTACTGTCTTATTACCCTGTC | |
| AAV 320 with ITRs and correction to GAG | CCTGCAGGCAGCTGCGCGCTCGCTCGCTCACTGAGGCCGCCCGGGCGTCGGGCGA<br>CCTTTGGTCGCCCGGCCTCAGTGAGCGAGCGAGCGCGCAGAGAGGGAGTGGCCAA<br>CTCCATCACTAGGGGTTCCTGCGGCCGCACGCGTCTTGCTTTGACAATTTTGGTC<br>TTTCAGAATACTATAAATATAACCTATATTATAATTTCATAAAGTCTGTGCATTT<br>TCTTTGACCCAGGATATTTGCAAAAGACATATTCAAACTTCCGCAGAACACTTTA<br>TTTCACATATACATGCCTCTTATATCAGGGATGTGAAACAGGGTCTTGAAAACTG<br>TCTAAATCTAAAACAATGCTAATGCAGGTTTAAATTTAATAAAATAAAATCCAAA<br>ATCTAACAGCCAAGTCAAATCTGCATGTTTTAACATTTAAAATATTTTAAAGACG<br>TCTTTTCCCAGGATTCAACATGTGAAATCTTTTCTCAGGGATACACGTGTGCCTA<br>GATCCTCATTGCTTTAGTTTTTTACAGAGGAATGAATATAAAAAGAAAATACTTA<br>AATTTTATCCCTCTTACCTCTATAATCATACATAGGCATAATTTTTTAACCTAGG<br>CTCCAGATAGCCATAGAAGAACCAAACACTTTCTGCGTGTGTGAGAATAATCAGA<br>GTGAGATTTTTTCACAAGTACCTGATGAGGGTTGAGACAGGTAGAAAAAGTGAGA<br>GATCTCTATTTATTTAGCAATAATAGAGAAAGCATTTAAGAGAATAAAGCAATGG<br>AAATAAGAAATTTGTAAATTTCCTTCTGATAACTAGAAATAGAGGATCCAGTTTC<br>TTTTGGTTAACCTAAATTTTATTTCATTTTATTGTTTTATTTTATTTTATTTTAT<br>TTTATTTTGTGTAATCGTAGTTTCAGAGTGTTAGAGCTGAAAGGAAGAAGTAGGA<br>GAAACATGCAAAGTAAAAGTATAACACTTTCCTTACTAAACCGACATGGGTTTCC<br>AGGTAGGGGCAGGATTCAGGATGACTGACAGGGCCCTTAGGGAACACTGAGACCC<br>TACGCTGACCTCATAAATGCTTGCTACCTTTGCTGTTTTAATTACATCTTTTAAT<br>AGCAGGAAGCAGAACTCTGCACTTCAAAAGTTTTTCCTCACCTGAGGAGTTAATT<br>TAGTACAAGGGGAAAAAGTACAGGGGGATGGGAGAAAGGCGATCACGTTGGGAAG<br>CTATAGAGAAAGAAGAGTAAATTTTAGTAAAGGAGGTTTAAACAAACAAAATATA<br>AAGAGAAATAGGAACTTGAATCAAGGAAATGATTTTAAAACGCAGTATTCTTAGT<br>GGACTAGAGGAAAAAAATAATCTGAGCCAAGTAGAAGACCTTTTCCCCTCCTACC<br>CCTACTTTCTAAGTCACAGAGGCTTTTTGTTCCCCCAGACACTCTTGCAGATTAG<br>TCCAGGCAGAAACAGTTAGATGTCCCCAGTTAACCTCCTATTTGACACCACTGAT<br>TACCCCATTGATAGTCACACTTTGGGTTGTAAGTGACTTTTTATTTATTTGTATT<br>TTTGACTGCATTAAGAGGTCTCTAGTTTTTTATCTCTTGTTTCCCAAAACCTAAT<br>AAGTAACTAATGCACAGAGCACATTGATTTGTATTTATTCTATTTTTAGACATAA<br>TTTATTAGCATGCATGAGCAAATTAAGAAAAACAACAACAAATGAATGCATATAT<br>ATGTATATGTATGTGTGTATATATACACACATATATATATATATTTTTTCTTTTC<br>TTACCAGAAGGTTTTAATCCAAATAAGGAGAAGATATGCTTAGAACCGAGGTAGA<br>GTTTTCATCCATTCTGTCCTGTAAGTATTTTGCATATTCTGGAGACGCAGGAAGA<br>GATCCATCTACATATCCCAAAGCTGAATTATGGTAGACAAAACTCTTCCACTTTT<br>AGTGCATCAACTTCTTATTTGTGTAATAAGAAAATTGGGAAAACGATCTTCAATA<br>TGCTTACCAAGCTGTGATTCCAAATATTACGTAAATACACTTGCAAAGGAGGATG<br>TTTTTAGTAGCAATTTGTACTGATGGTATGGGGCCAAGAGATATATCTTAGAGGG<br>AGGGCTGAGGGTTTGAAGTCCAACTCCTAAGCCAGTGCCAGAAGAGCCAAGGACA<br>GGTACGGCTGTCATCACTTAGACCTCACCCTGTGGAGCCACACCCTAGGGTTGGC<br>CAATCTACTCCCAGGAGCAGGGAGGGCAGGAGCCAGGGCTGGGCATAAAAGTCAG<br>GGCAGAGCCATCTATTGCTTACATTTGCTTCTGACACAACTGTGTTCACTAGCAA<br>CCTCAAACAGACACCATGGTGCATCTGACTCCTGAGGAGAAAGCGCTGTGACCG<br>CACTCTGGGGTAAAGTGAACGTCGACGAGGTGGGCGGTGAAGCTCTCGGAAGgtt<br>ggtatcaaggttacaagacaggtttaaggagacGaatagaaactgggCATGTGGA<br>GACAGAGAAGACTCTTGGGTTTCTGATAGGCACTGACTCTCTCTGCCTATTGGTC<br>TATTTTCCCACCCTTAGGCTGCTGGTGGTCTACCCTTGGACCCAGAGGTTCTTTG<br>AGTCCTTTGGGGATCTGTCCACTCCTGATGCTGTTATGGGCAACCCTAAGGTGAA<br>GGCTCATGGCAAGAAAGTGCTCGGTGCCTTTAGTGATGGCCTGGCTCACCTGGAC<br>AACCTCAAGGGCACCTTTGCCACACTGAGTGAGCTGCACTGTGACAAGCTGCACG<br>TGGATCCTGAGAACTTCAGGGTGAGTCTATGGGACGCTTGATGTTTTCTTTCCCC<br>TTCTTTTCTATGGTTAAGTTCATGTCATAGGAAGGGGATAAGTAACAGGGTACAG<br>TTTAGAATGGGAAACAGACGAATGATTGCATCAGTGTGGAAGTCTCAGGATCGTT<br>TTAGTTTCTTTTATTTGCTGTTCATAACAATTGTTTTCTTTTGTTTAATTCTTGC<br>TTTCTTTTTTTTTCTTCTCCGCAATTTTTACTATTATACTTAATGCCTTAACATT<br>GTGTATAACAAAAGGAAATATCTCTGAGATACATTAAGTAACTTAAAAAAAAACT<br>TTACACAGTCTGCCTAGTACATTACTATTTGGAATATATGTGTGCTTATTTGCAT<br>ATTCATAATCTCCCTACTTTATTTTCTTTTATTTTTAATTGATACATAATCATTA<br>TACATATTTATGGGTTAAAGTGTAATGTTTTAATATGTGTACACATATTGACCAA<br>ATCAGGGTAATTTTGCATTTGTAATTTTAAAAAATGCTTTCTTCTTTTAATATAC<br>TTTTTTGTTTATCTTATTTCTAATACTTTCCCTAATCTCTTTCTTTCAGGGCAAT<br>AATGATACAATGTATCATGCCTCTTTGCACCATTCTAAAGAATAACAGTGATAAT<br>TTCTGGGTTAAGGCAATAGCAATATCTCTGCATATAAATATTTCTGCATATAAAT<br>TGTAACTGATGTAAGAGGTTTCATATTGCTAATAGCAGCTACAATCCAGCTACCA | 9 |

-continued

SEQUENCE LISTING

| Name/Identifier | Sequence | SEQ ID NO |
|---|---|---|
| | TTCTGCTTTTATTTTATGGTTGGGATAAGGCTGGATTATTCTGAGTCCAAGCTAG<br>GCCCTTTTGCTAATCATGTTCATACCTCTTATCTTCCTCCCACAGCTCCTGGGCA<br>ACGTGCTGGTCTGTGTGCTGGCCCATCACTTTGGCAAAGAATTCACCCCACCAGT<br>GCAGGCTGCCTATCAGAAAGTGGTGGCTGGTGTGGCTAATGCCCTGGCCCACAAG<br>TATCACTAAGCTCGCTTTCTTGCTGTCCAATTTCTATTAAAGGTTCCTTTGTTCC<br>CTAAGTCCAACTACTAAACTGGGGGATATTATGAAGGGCCTTGAGCATCTGGATT<br>CTGCCTAATAAAAAACATTTATTTTCATTGCAATGATGTATTTAAATTATTTCTG<br>AATATTTTACTAAAAAGGGAATGTGGGAGGTCAGTGCATTTAAAACATAAAGAAA<br>TGAAGAGCTAGTTCAAACCTTGGGAAAATACACTATATCTTAAACTCCATGAAAG<br>AAGGTGAGGCTGCAAACAGCTAATGCACATTGGCAACAGCCCCTGATGCATATGC<br>CTTATTCATCCCTCAGAAAAGGATTCAAGTAGAGGCTTGATTTGGAGGTTAAAGT<br>TTTGCTATGCTGTATTTTACATTACTTATTGTTTTAGCTGTCCTCATGAATGTCT<br>TTTCACTACCCATTTGCTTATCCTGCATCTCTCAGCCTTGACTCCACTCAGTTCT<br>CTTGCTTAGAGATACCACCTTTCCCCTGAAGTGTTCCTTCCATGTTTTACGGCGA<br>GATGGTTTCTCCTCGCCTGGCCACTCAGCCTTAGTTGTCTCTGTTGTCTTATAGA<br>GGTCTACTTGAAGAAGGAAAAACAGGGGTCATGGTTTGACTGTCCTGTGAGCCCT<br>TCTTCCCTGCCTCCCCCACTCACAGTGACCCGGAATCTGCAGTGCTAGTCTCCCG<br>GAACTATCACTCTTTCACAGTCTGCTTTGGAAGGACTGGGCTTAGTATGAAAAGT<br>TAGGACTGAGAAGAATTTGAAAGGCGGCTTTTTGTAGCTTGATATTCACTACTGT<br>CTTATTACCCTGTCGGTAACCACGTGCGGCCGAGGCTGCAGCGTCGTCCTCCCTA<br>GGAACCCCTAGTGATGGAGTTGGCCACTCCCTCTCTGCGCGCTCGCTCGCTCACT<br>GAGGCCGGGCGACCAAAGGTCGCCCGACGCCCGGGCTTTGCCCGGGCGGCCTCAG<br>TGAGCGAGCGAGCGCGCAGCTGCCTGCAGG | |
| i53 mRNA ORF | AUGCUGAUCUUCGUGAAGACCCUGACCGGCAAGACCAUCACCCUGGAGGUGGAGC<br>CCAGCGACACCAUCGAGAACGUGAAGGCCAAGAUCCAGGACAAGGAGGGCAUCCC<br>CCCCGACCAGCAGAGGCUGGCCUUCGCCGGCAAGAGCCUGGAGGACGGCAGGACC<br>CUGAGCGACUACAACAUCCUGAAGGACAGCAAGCUGCACCCCCUGCUGAGGCUGA<br>GGUGA | 10 |
| i53 polypeptide | MLIFVKTLTGKTITLEVEPSDTIENVKAKIQDKEGIPPDQQRLAFAGKSLEDGRT<br>LSDYNILKDSKLHPLLRLR | 11 |
| R02 HBB Target Sequence | CTTGCCCCACAGGGCAGTAA | 12 |
| R02 HBB Target Sequence with PAM | CTTGCCCCACAGGGCAGTAA**CGG** | 13 |
| R02 Spacer Sequence | CUUGCCCCACAGGGCAGUAA | 14 |
| R02 sgRNA (spacer in bold) | **csususGCCCCACAGGGCAGUAA**GUUUUAGAGCUAGAAAUAGCAAGUUAAAAUAA<br>GGCUAGUCCGUUAUCAACUUGAAAAAGUGGCACCGAGUCGGUGCusususU<br>a, c, g, u: 2' O-methyl phosphorothioate nucleotides<br>s: phosphorothioate nucleotides<br>A, C, G, U, N: canonical RNA nucleotides | 15 |
| 200mer ssODN for use with R02 sgRNA E6V mutation in bold PAM mutation in bold underline Silent mutations relative to HBB in underline | GsCsAsTAAAAGTCAGGGCAGAGCCATCTATTGCTTACATTTGCTTCTGACACAA<br>CTGTGTTCACTAGCAACCTCAAACAGACACCATGGTGCATCTGACTCCT**GTC**GAA<br>AAATCCG**CTG**TCACCGCCCTCTGGGGCAAGGTGAACGTGGATGAAGTTGGTGGTG<br>AGGCCCTGGGCAGGTTGGTATCAAGGTTACAAGACAsGsG<br>s: phosphorothioate nucleotides | 16 |
| 200mer ssODN for use with T107 sgRNA E6V mutation in bold PAM mutation in bold underline Silent mutations relative to HBB in italics | AsAsCsAGACACCATGGTGCATCTGACTCCT**GTC**GAGAAAAGCGCTGTGACCGCA<br>CTCTGGGGTAAAGTGAACGTCGACGAGGTGGGCGGTGAAGCTCTCGGAAGGTTGG<br>TATCAAGGTTACAAGACACGTTTAAGGAGA**CGA**ATAGAAACTGCGCATGTGGAGA<br>CAGAGAAGACTCTTGGGTTTCTGATAGGCACTGACsTsCsT<br>s: phosphorothioate nucleotides | 17 |

-continued

SEQUENCE LISTING

| Name/Identifier | Sequence | SEQ ID NO |
|---|---|---|
| AAV.321 5' ITR | CCTGCAGGCAGCTGCGCGCTCGCTCGCTCACTGAGGCCGCCCGGGCAAAGCCCGG<br>GCGTCGGGCGACCTTTGGTCGCCCGGCCTCAGTGAGCGAGCGAGCGCGCAGAGAG<br>GGAGTGGCCAACTCCATCACTAGGGGTTCCT | 18 |
| AAV.321<br>sequence with<br>correction<br>E6V correction<br>in bold<br>PAM mutation in<br>underline | **GAG**GAGAAAAGCGCTGTGACCGCACTCTGGGGTAAAGTGAACGTCGACGAGGTGG<br>GCGGTGAAGCTCTCGGAAGGTTGGTATCAAGGTTACAAGACAGGTTTAAGGAGAC<br>CAATAGAAACTGCG | 19 |
| AAV.321 | CTTGCTTTGACAATTTTGGTCTTTCAGAATACTATAAATATAACCTATATTATAA<br>TTTCATAAAGTCTGTGCATTTTCTTTGACCCAGGATATTTGCAAAAGACATATTC<br>AAACTTCCGCAGAACACTTTATTTCACATATACATGCCTCTTATATCAGGGATGT<br>GAAACAGGGTCTTGAAAACTGTCTAAATCTAAAACAATGCTAATGCAGGTTTAAA<br>TTTAATAAAATAAAATCCAAAATCTAACAGCCAAGTCAAATCTGCATGTTTTAAC<br>ATTTAAAATATTTTAAAGACGTCTTTTCCCAGGATTCAACATGTGAAATCTTTTC<br>TCAGGGATACACGTGTGCCTAGATCCTCATTGCTTTAGTTTTTTACAGAGGAATG<br>AATATAAAAAGAAAATACTTAAATTTTATCCCTCTTACCTCTATAATCATACATA<br>GGCATAATTTTTTAACCTAGGCTCCAGATAGCCATAGAAGAACCAAACACTTTCT<br>GCGTGTGTGAGAATAATCAGAGTGAGATTTTTTCACAAGTACCTGATGAGGGTTG<br>AGACAGGTAGAAAAAGTGAGAGATCTCTATTTATTTAGCAATAATAGAGAAAGCA<br>TTTAAGAGAATAAAGCAATGGAAATAAGAAATTTGTAAATTTCCTTCTGATAACT<br>AGAAATAGAGGATCCAGTTTCTTTTGGTTAACCTAAATTTTATTTCATTTTATTG<br>TTTTATTTTATTTTATTTTATTTTATTTTGTGTAATCGTAGTTTCAGAGTGTTAG<br>AGCTGAAAGGAAGAAGTAGGAGAAACATGCAAAGTAAAAGTATAACACTTTCCTT<br>ACTAAACCGACATGGGTTTCCAGGTAGGGGCAGGATTCAGGATGACTGACAGGGC<br>CCTTAGGGAACACTGAGACCCTACGCTGACCTCATAAATGCTTGCTACCTTTGCT<br>GTTTTAATTACATCTTTTAATAGCAGGAAGCAGAACTCTGCACTTCAAAAGTTTT<br>TCCTCACCTGAGGAGTTAATTTAGTACAAGGGGAAAAAGTACAGGGGGATGGGAG<br>AAAGGCGATCACGTTGGGAAGCTATAGAGAAAGAAGAGTAAATTTTAGTAAAGGA<br>GGTTTAAACAAACAAAATATAAAGAGAAATAGGAACTTGAATCAAGGAAATGATT<br>TTAAAACGCAGTATTCTTAGTGGACTAGAGGAAAAAAATAATCTGAGCCAAGTAG<br>AAGACCTTTTCCCCTCCTACCCCTACTTTCTAAGTCACAGAGGCTTTTTGTTCCC<br>CCAGACACTCTTGCAGATTAGTCCAGGCAGAAACAGTTAGATGTCCCCAGTTAAC<br>CTCCTATTTGACACCACTGATTACCCCATTGATAGTCACACTTTGGGTTGTAAGT<br>GACTTTTTATTTATTTGTATTTTTGACTGCATTAAGAGGTCTCTAGTTTTTTATC<br>TCTTGTTTCCCAAAACCTAATAAGTAACTAATGCACAGAGCACATTGATTTGTAT<br>TTATTCTATTTTTAGACATAATTTATTAGCATGCATGAGCAAATTAAGAAAAACA<br>ACAACAAATGAATGCATATATATGTATATGTATGTGTGTATATATACACACATAT<br>ATATATATATTTTTTCTTTTCTTACCAGAAGGTTTTAATCCAAATAAGGAGAAGA<br>TATGCTTAGAACCGAGGTAGAGTTTTCATCCATTCTGTCCTGTAAGTATTTTGCA<br>TATTCTGGAGACGCAGGAAGAGATCCATCTACATATCCCAAAGCTGAATTATGGT<br>AGACAAAACTCTTCCACTTTTAGTGCATCAACTTCTTATTTGTGTAATAAGAAAA<br>TTGGGAAAACGATCTTCAATATGCTTACCAAGCTGTGATTCCAAATATTACGTAA<br>ATACACTTGCAAAGGAGGATGTTTTTAGTAGCAATTTGTACTGATGGTATGGGGC<br>CAAGAGATATATCTTAGAGGGAGGGCTGAGGGTTTGAAGTCCAACTCCTAAGCCA<br>GTGCCAGAAGAGCCAAGGACAGGTACGGCTGTCATCACTTAGACCTCACCCTGTG<br>GAGCCACACCCTAGGGTTGGCCAATCTACTCCCAGGAGCAGGGAGGGCAGGAGCC<br>AGGGCTGGGCATAAAAGTCAGGGCAGAGCCATCTATTGCTTACATTTGCTTCTGA<br>CACAACTGTGTTCACTAGCAACCTCAAACAGACACCATGGTGCATCTGACTCCTG<br>AGGAGAAAAGCGCTGTGACCGCACTCTGGGGTAAAGTGAACGTCGACGAGGTGGG<br>CGGTGAAGCTCTCGGAAGgttggtatcaaggttacaagacaggtttaaggagacc<br>aatagaaactgCgCATGTGGAGACAGAGAAGACTCTTGGGTTTCTGATAGGCACT<br>GACTCTCTCTGCCTATTGGTCTATTTTCCCACCCTTAGGCTGCTGGTGGTCTACC<br>CTTGGACCCAGAGGTTCTTTGAGTCCTTTGGGGATCTGTCCACTCCTGATGCTGT<br>TATGGGCAACCCTAAGGTGAAGGCTCATGGCAAGAAAGTGCTCGGTGCCTTTAGT<br>GATGGCCTGGCTCACCTGGACAACCTCAAGGGCACCTTTGCCACACTGAGTGAGC<br>TGCACTGTGACAAGCTGCACGTGGATCCTGAGAACTTCAGGGTGAGTCTATGGGA<br>CGCTTGATGTTTTCTTTCCCCTTCTTTTCTATGGTTAAGTTCATGTCATAGGAAG<br>GGGATAAGTAACAGGGTACAGTTTAGAATGGGAAACAGACGAATGATTGCATCAG<br>TGTGGAAGTCTCAGGATCGTTTTAGTTTCTTTTATTTGCTGTTCATAACAATTGT<br>TTTCTTTTGTTTAATTCTTGCTTTCTTTTTTTTTCTTCTCCGCAATTTTTACTAT<br>TATACTTAATGCCTTAACATTGTGTATAACAAAAGGAAATATCTCTGAGATACAT<br>TAAGTAACTTAAAAAAAAACTTTACACAGTCTGCCTAGTACATTACTATTTGGAA<br>TATATGTGTGCTTATTTGCATATTCATAATCTCCCTACTTTATTTTCTTTTATTT<br>TTAATTGATACATAATCATTATACATATTTATGGGTTAAAGTGTAATGTTTTAAT<br>ATGTGTACACATATTGACCAAATCAGGGTAATTTTGCATTTGTAATTTTAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCATT<br>CTAAAGAATAACAGTGATAATTTCTGGGTTAAGGCAATAGCAATATCTCTGCATA<br>TAAATATTTCTGCATATAAATTGTAACTGATGTAAGAGGTTTCATATTGCTAATA | 20 |

-continued

SEQUENCE LISTING

| Name/Identifier | Sequence | SEQ ID NO |
|---|---|---|
| | GCAGCTACAATCCAGCTACCATTCTGCTTTTATTTTATGGTTGGGATAAGGCTGG<br>ATTATTCTGAGTCCAAGCTAGGCCCTTTTGCTAATCATGTTCATACCTCTTATCT<br>TCCTCCCACAGCTCCTGGGCAACGTGCTGGTCTGTGTGCTGGCCCATCACTTTGG<br>CAAAGAATTCACCCCACCAGTGCAGGCTGCCTATCAGAAAGTGGTGGCTGGTGTG<br>GCTAATGCCCTGGCCCACAAGTATCACTAAGCTCGCTTTCTTGCTGTCCAATTTC<br>TATTAAAGGTTCCTTTGTTCCCTAAGTCCAACTACTAAACTGGGGGATATTATGA<br>AGGGCCTTGAGCATCTGGATTCTGCCTAATAAAAAACATTTATTTTCATTGCAAT<br>GATGTATTTAAATTATTTCTGAATATTTTACTAAAAAGGGAATGTGGGAGGTCAG<br>TGCATTTAAAACATAAAGAAATGAAGAGCTAGTTCAAACCTTGGGAAAATACACT<br>ATATCTTAAACTCCATGAAAGAAGGTGAGGCTGCAAACAGCTAATGCACATTGGC<br>AACAGCCCCTGATGCATATGCCTTATTCATCCCTCAGAAAAGGATTCAAGTAGAG<br>GCTTGATTTGGAGGTTAAAGTTTTGCTATGCTGTATTTTACATTACTTATTGTTT<br>TAGCTGTCCTCATGAATGTCTTTTCACTACCCATTTGCTTATCCTGCATCTCTCA<br>GCCTTGACTCCACTCAGTTCTCTTGCTTAGAGATACCACCTTTCCCCTGAAGTGT<br>TCCTTCCATGTTTTACGGCGAGATGGTTTCTCCTCGCCTGGCCACTCAGCCTTAG<br>TTGTCTCTGTTGTCTTATAGAGGTCTACTTGAAGAAGGAAAAACAGGGGTCATGG<br>TTTGACTGTCCTGTGAGCCCTTCTTCCCTGCCTCCCCCACTCACAGTGACCCGGA<br>ATCTGCAGTGCTAGTCTCCCGGAACTATCACTCTTTCACAGTCTGCTTTGGAAGG<br>ACTGGGCTTAGTATGAAAAGTTAGGACTGAGAAGAATTTGAAAGGCGGCTTTTTG<br>TAGCTTGATATTCACTACTGTCTTATTACCCTGTC | |
| AAV.321 with ITRs | *CCTGCAGGCAGCTGCGCGCTCGCTCGCTCACTGAGGCCGCCCGGGCAAAGCCCGG*<br>*GCGTCGGGCGACCTTTGGTCGCCCGGCCTCAGTGAGCGAGCGAGCGCGCAGAGAG*<br>*GGAGTGGCCAACTCCATCACTAGGGGTTCCT*GCGGCCGCACGCGTCTTGCTTTGA<br>CAATTTTGGTCTTTCAGAATACTATAAATATAACCTATATTATAATTTCATAAAG<br>TCTGTGCATTTTCTTTGACCCAGGATATTTGCAAAAGACATATTCAAACTTCCGC<br>AGAACACTTTATTTCACATATACATGCCTCTTATATCAGGGATGTGAAACAGGGT<br>CTTGAAAACTGTCTAAATCTAAAACAATGCTAATGCAGGTTTAAATTTAATAAAA<br>TAAAATCCAAAATCTAACAGCCAAGTCAAATCTGCATGTTTTAACATTTAAAATA<br>TTTTAAAGACGTCTTTTCCCAGGATTCAACATGTGAAATCTTTTCTCAGGGATAC<br>ACGTGTGCCTAGATCCTCATTGCTTTAGTTTTTTACAGAGGAATGAATATAAAAA<br>GAAAATACTTAAATTTTATCCCTCTTACCTCTATAATCATACATAGGCATAATTT<br>TTTAACCTAGGCTCCAGATAGCCATAGAAGAACCAAACACTTTCTGCGTGTGTGA<br>GAATAATCAGAGTGAGATTTTTTCACAAGTACCTGATGAGGGTTGAGACAGGTAG<br>AAAAAGTGAGAGATCTCTATTTATTTAGCAATAATAGAGAAAGCATTTAAGAGAA<br>TAAAGCAATGGAAATAAGAAATTTGTAAATTTCCTTCTGATAACTAGAAATAGAG<br>GATCCAGTTTCTTTTGGTTAACCTAAATTTTATTTCATTTTATTGTTTTATTTTA<br>TTTTATTTTATTTTATTTTGTGTAATCGTAGTTTCAGAGTGTTAGAGCTGAAAGG<br>AAGAAGTAGGAGAAACATGCAAAGTAAAAGTATAACACTTTCCTTACTAAACCGA<br>CATGGGTTTCCAGGTAGGGGCAGGATTCAGGATGACTGACAGGGCCCTTAGGGAA<br>CACTGAGACCCTACGCTGACCTCATAAATGCTTGCTACCTTTGCTGTTTTAATTA<br>CATCTTTTAATAGCAGGAAGCAGAACTCTGCACTTCAAAAGTTTTTCCTCACCTG<br>AGGAGTTAATTTAGTACAAGGGGAAAAAGTACAGGGGGATGGGAGAAAGGCGATC<br>ACGTTGGGAAGCTATAGAGAAAGAAGAGTAAATTTTAGTAAAGGAGGTTTAAACA<br>AACAAAATATAAAGAGAAATAGGAACTTGAATCAAGGAAATGATTTTAAAACGCA<br>GTATTCTTAGTGGACTAGAGGAAAAAAATAATCTGAGCCAAGTAGAAGACCTTTT<br>CCCCTCCTACCCCTACTTTCTAAGTCACAGAGGCTTTTTGTTCCCCCAGACACTC<br>TTGCAGATTAGTCCAGGCAGAAACAGTTAGATGTCCCCAGTTAACCTCCTATTTG<br>ACACCACTGATTACCCCATTGATAGTCACACTTTGGGTTGTAAGTGACTTTTTAT<br>TTATTTGTATTTTTGACTGCATTAAGAGGTCTCTAGTTTTTTATCTCTTGTTTCC<br>CAAAACCTAATAAGTAACTAATGCACAGAGCACATTGATTTGTATTTATTCTATT<br>TTTAGACATAATTTATTAGCATGCATGAGCAAATTAAGAAAAACAACAACAAATG<br>AATGCATATATATGTATATGTATGTGTGTATATATACACACATATATATATATAT<br>TTTTTCTTTTCTTACCAGAAGGTTTTAATCCAAATAAGGAGAAGATATGCTTAGA<br>ACCGAGGTAGAGTTTTCATCCATTCTGTCCTGTAAGTATTTTGCATATTCTGGAG<br>ACGCAGGAAGAGATCCATCTACATATCCCAAAGCTGAATTATGGTAGACAAAACT<br>CTTCCACTTTTAGTGCATCAACTTCTTATTTGTGTAATAAGAAAATTGGGAAAAC<br>GATCTTCAATATGCTTACCAAGCTGTGATTCCAAATATTACGTAAATACACTTGC<br>AAAGGAGGATGTTTTTAGTAGCAATTTGTACTGATGGTATGGGGCCAAGAGATAT<br>ATCTTAGAGGGAGGGCTGAGGGTTTGAAGTCCAACTCCTAAGCCAGTGCCAGAAG<br>AGCCAAGGACAGGTACGGCTGTCATCACTTAGACCTCACCCTGTGGAGCCACACC<br>CTAGGGTTGGCCAATCTACTCCCAGGAGCAGGGAGGGCAGGAGCCAGGGCTGGGC<br>ATAAAAGTCAGGGCAGAGCCATCTATTGCTTACATTTGCTTCTGACACAACTGTG<br>TTCACTAGCAACCTCAAACAGACACCATGGTGCATCTGACTCCTGAGGAGAAAAG<br>CGCTGTGACCGCACTCTGGGGTAAAGTGAACGTCGACGAGGTGGGCGGTGAAGCT<br>CTCGGAAGgttggtatcaaggttacaagacaggtttaaggagaccaatagaaact<br>gCgCATGTGGAGACAGAGAAGACTCTTGGGTTTCTGATAGGCACTGACTCTCTCT<br>GCCTATTGGTCTATTTTCCCACCCTTAGGCTGCTGGTGGTCTACCCTTGGACCCA<br>GAGGTTCTTTGAGTCCTTTGGGGATCTGTCCACTCCTGATGCTGTTATGGGCAAC<br>CCTAAGGTGAAGGCTCATGGCAAGAAAGTGCTCGGTGCCTTTAGTGATGGCCTGG<br>CTCACCTGGACAACCTCAAGGGCACCTTTGCCACACTGAGTGAGCTGCACTGTGA<br>CAAGCTGCACGTGGATCCTGAGAACTTCAGGGTGAGTCTATGGGACGCTTGATGT<br>TTTCTTTCCCCTTCTTTTCTATGGTTAAGTTCATGTCATAGGAAGGGGATAAGTA | 21 |

-continued

SEQUENCE LISTING

| Name/Identifier | Sequence | SEQ ID NO |
|---|---|---|
| | ACAGGGTACAGTTTAGAATGGGAAACAGACGAATGATTGCATCAGTGTGGAAGTC<br>TCAGGATCGTTTTAGTTTCTTTTATTTGCTGTTCATAACAATTGTTTTCTTTTGT<br>TTAATTCTTGCTTTCTTTTTTTTTCTTCTCCGCAATTTTTACTATTATACTTAAT<br>GCCTTAACATTGTGTATAACAAAAGGAAATATCTCTGAGATACATTAAGTAACTT<br>AAAAAAAAACTTTACACAGTCTGCCTAGTACATTACTATTTGGAATATATGTGTG<br>CTTATTTGCATATTCATAATCTCCCTACTTTATTTTCTTTTATTTTTAATTGATA<br>CATAATCATTATACATATTTATGGGTTAAAGTGTAATGTTTTAATATGTGTACAC<br>ATATTGACCAAATCAGGGTAATTTTGCATTTGTAATTTTAAAAAATGCTTTCTTC<br>TTTTAATATACTTTTTTGTTTATCTTATTTCTAATACTTTCCCTAATCTCTTTCT<br>TTCAGGGCAATAATGATACAATGTATCATGCCTCTTTGCACCATTCTAAAGAATA<br>ACAGTGATAATTTCTGGGTTAAGGCAATAGCAATATCTCTGCATATAAATATTTC<br>TGCATATAAATTGTAACTGATGTAAGAGGTTTCATATTGCTAATAGCAGCTACAA<br>TCCAGCTACCATTCTGCTTTTATTTTATGGTTGGGATAAGGCTGGATTATTCTGA<br>GTCCAAGCTAGGCCCTTTTGCTAATCATGTTCATACCTCTTATCTTCCTCCCACA<br>GCTCCTGGGCAACGTGCTGGTCTGTGTGCTGGCCCATCACTTTGGCAAAGAATTC<br>ACCCCACCAGTGCAGGCTGCCTATCAGAAAGTGGTGGCTGGTGTGGCTAATGCCC<br>TGGCCCACAAGTATCACTAAGCTCGCTTTCTTGCTGTCCAATTTCTATTAAAGGT<br>TCCTTTGTTCCCTAAGTCCAACTACTAAACTGGGGGATATTATGAAGGGCCTTGA<br>GCATCTGGATTCTGCCTAATAAAAAACATTTATTTTCATTGCAATGATGTATTTA<br>AATTATTTCTGAATATTTTACTAAAAAGGGAATGTGGGAGGTCAGTGCATTTAAA<br>ACATAAAGAAATGAAGAGCTAGTTCAAACCTTGGGAAAATACACTATATCTTAAA<br>CTCCATGAAAGAAGGTGAGGCTGCAAACAGCTAATGCACATTGGCAACAGCCCCT<br>GATGCATATGCCTTATTCATCCCTCAGAAAAGGATTCAAGTAGAGGCTTGATTTG<br>GAGGTTAAAGTTTTGCTATGCTGTATTTTACATTACTTATTGTTTTAGCTGTCCT<br>CATGAATGTCTTTTCACTACCCATTTGCTTATCCTGCATCTCTCAGCCTTGACTC<br>CACTCAGTTCTCTTGCTTAGAGATACCACCTTTCCCCTGAAGTGTTCCTTCCATG<br>TTTTACGGCGAGATGGTTTCTCCTCGCCTGGCCACTCAGCCTTAGTTGTCTCTGT<br>TGTCTTATAGAGGTCTACTTGAAGAAGGAAAAACAGGGGTCATGGTTTGACTGTC<br>CTGTGAGCCCTTCTTCCCTGCCTCCCCCACTCACAGTGACCCGGAATCTGCAGTG<br>CTAGTCTCCCGGAACTATCACTCTTTCACAGTCTGCTTTGGAAGGACTGGGCTTA<br>GTATGAAAAGTTAGGACTGAGAAGAATTTGAAAGGCGGCTTTTTGTAGCTTGATA<br>TTCACTACTGTCTTATTACCCTGTCGGTAACCACGTGCGGCCGAGGCTGCAGCGT<br>CGTCCTCCCT*AGGAACCCCTAGTGATGGAGTTGGCCACTCCCTCTCTGCGCGCTC*<br>*GCTCGCTCACTGAGGCCGGGCGACCAAAGGTCGCCCGACGCCCGGGCTTTGCCCG*<br>*GGCGGCCTCAGTGAGCGAGCGAGCGCGCAGCTGCCTGCAGG* | |
| AAV.310 sequence with E6V mutation in bold PAM mutation in underline | **GTC**GAGAAAAGCGCTGTGACCGCACTCTGGGGTAAAGTGAACGTCGACGAGGTGG<br>GCGGTGAAGCTCTCGGAAGgttggtatcaaggttacaagacaCgtttaaggagac<br>Ga | 22 |
| AAV.310 | CTTGCTTTGACAATTTTGGTCTTTCAGAATACTATAAATATAACCTATATTATAA<br>TTTCATAAAGTCTGTGCATTTTCTTTGACCCAGGATATTTGCAAAAGACATATTC<br>AAACTTCCGCAGAACACTTTATTTCACATATACATGCCTCTTATATCAGGGATGT<br>GAAACAGGGTCTTGAAAACTGTCTAAATCTAAAACAATGCTAATGCAGGTTTAAA<br>TTTAATAAAATAAAATCCAAAATCTAACAGCCAAGTCAAATCTGCATGTTTTAAC<br>ATTTAAAATATTTTAAAGACGTCTTTTCCCAGGATTCAACATGTGAAATCTTTTC<br>TCAGGGATACACGTGTGCCTAGATCCTCATTGCTTTAGTTTTTTACAGAGGAATG<br>AATATAAAAAGAAAATACTTAAATTTTATCCCTCTTACCTCTATAATCATACATA<br>GGCATAATTTTTTAACCTAGGCTCCAGATAGCCATAGAAGAACCAAACACTTTCT<br>GCGTGTGTGAGAATAATCAGAGTGAGATTTTTTCACAAGTACCTGATGAGGGTTG<br>AGACAGGTAGAAAAAGTGAGAGATCTCTATTTATTTAGCAATAATAGAGAAAGCA<br>TTTAAGAGAATAAAGCAATGGAAATAAGAAATTTGTAAATTTCCTTCTGATAACT<br>AGAAATAGAGGATCCAGTTTCTTTTGGTTAACCTAAATTTTATTTCATTTTATTG<br>TTTTATTTTATTTTATTTTATTTTATTTTGTGTAATCGTAGTTTCAGAGTGTTAG<br>AGCTGAAAGGAAGAAGTAGGAGAAACATGCAAAGTAAAAGTATAACACTTTCCTT<br>ACTAAACCGACATGGGTTTCCAGGTAGGGGCAGGATTCAGGATGACTGACAGGGC<br>CCTTAGGGAACACTGAGACCCTACGCTGACCTCATAAATGCTTGCTACCTTTGCT<br>GTTTTAATTACATCTTTTAATAGCAGGAAGCAGAACTCTGCACTTCAAAAGTTTT<br>TCCTCACCTGAGGAGTTAATTTAGTACAAGGGGAAAAAGTACAGGGGGATGGGAG<br>AAAGGCGATCACGTTGGGAAGCTATAGAGAAAGAAGAGTAAATTTTAGTAAAGGA<br>GGTTTAAACAAACAAAATATAAAGAGAAATAGGAACTTGAATCAAGGAAATGATT<br>TTAAAACGCAGTATTCTTAGTGGACTAGAGGAAAAAAATAATCTGAGCCAAGTAG<br>AAGACCTTTTCCCCTCCTACCCCTACTTTCTAAGTCACAGAGGCTTTTTGTTCCC<br>CCAGACACTCTTGCAGATTAGTCCAGGCAGAAACAGTTAGATGTCCCCAGTTAAC<br>CTCCTATTTGACACCACTGATTACCCCATTGATAGTCACACTTTGGGTTGTAAGT<br>GACTTTTTATTTATTTGTATTTTTGACTGCATTAAGAGGTCTCTAGTTTTTTATC<br>TCTTGTTTCCCAAAACCTAATAAGTAACTAATGCACAGAGCACATTGATTTGTAT<br>TTATTCTATTTTTAGACATAATTTATTAGCATGCATGAGCAAATTAAGAAAAACA | 23 |

-continued

SEQUENCE LISTING

| Name/Identifier | Sequence | SEQ ID NO |
|---|---|---|
| | ACAACAAATGAATGCATATATATGTATATGTATGTGTGTATATATACACACATAT<br>ATATATATATTTTTTCTTTTCTTACCAGAAGGTTTTAATCCAAATAAGGAGAAGA<br>TATGCTTAGAACCGAGGTAGAGTTTTCATCCATTCTGTCCTGTAAGTATTTTGCA<br>TATTCTGGAGACGCAGGAAGAGATCCATCTACATATCCCAAAGCTGAATTATGGT<br>AGACAAAACTCTTCCACTTTTAGTGCATCAACTTCTTATTTGTGTAATAAGAAAA<br>TTGGGAAAACGATCTTCAATATGCTTACCAAGCTGTGATTCCAAATATTACGTAA<br>ATACACTTGCAAAGGAGGATGTTTTTAGTAGCAATTTGTACTGATGGTATGGGGC<br>CAAGAGATATATCTTAGAGGGAGGGCTGAGGGTTTGAAGTCCAACTCCTAAGCCA<br>GTGCCAGAAGAGCCAAGGACAGGTACGGCTGTCATCACTTAGACCTCACCCTGTG<br>GAGCCACACCCTAGGGTTGGCCAATCTACTCCCAGGAGCAGGGAGGGCAGGAGCC<br>AGGGCTGGGCATAAAAGTCAGGGCAGAGCCATCTATTGCTTACATTTGCTTCTGA<br>CACAACTGTGTTCACTAGCAACCTCAAACAGACACCATGGTGCATCTGACTCCTG<br>TCGAGAAAAGCGCTGTGACCGCACTCTGGGGTAAAGTGAACGTCGACGAGGTGGG<br>CGGTGAAGCTCTCGGAAGgttggtatcaaggttacaagacaCgtttaaggagacG<br>aatagaaactgCgCATGTGGAGACAGAGAAGACTCTTGGGTTTCTGATAGGCACT<br>GACTCTCTCTGCCTATTGGTCTATTTTCCCACCCTTAGGCTGCTGGTGGTCTACC<br>CTTGGACCCAGAGGTTCTTTGAGTCCTTTGGGGATCTGTCCACTCCTGATGCTGT<br>TATGGGCAACCCTAAGGTGAAGGCTCATGGCAAGAAAGTGCTCGGTGCCTTTAGT<br>GATGGCCTGGCTCACCTGGACAACCTCAAGGGCACCTTTGCCACACTGAGTGAGC<br>TGCACTGTGACAAGCTGCACGTGGATCCTGAGAACTTCAGGGTGAGTCTATGGGA<br>CGCTTGATGTTTTCTTTCCCCTTCTTTTCTATGGTTAAGTTCATGTCATAGGAAG<br>GGGATAAGTAACAGGGTACAGTTTAGAATGGGAAACAGACGAATGATTGCATCAG<br>TGTGGAAGTCTCAGGATCGTTTTAGTTTCTTTTATTTGCTGTTCATAACAATTGT<br>TTTCTTTTGTTTAATTCTTGCTTTCTTTTTTTTTCTTCTCCGCAATTTTTACTAT<br>TATACTTAATGCCTTAACATTGTGTATAACAAAAGGAAATATCTCTGAGATACAT<br>TAAGTAACTTAAAAAAAAACTTTACACAGTCTGCCTAGTACATTACTATTTGGAA<br>TATATGTGTGCTTATTTGCATATTCATAATCTCCCTACTTTATTTTCTTTTATTT<br>TTAATTGATACATAATCATTATACATATTTATGGGTTAAAGTGTAATGTTTTAAT<br>ATGTGTACACATATTGACCAAATCAGGGTAATTTTGCATTTGTAATTTTAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCATT<br>CTAAAGAATAACAGTGATAATTTCTGGGTTAAGGCAATAGCAATATCTCTGCATA<br>TAAATATTTCTGCATATAAATTGTAACTGATGTAAGAGGTTTCATATTGCTAATA<br>GCAGCTACAATCCAGCTACCATTCTGCTTTTATTTTATGGTTGGGATAAGGCTGG<br>ATTATTCTGAGTCCAAGCTAGGCCCTTTTGCTAATCATGTTCATACCTCTTATCT<br>TCCTCCCACAGCTCCTGGGCAACGTGCTGGTCTGTGTGCTGGCCCATCACTTTGG<br>CAAAGAATTCACCCCACCAGTGCAGGCTGCCTATCAGAAAGTGGTGGCTGGTGTG<br>GCTAATGCCCTGGCCCACAAGTATCACTAAGCTCGCTTTCTTGCTGTCCAATTTC<br>TATTAAAGGTTCCTTTGTTCCCTAAGTCCAACTACTAAACTGGGGGATATTATGA<br>AGGGCCTTGAGCATCTGGATTCTGCCTAATAAAAAACATTTATTTTCATTGCAAT<br>GATGTATTTAAATTATTTCTGAATATTTTACTAAAAAGGGAATGTGGGAGGTCAG<br>TGCATTTAAAACATAAAGAAATGAAGAGCTAGTTCAAACCTTGGGAAAATACACT<br>ATATCTTAAACTCCATGAAAGAAGGTGAGGCTGCAAACAGCTAATGCACATTGGC<br>AACAGCCCCTGATGCATATGCCTTATTCATCCCTCAGAAAAGGATTCAAGTAGAG<br>GCTTGATTTGGAGGTTAAAGTTTTGCTATGCTGTATTTTACATTACTTATTGTTT<br>TAGCTGTCCTCATGAATGTCTTTTCACTACCCATTTGCTTATCCTGCATCTCTCA<br>GCCTTGACTCCACTCAGTTCTCTTGCTTAGAGATACCACCTTTCCCCTGAAGTGT<br>TCCTTCCATGTTTTACGGCGAGATGGTTTCTCCTCGCCTGGCCACTCAGCCTTAG<br>TTGTCTCTGTTGTCTTATAGAGGTCTACTTGAAGAAGGAAAAACAGGGGTCATGG<br>TTTGACTGTCCTGTGAGCCCTTCTTCCCTGCCTCCCCCACTCACAGTGACCCGGA<br>ATCTGCAGTGCTAGTCTCCCGGAACTATCACTCTTTCACAGTCTGCTTTGGAAGG<br>ACTGGGCTTAGTATGAAAAGTTAGGACTGAGAAGAATTTGAAAGGCGGCTTTTTG<br>TAGCTTGATATTCACTACTGTCTTATTACCCTGTC | |
| AAV.310<br>with<br>ITRs | CCTGCAGGCAGCTGCGCGCTCGCTCGCTCACTGAGGCCGCCCGGGCGTCGGGCGA<br>CCTTTGGTCGCCCGGCCTCAGTGAGCGAGCGAGCGCGCAGAGAGGGAGTGGCCAA<br>CTCCATCACTAGGGGTTCCTGCGGCCGCACGCGTCTTGCTTTGACAATTTTGGTC<br>TTTCAGAATACTATAAATATAACCTATATTATAATTTCATAAAGTCTGTGCATTT<br>TCTTTGACCCAGGATATTTGCAAAAGACATATTCAAACTTCCGCAGAACACTTTA<br>TTTCACATATACATGCCTCTTATATCAGGGATGTGAAACAGGGTCTTGAAAACTG<br>TCTAAATCTAAAACAATGCTAATGCAGGTTTAAATTTAATAAAATAAAATCCAAA<br>ATCTAACAGCCAAGTCAAATCTGCATGTTTTAACATTTAAAATATTTTAAAGACG<br>TCTTTTCCCAGGATTCAACATGTGAAATCTTTTCTCAGGGATACACGTGTGCCTA<br>GATCCTCATTGCTTTAGTTTTTTACAGAGGAATGAATATAAAAAGAAAATACTTA<br>AATTTTATCCCTCTTACCTCTATAATCATACATAGGCATAATTTTTTAACCTAGG<br>CTCCAGATAGCCATAGAAGAACCAAACACTTTCTGCGTGTGTGAGAATAATCAGA<br>GTGAGATTTTTTCACAAGTACCTGATGAGGGTTGAGACAGGTAGAAAAAGTGAGA<br>GATCTCTATTTATTTAGCAATAATAGAGAAAGCATTTAAGAGAATAAAGCAATGG<br>AAATAAGAAATTTGTAAATTTCCTTCTGATAACTAGAAATAGAGGATCCAGTTTC<br>TTTTGGTTAACCTAAATTTTATTTCATTTTATTGTTTTATTTTATTTTATTTTAT<br>TTTATTTTGTGTAATCGTAGTTTCAGAGTGTTAGAGCTGAAAGGAAGAAGTAGGA<br>GAAACATGCAAAGTAAAAGTATAACACTTTCCTTACTAAACCGACATGGGTTTCC<br>AGGTAGGGGCAGGATTCAGGATGACTGACAGGGCCCTTAGGGAACACTGAGACCC | 24 |

-continued

SEQUENCE LISTING

| Name/Identifier | Sequence | SEQ ID NO |
|---|---|---|
| | TACGCTGACCTCATAAATGCTTGCTACCTTTGCTGTTTTAATTACATCTTTTAAT<br>AGCAGGAAGCAGAACTCTGCACTTCAAAAGTTTTTCCTCACCTGAGGAGTTAATT<br>TAGTACAAGGGGAAAAAGTACAGGGGGATGGGAGAAAGGCGATCACGTTGGGAAG<br>CTATAGAGAAAGAAGAGTAAATTTTAGTAAAGGAGGTTTAAACAAACAAAATATA<br>AAGAGAAATAGGAACTTGAATCAAGGAAATGATTTTAAAACGCAGTATTCTTAGT<br>GGACTAGAGGAAAAAAAATAATCTGAGCCAAGTAGAAGACCTTTTCCCCTCCTACC<br>CCTACTTTCTAAGTCACAGAGGCTTTTTGTTCCCCCAGACACTCTTGCAGATTAG<br>TCCAGGCAGAAACAGTTAGATGTCCCCAGTTAACCTCCTATTTGACACCACTGAT<br>TACCCCATTGATAGTCACACTTTGGGTTGTAAGTGACTTTTTATTTATTTGTATT<br>TTTGACTGCATTAAGAGGTCTCTAGTTTTTTATCTCTTGTTTCCCAAAACCTAAT<br>AAGTAACTAATGCACAGAGCACATTGATTTGTATTTATTCTATTTTTAGACATAA<br>TTTATTAGCATGCATGAGCAAATTAAGAAAAACAACAACAAATGAATGCATATAT<br>ATGTATATGTATGTGTGTATATATACACACATATATATATATATTTTTTCTTTTC<br>TTACCAGAAGGTTTTAATCCAAATAAGGAGAAGATATGCTTAGAACCGAGGTAGA<br>GTTTTCATCCATTCTGTCCTGTAAGTATTTTGCATATTCTGGAGACGCAGGAAGA<br>GATCCATCTACATATCCCAAAGCTGAATTATGGTAGACAAAACTCTTCCACTTTT<br>AGTGCATCAACTTCTTATTTGTGTAATAAGAAAATTGGGAAAACGATCTTCAATA<br>TGCTTACCAAGCTGTGATTCCAAATATTACGTAAATACACTTGCAAAGGAGGATG<br>TTTTTAGTAGCAATTTGTACTGATGGTATGGGGCCAAGAGATATATCTTAGAGGG<br>AGGGCTGAGGGTTTGAAGTCCAACTCCTAAGCCAGTGCCAGAAGAGCCAAGGACA<br>GGTACGGCTGTCATCACTTAGACCTCACCCTGTGGAGCCACACCCTAGGGTTGGC<br>CAATCTACTCCCAGGAGCAGGGAGGGCAGGAGCCAGGGCTGGGCATAAAAGTCAG<br>GGCAGAGCCATCTATTGCTTACATTTGCTTCTGACACAACTGTGTTCACTAGCAA<br>CCTCAAACAGACACCATGGTGCATCTGACTCCTGTCGAGAAAAGCGCTGTGACCG<br>CACTCTGGGGTAAAGTGAACGTCGACGAGGTGGGCGGTGAAGCTCTCGGAAGgtt<br>ggtatcaaggttacaagacaCgtttaaggagacGaatagaaactgCgCATGTGGA<br>GACAGAGAAGACTCTTGGGTTTCTGATAGGCACTGACTCTCTCTGCCTATTGGTC<br>TATTTTCCCACCCTTAGGCTGCTGGTGGTCTACCCTTGGACCCAGAGGTTCTTTG<br>AGTCCTTTGGGGATCTGTCCACTCCTGATGCTGTTATGGGCAACCCTAAGGTGAA<br>GGCTCATGGCAAGAAAGTGCTCGGTGCCTTTAGTGATGGCCTGGCTCACCTGGAC<br>AACCTCAAGGGCACCTTTGCCACACTGAGTGAGCTGCACTGTGACAAGCTGCACG<br>TGGATCCTGAGAACTTCAGGGTGAGTCTATGGGACGCTTGATGTTTTCTTTCCCC<br>TTCTTTTCTATGGTTAAGTTCATGTCATAGGAAGGGGATAAGTAACAGGGTACAG<br>TTTAGAATGGGAAACAGACGAATGATTGCATCAGTGTGGAAGTCTCAGGATCGTT<br>TTAGTTTCTTTTATTTGCTGTTCATAACAATTGTTTTCTTTTGTTTAATTCTTGC<br>TTTCTTTTTTTTTCTTCTCCGCAATTTTTACTATTATACTTAATGCCTTAACATT<br>GTGTATAACAAAAGGAAATATCTCTGAGATACATTAAGTAACTTAAAAAAAAACT<br>TTACACAGTCTGCCTAGTACATTACTATTTGGAATATATGTGTGCTTATTTGCAT<br>ATTCATAATCTCCCTACTTTATTTTCTTTTATTTTTAATTGATACATAATCATTA<br>TACATATTTATGGGTTAAAGTGTAATGTTTTAATATGTGTACACATATTGACCAA<br>ATCAGGGTAATTTTGCATTTGTAATTTTAAAAAATGCTTTCTTCTTTTAATATAC<br>TTTTTTGTTTATCTTATTTCTAATACTTTCCCTAATCTCTTTCTTTCAGGGCAAT<br>AATGATACAATGTATCATGCCTCTTTGCACCATTCTAAAGAATAACAGTGATAAT<br>TTCTGGGTTAAGGCAATAGCAATATCTCTGCATATAAATATTTCTGCATATAAAT<br>TGTAACTGATGTAAGAGGTTTCATATTGCTAATAGCAGCTACAATCCAGCTACCA<br>TTCTGCTTTTATTTTATGGTTGGGATAAGGCTGGATTATTCTGAGTCCAAGCTAG<br>GCCCTTTTGCTAATCATGTTCATACCTCTTATCTTCCTCCCACAGCTCCTGGGCA<br>ACGTGCTGGTCTGTGTGCTGGCCCATCACTTTGGCAAAGAATTCACCCCACCAGT<br>GCAGGCTGCCTATCAGAAAGTGGTGGCTGGTGTGGCTAATGCCCTGGCCCACAAG<br>TATCACTAAGCTCGCTTTCTTGCTGTCCAATTTCTATTAAAGGTTCCTTTGTTCC<br>CTAAGTCCAACTACTAAACTGGGGGATATTATGAAGGGCCTTGAGCATCTGGATT<br>CTGCCTAATAAAAAACATTTATTTTCATTGCAATGATGTATTTAAATTATTTCTG<br>AATATTTTACTAAAAAGGGAATGTGGGAGGTCAGTGCATTTAAAACATAAAGAAA<br>TGAAGAGCTAGTTCAAACCTTGGGAAAATACACTATATCTTAAACTCCATGAAAG<br>AAGGTGAGGCTGCAAACAGCTAATGCACATTGGCAACAGCCCCTGATGCATATGC<br>CTTATTCATCCCTCAGAAAAGGATTCAAGTAGAGGCTTGATTTGGAGGTTAAAGT<br>TTTGCTATGCTGTATTTTACATTACTTATTGTTTTAGCTGTCCTCATGAATGTCT<br>TTTCACTACCCATTTGCTTATCCTGCATCTCTCAGCCTTGACTCCACTCAGTTCT<br>CTTGCTTAGAGATACCACCTTTCCCCTGAAGTGTTCCTTCCATGTTTTACGGCGA<br>GATGGTTTCTCCTCGCCTGGCCACTCAGCCTTAGTTGTCTCTGTTGTCTTATAGA<br>GGTCTACTTGAAGAAGGAAAAACAGGGGTCATGGTTTGACTGTCCTGTGAGCCCT<br>TCTTCCCTGCCTCCCCCACTCACAGTGACCCGGAATCTGCAGTGCTAGTCTCCCG<br>GAACTATCACTCTTTCACAGTCTGCTTTGGAAGGACTGGGCTTAGTATGAAAAGT<br>TAGGACTGAGAAGAATTTGAAAGGCGGCTTTTTGTAGCTTGATATTCACTACTGT<br>CTTATTACCCTGTCGGTAACCACGTGCGGCCGAGGCTGCAGCGTCGTCCTCCCTC<br>CTGCAGGCAGCTGCGCGCTCGCTCGCTCACTGAGGCCGCCCGGGCGTCGGGCGAC<br>CTTTGGTCGCCCGGCCTCAGTGAGCGAGCGAGCGCGCAGAGAGGGAGTGGCCAAC<br>TCCATCACTAGGGGTTCCT | |
| SV40 NLS | PKKKRKV | 25 |
| SV40 NLS | PKKKRRV | 26 |

-continued

SEQUENCE LISTING

| Name/Identifier | Sequence | SEQ ID NO |
|---|---|---|
| Nucleoplasmin NLS | KRPAATKKAGQAKKKK | 27 |
| A10 (DNA) | ATGCAGATTTACGTGAAGACCTTTGCCCGGAAGCCCATCACCCTCGAGGTTGAAC CCTCGGATACGATAGAAAATGTAAAGGCCAAGATCCAGGATAAGGAAGGAATTCC TCCTGATCAGCAGCGACTGATCTTTGCTGAAATGCGGCTGGAAGATGGACGTACT TTGTCTGACTACAATATTAAAAACGACTCTACTCTTTTTCTTGTGTTGAAAAATA GTGTTACT | 28 |
| A10 (RNA) | AUGCAGAUUUACGUGAAGACCUUUGCCCGGAAGCCCAUCACCCUCGAGGUUGAAC CCUCGGAUACGAUAGAAAAUGUAAAGGCCAAGAUCCAGGAUAAGGAAGGAAUUCC UCCUGAUCAGCAGCGACUGAUCUUUGCUGAAAUGCGGCUGGAAGAUGGACGUACU UUGUCUGACUACAAUAUUAAAAACGACUCUACUCUUUUUCUUGUGUUGAAAAAUA GUGUUACU | 29 |
| A10 (aa) | MQIYVKTFARKPITLEVEPSDTIENVKAKIQDKEGIPPDQQRLIFAEMRLEDGRT LSDYNIKNDSTLFLVLKNSVT | 30 |
| A11 (DNA) | ATGCTGATTTTCGTGACCACCGATATGGGGATGACAATCTCACTCGAGGTTGAAC CCTCGGATACGATAGAAAATGTAAAGGCCAAGATCCAGGATAAGGAAGGAATTCC TCCTGATCAGCAGAGACTGATCTTTGGTGACAAGGATCTGGAAGATGGACGTACT TTGTCTGACTACAATATTCAAAAGGAGTCTAGCCTTAATCTTGTGCTGAAACTTC GTGGTGGT | 31 |
| A11 (RNA) | AUGCUGAUUUUCGUGACCACCGAUAUGGGGAUGACAAUCUCACUCGAGGUUGAAC CCUCGGAUACGAUAGAAAAUGUAAAGGCCAAGAUCCAGGAUAAGGAAGGAAUUCC UCCUGAUCAGCAGAGACUGAUCUUUGGUGACAAGGAUCUGGAAGAUGGACGUACU UUGUCUGACUACAAUAUUCAAAAGGAGUCUAGCCUUAAUCUUGUGCUGAAACUUC GUGGUGGU | 32 |
| A11 (aa) | MLIFVTTDMGMTISLEVEPSDTIENVKAKIQDKEGIPPDQQRLIFGDKDLEDGRT LSDYNIQKESSLNLVLKLRGG | 33 |
| C08 (DNA) | ATGCAGATTTTCGTGACCACCGATATGTGGATGAGAATCTCACTCGAGGTTGAAC CCTCGGATACGATAGAAAATGTAAAGGCCAAGATCCAGGATAAGGAAGGAATTCC TCCTGATCAGCAGAGACTGATCTTTGGTGACAAGGATCTGGAAGATGGACGTACT TTGTCTGACTACAATATTCAAAAGGAGTCTAGCCTTAATCTTGTGCTGAACCTTC GTGGTGGT | 34 |
| C08 (RNA) | AUGCAGAUUUUCGUGACCACCGAUAUGUGGAUGAGAAUCUCACUCGAGGUUGAAC CCUCGGAUACGAUAGAAAAUGUAAAGGCCAAGAUCCAGGAUAAGGAAGGAAUUCC UCCUGAUCAGCAGAGACUGAUCUUUGGUGACAAGGAUCUGGAAGAUGGACGUACU UUGUCUGACUACAAUAUUCAAAAGGAGUCUAGCCUUAAUCUUGUGCUGAACCUUC GUGGUGGU | 35 |
| C08 (aa) | MQIFVTTDMWMRISLEVEPSDTIENVKAKIQDKEGIPPDQQRLIFGDKDLEDGRT LSDYNIQKESSLNLVLNLRGG | 36 |
| G08 (DNA) | ATGTTGATTTTCGTGAAAACCCTTACCGGGAAAACCATCACCCTCGAGGTTGAAC CCTCGGATACGATAGAAAATGTAAAGGCCAAGATCCAGGATAAGGAAGGAATTCC TCCTGATCAGCAGAGACTGATCTTTGCTGGCAAATCGCTGGAAGATGGACGTACT TTGTCTGACTACAATATTCTAAAGGACTCTAAACTTCATCCTCTGTTGAGACTTC GTGGTGGT | 37 |
| G08 (RNA) | AUGUUGAUUUUCGUGAAAACCCUUACCGGGAAAACCAUCACCCUCGAGGUUGAAC CCUCGGAUACGAUAGAAAAUGUAAAGGCCAAGAUCCAGGAUAAGGAAGGAAUUCC UCCUGAUCAGCAGAGACUGAUCUUUGCUGGCAAAUCGCUGGAAGAUGGACGUACU UUGUCUGACUACAAUAUUCUAAAGGACUCUAAACUUCAUCCUCUGUUGAGACUUC GUGGUGGU | 38 |
| G08 (aa) | MLIFVKTLTGKTITLEVEPSDTIENVKAKIQDKEGIPPDQQRLIFAGKSLEDGRT LSDYNILKDSKLHPLLRLRGG | 39 |
| H04 (DNA) | ATGCGAATTATCGTGAAAACCTTTATGCGGAAGCCGATCACGCTCGAGGTTGAAC CCTCGGATACGATAGAAAATGTAAAGGCCAAGATCCAGGATAAGGAAGGAATTCC TCCTGATCAGCAGAGACTGTATTTTGCGGCCAGTCAGCTGGAAGATGGACGTACT TTGTCTGACTACAATATTCAAAAGGAGTCTACTCTTCTTCTTGTGGTAAGGCTGC TCCGCGTT | 40 |

-continued

SEQUENCE LISTING

| Name/Identifier | Sequence | SEQ ID NO |
|---|---|---|
| H04 (RNA) | AUGCGAAUUAUCGUGAAAACCUUUAUGCGGAAGCCGAUCACGCUCGAGGUUGAAC CCUCGGAUACGAUAGAAAAUGUAAAGGCCAAGAUCCAGGAUAAGGAAGGAAUUCC UCCUGAUCAGCAGAGACUGUAUUUUGCGGCCAGUCAGCUGGAAGAUGGACGUACU UUGUCUGACUACAAUAUUCAAAAGGAGUCUACUCUUCUUCUUGUGGUAAGGCUGC UCCGCGUU | 41 |
| H04 (aa) | MRIIVKTFMRKPITLEVEPSDTIENVKAKIQDKEGIPPDQQRLYFAASQLEDGRT LSDYNIQKESTLLLWRLLRV | 42 |
| i53 alt (RNA) | AUGUUGAUUUUCGUGAAAACCCUUACCGGGAAAACCAUCACCCUCGAGGUUGAAC CCUCGGAUACGAUAGAAAAUGUAAAGGCCAAGAUCCAGGAUAAGGAAGGAAUUCC UCCUGAUCAGCAGAGACUGGCCUUUGCUGGCAAAUCGCUGGAAGAUGGACGUACU UUGUCUGACUACAAUAUUCUAAAGGACUCUAAACUUCAUCCUCUGUUGAGACUUC GU | 43 |
| AAV.323 | CTTGCTTTGACAATTTTGGTCTTTCAGAATACTATAAATATAACCTATATTATAA TTTCATAAAGTCTGTGCATTTTCTTTGACCCAGGATATTTGCAAAAGACATATTC AAACTTCCGCAGAACACTTTATTTCACATATACATGCCTCTTATATCAGGGATGT GAAACAGGGTCTTGAAAACTGTCTAAATCTAAAACAATGCTAATGCAGGTTTAAA TTTAATAAAATAAAATCCAAAATCTAACAGCCAAGTCAAATCTGCATGTTTTAAC ATTTAAAATATTTTAAAGACGTCTTTTCCCAGGATTCAACATGTGAAATCTTTTC TCAGGGATACACGTGTGCCTAGATCCTCATTGCTTTAGTTTTTTACAGAGGAATG AATATAAAAAGAAAATACTTAAATTTTATCCCTCTTACCTCTATAATCATACATA GGCATAATTTTTTAACCTAGGCTCCAGATAGCCATAGAAGAACCAAACACTTTCT GCGTGTGTGAGAATAATCAGAGTGAGATTTTTTCACAAGTACCTGATGAGGGTTG AGACAGGTAGAAAAAGTGAGAGATCTCTATTTATTTAGCAATAATAGAGAAAGCA TTTAAGAGAATAAAGCAATGGAAATAAGAAATTTGTAAATTTCCTTCTGATAACT AGAAATAGAGGATCCAGTTTCTTTTGGTTAACCTAAATTTTATTTCATTTTATTG TTTTATTTTATTTTATTTTATTTTATTTTGTGTAATCGTAGTTTCAGAGTGTTAG AGCTGAAAGGAAGAAGTAGGAGAAACATGCAAAGTAAAAGTATAACACTTTCCTT ACTAAACCGACATGGGTTTCCAGGTAGGGGCAGGATTCAGGATGACTGACAGGGC CCTTAGGGAACACTGAGACCCTACGCTGACCTCATAAATGCTTGCTACCTTTGCT GTTTTAATTACATCTTTTAATAGCAGGAAGCAGAACTCTGCACTTCAAAAGTTTT TCCTCACCTGAGGAGTTAATTTAGTACAAGGGGAAAAAGTACAGGGGGATGGGAG AAAGGCGATCACGTTGGGAAGCTATAGAGAAAGAAGAGTAAATTTTAGTAAAGGA GGTTTAAACAAACAAAATATAAAGAGAAATAGGAACTTGAATCAAGGAAATGATT TTAAAACGCAGTATTCTTAGTGGACTAGAGGAAAAAAATAATCTGAGCCAAGTAG AAGACCTTTTCCCCTCCTACCCCTACTTTCTAAGTCACAGAGGCTTTTTGTTCCC CCAGACACTCTTGCAGATTAGTCCAGGCAGAAACAGTTAGATGTCCCCAGTTAAC CTCCTATTTGACACCACTGATTACCCCATTGATAGTCACACTTTGGGTTGTAAGT GACTTTTTATTTATTTGTATTTTTGACTGCATTAAGAGGTCTCTAGTTTTTTATC TCTTGTTTCCCAAAACCTAATAAGTAACTAATGCACAGAGCACATTGATTTGTAT TTATTCTATTTTTAGACATAATTTATTAGCATGCATGAGCAAATTAAGAAAAACA ACAACAAATGAATGCATATATATGTATATGTATGTGTGTATATATACACACATAT ATATATATATTTTTTCTTTTCTTACCAGAAGGTTTTAATCCAAATAAGGAGAAGA TATGCTTAGAACCGAGGTAGAGTTTTCATCCATTCTGTCCTGTAAGTATTTTGCA TATTCTGGAGACGCAGGAAGAGATCCATCTACATATCCCAAAGCTGAATTATGGT AGACAAAACTCTTCCACTTTTAGTGCATCAACTTCTTATTTGTGTAATAAGAAAA TTGGGAAAACGATCTTCAATATGCTTACCAAGCTGTGATTCCAAATATTACGTAA ATACACTTGCAAAGGAGGATGTTTTTAGTAGCAATTTGTACTGATGGTATGGGGC CAAGAGATATATCTTAGAGGGAGGGCTGAGGGTTTGAAGTCCAACTCCTAAGCCA GTGCCAGAAGAGCCAAGGACAGGTACGGCTGTCATCACTTAGACCTCACCCTGTG GAGCCACACCCTAGGGTTGGCCAATCTACTCCCAGGAGCAGGGAGGGCAGGAGCC AGGGCTGGGCATAAAAGTCAGGGCAGAGCCATCTATTGCTTACATTTGCTTCTGA CACAACTGTGTTCACTAGCAACCTCAAACAGACACCATGGTGCATCTGACTCCTG AAGAAAAATCCGCTGTCACTGCCCTGTGGGGCAAGGTGAACGTGGATGAAGTTGG TGGTGAGGCCCTGGGCAGGTTGGTATCAAGGTTACAAGACAGGTTTAAGGAGACC AATAGAAACTGGGCATGTGGAGACAGAGAAGACTCTTGGGTTTCTGATAGGCACT GACTCTCTCTGCCTATTGGTCTATTTTCCCACCCTTAGGCTGCTGGTGGTCTACC CTTGGACCCAGAGGTTCTTTGAGTCCTTTGGGGATCTGTCCACTCCTGATGCTGT TATGGGCAACCCTAAGGTGAAGGCTCATGGCAAGAAAGTGCTCGGTGCCTTTAGT GATGGCCTGGCTCACCTGGACAACCTCAAGGGCACCTTTGCCACACTGAGTGAGC TGCACTGTGACAAGCTGCACGTGGATCCTGAGAACTTCAGGGTGAGTCTATGGGA CGCTTGATGTTTTCTTTCCCCTTCTTTTCTATGGTTAAGTTCATGTCATAGGAAG GGGATAAGTAACAGGGTACAGTTTAGAATGGGAAACAGACGAATGATTGCATCAG TGTGGAAGTCTCAGGATCGTTTTAGTTTCTTTTATTTGCTGTTCATAACAATTGT TTTCTTTTGTTTAATTCTTGCTTTCTTTTTTTTTCTTCTCCGCAATTTTTACTAT TATACTTAATGCCTTAACATTGTGTATAACAAAAGGAAATATCTCTGAGATACAT TAAGTAACTTAAAAAAAAACTTTACACAGTCTGCCTAGTACATTACTATTTGGAA TATATGTGTGCTTATTTGCATATTCATAATCTCCCTACTTTATTTTCTTTTATTT TTAATTGATACATAATCATTATACATATTTATGGGTTAAAGTGTAATGTTTTAAT ATGTGTACACATATTGACCAAATCAGGGTAATTTTGCATTTGTAATTTTAAAAA | 44 |

-continued

| SEQUENCE LISTING | | |
|---|---|---|
| Name/Identifier | Sequence | SEQ ID NO |
| | TGCTTTCTTCTTTTAATATACTTTTTTGTTTATCTTATTTCTAATACTTTCCCTA ATCTCTTTCTTTCAGGGCAATAATGATACAATGTATCATGCCTCTTTGCACCATT CTAAAGAATAACAGTGATAATTTCTGGGTTAAGGCAATAGCAATATCTCTGCATA TAAATATTTCTGCATATAAATTGTAACTGATGTAAGAGGTTTCATATTGCTAATA GCAGCTACAATCCAGCTACCATTCTGCTTTTATTTTATGGTTGGGATAAGGCTGG ATTATTCTGAGTCCAAGCTAGGCCCTTTTGCTAATCATGTTCATACCTCTTATCT TCCTCCCACAGCTCCTGGGCAACGTGCTGGTCTGTGTGCTGGCCCATCACTTTGG CAAAGAATTCACCCCACCAGTGCAGGCTGCCTATCAGAAAGTGGTGGCTGGTGTG GCTAATGCCCTGGCCCACAAGTATCACTAAGCTCGCTTTCTTGCTGTCCAATTTC TATTAAAGGTTCCTTTGTTCCCTAAGTCCAACTACTAAACTGGGGGATATTATGA AGGGCCTTGAGCATCTGGATTCTGCCTAATAAAAAACATTTATTTTCATTGCAAT GATGTATTTAAATTATTTCTGAATATTTTACTAAAAAGGGAATGTGGGAGGTCAG TGCATTTAAAACATAAAGAAATGAAGAGCTAGTTCAAACCTTGGGAAAATACACT ATATCTTAAACTCCATGAAAGAAGGTGAGGCTGCAAACAGCTAATGCACATTGGC AACAGCCCCTGATGCATATGCCTTATTCATCCCTCAGAAAAGGATTCAAGTAGAG GCTTGATTTGGAGGTTAAAGTTTTGCTATGCTGTATTTTACATTACTTATTGTTT TAGCTGTCCTCATGAATGTCTTTTCACTACCCATTTGCTTATCCTGCATCTCTCA GCCTTGACTCCACTCAGTTCTCTTGCTTAGAGATACCACCTTTCCCCTGAAGTGT TCCTTCCATGTTTTACGGCGAGATGGTTTCTCCTCGCCTGGCCACTCAGCCTTAG TTGTCTCTGTTGTCTTATAGAGGTCTACTTGAAGAAGGAAAAACAGGGGTCATGG TTTGACTGTCCTGTGAGCCCTTCTTCCCTGCCTCCCCCACTCACAGTGACCCGGA ATCTGCAGTGCTAGTCTCCCGGAACTATCACTCTTTCACAGTCTGCTTTGGAAGG ACTGGGCTTAGTATGAAAAGTTAGGACTGAGAAGAATTTGAAAGGCGGCTTTTTG TAGCTTGATATTCACTACTGTCTTATTACCCTGTC | |
| AAV.323 sequence with E6V correction in bold PAM mutation in underline | **GAA**GAAAAATCCG<u>CTG</u> | 45 |
| AAV.323 with ITRs | CCTGCAGGCAGCTGCGCGCTCGCTCGCTCACTGAGGCCGCCCGGGCGTCGGGCGA CCTTTGGTCGCCCGGCCTCAGTGAGCGAGCGAGCGCGCAGAGAGGGAGTGGCCAA CTCCATCACTAGGGGTTCCTGCGGCCGCACGCGTCTTGCTTTGACAATTTTGGTC TTTCAGAATACTATAAATATAACCTATATTATAATTTCATAAAGTCTGTGCATTT TCTTTGACCCAGGATATTTGCAAAAGACATATTCAAACTTCCGCAGAACACTTTA TTTCACATATACATGCCTCTTATATCAGGGATGTGAAACAGGGTCTTGAAAACTG TCTAAATCTAAAACAATGCTAATGCAGGTTTAAATTTAATAAAATAAAATCCAAA ATCTAACAGCCAAGTCAAATCTGCATGTTTTAACATTTAAAATATTTTAAAGACG TCTTTTCCCAGGATTCAACATGTGAAATCTTTTCTCAGGGATACACGTGTGCCTA GATCCTCATTGCTTTAGTTTTTTACAGAGGAATGAATATAAAAAGAAAATACTTA AATTTTATCCCTCTTACCTCTATAATCATACATAGGCATAATTTTTTAACCTAGG CTCCAGATAGCCATAGAAGAACCAAACACTTTCTGCGTGTGTGAGAATAATCAGA GTGAGATTTTTTCACAAGTACCTGATGAGGGTTGAGACAGGTAGAAAAAGTGAGA GATCTCTATTTATTTAGCAATAATAGAGAAAGCATTTAAGAGAATAAAGCAATGG AAATAAGAAATTTGTAAATTTCCTTCTGATAACTAGAAATAGAGGATCCAGTTTC TTTTGGTTAACCTAAATTTTATTTCATTTTATTGTTTTATTTTATTTTATTTTAT TTTATTTTGTGTAATCGTAGTTTCAGAGTGTTAGAGCTGAAAGGAAGAAGTAGGA GAAACATGCAAAGTAAAAGTATAACACTTTCCTTACTAAACCGACATGGGTTTCC AGGTAGGGGCAGGATTCAGGATGACTGACAGGGCCCTTAGGGAACACTGAGACCC TACGCTGACCTCATAAATGCTTGCTACCTTTGCTGTTTTAATTACATCTTTTAAT AGCAGGAAGCAGAACTCTGCACTTCAAAAGTTTTTCCTCACCTGAGGAGTTAATT TAGTACAAGGGGAAAAAGTACAGGGGGATGGGAGAAAGGCGATCACGTTGGGAAG CTATAGAGAAAGAAGAGTAAATTTTAGTAAAGGAGGTTTAAACAAACAAAATATA AAGAGAAATAGGAACTTGAATCAAGGAAATGATTTTAAAACGCAGTATTCTTAGT GGACTAGAGGAAAAAAAATAATCTGAGCCAAGTAGAAGACCTTTTCCCCTCCTACC CCTACTTTCTAAGTCACAGAGGCTTTTTGTTCCCCCAGACACTCTTGCAGATTAG TCCAGGCAGAAACAGTTAGATGTCCCCAGTTAACCTCCTATTTGACACCACTGAT TACCCCATTGATAGTCACACTTTGGGTTGTAAGTGACTTTTTATTTATTTGTATT TTTGACTGCATTAAGAGGTCTCTAGTTTTTTATCTCTTGTTTCCCAAAACCTAAT AAGTAACTAATGCACAGAGCACATTGATTTGTATTTATTCTATTTTTAGACATAA TTTATTAGCATGCATGAGCAAATTAAGAAAAACAACAACAAATGAATGCATATAT ATGTATATGTATGTGTGTATATATACACACATATATATATATATTTTTTCTTTTC TTACCAGAAGGTTTTAATCCAAATAAGGAGAAGATATGCTTAGAACCGAGGTAGA GTTTTCATCCATTCTGTCCTGTAAGTATTTTGCATATTCTGGAGACGCAGGAAGA GATCCATCTACATATCCCAAAGCTGAATTATGGTAGACAAAACTCTTCCACTTTT AGTGCATCAACTTCTTATTTGTGTAATAAGAAAATTGGGAAAACGATCTTCAATA TGCTTACCAAGCTGTGATTCCAAATATTACGTAAATACACTTGCAAAGGAGGATG TTTTTAGTAGCAATTTGTACTGATGGTATGGGGCCAAGAGATATATCTTAGAGGG AGGGCTGAGGGTTTGAAGTCCAACTCCTAAGCCAGTGCCAGAAGAGCCAAGGACA GGTACGGCTGTCATCACTTAGACCTCACCCTGTGGAGCCACACCCTAGGGTTGGC CAATCTACTCCCAGGAGCAGGGAGGGCAGGAGCCAGGGCTGGGCATAAAAGTCAG | 46 |

-continued

SEQUENCE LISTING

| Name/Identifier | Sequence | SEQ ID NO |
|---|---|---|
| | GGCAGAGCCATCTATTGCTTACATTTGCTTCTGACACAACTGTGTTCACTAGCAA<br>CCTCAAACAGACACCATGGTGCATCTGACTCCTGAAGAAAAATCCGCTGTCACTG<br>CCCTGTGGGGCAAGGTGAACGTGGATGAAGTTGGTGGTGAGGCCCTGGGCAGGTT<br>GGTATCAAGGTTACAAGACAGGTTTAAGGAGACCAATAGAAACTGGGCATGTGGA<br>GACAGAGAAGACTCTTGGGTTTCTGATAGGCACTGACTCTCTCTGCCTATTGGTC<br>TATTTTCCCACCCTTAGGCTGCTGGTGGTCTACCCTTGGACCCAGAGGTTCTTTG<br>AGTCCTTTGGGGATCTGTCCACTCCTGATGCTGTTATGGGCAACCCTAAGGTGAA<br>GGCTCATGGCAAGAAAGTGCTCGGTGCCTTTAGTGATGGCCTGGCTCACCTGGAC<br>AACCTCAAGGGCACCTTTGCCACACTGAGTGAGCTGCACTGTGACAAGCTGCACG<br>TGGATCCTGAGAACTTCAGGGTGAGTCTATGGGACGCTTGATGTTTTCTTTCCCC<br>TTCTTTTCTATGGTTAAGTTCATGTCATAGGAAGGGGATAAGTAACAGGGTACAG<br>TTTAGAATGGGAAACAGACGAATGATTGCATCAGTGTGGAAGTCTCAGGATCGTT<br>TTAGTTTCTTTTATTTGCTGTTCATAACAATTGTTTTCTTTTGTTTAATTCTTGC<br>TTTCTTTTTTTTTCTTCTCCGCAATTTTTACTATTATACTTAATGCCTTAACATT<br>GTGTATAACAAAAGGAAATATCTCTGAGATACATTAAGTAACTTAAAAAAAAACT<br>TTACACAGTCTGCCTAGTACATTACTATTTGGAATATATGTGTGCTTATTTGCAT<br>ATTCATAATCTCCCTACTTTATTTTCTTTTATTTTTAATTGATACATAATCATTA<br>TACATATTTATGGGTTAAAGTGTAATGTTTTAATATGTGTACACATATTGACCAA<br>ATCAGGGTAATTTTGCATTTGTAATTTTAAAAAATGCTTTCTTCTTTTAATATAC<br>TTTTTTGTTTATCTTATTTCTAATACTTTCCCTAATCTCTTTCTTTCAGGGCAAT<br>AATGATACAATGTATCATGCCTCTTTGCACCATTCTAAAGAATAACAGTGATAAT<br>TTCTGGGTTAAGGCAATAGCAATATCTCTGCATATAAATATTTCTGCATATAAAT<br>TGTAACTGATGTAAGAGGTTTCATATTGCTAATAGCAGCTACAATCCAGCTACCA<br>TTCTGCTTTTATTTTATGGTTGGGATAAGGCTGGATTATTCTGAGTCCAAGCTAG<br>GCCCTTTTGCTAATCATGTTCATACCTCTTATCTTCCTCCCACAGCTCCTGGGCA<br>ACGTGCTGGTCTGTGTGCTGGCCCATCACTTTGGCAAAGAATTCACCCCACCAGT<br>GCAGGCTGCCTATCAGAAAGTGGTGGCTGGTGTGGCTAATGCCCTGGCCCACAAG<br>TATCACTAAGCTCGCTTTCTTGCTGTCCAATTTCTATTAAAGGTTCCTTTGTTCC<br>CTAAGTCCAACTACTAAACTGGGGGATATTATGAAGGGCCTTGAGCATCTGGATT<br>CTGCCTAATAAAAAACATTTATTTTCATTGCAATGATGTATTTAAATTATTTCTG<br>AATATTTTACTAAAAAGGGAATGTGGGAGGTCAGTGCATTTAAAACATAAAGAAA<br>TGAAGAGCTAGTTCAAACCTTGGGAAAATACACTATATCTTAAACTCCATGAAAG<br>AAGGTGAGGCTGCAAACAGCTAATGCACATTGGCAACAGCCCCTGATGCATATGC<br>CTTATTCATCCCTCAGAAAAGGATTCAAGTAGAGGCTTGATTTGGAGGTTAAAGT<br>TTTGCTATGCTGTATTTTACATTACTTATTGTTTTAGCTGTCCTCATGAATGTCT<br>TTTCACTACCCATTTGCTTATCCTGCATCTCTCAGCCTTGACTCCACTCAGTTCT<br>CTTGCTTAGAGATACCACCTTTCCCCTGAAGTGTTCCTTCCATGTTTTACGGCGA<br>GATGGTTTCTCCTCGCCTGGCCACTCAGCCTTAGTTGTCTCTGTTGTCTTATAGA<br>GGTCTACTTGAAGAAGGAAAAACAGGGGTCATGGTTTGACTGTCCTGTGAGCCCT<br>TCTTCCCTGCCTCCCCCACTCACAGTGACCCGGAATCTGCAGTGCTAGTCTCCCG<br>GAACTATCACTCTTTCACAGTCTGCTTTGGAAGGACTGGGCTTAGTATGAAAAGT<br>TAGGACTGAGAAGAATTTGAAAGGCGGCTTTTTGTAGCTTGATATTCACTACTGT<br>CTTATTACCCTGTCGGTAACCACGTGCGGCCGAGGCTGCAGCGTCGTCCTCCCTA<br>GGAACCCCTAGTGATGGAGTTGGCCACTCCCTCTCTGCGCGCTCGCTCGCTCACT<br>GAGGCCGGGCGACCAAAGGTCGCCCGACGCCCGGGCTTTGCCCGGGCGGCCTCAG<br>TGAGCGAGCGAGCGCGCAGCTGCCTGCAGG | |
| HBB exons 1-3 | ATGGTGCATCTGACTCCTGAAGAAAAATCCGCTGTCACTGCCCTGTGGGGCAAGG<br>TGAACGTGGATGAAGTTGGTGGTGAGGCCCTGGGCAGGTTGGTATCAAGGTTACA<br>AGACAGGTTTAAGGAGACCAATAGAAACTGGGCATGTGGAGACAGAGAAGACTCT<br>TGGGTTTCTGATAGGCACTGACTCTCTCTGCCTATTGGTCTATTTTCCCACCCTT<br>AGGCTGCTGGTGGTCTACCCTTGGACCCAGAGGTTCTTTGAGTCCTTTGGGGATC<br>TGTCCACTCCTGATGCTGTTATGGGCAACCCTAAGGTGAAGGCTCATGGCAAGAA<br>AGTGCTCGGTGCCTTTAGTGATGGCCTGGCTCACCTGGACAACCTCAAGGGCACC<br>TTTGCCACACTGAGTGAGCTGCACTGTGACAAGCTGCACGTGGATCCTGAGAACT<br>TCAGGGTGAGTCTATGGGACGCTTGATGTTTTCTTTCCCCTTCTTTTCTATGGTT<br>AAGTTCATGTCATAGGAAGGGGATAAGTAACAGGGTACAGTTTAGAATGGGAAAC<br>AGACGAATGATTGCATCAGTGTGGAAGTCTCAGGATCGTTTTAGTTTCTTTTATT<br>TGCTGTTCATAACAATTGTTTTCTTTTGTTTAATTCTTGCTTTCTTTTTTTTTCT<br>TCTCCGCAATTTTTACTATTATACTTAATGCCTTAACATTGTGTATAACAAAAGG<br>AAATATCTCTGAGATACATTAAGTAACTTAAAAAAAAACTTTACACAGTCTGCCT<br>AGTACATTACTATTTGGAATATATGTGTGCTTATTTGCATATTCATAATCTCCCT<br>ACTTTATTTTCTTTTATTTTTAATTGATACATAATCATTATACATATTTATGGGT<br>TAAAGTGTAATGTTTTAATATGTGTACACATATTGACCAAATCAGGGTAATTTTG<br>CATTTGTAATTTTAAAAAATGCTTTCTTCTTTTAATATACTTTTTTGTTTATCTT<br>ATTTCTAATACTTTCCCTAATCTCTTTCTTTCAGGGCAATAATGATACAATGTAT<br>CATGCCTCTTTGCACCATTCTAAAGAATAACAGTGATAATTTCTGGGTTAAGGCA<br>ATAGCAATATCTCTGCATATAAATATTTCTGCATATAAATTGTAACTGATGTAAG<br>AGGTTTCATATTGCTAATAGCAGCTACAATCCAGCTACCATTCTGCTTTTATTTT<br>ATGGTTGGGATAAGGCTGGATTATTCTGAGTCCAAGCTAGGCCCTTTTGCTAATC<br>ATGTTCATACCTCTTATCTTCCTCCCACAGCTCCTGGGCAACGTGCTGGTCTGTG<br>TGCTGGCCCATCACTTTGGCAAAGAATTCACCCCACCAGTGCAGGCTGCCTATCA<br>GAAAGTGGTGGCTGGTGTGGCTAATGCCCTGGCCCACAAGTATCAC | 47 |

-continued

SEQUENCE LISTING

| Name/Identifier | Sequence | SEQ ID NO |
|---|---|---|
| Wild-type *S. pyogenes* Cas9 | MAPKKKRKVGSGGSGGSGDKKYSIGLDIGTNSVGWAVITDEYKVPSKKFKVLGNT<br>DRHSIKKNLIGALLFDSGETAEATRLKRTARRRYTRRKNRICYLQEIFSNEMAKV<br>DDSFFHRLEESFLVEEDKKHERHPIFGNIVDEVAYHEKYPTIYHLRKKLVDSTDK<br>ADLRLIYLALAHMIKFRGHFLIEGDLNPDNSDVDKLFIQLVQTYNQLFEENPINA<br>SGVDAKAILSARLSKSRRLENLIAQLPGEKKNGLFGNLIALSLGLTPNFKSNFDL<br>AEDAKLQLSKDTYDDDLDNLLAQIGDQYADLFLAAKNLSDAILLSDILRVNTEIT<br>KAPLSASMIKRYDEHHQDLTLLKALVRQQLPEKYKEIFFDQSKNGYAGYIDGGAS<br>QEEFYKFIKPILEKMDGTEELLVKLNREDLLRKQRTFDNGSIPHQIHLGELHAIL<br>RRQEDFYPFLKDNREKIEKILTFRIPYYVGPLARGNSRFAWMTRKSEETITPWNF<br>EEVVDKGASAQSFIERMTNFDKNLPNEKVLPKHSLLYEYFTVYNELTKVKYVTEG<br>MRKPAFLSGEQKKAIVDLLFKTNRKVTVKQLKEDYFKKIECFDSVEISGVEDRFN<br>ASLGTYHDLLKIIKDKDFLDNEENEDILEDIVLTLTLFEDREMIEERLKTYAHLF<br>DDKVMKQLKRRRYTGWGRLSRKLINGIRDKQSGKTILDFLKSDGFANRNFMQLIH<br>DDSLTFKEDIQKAQVSGQGDSLHEHIANLAGSPAIKKGILQTVKVVDELVKVMGR<br>HKPENIVIEMARENQTTQKGQKNSRERMKRIEEGIKELGSQILKEHPVENTQLQN<br>EKLYLYYLQNGRDMYVDQELDINRLSDYDVDHIVPQSFLKDDSIDNKVLTRSDKN<br>RGKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQFY<br>KVREINNYHHAHDAYLNAVVGTALIKKYPKLESEFVYGDYKVYDVRKMIAKSEQE<br>IGKATAKYFFYSNIMNFFKTEITLANGEIRKRPLIETNGETGEIVWDKGRDFATV<br>RKVLSMPQVNIVKKTEVQTGGFSKESILPKRNSDKLIARKKDWDPKKYGGFDSPT<br>VAYSVLVVAKVEKGKSKKLKSVKELLGITIMERSSFEKNPIDFLEAKGYKEVKKD<br>LIIKLPKYSLFELENGRKRMLASAGELQKGNELALPSKYVNFLYLASHYEKLKGS<br>PEDNEQKQLFVEQHKHYLDEIIEQISEFSKRVILADANLDKVLSAYNKHRDKPIR<br>EQAENIIHLFTLTNLGAPAAFKYFDTTIDRKRYTSTKEVLDATLIHQSITGLYET<br>RIDLSQLGGDGSAGSGGSGGSGPKKKRKV | 48 |
| T223 Target Sequence | TAAGGAGACCAATAGAAACT | 49 |
| T223 Target Sequence PAM in bold | TAAGGAGACCAATAGAAACT**GGG** | 50 |
| T223 Spacer Sequence | UAAGGAGACCAAUAGAAACU | 51 |
| T223 sgRNA Spacer in bold | **usasasGGAGACCAAUAGAAACU**GUUUUAGAGCUAGAAAUAGCAAGUUAA<br>AAUAAGGCUAGUCCGUUAUCAACUUGAAAAAGUGGCACCGAGUCGGUGCu<br>sususU<br>a, c, g, u: 2' O-methyl phosphorothioate nucleotides<br>s: phosphorothioate nucleotides<br>A, C, G, U, N: canonical RNA nucleotides | 52 |
| Segment of wild-type HBB gene | CATCTGACTCCTGAGGAGAAGTCTGCCGTTACTGCCCTGTGGGGCAAGGT<br>GAACGTGGATGAAGTTGGTGGTGAGGCCCTGGGCAGGTTGGTATCAAGGT<br>TACAAGACAGGTTTAAGGAGACCAATAGAAACTGGGCAT | 53 |
| Segment of HBB gene with beta-thal mutation | CATCTGACTCCTGAGGAGAAGTCTGCAGTTACTGCCCTGTGGGGCAAGGT<br>GAACGTGGATGAAGTTGGAGGTGAGGCCCTGGGCAGGTTGGTATCAAGGT<br>TACAAGACAGGTTTAAGGAGACCAATAGAAACTGGGCAT | 54 |
| EF1α promoter | GGCTCCGGTGCCCGTCAGTGGGCAGAGCGCACATCGCCCACAGTCCCCGA<br>GAAGTTGGGGGGAGGGGTCGGCAATTGAACCGGTGCCTAGAGAAGGTGGC<br>GCGGGGTAAACTGGGAAAGTGATGTCGTGTACTGGCTCCGCCTTTTTCCC<br>GAGGGTGGGGGAGAACCGTATATAAGTGCAGTAGTCGCCGTGAACGTTCT<br>TTTTCGCAACGGGTTTGCCGCCAGAACACAGGTAAGTGCCGTGTGTGGTT<br>CCCGCGGGCCTGGCCTCTTTACGGGTTATGGCCCTTGCGTGCCTTGAATT<br>ACTTCCACTGGCTGCAGTACGTGATTCTTGATCCCGAGCTTCGGGTTGGA<br>AGTGGGTGGGAGAGTTCGAGGCCTTGCGCTTAAGGAGCCCCTTCGCCTCG<br>TGCTTGAGTTGAGGCCTGGCCTGGGCGCTGGGGCCGCCGCGTGCGAATCT<br>GGTGGCACCTTCGCGCCTGTCTCGCTGCTTTCGATAAGTCTCTAGCCATT<br>TAAAATTTTTGATGACCTGCTGCGACGCTTTTTTTCTGGCAAGATAGTCT<br>TGTAAATGCGGGCCAAGATCTGCACACTGGTATTTCGGTTTTTGGGGCCG<br>CGGGCGGCGACGGGGCCCGTGCGTCCCAGCGCACATGTTCGGCGAGGCGG<br>GGCCTGCGAGCGCGGCCACCGAGAATCGGACGGGGGTAGTCTCAAGCTGG<br>CCGGCCTGCTCTGGTGCCTGGCCTCGCGCCGCCGTGTATCGCCCCGCCCT<br>GGGCGGCAAGGCTGGCCCGGTCGGCACCAGTTGCGTGAGCGGAAAGATGG<br>CCGCTTCCCGGCCCTGCTGCAGGGAGCTCAAAATGGAGGACGCGGCGCTC<br>GGGAGAGCGGGCGGGTGAGTCACCCACACAAAGGAAAAGGGCCTTTCCGT | 55 |

-continued

SEQUENCE LISTING

| Name/Identifier | Sequence | SEQ ID NO |
|---|---|---|
| | CCTCAGCCGTCGCTTCATGTGACTCCACGGAGTACCGGGCGCCGTCCAGG<br>CACCTCGATTAGTTCTCGAGCTTTTGGAGTACGTCGTCTTTAGGTTGGGG<br>GGAGGGGTTTTATGCGATGGAGTTTCCCCACACTGAGTGGGTGGAGACTG<br>AAGTTAGGCCAGCTTGGCACTTGATGTAATTCTCCTTGGAATTTGCCCTT<br>TTTGAGTTTGGATCTTGGTTCATTCTCAAGCCTCAGACAGTGGTTCAAAG<br>TTTTTTTCTTCCATTTCAGGTGTCGTGA | |
| AAV.320 sequence with correction to GAA<br>E6V correction in bold<br>PAM mutation in underline | **GAA**GAGAAAAGCGCTGTGACCGCACTCTGGGGTAAAGTGAACGTCGACGAG<br>GTGGGCGGTGAAGCTCTCGGAAGgttggtatcaaggttacaagacaggttt<br>aaggagacGa | 56 |
| AAV.320 with correction to GAA | CTTGCTTTGACAATTTTGGTCTTTCAGAATACTATAAATATAACCTATATTATAA<br>TTTCATAAAGTCTGTGCATTTTCTTTGACCCAGGATATTTGCAAAAGACATATTC<br>AAACTTCCGCAGAACACTTTATTTCACATATACATGCCTCTTATATCAGGGATGT<br>GAAACAGGGTCTTGAAAACTGTCTAAATCTAAAACAATGCTAATGCAGGTTTAAA<br>TTTAATAAAATAAAATCCAAAATCTAACAGCCAAGTCAAATCTGCATGTTTTAAC<br>ATTTAAAATATTTTAAAGACGTCTTTTCCCAGGATTCAACATGTGAAATCTTTTC<br>TCAGGGATACACGTGTGCCTAGATCCTCATTGCTTTAGTTTTTTACAGAGGAATG<br>AATATAAAAAGAAAATACTTAAATTTTATCCCTCTTACCTCTATAATCATACATA<br>GGCATAATTTTTTAACCTAGGCTCCAGATAGCCATAGAAGAACCAAACACTTTCT<br>GCGTGTGTGAGAATAATCAGAGTGAGATTTTTTCACAAGTACCTGATGAGGGTTG<br>AGACAGGTAGAAAAAGTGAGAGATCTCTATTTATTTAGCAATAATAGAGAAAGCA<br>TTTAAGAGAATAAAGCAATGGAAATAAGAAATTTGTAAATTTCCTTCTGATAACT<br>AGAAATAGAGGATCCAGTTTCTTTTGGTTAACCTAAATTTTATTTCATTTTATTG<br>TTTTATTTTATTTTATTTTATTTTATTTTGTGTAATCGTAGTTTCAGAGTGTTAG<br>AGCTGAAAGGAAGAAGTAGGAGAAACATGCAAAGTAAAAGTATAACACTTTCCTT<br>ACTAAACCGACATGGGTTTCCAGGTAGGGGCAGGATTCAGGATGACTGACAGGGC<br>CCTTAGGGAACACTGAGACCCTACGCTGACCTCATAAATGCTTGCTACCTTTGCT<br>GTTTTAATTACATCTTTTAATAGCAGGAAGCAGAACTCTGCACTTCAAAAGTTTT<br>TCCTCACCTGAGGAGTTAATTTAGTACAAGGGGAAAAAGTACAGGGGGATGGGAG<br>AAAGGCGATCACGTTGGGAAGCTATAGAGAAAGAAGAGTAAATTTTAGTAAAGGA<br>GGTTTAAACAAACAAAATATAAAGAGAAATAGGAACTTGAATCAAGGAAATGATT<br>TTAAAACGCAGTATTCTTAGTGGACTAGAGGAAAAAAATAATCTGAGCCAAGTAG<br>AAGACCTTTTCCCCTCCTACCCCTACTTTCTAAGTCACAGAGGCTTTTTGTTCCC<br>CCAGACACTCTTGCAGATTAGTCCAGGCAGAAACAGTTAGATGTCCCCAGTTAAC<br>CTCCTATTTGACACCACTGATTACCCCATTGATAGTCACACTTTGGGTTGTAAGT<br>GACTTTTTATTTATTTGTATTTTTGACTGCATTAAGAGGTCTCTAGTTTTTTATC<br>TCTTGTTTCCCAAAACCTAATAAGTAACTAATGCACAGAGCACATTGATTTGTAT<br>TTATTCTATTTTTAGACATAATTTATTAGCATGCATGAGCAAATTAAGAAAAACA<br>ACAACAAATGAATGCATATATATGTATATGTATGTGTGTATATATACACACATAT<br>ATATATATATTTTTTCTTTTCTTACCAGAAGGTTTTAATCCAAATAAGGAGAAGA<br>TATGCTTAGAACCGAGGTAGAGTTTTCATCCATTCTGTCCTGTAAGTATTTTGCA<br>TATTCTGGAGACGCAGGAAGAGATCCATCTACATATCCCAAAGCTGAATTATGGT<br>AGACAAAACTCTTCCACTTTTAGTGCATCAACTTCTTATTTGTGTAATAAGAAAA<br>TTGGGAAAACGATCTTCAATATGCTTACCAAGCTGTGATTCCAAATATTACGTAA<br>ATACACTTGCAAAGGAGGATGTTTTTAGTAGCAATTTGTACTGATGGTATGGGGC<br>CAAGAGATATATCTTAGAGGGAGGGCTGAGGGTTTGAAGTCCAACTCCTAAGCCA<br>GTGCCAGAAGAGCCAAGGACAGGTACGGCTGTCATCACTTAGACCTCACCCTGTG<br>GAGCCACACCCTAGGGTTGGCCAATCTACTCCCAGGAGCAGGGAGGGCAGGAGCC<br>AGGGCTGGGCATAAAAGTCAGGGCAGAGCCATCTATTGCTTACATTTGCTTCTGA<br>CACAACTGTGTTCACTAGCAACCTCAAACAGACACCATGGTGCATCTGACTCCTG<br>AAGAGAAAAGCGCTGTGACCGCACTCTGGGGTAAAGTGAACGTCGACGAGGTGGG<br>CGGTGAAGCTCTCGGAAGgttggtatcaaggttacaagacaggtttaaggagacG<br>aatagaaactgggCATGTGGAGACAGAGAAGACTCTTGGGTTTCTGATAGGCACT<br>GACTCTCTCTGCCTATTGGTCTATTTTCCCACCCTTAGGCTGCTGGTGGTCTACC<br>CTTGGACCCAGAGGTTCTTTGAGTCCTTTGGGGATCTGTCCACTCCTGATGCTGT<br>TATGGGCAACCCTAAGGTGAAGGCTCATGGCAAGAAAGTGCTCGGTGCCTTTAGT<br>GATGGCCTGGCTCACCTGGACAACCTCAAGGGCACCTTTGCCACACTGAGTGAGC<br>TGCACTGTGACAAGCTGCACGTGGATCCTGAGAACTTCAGGGTGAGTCTATGGGA<br>CGCTTGATGTTTTCTTTCCCCTTCTTTTCTATGGTTAAGTTCATGTCATAGGAAG<br>GGGATAAGTAACAGGGTACAGTTTAGAATGGGAAACAGACGAATGATTGCATCAG<br>TGTGGAAGTCTCAGGATCGTTTTAGTTTCTTTTATTTGCTGTTCATAACAATTGT<br>TTTCTTTTGTTTAATTCTTGCTTTCTTTTTTTTTCTTCTCCGCAATTTTTACTAT<br>TATACTTAATGCCTTAACATTGTGTATAACAAAAGGAAATATCTCTGAGATACAT<br>TAAGTAACTTAAAAAAAAACTTTACACAGTCTGCCTAGTACATTACTATTTGGAA<br>TATATGTGTGCTTATTTGCATATTCATAATCTCCCTACTTTATTTTCTTTTATTT<br>TTAATTGATACATAATCATTATACATATTTATGGGTTAAAGTGTAATGTTTTAAT<br>ATGTGTACACATATTGACCAAATCAGGGTAATTTTGCATTTGTAATTTTAAAAAA | 57 |

-continued

SEQUENCE LISTING

| Name/Identifier | Sequence | SEQ ID NO |
|---|---|---|
| | TGCTTTCTTCTTTTAATATACTTTTTTGTTTATCTTATTTCTAATACTTTCCCTA ATCTCTTTCTTTCAGGGCAATAATGATACAATGTATCATGCCTCTTTGCACCATT CTAAAGAATAACAGTGATAATTTCTGGGTTAAGGCAATAGCAATATCTCTGCATA TAAATATTTCTGCATATAAATTGTAACTGATGTAAGAGGTTTCATATTGCTAATA GCAGCTACAATCCAGCTACCATTCTGCTTTTATTTTATGGTTGGGATAAGGCTGG ATTATTCTGAGTCCAAGCTAGGCCCTTTTGCTAATCATGTTCATACCTCTTATCT TCCTCCCACAGCTCCTGGGCAACGTGCTGGTCTGTGTGCTGGCCCATCACTTTGG CAAAGAATTCACCCCACCAGTGCAGGCTGCCTATCAGAAAGTGGTGGCTGGTGTG GCTAATGCCCTGGCCCACAAGTATCACTAAGCTCGCTTTCTTGCTGTCCAATTTC TATTAAAGGTTCCTTTGTTCCCTAAGTCCAACTACTAAACTGGGGGATATTATGA AGGGCCTTGAGCATCTGGATTCTGCCTAATAAAAAACATTTATTTTCATTGCAAT GATGTATTTAAATTATTTCTGAATATTTTACTAAAAAGGGAATGTGGGAGGTCAG TGCATTTAAAACATAAAGAAATGAAGAGCTAGTTCAAACCTTGGGAAAATACACT ATATCTTAAACTCCATGAAAGAAGGTGAGGCTGCAAACAGCTAATGCACATTGGC AACAGCCCCTGATGCATATGCCTTATTCATCCCTCAGAAAAGGATTCAAGTAGAG GCTTGATTTGGAGGTTAAAGTTTTGCTATGCTGTATTTTACATTACTTATTGTTT TAGCTGTCCTCATGAATGTCTTTTCACTACCCATTTGCTTATCCTGCATCTCTCA GCCTTGACTCCACTCAGTTCTCTTGCTTAGAGATACCACCTTTCCCCTGAAGTGT TCCTTCCATGTTTTACGGCGAGATGGTTTCTCCTCGCCTGGCCACTCAGCCTTAG TTGTCTCTGTTGTCTTATAGAGGTCTACTTGAAGAAGGAAAAACAGGGGTCATGG TTTGACTGTCCTGTGAGCCCTTCTTCCCTGCCTCCCCCACTCACAGTGACCCGGA ATCTGCAGTGCTAGTCTCCCGGAACTATCACTCTTTCACAGTCTGCTTTGGAAGG ACTGGGCTTAGTATGAAAAGTTAGGACTGAGAAGAATTTGAAAGGCGGCTTTTTG TAGCTTGATATTCACTACTGTCTTATTACCCTGTC | |
| AAV 320 with ITRs and correction to GAA | CCTGCAGGCAGCTGCGCGCTCGCTCGCTCACTGAGGCCGCCCGGGCGTCGGGCGA CCTTTGGTCGCCCGGCCTCAGTGAGCGAGCGAGCGCGCAGAGAGGGAGTGGCCAA CTCCATCACTAGGGGTTCCTGCGGCCGCACGCGTCTTGCTTTGACAATTTTGGTC TTTCAGAATACTATAAATATAACCTATATTATAATTTCATAAAGTCTGTGCATTT TCTTTGACCCAGGATATTTGCAAAAGACATATTCAAACTTCCGCAGAACACTTTA TTTCACATATACATGCCTCTTATATCAGGGATGTGAAACAGGGTCTTGAAAACTG TCTAAATCTAAAACAATGCTAATGCAGGTTTAAATTTAATAAAATAAAATCCAAA ATCTAACAGCCAAGTCAAATCTGCATGTTTTAACATTTAAAATATTTTAAAGACG TCTTTTCCCAGGATTCAACATGTGAAATCTTTTCTCAGGGATACACGTGTGCCTA GATCCTCATTGCTTTAGTTTTTTACAGAGGAATGAATATAAAAAGAAAATACTTA AATTTTATCCCTCTTACCTCTATAATCATACATAGGCATAATTTTTTAACCTAGG CTCCAGATAGCCATAGAAGAACCAAACACTTTCTGCGTGTGTGAGAATAATCAGA GTGAGATTTTTTCACAAGTACCTGATGAGGGTTGAGACAGGTAGAAAAAGTGAGA GATCTCTATTTATTTAGCAATAATAGAGAAAGCATTTAAGAGAATAAAGCAATGG AAATAAGAAATTTGTAAATTTCCTTCTGATAACTAGAAATAGAGGATCCAGTTTC TTTTGGTTAACCTAAATTTTATTTCATTTTATTGTTTTATTTTATTTTATTTTAT TTTATTTTGTGTAATCGTAGTTTCAGAGTGTTAGAGCTGAAAGGAAGAAGTAGGA GAAACATGCAAAGTAAAAGTATAACACTTTCCTTACTAAACCGACATGGGTTTCC AGGTAGGGGCAGGATTCAGGATGACTGACAGGGCCCTTAGGGAACACTGAGACCC TACGCTGACCTCATAAATGCTTGCTACCTTTGCTGTTTTAATTACATCTTTTAAT AGCAGGAAGCAGAACTCTGCACTTCAAAAGTTTTTCCTCACCTGAGGAGTTAATT TAGTACAAGGGGAAAAAGTACAGGGGGATGGGAGAAAGGCGATCACGTTGGGAAG CTATAGAGAAAGAAGAGTAAATTTTAGTAAAGGAGGTTTAAACAAACAAAATATA AAGAGAAATAGGAACTTGAATCAAGGAAATGATTTTAAAACGCAGTATTCTTAGT GGACTAGAGGAAAAAAATAATCTGAGCCAAGTAGAAGACCTTTTCCCCTCCTACC CCTACTTTCTAAGTCACAGAGGCTTTTTGTTCCCCCAGACACTCTTGCAGATTAG TCCAGGCAGAAACAGTTAGATGTCCCCAGTTAACCTCCTATTTGACACCACTGAT TACCCCATTGATAGTCACACTTTGGGTTGTAAGTGACTTTTTATTTATTTGTATT TTTGACTGCATTAAGAGGTCTCTAGTTTTTTATCTCTTGTTTCCCAAAACCTAAT AAGTAACTAATGCACAGAGCACATTGATTTGTATTTATTCTATTTTTAGACATAA TTTATTAGCATGCATGAGCAAATTAAGAAAAACAACAACAAATGAATGCATATAT ATGTATATGTATGTGTGTATATATACACACATATATATATATATATTTTTTCTTTTC TTACCAGAAGGTTTTAATCCAAATAAGGAGAAGATATGCTTAGAACCGAGGTAGA GTTTTCATCCATTCTGTCCTGTAAGTATTTTGCATATTCTGGAGACGCAGGAAGA GATCCATCTACATATCCCAAAGCTGAATTATGGTAGACAAAACTCTTCCACTTTT AGTGCATCAACTTCTTATTTGTGTAATAAGAAAATTGGGAAAACGATCTTCAATA TGCTTACCAAGCTGTGATTCCAAATATTACGTAAATACACTTGCAAAGGAGGATG TTTTTAGTAGCAATTTGTACTGATGGTATGGGGCCAAGAGATATATCTTAGAGGG AGGGCTGAGGGTTTGAAGTCCAACTCCTAAGCCAGTGCCAGAAGAGCCAAGGACA GGTACGGCTGTCATCACTTAGACCTCACCCTGTGGAGCCACACCCTAGGGTTGGC CAATCTACTCCCAGGAGCAGGGAGGGCAGGAGCCAGGGCTGGGCATAAAAGTCAG GGCAGAGCCATCTATTGCTTACATTTGCTTCTGACACAACTGTGTTCACTAGCAA CCTCAAACAGACACCATGGTGCATCTGACTCCTGAAGAGAAAGCGCTGTGACCG CACTCTGGGGTAAAGTGAACGTCGACGAGGTGGGCGGTGAAGCTCTCGGAAGgtt ggtatcaaggttacaagacaggtttaaggagacGaatagaaactgggCATGTGGA GACAGAGAAGACTCTTGGGTTTCTGATAGGCACTGACTCTCTCTGCCTATTGGTC TATTTTCCCACCCTTAGGCTGCTGGTGGTCTACCCTTGGACCCAGAGGTTCTTTG AGTCCTTTGGGGATCTGTCCACTCCTGATGCTGTTATGGGCAACCCTAAGGTGAA | 58 |

-continued

SEQUENCE LISTING

| Name/Identifier | Sequence | SEQ ID NO |
|---|---|---|
| | GGCTCATGGCAAGAAAGTGCTCGGTGCCTTTAGTGATGGCCTGGCTCACCTGGAC<br>AACCTCAAGGGCACCTTTGCCACACTGAGTGAGCTGCACTGTGACAAGCTGCACG<br>TGGATCCTGAGAACTTCAGGGTGAGTCTATGGGACGCTTGATGTTTTCTTTCCCC<br>TTCTTTTCTATGGTTAAGTTCATGTCATAGGAAGGGGATAAGTAACAGGGTACAG<br>TTTAGAATGGGAAACAGACGAATGATTGCATCAGTGTGGAAGTCTCAGGATCGTT<br>TTAGTTTCTTTTATTTGCTGTTCATAACAATTGTTTTCTTTTGTTTAATTCTTGC<br>TTTCTTTTTTTTTCTTCTCCGCAATTTTTACTATTATACTTAATGCCTTAACATT<br>GTGTATAACAAAAGGAAATATCTCTGAGATACATTAAGTAACTTAAAAAAAAACT<br>TTACACAGTCTGCCTAGTACATTACTATTTGGAATATATGTGTGCTTATTTGCAT<br>ATTCATAATCTCCCTACTTTATTTTCTTTTATTTTTAATTGATACATAATCATTA<br>TACATATTTATGGGTTAAAGTGTAATGTTTTAATATGTGTACACATATTGACCAA<br>ATCAGGGTAATTTTGCATTTGTAATTTTAAAAAATGCTTTCTTCTTTTAATATAC<br>TTTTTTGTTTATCTTATTTCTAATACTTTCCCTAATCTCTTTCTTTGAGGGCAAT<br>AATGATACAATGTATCATGCCTCTTTGCACCATTCTAAAGAATAACAGTGATAAT<br>TTCTGGGTTAAGGCAATAGCAATATCTCTGCATATAAATATTTCTGCATATAAAT<br>TGTAACTGATGTAAGAGGTTTCATATTGCTAATAGCAGCTACAATCCAGCTACCA<br>TTCTGCTTTTATTTTATGGTTGGGATAAGGCTGGATTATTCTGAGTCCAAGCTAG<br>GCCCTTTTGCTAATCATGTTCATACCTCTTATCTTCCTCCCACAGCTCCTGGGCA<br>ACGTGCTGGTCTGTGTGCTGGCCCATCACTTTGGCAAAGAATTCACCCCACCAGT<br>GCAGGCTGCCTATCAGAAAGTGGTGGCTGGTGTGGCTAATGCCCTGGCCCACAAG<br>TATCACTAAGCTCGCTTTCTTGCTGTCCAATTTCTATTAAAGGTTCCTTTGTTCC<br>CTAAGTCCAACTACTAAACTGGGGGATATTATGAAGGGCCTTGAGCATCTGGATT<br>CTGCCTAATAAAAAACATTTATTTTCATTGCAATGATGTATTTAAATTATTTCTG<br>AATATTTTACTAAAAAGGGAATGTGGGAGGTCAGTGCATTTAAAACATAAAGAAA<br>TGAAGAGCTAGTTCAAACCTTGGGAAAATACACTATATCTTAAACTCCATGAAAG<br>AAGGTGAGGCTGCAAACAGCTAATGCACATTGGCAACAGCCCCTGATGCATATGC<br>CTTATTCATCCCTCAGAAAAGGATTCAAGTAGAGGCTTGATTTGGAGGTTAAAGT<br>TTTGCTATGCTGTATTTTACATTACTTATTGTTTTAGCTGTCCTCATGAATGTCT<br>TTTCACTACCCATTTGCTTATCCTGCATCTCTCAGCCTTGACTCCACTCAGTTCT<br>CTTGCTTAGAGATACCACCTTTCCCCTGAAGTGTTCCTTCCATGTTTTACGGCGA<br>GATGGTTTCTCCTCGCCTGGCCACTCAGCCTTAGTTGTCTCTGTTGTCTTATAGA<br>GGTCTACTTGAAGAAGGAAAAACAGGGGTCATGGTTTGACTGTCCTGTGAGCCCT<br>TCTTCCCTGCCTCCCCCACTCACAGTGACCCGGAATCTGCAGTGCTAGTCTCCCG<br>GAACTATCACTCTTTCACAGTCTGCTTTGGAAGGACTGGGCTTAGTATGAAAAGT<br>TAGGACTGAGAAGAATTTGAAAGGCGGCTTTTTGTAGCTTGATATTCACTACTGT<br>CTTATTACCCTGTCGGTAACCACGTGCGGCCGAGGCTGCAGCGTCGTCCTCCCTA<br>GGAACCCCTAGTGATGGAGTTGGCCACTCCCTCTCTGCGCGCTCGCTCGCTCACT<br>GAGGCCGGGCGACCAAAGGTCGCCCGACGCCCGGGCTTTGCCCGGGCGGCCTCAG<br>TGAGCGAGCGAGCGCGCAGCTGCCTGCAGG | |

What is claimed:

1. A system for correcting an E6V mutation in human beta-globin (HBB) in a cell or population of cells, the system comprising:
   (a) a Cas9 endonuclease, an mRNA encoding the Cas9 endonuclease, or a recombinant expression vector comprising a nucleotide sequence encoding the Cas9 endonuclease;
   (b) a single guide RNA (sgRNA) comprising a spacer sequence corresponding to a target sequence adjacent to a PAM, the target sequence comprising a target site within intron 1 of HBB; and
   (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, and wherein the nucleotide sequence homologous with a region of the HBB gene encoding the E6V mutation comprises the nucleotide sequence of SEQ ID NO: 6 or SEQ ID NO: 19.

2. The system of claim 1, wherein the target site is about 70 to about 200 bp downstream of the E6V mutation, or wherein the target site is about 90, 95, 100, 105, 110, 115, 120, 125, 130, 135, 140, 145 or 150 bp downstream of the E6V mutation.

3. The system of claim 1, wherein the target sequence comprises the nucleotide sequence of SEQ ID NO: 1 or SEQ ID NO: 49.

4. The system of claim 1, wherein the nucleic acid of (c) comprises a nucleotide sequence of about 0.5 kb to about 5.5 kb in length, about 1 kb to about 5 kb, about 1.5 kb to about 4.6 kb, about 2 kb to about 4.6 kb, about 2.5 kb to about 4.6 kb, about 3 kb to about 4.6 kb, about 3.5 kb to about 4.6 kb, about 4 kb to about 4.6 kb, or less than 5 kb.

5. The system of claim 1, wherein the nucleotide sequence of (c) comprises a mutation to delete the PAM.

6. The system of claim 1, wherein the target sequence comprises the nucleotide sequence of SEQ ID NO: 1 and the nucleic acid of (c) comprises a nucleotide sequence with at least 90% sequence identity to the nucleotide sequence of SEQ ID NO: 8; or wherein the target sequence comprises the nucleotide sequence of SEQ ID NO: 49 and the nucleic acid of (c) comprises a nucleotide sequence with at least 90% sequence identity to the nucleotide sequence of SEQ ID NO: 20.

7. The system of claim 1, wherein the recombinant expression vector is an AAV vector.

8. The system of claim 7, wherein the AAV vector is about 2.5 kb-4.6 kb in length, and/or wherein the AAV vector is an AAV type 6 (AAV6).

9. The system of claim 7, wherein the AAV vector comprises 5' and 3' inverted terminal repeats (ITRs) derived from AAV type 2 (AAV2).

10. The system of claim 1, wherein the target sequence comprises the nucleotide sequence of SEQ ID NO: 1 and wherein the recombinant vector is an AAV vector comprising a nucleotide sequence having at least 90% sequence identity to the nucleotide sequence of SEQ ID NO: 9; or wherein the target sequence comprises the nucleotide sequence of SEQ ID NO: 49 and wherein the recombinant vector is an AAV vector comprising a nucleotide sequence having at least 90% sequence identity to the nucleotide sequence of SEQ ID NO: 21.

11. The system of claim 1, wherein the Cas9 endonuclease is a *S. pyogenes* Cas9 (SpCas9) endonuclease.

12. The system of claim 11, wherein the SpCas9 endonuclease is a high fidelity SpCas9 endonuclease.

13. The system of claim 1, wherein the system comprises the Cas9 endonuclease as a polypeptide, and wherein the system comprises a ribonucleoprotein complex of the sgRNA and the Cas9 endonuclease.

14. The system of claim 1, wherein the system comprises the mRNA encoding the Cas9 endonuclease.

15. The system of claim 1, wherein the system comprises the recombinant expression vector comprising a nucleotide sequence encoding the Cas9 endonuclease.

16. The system of claim 1, wherein the cell is a hematopoietic stem or progenitor cell (HSPC) or the population of cells comprises HSPCs.

17. The system of claim 16, wherein the HSPC is a CD34-expressing cell.

18. The system of claim 1, wherein the cell or population of cells is isolated from a tissue sample obtained from a human donor having sickle cell disease.

19. The system of claim 18, wherein the tissue sample is a peripheral blood sample, and wherein the human donor is administered one or more HSPC mobilizing agent(s) prior to obtaining the tissue sample.

20. A pharmaceutical composition comprising the system of claim 1, and a pharmaceutically acceptable carrier.

21. A kit comprising the pharmaceutical composition of claim 20, and instructions for correcting an E6V mutation in human beta-globin (HBB) in a population of cells by contacting the population with the system or pharmaceutical composition.

22. A method for correcting an E6V mutation in HBB in a cell or population of cells, the method comprising contacting the cell or population of cells comprising an HBB gene encoding the E6V mutation with:

(a) a Cas9 endonuclease, an mRNA encoding the Cas9 endonuclease, or a recombinant expression vector comprising a nucleotide sequence encoding the Cas9 endonuclease;

(b) a single guide RNA (sgRNA) comprises a spacer sequence corresponding to a target sequence adjacent to a PAM, the target sequence comprising a target site within intron 1 of HBB; and (c) a recombinant vector comprising a nucleic acid for correcting the E6V mutation, the nucleic acid comprising a nucleotide sequence homologous with a region of the HBB gene encoding the E6V mutation, wherein the nucleotide sequence comprises a codon encoding E6, and wherein the nucleotide sequence comprises the nucleotide sequence of SEQ ID NO: 6 or SEQ ID NO: 19, thereby correcting the E6V mutation in the HBB gene in the cell or population of cells.

23. A cell or population of cells generated by the method of claim 22.

24. An isolated cell or population of isolated cells, comprising at least one chromosomal copy of an HBB gene comprising a nucleotide sequence selected from: SEQ ID NO: 6, SEQ ID NO: 19, SEQ ID NO: 8, and SEQ ID NO: 20.

* * * * *

SEQUENCE LISTING

<160> NUMBER OF SEQ ID NOS: 58

<210> SEQ ID NO 1
<211> LENGTH: 20
<212> TYPE: DNA
<213> ORGANISM: Artificial Sequence
<220> FEATURE:
<223> OTHER INFORMATION: HBB Target Sequence

<400> SEQUENCE: 1
tccacatgcc cagtttctat 20

<210> SEQ ID NO 2
<211> LENGTH: 23
<212> TYPE: DNA
<213> ORGANISM: Artificial Sequence
<220> FEATURE:
<223> OTHER INFORMATION: HBB Target Sequence with PAM

<400> SEQUENCE: 2
tccacatgcc cagtttctat tgg 23

<210> SEQ ID NO 3

<211> LENGTH: 20
<212> TYPE: RNA
<213> ORGANISM: Artificial Sequence
<220> FEATURE:
<223> OTHER INFORMATION: Spacer Sequence

<400> SEQUENCE: 3
uccacaugcc caguuucuau 20

<210> SEQ ID NO 4
<211> LENGTH: 100
<212> TYPE: RNA
<213> ORGANISM: Artificial Sequence
<220> FEATURE:
<223> OTHER INFORMATION: sgRNA
<220> FEATURE:
<221> NAME/KEY: misc_feature
<222> LOCATION: (1)..(3)
<223> OTHER INFORMATION: 2' O-methyl phosphorothioate nucleotide
<220> FEATURE:
<221> NAME/KEY: misc_feature
<222> LOCATION: (1)..(4)
<223> OTHER INFORMATION: joined by phosphorothioate bond
<220> FEATURE:
<221> NAME/KEY: misc_feature
<222> LOCATION: (97)..(99)
<223> OTHER INFORMATION: 2' O-methyl phosphorothioate nucleotide
<220> FEATURE:
<221> NAME/KEY: misc_feature
<222> LOCATION: (97)..(100)
<223> OTHER INFORMATION: joined by phosphorothioate bond

<400> SEQUENCE: 4
uccacaugcc caguuucuau guuuuagagc uagaaauagc aaguuaaaau aaggcuaguc 60
cguuaucaac uugaaaaagu ggcaccgagu cggugcuuuu 100

<210> SEQ ID NO 5
<211> LENGTH: 130
<212> TYPE: DNA
<213> ORGANISM: Artificial Sequence
<220> FEATURE:
<223> OTHER INFORMATION: 5' ITR

<400> SEQUENCE: 5
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct 130

<210> SEQ ID NO 6
<211> LENGTH: 112
<212> TYPE: DNA
<213> ORGANISM: Artificial Sequence
<220> FEATURE:
<223> OTHER INFORMATION: Region encoding E6V to E6 and PAM mutation

<400> SEQUENCE: 6
gaggagaaaa gcgctgtgac cgcactctgg ggtaaagtga acgtcgacga ggtgggcggt 60
gaagctctcg gaaggttggt atcaaggtta caagacaggt ttaaggagac ga 112

<210> SEQ ID NO 7
<211> LENGTH: 141
<212> TYPE: DNA
<213> ORGANISM: Artificial Sequence
<220> FEATURE:
<223> OTHER INFORMATION: 3' ITR

<400> SEQUENCE: 7

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgcag g                                              141


<210> SEQ ID NO 8
<211> LENGTH: 4435
<212> TYPE: DNA
<213> ORGANISM: Artificial Sequence
<220> FEATURE:
<223> OTHER INFORMATION: AAV.320

<400> SEQUENCE: 8

cttgctttga caattttggt ctttcagaat actataaata taacctatat tataatttca     60

taaagtctgt gcattttctt tgacccagga tatttgcaaa agacatattc aaacttccgc    120

agaacacttt atttcacata tacatgcctc ttatatcagg gatgtgaaac agggtcttga    180

aaactgtcta aatctaaaac aatgctaatg caggtttaaa tttaataaaa taaaatccaa    240

aatctaacag ccaagtcaaa tctgcatgtt ttaacattta aaatatttta aagacgtctt    300

ttcccaggat tcaacatgtg aaatcttttc tcagggatac acgtgtgcct agatcctcat    360

tgctttagtt ttttacagag gaatgaatat aaaaagaaaa tacttaaatt ttatccctct    420

tacctctata atcatacata ggcataattt tttaacctag gctccagata gccatagaag    480

aaccaaacac tttctgcgtg tgtgagaata atcagagtga gatttttca caagtacctg     540

atgagggttg agacaggtag aaaaagtgag agatctctat ttatttagca ataatagaga    600

aagcatttaa gagaataaag caatggaaat aagaaatttg taaatttcct tctgataact    660

agaaatagag gatccagttt cttttggtta acctaaattt tatttcattt tattgtttta    720

ttttatttta ttttatttta ttttgtgtaa tcgtagtttc agagtgttag agctgaaagg    780

aagaagtagg agaaacatgc aaagtaaaag tataacactt tccttactaa accgacatgg    840

gtttccaggt aggggcagga ttcaggatga ctgacagggc ccttagggaa cactgagacc    900

ctacgctgac ctcataaatg cttgctacct ttgctgtttt aattacatct tttaatagca    960

ggaagcagaa ctctgcactt caaaagtttt tcctcacctg aggagttaat ttagtacaag   1020

gggaaaaagt acagggggat gggagaaagg cgatcacgtt gggaagctat agagaaagaa   1080

gagtaaattt tagtaaagga ggtttaaaca aacaaaatat aaagagaaat aggaacttga   1140

atcaaggaaa tgattttaaa acgcagtatt cttagtggac tagaggaaaa aaataatctg   1200

agccaagtag aagacctttt cccctcctac ccctactttc taagtcacag aggctttttg   1260

ttcccccaga cactcttgca gattagtcca ggcagaaaca gttagatgtc cccagttaac   1320

ctcctatttg acaccactga ttaccccatt gatagtcaca ctttgggttg taagtgactt   1380

tttatttatt tgtatttttg actgcattaa gaggtctcta gtttttatc tcttgtttcc    1440

caaaacctaa taagtaacta atgcacagag cacattgatt tgtatttatt ctatttttag   1500

acataattta ttagcatgca tgagcaaatt aagaaaaaca acaacaaatg aatgcatata   1560

tatgtatatg tatgtgtgta tatatacaca catatatata tatatttttt cttttcttac   1620

cagaaggttt taatccaaat aaggagaaga tatgcttaga accgaggtag agttttcatc   1680

cattctgtcc tgtaagtatt ttgcatattc tggagacgca ggaagagatc catctacata   1740

tcccaaagct gaattatggt agacaaaact cttccacttt tagtgcatca acttcttatt   1800

tgtgtaataa gaaaattggg aaaacgatct tcaatatgct taccaagctg tgattccaaa   1860
```

-continued

```
tattacgtaa atacacttgc aaaggaggat gtttttagta gcaatttgta ctgatggtat   1920
ggggccaaga gatatatctt agagggaggg ctgagggttt gaagtccaac tcctaagcca   1980
gtgccagaag agccaaggac aggtacggct gtcatcactt agacctcacc ctgtggagcc   2040
acaccctagg gttggccaat ctactcccag gagcagggag ggcaggagcc agggctgggc   2100
ataaaagtca gggcagagcc atctattgct tacatttgct tctgacacaa ctgtgttcac   2160
tagcaacctc aaacagacac catggtgcat ctgactcctg aggagaaaag cgctgtgacc   2220
gcactctggg gtaaagtgaa cgtcgacgag gtgggcggtg aagctctcgg aaggttggta   2280
tcaaggttac aagacaggtt taaggagacg aatagaaact gggcatgtgg agacagagaa   2340
gactcttggg tttctgatag gcactgactc tctctgccta ttggtctatt ttcccaccct   2400
taggctgctg gtggtctacc cttggaccca gaggttcttt gagtcctttg gggatctgtc   2460
cactcctgat gctgttatgg gcaaccctaa ggtgaaggct catggcaaga aagtgctcgg   2520
tgcctttagt gatggcctgg ctcacctgga caacctcaag ggcacctttg ccacactgag   2580
tgagctgcac tgtgacaagc tgcacgtgga tcctgagaac ttcagggtga gtctatggga   2640
cgcttgatgt tttctttccc cttcttttct atggttaagt tcatgtcata ggaaggggat   2700
aagtaacagg gtacagttta gaatgggaaa cagacgaatg attgcatcag tgtggaagtc   2760
tcaggatcgt ttagtttctt ttatttgct gttcataaca attgttttct tttgtttaat    2820
tcttgctttc tttttttttc ttctccgcaa tttttactat tatacttaat gccttaacat   2880
tgtgtataac aaaaggaaat atctctgaga tacattaagt aacttaaaaa aaaactttac   2940
acagtctgcc tagtacatta ctatttggaa tatatgtgtg cttatttgca tattcataat   3000
ctccctactt tattttcttt tatttttaat tgatacataa tcattataca tatttatggg   3060
ttaaagtgta atgttttaat atgtgtacac atattgacca aatcagggta attttgcatt   3120
tgtaatttta aaaaatgctt tcttctttta atatactttt ttgtttatct tatttctaat   3180
actttcccta atctctttct ttcagggcaa taatgataca atgtatcatg cctctttgca   3240
ccattctaaa gaataacagt gataatttct gggttaaggc aatagcaata tctctgcata   3300
taaatatttc tgcatataaa ttgtaactga tgtaagaggt ttcatattgc taatagcagc   3360
tacaatccag ctaccattct gcttttattt tatggttggg ataaggctgg attattctga   3420
gtccaagcta ggcccttttg ctaatcatgt tcatacctct tatcttcctc ccacagctcc   3480
tgggcaacgt gctggtctgt gtgctggccc atcactttgg caaagaattc accccaccag   3540
tgcaggctgc ctatcagaaa gtggtggctg gtgtggctaa tgccctggcc cacaagtatc   3600
actaagctcg ctttcttgct gtccaatttc tattaaaggt tcctttgttc cctaagtcca   3660
actactaaac tgggggatat tatgaagggc cttgagcatc tggattctgc ctaataaaaa   3720
acatttattt tcattgcaat gatgtattta aattatttct gaatatttta ctaaaaaggg   3780
aatgtgggag gtcagtgcat ttaaaacata aagaaatgaa gagctagttc aaaccttggg   3840
aaaatacact atatcttaaa ctccatgaaa gaaggtgagg ctgcaaacag ctaatgcaca   3900
ttggcaacag cccctgatgc atatgcctta ttcatccctc agaaaaggat tcaagtagag   3960
gcttgatttg gaggttaaag ttttgctatg ctgtatttta cattacttat tgttttagct   4020
gtcctcatga atgtcttttc actacccatt tgcttatcct gcatctctca gccttgactc   4080
cactcagttc tcttgcttag agataccacc tttcccctga agtgttcctt ccatgtttta   4140
cggcgagatg gtttctcctc gcctggccac tcagccttag ttgtctctgt tgtcttatag   4200
aggtctactt gaagaaggaa aaacaggggt catggtttga ctgtcctgtg agcccttctt   4260
```

ccctgcctcc cccactcaca gtgacccgga atctgcagtg ctagtctccc ggaactatca 4320
ctctttcaca gtctgctttg gaaggactgg gcttagtatg aaaagttagg actgagaaga 4380
atttgaaagg cggctttttg tagcttgata ttcactactg tcttattacc ctgtc 4435

<210> SEQ ID NO 9
<211> LENGTH: 4760
<212> TYPE: DNA
<213> ORGANISM: Artificial Sequence
<220> FEATURE:
<223> OTHER INFORMATION: AAV.320 with ITRs

<400> SEQUENCE: 9
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtcttgct ttgacaattt tggtctttca gaatactata 180
aatataacct atattataat ttcataaagt ctgtgcattt tctttgaccc aggatatttg 240
caaaagacat attcaaactt ccgcagaaca ctttatttca catatacatg cctcttatat 300
cagggatgtg aaacagggtc ttgaaaactg tctaaatcta aaacaatgct aatgcaggtt 360
taaatttaat aaaataaaat ccaaaatcta acagccaagt caaatctgca tgttttaaca 420
tttaaaatat tttaaagacg tcttttccca ggattcaaca tgtgaaatct tttctcaggg 480
atacacgtgt gcctagatcc tcattgcttt agttttttac agaggaatga atataaaaag 540
aaaatactta aattttatcc ctcttacctc tataatcata cataggcata attttttaac 600
ctaggctcca gatagccata gaagaaccaa acactttctg cgtgtgtgag aataatcaga 660
gtgagatttt ttcacaagta cctgatgagg gttgagacag gtagaaaaag tgagagatct 720
ctatttattt agcaataata gagaaagcat ttaagagaat aaagcaatgg aaataagaaa 780
tttgtaaatt tccttctgat aactagaaat agaggatcca gtttcttttg gttaacctaa 840
attttatttc attttattgt tttattttat tttattttat tttattttgt gtaatcgtag 900
tttcagagtg ttagagctga aaggaagaag taggagaaac atgcaaagta aaagtataac 960
actttcctta ctaaaccgac atgggtttcc aggtaggggc aggattcagg atgactgaca 1020
gggcccttag ggaacactga gaccctacgc tgacctcata aatgcttgct acctttgctg 1080
ttttaattac atcttttaat agcaggaagc agaactctgc acttcaaaag tttttcctca 1140
cctgaggagt taatttagta caaggggaaa aagtacaggg ggatgggaga aaggcgatca 1200
cgttgggaag ctatagagaa agaagagtaa attttagtaa aggaggttta aacaaacaaa 1260
atataaagag aaataggaac ttgaatcaag gaaatgattt taaaacgcag tattcttagt 1320
ggactagagg aaaaaaataa tctgagccaa gtagaagacc ttttcccctc ctacccctac 1380
tttctaagtc acagaggctt tttgttcccc cagacactct tgcagattag tccaggcaga 1440
aacagttaga tgtccccagt taacctccta tttgacacca ctgattaccc cattgatagt 1500
cacactttgg gttgtaagtg actttttatt tatttgtatt tttgactgca ttaagaggtc 1560
tctagttttt tatctcttgt ttcccaaaac ctaataagta actaatgcac agagcacatt 1620
gatttgtatt tattctattt ttagacataa tttattagca tgcatgagca aattaagaaa 1680
aacaacaaca aatgaatgca tatatatgta tatgtatgtg tgtatatata cacacatata 1740
tatatatatt ttttcttttc ttaccagaag gttttaatcc aaataaggag aagatatgct 1800
tagaaccgag gtagagtttt catccattct gtcctgtaag tattttgcat attctggaga 1860

-continued

```
cgcaggaaga gatccatcta catatcccaa agctgaatta tggtagacaa aactcttcca   1920
cttttagtgc atcaacttct tatttgtgta ataagaaaat tgggaaaacg atcttcaata   1980
tgcttaccaa gctgtgattc caaatattac gtaaatacac ttgcaaagga ggatgttttt   2040
agtagcaatt tgtactgatg gtatggggcc aagagatata tcttagaggg agggctgagg   2100
gtttgaagtc caactcctaa gccagtgcca gaagagccaa ggacaggtac ggctgtcatc   2160
acttagacct caccctgtgg agccacaccc tagggttggc caatctactc ccaggagcag   2220
ggagggcagg agccagggct gggcataaaa gtcagggcag agccatctat tgcttacatt   2280
tgcttctgac acaactgtgt tcactagcaa cctcaaacag acaccatggt gcatctgact   2340
cctgaggaga aaagcgctgt gaccgcactc tggggtaaag tgaacgtcga cgaggtgggc   2400
ggtgaagctc tcggaaggtt ggtatcaagg ttacaagaca ggtttaagga gacgaataga   2460
aactgggcat gtggagacag agaagactct tgggtttctg ataggcactg actctctctg   2520
cctattggtc tattttccca cccttaggct gctggtggtc tacccttgga cccagaggtt   2580
ctttgagtcc tttggggatc tgtccactcc tgatgctgtt atgggcaacc ctaaggtgaa   2640
ggctcatggc aagaaagtgc tcggtgcctt tagtgatggc ctggctcacc tggacaacct   2700
caagggcacc tttgccacac tgagtgagct gcactgtgac aagctgcacg tggatcctga   2760
gaacttcagg gtgagtctat gggacgcttg atgttttctt tccccttctt ttctatggtt   2820
aagttcatgt cataggaagg ggataagtaa cagggtacag tttagaatgg gaaacagacg   2880
aatgattgca tcagtgtgga agtctcagga tcgttttagt ttcttttatt tgctgttcat   2940
aacaattgtt ttcttttgtt taattcttgc tttctttttt tttcttctcc gcaattttta   3000
ctattatact taatgcctta acattgtgta taacaaaagg aaatatctct gagatacatt   3060
aagtaactta aaaaaaaact ttacacagtc tgcctagtac attactattt ggaatatatg   3120
tgtgcttatt tgcatattca taatctccct actttatttt cttttatttt taattgatac   3180
ataatcatta tacatattta tgggttaaag tgtaatgttt taatatgtgt acacatattg   3240
accaaatcag ggtaattttg catttgtaat tttaaaaaat gctttcttct tttaatatac   3300
tttttttgttt atcttatttc taatactttc cctaatctct ttctttcagg gcaataatga   3360
tacaatgtat catgcctctt tgcaccattc taaagaataa cagtgataat ttctgggtta   3420
aggcaatagc aatatctctg catataaata tttctgcata taaattgtaa ctgatgtaag   3480
aggtttcata ttgctaatag cagctacaat ccagctacca ttctgctttt attttatggt   3540
tgggataagg ctggattatt ctgagtccaa gctaggccct tttgctaatc atgttcatac   3600
ctcttatctt cctcccacag ctcctgggca acgtgctggt ctgtgtgctg gcccatcact   3660
ttggcaaaga attcacccca ccagtgcagg ctgcctatca gaaagtggtg gctggtgtgg   3720
ctaatgccct ggcccacaag tatcactaag ctcgctttct tgctgtccaa tttctattaa   3780
aggttccttt gttccctaag tccaactact aaactggggg atattatgaa gggccttgag   3840
catctggatt ctgcctaata aaaaacattt attttcattg caatgatgta tttaaattat   3900
ttctgaatat tttactaaaa agggaatgtg ggaggtcagt gcatttaaaa cataaagaaa   3960
tgaagagcta gttcaaacct tgggaaaata cactatatct taaactccat gaaagaaggt   4020
gaggctgcaa acagctaatg cacattggca acagcccctg atgcatatgc cttattcatc   4080
cctcagaaaa ggattcaagt agaggcttga tttggaggtt aaagttttgc tatgctgtat   4140
tttacattac ttattgtttt agctgtcctc atgaatgtct tttcactacc catttgctta   4200
tcctgcatct ctcagccttg actccactca gttctcttgc ttagagatac cacctttccc   4260
```

-continued

```
ctgaagtgtt ccttccatgt tttacggcga gatggtttct cctcgcctgg ccactcagcc   4320

ttagttgtct ctgttgtctt atagaggtct acttgaagaa ggaaaaacag gggtcatggt   4380

ttgactgtcc tgtgagccct tcttccctgc ctcccccact cacagtgacc cggaatctgc   4440

agtgctagtc tcccggaact atcactcttt cacagtctgc tttggaagga ctgggcttag   4500

tatgaaaagt taggactgag aagaatttga aaggcggctt tttgtagctt gatattcact   4560

actgtcttat taccctgtcg gtaaccacgt gcggccgagg ctgcagcgtc gtcctcccta   4620

ggaaccccta gtgatggagt tggccactcc ctctctgcgc gctcgctcgc tcactgaggc   4680

cgggcgacca aaggtcgccc gacgcccggg ctttgcccgg gcggcctcag tgagcgagcg   4740

agcgcgcagc tgcctgcagg                                               4760
```

```
<210> SEQ ID NO 10
<211> LENGTH: 225
<212> TYPE: RNA
<213> ORGANISM: Artificial Sequence
<220> FEATURE:
<223> OTHER INFORMATION: i53 mRNA ORF

<400> SEQUENCE: 10

augcugaucu ucgugaagac ccugaccggc aagaccauca cccuggaggu ggagcccagc     60

gacaccaucg agaacgugaa ggccaagauc caggacaagg agggcauccc ccccgaccag    120

cagaggcugg ccuucgccgg caagagccug gaggacggca ggacccugag cgacuacaac    180

auccugaagg acagcaagcu gcacccccug cugaggcuga gguga                    225
```

```
<210> SEQ ID NO 11
<211> LENGTH: 74
<212> TYPE: PRT
<213> ORGANISM: Artificial Sequence
<220> FEATURE:
<223> OTHER INFORMATION: i53 polypeptide

<400> SEQUENCE: 11

Met Leu Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ala Phe Ala Gly Lys
        35                  40                  45

Ser Leu Glu Asp Gly Arg Thr Leu Ser Asp Tyr Asn Ile Leu Lys Asp
    50                  55                  60

Ser Lys Leu His Pro Leu Leu Arg Leu Arg
65                  70
```

```
<210> SEQ ID NO 12
<211> LENGTH: 20
<212> TYPE: DNA
<213> ORGANISM: Artificial Sequence
<220> FEATURE:
<223> OTHER INFORMATION: HBB Target Sequence

<400> SEQUENCE: 12

cttgccccac agggcagtaa                                                 20
```

```
<210> SEQ ID NO 13
<211> LENGTH: 23
<212> TYPE: DNA
<213> ORGANISM: Artificial Sequence
```

<220> FEATURE:
<223> OTHER INFORMATION: HBB Target Sequence with PAM

<400> SEQUENCE: 13
cttgccccac agggcagtaa cgg 23

<210> SEQ ID NO 14
<211> LENGTH: 20
<212> TYPE: RNA
<213> ORGANISM: Artificial Sequence
<220> FEATURE:
<223> OTHER INFORMATION: R02 Spacer Sequence

<400> SEQUENCE: 14
cuugccccac agggcaguaa 20

<210> SEQ ID NO 15
<211> LENGTH: 100
<212> TYPE: RNA
<213> ORGANISM: Artificial Sequence
<220> FEATURE:
<223> OTHER INFORMATION: R02 sgRNA
<220> FEATURE:
<221> NAME/KEY: misc_feature
<222> LOCATION: (1)..(3)
<223> OTHER INFORMATION: 2' O-methyl phosphorothioate nucleotide
<220> FEATURE:
<221> NAME/KEY: misc_feature
<222> LOCATION: (1)..(4)
<223> OTHER INFORMATION: joined by phosphorothioate bond
<220> FEATURE:
<221> NAME/KEY: misc_feature
<222> LOCATION: (97)..(99)
<223> OTHER INFORMATION: 2' O-methyl phosphorothioate nucleotide
<220> FEATURE:
<221> NAME/KEY: misc_feature
<222> LOCATION: (97)..(100)
<223> OTHER INFORMATION: joined by phosphorothioate bond

<400> SEQUENCE: 15
cuugccccac agggcaguaa guuuuagagc uagaaauagc aaguuaaaau aaggcuaguc 60
cguuaucaac uugaaaaagu ggcaccgagu cggugcuuuu 100

<210> SEQ ID NO 16
<211> LENGTH: 200
<212> TYPE: DNA
<213> ORGANISM: Artificial Sequence
<220> FEATURE:
<223> OTHER INFORMATION: 200mer ssODN for use with R02 sgRNA
<220> FEATURE:
<221> NAME/KEY: misc_feature
<222> LOCATION: (1)..(3)
<223> OTHER INFORMATION: 2' O-methyl phosphorothioate nucleotide
<220> FEATURE:
<221> NAME/KEY: misc_feature
<222> LOCATION: (1)..(4)
<223> OTHER INFORMATION: joined by phosphorothioate bond
<220> FEATURE:
<221> NAME/KEY: misc_feature
<222> LOCATION: (198)..(199)
<223> OTHER INFORMATION: 2' O-methyl phosphorothioate nucleotide
<220> FEATURE:
<221> NAME/KEY: misc_feature
<222> LOCATION: (198)..(200)
<223> OTHER INFORMATION: joined by phosphorothioate bond

<400> SEQUENCE: 16
gcataaaagt cagggcagag ccatctattg cttacatttg cttctgacac aactgtgttc 60
actagcaacc tcaaacagac accatggtgc atctgactcc tgtcgaaaaa tccgctgtca 120
ccgccctctg gggcaaggtg aacgtggatg aagttggtgg tgaggccctg ggcaggttgg 180
tatcaaggtt acaagacagg 200

<210> SEQ ID NO 17
<211> LENGTH: 200
<212> TYPE: DNA
<213> ORGANISM: Artificial Sequence
<220> FEATURE:
<223> OTHER INFORMATION: 200mer ssODN for use with T107 sgRNA
<220> FEATURE:
<221> NAME/KEY: misc_feature
<222> LOCATION: (1)..(3)
<223> OTHER INFORMATION: 2' O-methyl phosphorothioate nucleotide
<220> FEATURE:
<221> NAME/KEY: misc_feature
<222> LOCATION: (1)..(4)
<223> OTHER INFORMATION: joined by phosphorothioate bond
<220> FEATURE:
<221> NAME/KEY: misc_feature
<222> LOCATION: (197)..(199)
<223> OTHER INFORMATION: 2' O-methyl phosphorothioate nucleotide
<220> FEATURE:
<221> NAME/KEY: misc_feature
<222> LOCATION: (197)..(200)
<223> OTHER INFORMATION: joined by phosphorothioate bond

<400> SEQUENCE: 17
aacagacacc atggtgcatc tgactcctgt cgagaaaagc gctgtgaccg cactctgggg 60
taaagtgaac gtcgacgagg tgggcggtga agctctcgga aggttggtat caaggttaca 120
agacacgttt aaggagacga atagaaactg cgcatgtgga gacagagaag actcttgggt 180
ttctgatagg cactgactct 200

<210> SEQ ID NO 18
<211> LENGTH: 141
<212> TYPE: DNA
<213> ORGANISM: Artificial Sequence
<220> FEATURE:
<223> OTHER INFORMATION: 5' ITR

<400> SEQUENCE: 18
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc t 141

<210> SEQ ID NO 19
<211> LENGTH: 124
<212> TYPE: DNA
<213> ORGANISM: Artificial Sequence
<220> FEATURE:
<223> OTHER INFORMATION: Region encoding E6V to E6 and PAM mutation

<400> SEQUENCE: 19
gaggagaaaa gcgctgtgac cgcactctgg ggtaaagtga acgtcgacga ggtgggcggt 60
gaagctctcg gaaggttggt atcaaggtta caagacaggt ttaaggagac caatagaaac 120
tgcg 124

<210> SEQ ID NO 20
<211> LENGTH: 4435
<212> TYPE: DNA
<213> ORGANISM: Artificial Sequence
<220> FEATURE:
<223> OTHER INFORMATION: AAV.321

<400> SEQUENCE: 20

```
cttgctttga caattttggt ctttcagaat actataaata taacctatat tataatttca     60
taaagtctgt gcattttctt tgacccagga tatttgcaaa agacatattc aaacttccgc    120
agaacacttt atttcacata tacatgcctc ttatatcagg gatgtgaaac agggtcttga    180
aaactgtcta aatctaaaac aatgctaatg caggtttaaa tttaataaaa taaaatccaa    240
aatctaacag ccaagtcaaa tctgcatgtt ttaacattta aaatatttta aagacgtctt    300
ttcccaggat tcaacatgtg aaatcttttc tcagggatac acgtgtgcct agatcctcat    360
tgctttagtt ttttacagag gaatgaatat aaaaagaaaa tacttaaatt ttatccctct    420
tacctctata atcatacata ggcataattt tttaacctag gctccagata gccatagaag    480
aaccaaacac tttctgcgtg tgtgagaata atcagagtga gatttttca caagtacctg    540
atgagggttg agacaggtag aaaaagtgag agatctctat ttatttagca ataatagaga    600
aagcatttaa gagaataaag caatggaaat aagaaatttg taaatttcct tctgataact    660
agaaatagag gatccagttt cttttggtta acctaaattt tatttcattt tattgtttta    720
ttttatttta ttttatttta ttttgtgtaa tcgtagtttc agagtgttag agctgaaagg    780
aagaagtagg agaaacatgc aaagtaaaag tataacactt tccttactaa accgacatgg    840
gtttccaggt aggggcagga ttcaggatga ctgacagggc ccttagggaa cactgagacc    900
ctacgctgac ctcataaatg cttgctacct ttgctgtttt aattacatct tttaatagca    960
ggaagcagaa ctctgcactt caaaagtttt tcctcacctg aggagttaat ttagtacaag   1020
gggaaaaagt acagggggat gggagaaagg cgatcacgtt gggaagctat agagaaagaa   1080
gagtaaattt tagtaaagga ggtttaaaca aacaaaatat aaagagaaat aggaacttga   1140
atcaaggaaa tgattttaaa acgcagtatt cttagtggac tagaggaaaa aaataatctg   1200
agccaagtag aagacctttt cccctcctac ccctacttc taagtcacag aggcttttttg   1260
ttcccccaga cactcttgca gattagtcca ggcagaaaca gttagatgtc cccagttaac   1320
ctcctatttg acaccactga ttaccccatt gatagtcaca ctttgggttg taagtgactt   1380
tttatttatt tgtattttttg actgcattaa gaggtctcta gtttttatc tcttgtttcc   1440
caaaacctaa taagtaacta atgcacagag cacattgatt tgtatttatt ctatttttag   1500
acataattta ttagcatgca tgagcaaatt aagaaaaaca acaacaaatg aatgcatata   1560
tatgtatatg tatgtgtgta tatatacaca catatatata tatatttttt cttttcttac   1620
cagaaggttt taatccaaat aaggagaaga tatgcttaga accgaggtag agttttcatc   1680
cattctgtcc tgtaagtatt ttgcatattc tggagacgca ggaagagatc catctacata   1740
tcccaaagct gaattatggt agacaaaact cttccacttt tagtgcatca acttcttatt   1800
tgtgtaataa gaaaattggg aaaacgatct tcaatatgct taccaagctg tgattccaaa   1860
tattacgtaa atacacttgc aaaggaggat gtttttagta gcaatttgta ctgatggtat   1920
ggggccaaga gatatatctt agagggaggg ctgagggttt gaagtccaac tcctaagcca   1980
gtgccagaag agccaaggac aggtacggct gtcatcactt agacctcacc ctgtggagcc   2040
acaccctagg gttggccaat ctactcccag gagcagggag ggcaggagcc agggctgggc   2100
ataaaagtca gggcagagcc atctattgct tacatttgct tctgacacaa ctgtgttcac   2160
tagcaacctc aaacagacac catggtgcat ctgactcctg aggagaaaag cgctgtgacc   2220
gcactctggg gtaaagtgaa cgtcgacgag gtgggcggtg aagctctcgg aaggttggta   2280
tcaaggttac aagacaggtt taaggagacc aatagaaact gcgcatgtgg agacagagaa   2340
```

```
gactcttggg tttctgatag gcactgactc tctctgccta ttggtctatt ttcccaccct   2400
taggctgctg gtggtctacc cttggaccca gaggttcttt gagtcctttg gggatctgtc   2460
cactcctgat gctgttatgg gcaaccctaa ggtgaaggct catggcaaga aagtgctcgg   2520
tgcctttagt gatggcctgg ctcacctgga caacctcaag ggcacctttg ccacactgag   2580
tgagctgcac tgtgacaagc tgcacgtgga tcctgagaac ttcagggtga gtctatggga   2640
cgcttgatgt tttctttccc cttcttttct atggttaagt tcatgtcata ggaaggggat   2700
aagtaacagg gtacagttta gaatgggaaa cagacgaatg attgcatcag tgtggaagtc   2760
tcaggatcgt tttagtttct tttatttgct gttcataaca attgttttct tttgtttaat   2820
tcttgctttc tttttttttc ttctccgcaa tttttactat tatacttaat gccttaacat   2880
tgtgtataac aaaaggaaat atctctgaga tacattaagt aacttaaaaa aaaactttac   2940
acagtctgcc tagtacatta ctatttggaa tatatgtgtg cttatttgca tattcataat   3000
ctccctactt tattttcttt tatttttaat tgatacataa tcattataca tatttatggg   3060
ttaaagtgta atgttttaat atgtgtacac atattgacca aatcagggta attttgcatt   3120
tgtaatttta aaaaatgctt tcttctttta atatactttt ttgtttatct tatttctaat   3180
actttcccta atctctttct ttcagggcaa taatgataca atgtatcatg cctctttgca   3240
ccattctaaa gaataacagt gataatttct gggttaaggc aatagcaata tctctgcata   3300
taaatatttc tgcatataaa ttgtaactga tgtaagaggt ttcatattgc taatagcagc   3360
tacaatccag ctaccattct gcttttattt tatggttggg ataaggctgg attattctga   3420
gtccaagcta ggcccttttg ctaatcatgt tcatacctct tatcttcctc ccacagctcc   3480
tgggcaacgt gctggtctgt gtgctggccc atcactttgg caaagaattc accccaccag   3540
tgcaggctgc ctatcagaaa gtggtggctg gtgtggctaa tgccctggcc cacaagtatc   3600
actaagctcg ctttcttgct gtccaatttc tattaaaggt tcctttgttc cctaagtcca   3660
actactaaac tgggggatat tatgaagggc cttgagcatc tggattctgc ctaataaaaa   3720
acatttattt tcattgcaat gatgtattta aattatttct gaatatttta ctaaaaaggg   3780
aatgtgggag gtcagtgcat ttaaaacata aagaaatgaa gagctagttc aaaccttggg   3840
aaaatacact atatcttaaa ctccatgaaa gaaggtgagg ctgcaaacag ctaatgcaca   3900
ttggcaacag cccctgatgc atatgcctta ttcatccctc agaaaaggat tcaagtagag   3960
gcttgatttg gaggttaaag ttttgctatg ctgtatttta cattacttat tgttttagct   4020
gtcctcatga atgtcttttc actacccatt tgcttatcct gcatctctca gccttgactc   4080
cactcagttc tcttgcttag agataccacc tttcccctga agtgttcctt ccatgtttta   4140
cggcgagatg gtttctcctc gcctggccac tcagccttag ttgtctctgt tgtcttatag   4200
aggtctactt gaagaaggaa aaacaggggt catggtttga ctgtcctgtg agcccttctt   4260
ccctgcctcc cccactcaca gtgacccgga atctgcagtg ctagtctccc ggaactatca   4320
ctctttcaca gtctgctttg gaaggactgg gcttagtatg aaaagttagg actgagaaga   4380
atttgaaagg cggctttttg tagcttgata ttcactactg tcttattacc ctgtc        4435
```

<210> SEQ ID NO 21
<211> LENGTH: 4771
<212> TYPE: DNA
<213> ORGANISM: Artificial Sequence
<220> FEATURE:
<223> OTHER INFORMATION: AAV.321 with ITRs

<400> SEQUENCE: 21

-continued

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtcttgc tttgacaatt ttggtctttc    180
agaatactat aaatataacc tatattataa tttcataaag tctgtgcatt ttctttgacc    240
caggatattt gcaaaagaca tattcaaact tccgcagaac actttatttc acatatacat    300
gcctcttata tcagggatgt gaaacagggt cttgaaaact gtctaaatct aaaacaatgc    360
taatgcaggt ttaaatttaa taaaataaaa tccaaaatct aacagccaag tcaaatctgc    420
atgttttaac atttaaaata ttttaaagac gtcttttccc aggattcaac atgtgaaatc    480
ttttctcagg gatacacgtg tgcctagatc ctcattgctt tagtttttta cagaggaatg    540
aatataaaaa gaaaatactt aaattttatc cctcttacct ctataatcat acataggcat    600
aattttttaa cctaggctcc agatagccat agaagaacca aacactttct gcgtgtgtga    660
gaataatcag agtgagattt tttcacaagt acctgatgag ggttgagaca ggtagaaaaa    720
gtgagagatc tctatttatt tagcaataat agagaaagca tttaagagaa taaagcaatg    780
gaaataagaa atttgtaaat ttccttctga taactagaaa tagaggatcc agtttctttt    840
ggttaaccta aattttattt cattttattg ttttatttta ttttatttta ttttattttg    900
tgtaatcgta gtttcagagt gttagagctg aaaggaagaa gtaggagaaa catgcaaagt    960
aaaagtataa cactttcctt actaaaccga catgggtttc caggtagggg caggattcag   1020
gatgactgac agggccctta gggaacactg agaccctacg ctgacctcat aaatgcttgc   1080
tacctttgct gttttaatta catcttttaa tagcaggaag cagaactctg cacttcaaaa   1140
gtttttcctc acctgaggag ttaatttagt acaaggggaa aaagtacagg gggatgggag   1200
aaaggcgatc acgttgggaa gctatagaga aagaagagta aattttagta aaggaggttt   1260
aaacaaacaa aatataaaga gaaataggaa cttgaatcaa ggaaatgatt ttaaaacgca   1320
gtattcttag tggactagag gaaaaaaata atctgagcca agtagaagac cttttcccct   1380
cctacccta ctttctaagt cacagaggct ttttgttccc ccagacactc ttgcagatta   1440
gtccaggcag aaacagttag atgtccccag ttaacctcct atttgacacc actgattacc   1500
ccattgatag tcacactttg ggttgtaagt gactttttat ttatttgtat ttttgactgc   1560
attaagaggt ctctagtttt ttatctcttg tttcccaaaa cctaataagt aactaatgca   1620
cagagcacat tgatttgtat ttattctatt tttagacata atttattagc atgcatgagc   1680
aaattaagaa aaacaacaac aaatgaatgc atatatatgt atatgtatgt gtgtatatat   1740
acacacatat atatatatat tttttctttt cttaccagaa ggttttaatc caaataagga   1800
gaagatatgc ttagaaccga ggtagagttt tcatccattc tgtcctgtaa gtattttgca   1860
tattctggag acgcaggaag agatccatct acatatccca aagctgaatt atggtagaca   1920
aaactcttcc acttttagtg catcaacttc ttatttgtgt aataagaaaa ttgggaaaac   1980
gatcttcaat atgcttacca agctgtgatt ccaaatatta cgtaaataca cttgcaaagg   2040
aggatgtttt tagtagcaat ttgtactgat ggtatggggc caagagatat atcttagagg   2100
gagggctgag ggtttgaagt ccaactccta agccagtgcc agaagagcca aggacaggta   2160
cggctgtcat cacttagacc tcaccctgtg gagccacacc ctagggttgg ccaatctact   2220
cccaggagca gggagggcag gagccagggc tgggcataaa agtcagggca gagccatcta   2280
ttgcttacat ttgcttctga cacaactgtg ttcactagca acctcaaaca gacaccatgg   2340
```

-continued

```
tgcatctgac tcctgaggag aaaagcgctg tgaccgcact ctggggtaaa gtgaacgtcg   2400
acgaggtggg cggtgaagct ctcggaaggt tggtatcaag gttacaagac aggtttaagg   2460
agaccaatag aaactgcgca tgtggagaca gagaagactc ttgggtttct gataggcact   2520
gactctctct gcctattggt ctattttccc acccttaggc tgctggtggt ctacccttgg   2580
acccagaggt tctttgagtc ctttggggat ctgtccactc ctgatgctgt tatgggcaac   2640
cctaaggtga aggctcatgg caagaaagtg ctcggtgcct ttagtgatgg cctggctcac   2700
ctggacaacc tcaagggcac ctttgccaca ctgagtgagc tgcactgtga caagctgcac   2760
gtggatcctg agaacttcag ggtgagtcta tgggacgctt gatgttttct ttccccttct   2820
tttctatggt taagttcatg tcataggaag gggataagta acagggtaca gtttagaatg   2880
ggaaacagac gaatgattgc atcagtgtgg aagtctcagg atcgttttag tttcttttat   2940
ttgctgttca taacaattgt tttcttttgt ttaattcttg ctttcttttt ttttcttctc   3000
cgcaattttt actattatac ttaatgcctt aacattgtgt ataacaaaag gaaatatctc   3060
tgagatacat taagtaactt aaaaaaaaac tttacacagt ctgcctagta cattactatt   3120
tggaatatat gtgtgcttat ttgcatattc ataatctccc tactttattt tcttttattt   3180
ttaattgata cataatcatt atacatattt atgggttaaa gtgtaatgtt ttaatatgtg   3240
tacacatatt gaccaaatca gggtaatttt gcatttgtaa ttttaaaaaa tgctttcttc   3300
ttttaatata cttttttgtt tatcttattt ctaatacttt ccctaatctc tttctttcag   3360
ggcaataatg atacaatgta tcatgcctct ttgcaccatt ctaaagaata acagtgataa   3420
tttctgggtt aaggcaatag caatatctct gcatataaat atttctgcat ataaattgta   3480
actgatgtaa gaggtttcat attgctaata gcagctacaa tccagctacc attctgcttt   3540
tattttatgg ttgggataag gctggattat tctgagtcca agctaggccc ttttgctaat   3600
catgttcata cctcttatct tcctcccaca gctcctgggc aacgtgctgg tctgtgtgct   3660
ggcccatcac tttggcaaag aattcacccc accagtgcag gctgcctatc agaaagtggt   3720
ggctggtgtg gctaatgccc tggcccacaa gtatcactaa gctcgctttc ttgctgtcca   3780
atttctatta aaggttcctt tgttccctaa gtccaactac taaactgggg gatattatga   3840
agggccttga gcatctggat tctgcctaat aaaaaacatt tattttcatt gcaatgatgt   3900
atttaaatta tttctgaata ttttactaaa aagggaatgt gggaggtcag tgcatttaaa   3960
acataaagaa atgaagagct agttcaaacc ttgggaaaat acactatatc ttaaactcca   4020
tgaaagaagg tgaggctgca aacagctaat gcacattggc aacagcccct gatgcatatg   4080
ccttattcat ccctcagaaa aggattcaag tagaggcttg atttggaggt taaagttttg   4140
ctatgctgta ttttacatta cttattgttt tagctgtcct catgaatgtc ttttcactac   4200
ccatttgctt atcctgcatc tctcagcctt gactccactc agttctcttg cttagagata   4260
ccacctttcc cctgaagtgt tccttccatg ttttacggcg agatggtttc tcctcgcctg   4320
gccactcagc cttagttgtc tctgttgtct tatagaggtc tacttgaaga aggaaaaaca   4380
ggggtcatgg tttgactgtc ctgtgagccc ttcttccctg cctcccccac tcacagtgac   4440
ccggaatctg cagtgctagt ctcccggaac tatcactctt tcacagtctg ctttggaagg   4500
actgggctta gtatgaaaag ttaggactga gaagaatttg aaaggcggct tttgtagct   4560
tgatattcac tactgtctta ttaccctgtc ggtaaccacg tgcggccgag gctgcagcgt   4620
cgtcctccct aggaacccct agtgatggag ttggccactc cctctctgcg cgctcgctcg   4680
ctcactgagg ccgggcgacc aaaggtcgcc cgacgcccgg gctttgcccg ggcggcctca   4740
```

gtgagcgagc gagcgcgcag ctgcctgcag g 4771

<210> SEQ ID NO 22
<211> LENGTH: 112
<212> TYPE: DNA
<213> ORGANISM: Artificial Sequence
<220> FEATURE:
<223> OTHER INFORMATION: Region encoding E6 to E6V and PAM mutation

<400> SEQUENCE: 22
gtcgagaaaa gcgctgtgac cgcactctgg ggtaaagtga acgtcgacga ggtgggcggt 60
gaagctctcg gaaggttggt atcaaggtta caagacacgt ttaaggagac ga 112

<210> SEQ ID NO 23
<211> LENGTH: 4435
<212> TYPE: DNA
<213> ORGANISM: Artificial Sequence
<220> FEATURE:
<223> OTHER INFORMATION: AAV.310

<400> SEQUENCE: 23
cttgctttga caattttggt ctttcagaat actataaata taacctatat tataatttca 60
taaagtctgt gcattttctt tgacccagga tatttgcaaa agacatattc aaacttccgc 120
agaacacttt atttcacata tacatgcctc ttatatcagg gatgtgaaac agggtcttga 180
aaactgtcta aatctaaaac aatgctaatg caggtttaaa tttaataaaa taaaatccaa 240
aatctaacag ccaagtcaaa tctgcatgtt ttaacattta aaatatttta aagacgtctt 300
ttcccaggat tcaacatgtg aaatcttttc tcagggatac acgtgtgcct agatcctcat 360
tgctttagtt ttttacagag gaatgaatat aaaaagaaaa tacttaaatt ttatccctct 420
tacctctata atcatacata ggcataattt tttaacctag gctccagata gccatagaag 480
aaccaaacac tttctgcgtg tgtgagaata atcagagtga gatttttca caagtacctg 540 atgagggttg agacaggtag aaaaagtgag agatctctat ttatttagca ataatagaga 600
aagcatttaa gagaataaag caatggaaat aagaaatttg taaatttcct tctgataact 660
agaaatagag gatccagttt cttttggtta acctaaattt tatttcattt tattgtttta 720
ttttatttta ttttatttta ttttgtgtaa tcgtagtttc agagtgttag agctgaaagg 780
aagaagtagg agaaacatgc aaagtaaaag tataacactt tccttactaa accgacatgg 840
gtttccaggt aggggcagga ttcaggatga ctgacagggc ccttagggaa cactgagacc 900
ctacgctgac ctcataaatg cttgctacct ttgctgtttt aattacatct tttaatagca 960
ggaagcagaa ctctgcactt caaaagtttt tcctcacctg aggagttaat ttagtacaag 1020
gggaaaaagt acagggggat gggagaaagg cgatcacgtt gggaagctat agagaaagaa 1080
gagtaaattt tagtaaagga ggtttaaaca aacaaaatat aaagagaaat aggaacttga 1140
atcaaggaaa tgattttaaa acgcagtatt cttagtggac tagaggaaaa aaataatctg 1200
agccaagtag aagacctttt cccctcctac ccctactttc taagtcacag aggctttttg 1260
ttcccccaga cactcttgca gattagtcca ggcagaaaca gttagatgtc cccagttaac 1320
ctcctatttg acaccactga ttaccccatt gatagtcaca ctttgggttg taagtgactt 1380
tttatttatt tgtatttttg actgcattaa gaggtctcta gttttttatc tcttgtttcc 1440
caaaacctaa taagtaacta atgcacagag cacattgatt tgtatttatt ctatttttag 1500
acataattta ttagcatgca tgagcaaatt aagaaaaaca acaacaaatg aatgcatata 1560
tatgtatatg tatgtgtgta tatatacaca catatatata tatatttttt cttttcttac 1620
cagaaggttt taatccaaat aaggagaaga tatgcttaga accgaggtag agttttcatc 1680
cattctgtcc tgtaagtatt ttgcatattc tggagacgca ggaagagatc catctacata 1740
tcccaaagct gaattatggt agacaaaact cttccacttt tagtgcatca acttcttatt 1800
tgtgtaataa gaaaattggg aaaacgatct tcaatatgct taccaagctg tgattccaaa 1860
tattacgtaa atacacttgc aaaggaggat gtttttagta gcaatttgta ctgatggtat 1920
ggggccaaga gatatatctt agagggaggg ctgagggttt gaagtccaac tcctaagcca 1980
gtgccagaag agccaaggac aggtacggct gtcatcactt agacctcacc ctgtggagcc 2040
acaccctagg gttggccaat ctactcccag gagcagggag ggcaggagcc agggctgggc 2100
ataaaagtca gggcagagcc atctattgct tacatttgct tctgacacaa ctgtgttcac 2160
tagcaacctc aaacagacac catggtgcat ctgactcctg tcgagaaaag cgctgtgacc 2220
gcactctggg gtaaagtgaa cgtcgacgag gtgggcggtg aagctctcgg aaggttggta 2280
tcaaggttac aagacacgtt taaggagacg aatagaaact gcgcatgtgg agacagagaa 2340
gactcttggg tttctgatag gcactgactc tctctgccta ttggtctatt ttcccaccct 2400
taggctgctg gtggtctacc cttggaccca gaggttcttt gagtcctttg gggatctgtc 2460
cactcctgat gctgttatgg gcaaccctaa ggtgaaggct catggcaaga aagtgctcgg 2520
tgcctttagt gatggcctgg ctcacctgga caacctcaag ggcacctttg ccacactgag 2580
tgagctgcac tgtgacaagc tgcacgtgga tcctgagaac ttcagggtga gtctatggga 2640
cgcttgatgt ttctttcccc cttcttttct atggttaagt tcatgtcata ggaaggggat 2700
aagtaacagg gtacagttta gaatgggaaa cagacgaatg attgcatcag tgtggaagtc 2760
tcaggatcgt tttagtttct tttatttgct gttcataaca attgttttct tttgtttaat 2820
tcttgctttc tttttttttc ttctccgcaa tttttactat tatacttaat gccttaacat 2880
tgtgtataac aaaaggaaat atctctgaga tacattaagt aacttaaaaa aaaactttac 2940
acagtctgcc tagtacatta ctatttggaa tatatgtgtg cttatttgca tattcataat 3000
ctccctactt tattttcttt tatttttaat tgatacataa tcattataca tatttatggg 3060
ttaaagtgta atgttttaat atgtgtacac atattgacca aatcagggta attttgcatt 3120
tgtaatttta aaaaatgctt tcttctttta atatactttt ttgtttatct tatttctaat 3180
actttcccta atctctttct ttcagggcaa taatgataca atgtatcatg cctctttgca 3240
ccattctaaa gaataacagt gataatttct gggttaaggc aatagcaata tctctgcata 3300
taaatatttc tgcatataaa ttgtaactga tgtaagaggt ttcatattgc taatagcagc 3360
tacaatccag ctaccattct gcttttattt tatggttggg ataaggctgg attattctga 3420
gtccaagcta ggcccttttg ctaatcatgt tcatacctct tatcttcctc ccacagctcc 3480
tgggcaacgt gctggtctgt gtgctggccc atcactttgg caaagaattc accccaccag 3540
tgcaggctgc ctatcagaaa gtggtggctg gtgtggctaa tgccctggcc cacaagtatc 3600
actaagctcg ctttcttgct gtccaatttc tattaaaggt tcctttgttc cctaagtcca 3660
actactaaac tgggggatat tatgaagggc cttgagcatc tggattctgc ctaataaaaa 3720
acatttattt tcattgcaat gatgtattta aattatttct gaatatttta ctaaaaaggg 3780
aatgtgggag gtcagtgcat ttaaaacata aagaaatgaa gagctagttc aaaccttggg 3840
aaaatacact atatcttaaa ctccatgaaa gaaggtgagg ctgcaaacag ctaatgcaca 3900
ttggcaacag cccctgatgc atatgcctta ttcatccctc agaaaaggat tcaagtagag 3960
gcttgatttg gaggttaaag ttttgctatg ctgtatttta cattacttat tgttttagct 4020
gtcctcatga atgtcttttc actacccatt tgcttatcct gcatctctca gccttgactc 4080
cactcagttc tcttgcttag agataccacc tttcccctga agtgttcctt ccatgtttta 4140
cggcgagatg gtttctcctc gcctggccac tcagccttag ttgtctctgt tgtcttatag 4200
aggtctactt gaagaaggaa aaacaggggt catggtttga ctgtcctgtg agcccttctt 4260
ccctgcctcc cccactcaca gtgacccgga atctgcagtg ctagtctccc ggaactatca 4320
ctctttcaca gtctgctttg gaaggactgg gcttagtatg aaaagttagg actgagaaga 4380
atttgaaagg cggctttttg tagcttgata ttcactactg tcttattacc ctgtc 4435

<210> SEQ ID NO 24
<211> LENGTH: 4749
<212> TYPE: DNA
<213> ORGANISM: Artificial Sequence
<220> FEATURE:
<223> OTHER INFORMATION: AAV.310 with ITRs

<400> SEQUENCE: 24
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtcttgct ttgacaattt tggtctttca gaatactata 180
aatataacct atattataat ttcataaagt ctgtgcattt tctttgaccc aggatatttg 240
caaaagacat attcaaactt ccgcagaaca ctttatttca catatacatg cctcttatat 300
cagggatgtg aaacagggtc ttgaaaactg tctaaatcta aaacaatgct aatgcaggtt 360
taaatttaat aaaataaaat ccaaaatcta acagccaagt caaatctgca tgttttaaca 420
tttaaaatat tttaaagacg tcttttccca ggattcaaca tgtgaaatct tttctcaggg 480
atacacgtgt gcctagatcc tcattgcttt agtttttttac agaggaatga atataaaaag 540
aaaatactta aattttatcc ctcttacctc tataatcata cataggcata attttttaac 600
ctaggctcca gatagccata gaagaaccaa acactttctg cgtgtgtgag aataatcaga 660
gtgagatttt ttcacaagta cctgatgagg gttgagacag gtagaaaaag tgagagatct 720
ctatttattt agcaataata gagaaagcat ttaagagaat aaagcaatgg aaataagaaa 780
tttgtaaatt tccttctgat aactagaaat agaggatcca gtttcttttg gttaacctaa 840
attttatttc attttattgt tttattttat tttattttat tttattttgt gtaatcgtag 900
tttcagagtg ttagagctga aaggaagaag taggagaaac atgcaaagta aaagtataac 960
actttcctta ctaaaccgac atgggtttcc aggtaggggc aggattcagg atgactgaca 1020
gggcccttag ggaacactga gaccctacgc tgacctcata aatgcttgct acctttgctg 1080
ttttaattac atcttttaat agcaggaagc agaactctgc acttcaaaag tttttcctca 1140
cctgaggagt taatttagta caaggggaaa aagtacaggg ggatgggaga aaggcgatca 1200
cgttgggaag ctatagagaa agaagagtaa attttagtaa aggaggttta aacaaacaaa 1260
atataaagag aaataggaac ttgaatcaag gaaatgattt taaaacgcag tattcttagt 1320
ggactagagg aaaaaaataa tctgagccaa gtagaagacc ttttccccctc ctacccctac 1380 tttctaagtc acagaggctt tttgttcccc cagacactct tgcagattag tccaggcaga 1440
aacagttaga tgtccccagt taacctccta tttgacacca ctgattaccc cattgatagt 1500
cacactttgg gttgtaagtg actttttatt tatttgtatt tttgactgca ttaagaggtc 1560

-continued

```
tctagttttt tatctcttgt ttcccaaaac ctaataagta actaatgcac agagcacatt   1620
gatttgtatt tattctattt ttagacataa tttattagca tgcatgagca aattaagaaa   1680
aacaacaaca aatgaatgca tatatatgta tatgtatgtg tgtatatata cacacatata   1740
tatatatatt ttttcttttc ttaccagaag gttttaatcc aaataaggag aagatatgct   1800
tagaaccgag gtagagtttt catccattct gtcctgtaag tattttgcat attctggaga   1860
cgcaggaaga gatccatcta catatcccaa agctgaatta tggtagacaa aactcttcca   1920
cttttagtgc atcaacttct tatttgtgta ataagaaaat tgggaaaacg atcttcaata   1980
tgcttaccaa gctgtgattc caaatattac gtaaatacac ttgcaaagga ggatgttttt   2040
agtagcaatt tgtactgatg gtatggggcc aagagatata tcttagaggg agggctgagg   2100
gtttgaagtc caactcctaa gccagtgcca gaagagccaa ggacaggtac ggctgtcatc   2160
acttagacct caccctgtgg agccacaccc tagggttggc caatctactc ccaggagcag   2220
ggagggcagg agccagggct gggcataaaa gtcagggcag agccatctat tgcttacatt   2280
tgcttctgac acaactgtgt tcactagcaa cctcaaacag acaccatggt gcatctgact   2340
cctgtcgaga aaagcgctgt gaccgcactc tggggtaaag tgaacgtcga cgaggtgggc   2400
ggtgaagctc tcggaaggtt ggtatcaagg ttacaagaca cgtttaagga gacgaataga   2460
aactgcgcat gtggagacag agaagactct tgggtttctg ataggcactg actctctctg   2520
cctattggtc tattttccca cccttaggct gctggtggtc tacccttgga cccagaggtt   2580
ctttgagtcc tttggggatc tgtccactcc tgatgctgtt atgggcaacc ctaaggtgaa   2640
ggctcatggc aagaaagtgc tcggtgcctt tagtgatggc ctggctcacc tggacaacct   2700
caagggcacc tttgccacac tgagtgagct gcactgtgac aagctgcacg tggatcctga   2760
gaacttcagg gtgagtctat gggacgcttg atgttttctt tccccttctt ttctatggtt   2820
aagttcatgt cataggaagg ggataagtaa cagggtacag tttagaatgg gaaacagacg   2880
aatgattgca tcagtgtgga agtctcagga tcgttttagt ttcttttatt tgctgttcat   2940
aacaattgtt ttcttttgtt taattcttgc tttctttttt tttcttctcc gcaattttta   3000
ctattatact taatgcctta acattgtgta taacaaaagg aaatatctct gagatacatt   3060
aagtaactta aaaaaaaact ttacacagtc tgcctagtac attactattt ggaatatatg   3120
tgtgcttatt tgcatattca taatctccct actttatttt cttttatttt taattgatac   3180
ataatcatta tacatattta tgggttaaag tgtaatgttt taatatgtgt acacatattg   3240
accaaatcag ggtaattttg catttgtaat tttaaaaaat gctttcttct tttaatatac   3300
tttttgttt atcttatttc taatactttc cctaatctct ttctttcagg gcaataatga   3360
tacaatgtat catgcctctt tgcaccattc taaagaataa cagtgataat ttctgggtta   3420
aggcaatagc aatatctctg catataaata tttctgcata taaattgtaa ctgatgtaag   3480
aggtttcata ttgctaatag cagctacaat ccagctacca ttctgctttt attttatggt   3540
tgggataagg ctggattatt ctgagtccaa gctaggccct tttgctaatc atgttcatac   3600
ctcttatctt cctcccacag ctcctgggca acgtgctggt ctgtgtgctg gcccatcact   3660
ttggcaaaga attcacccca ccagtgcagg ctgcctatca gaaagtggtg gctggtgtgg   3720
ctaatgccct ggcccacaag tatcactaag ctcgctttct tgctgtccaa tttctattaa   3780
aggttccttt gttccctaag tccaactact aaactggggg atattatgaa gggccttgag   3840
catctggatt ctgcctaata aaaaacattt attttcattg caatgatgta tttaaattat   3900
ttctgaatat tttactaaaa agggaatgtg ggaggtcagt gcatttaaaa cataaagaaa   3960
```

tgaagagcta gttcaaacct tgggaaaata cactatatct taaactccat gaaagaaggt 4020
gaggctgcaa acagctaatg cacattggca acagcccctg atgcatatgc cttattcatc 4080
cctcagaaaa ggattcaagt agaggcttga tttggaggtt aaagttttgc tatgctgtat 4140
tttacattac ttattgtttt agctgtcctc atgaatgtct tttcactacc catttgctta 4200
tcctgcatct ctcagccttg actccactca gttctcttgc ttagagatac cacctttccc 4260
ctgaagtgtt ccttccatgt tttacggcga gatggtttct cctcgcctgg ccactcagcc 4320
ttagttgtct ctgttgtctt atagaggtct acttgaagaa ggaaaaacag gggtcatggt 4380
ttgactgtcc tgtgagccct tcttccctgc ctcccccact cacagtgacc cggaatctgc 4440
agtgctagtc tcccggaact atcactcttt cacagtctgc tttggaagga ctgggcttag 4500
tatgaaaagt taggactgag aagaatttga aaggcggctt tttgtagctt gatattcact 4560
actgtcttat taccctgtcg gtaaccacgt gcggccgagg ctgcagcgtc gtcctccctc 4620
ctgcaggcag ctgcgcgctc gctcgctcac tgaggccgcc cgggcgtcgg gcgacctttg 4680
gtcgcccggc ctcagtgagc gagcgagcgc gcagagaggg agtggccaac tccatcacta 4740
ggggttcct 4749

<210> SEQ ID NO 25
<211> LENGTH: 7
<212> TYPE: PRT
<213> ORGANISM: Artificial Sequence
<220> FEATURE:
<223> OTHER INFORMATION: SV40 nuclear localization signal

<400> SEQUENCE: 25

Pro Lys Lys Lys Arg Lys Val
1 5

<210> SEQ ID NO 26
<211> LENGTH: 7
<212> TYPE: PRT
<213> ORGANISM: Artificial Sequence
<220> FEATURE:
<223> OTHER INFORMATION: SV40 nuclear localization signal

<400> SEQUENCE: 26

Pro Lys Lys Lys Arg Arg Val
1 5

<210> SEQ ID NO 27
<211> LENGTH: 16
<212> TYPE: PRT
<213> ORGANISM: Artificial Sequence
<220> FEATURE:
<223> OTHER INFORMATION: Nucleoplasmin nuclear localization signal

<400> SEQUENCE: 27

Lys Arg Pro Ala Ala Thr Lys Lys Ala Gly Gln Ala Lys Lys Lys Lys
1 5 10 15

<210> SEQ ID NO 28
<211> LENGTH: 228
<212> TYPE: DNA
<213> ORGANISM: Artificial Sequence
<220> FEATURE:
<223> OTHER INFORMATION: A10

<400> SEQUENCE: 28
atgcagattt acgtgaagac ctttgcccgg aagcccatca ccctcgaggt tgaaccctcg 60

```
gatacgatag aaaatgtaaa ggccaagatc caggataagg aaggaattcc tcctgatcag    120

cagcgactga tctttgctga aatgcggctg gaagatggac gtactttgtc tgactacaat    180

attaaaaacg actctactct tttcttgtg ttgaaaaata gtgttact                  228


<210> SEQ ID NO 29
<211> LENGTH: 228
<212> TYPE: RNA
<213> ORGANISM: Artificial Sequence
<220> FEATURE:
<223> OTHER INFORMATION: A10

<400> SEQUENCE: 29

augcagauuu acgugaagac cuuugcccgg aagcccauca cccucgaggu ugaacccucg     60

gauacgauag aaaauguaaa ggccaagauc caggauaagg aaggaauucc uccugaucag    120

cagcgacuga ucuuugcuga aaugcggcug gaagauggac guacuuuguc ugacuacaau    180

auuaaaaacg acucuacucu uuuucuugug uugaaaaaua guguuacu                 228


<210> SEQ ID NO 30
<211> LENGTH: 76
<212> TYPE: PRT
<213> ORGANISM: Artificial Sequence
<220> FEATURE:
<223> OTHER INFORMATION: A10

<400> SEQUENCE: 30

Met Gln Ile Tyr Val Lys Thr Phe Ala Arg Lys Pro Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Glu Met
        35                  40                  45

Arg Leu Glu Asp Gly Arg Thr Leu Ser Asp Tyr Asn Ile Lys Asn Asp
    50                  55                  60

Ser Thr Leu Phe Leu Val Leu Lys Asn Ser Val Thr
65                  70                  75


<210> SEQ ID NO 31
<211> LENGTH: 228
<212> TYPE: DNA
<213> ORGANISM: Artificial Sequence
<220> FEATURE:
<223> OTHER INFORMATION: A11

<400> SEQUENCE: 31

atgctgattt tcgtgaccac cgatatgggg atgacaatct cactcgaggt tgaaccctcg     60

gatacgatag aaaatgtaaa ggccaagatc caggataagg aaggaattcc tcctgatcag    120

cagagactga tctttggtga caaggatctg gaagatggac gtactttgtc tgactacaat    180

attcaaaagg agtctagcct taatcttgtg ctgaaacttc gtggtggt                 228


<210> SEQ ID NO 32
<211> LENGTH: 228
<212> TYPE: RNA
<213> ORGANISM: Artificial Sequence
<220> FEATURE:
<223> OTHER INFORMATION: A11

<400> SEQUENCE: 32

augcugauuu ucgugaccac cgauaugggg augacaaucu cacucgaggu ugaacccucg     60
```

gauacgauag aaaauguaaa ggccaagauc caggauaagg aaggaauucc uccugaucag 120
cagagacuga ucuuugguga caaggaucug gaagauggac guacuuuguc ugacuacaau 180
auucaaaagg agucuagccu uaaucuugug cugaaacuuc gugguggu 228

<210> SEQ ID NO 33
<211> LENGTH: 76
<212> TYPE: PRT
<213> ORGANISM: Artificial Sequence
<220> FEATURE:
<223> OTHER INFORMATION: A11

<400> SEQUENCE: 33

Met Leu Ile Phe Val Thr Thr Asp Met Gly Met Thr Ile Ser Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Gly Asp Lys
35 40 45

Asp Leu Glu Asp Gly Arg Thr Leu Ser Asp Tyr Asn Ile Gln Lys Glu
50 55 60

Ser Ser Leu Asn Leu Val Leu Lys Leu Arg Gly Gly
65 70 75

<210> SEQ ID NO 34
<211> LENGTH: 228
<212> TYPE: DNA
<213> ORGANISM: Artificial Sequence
<220> FEATURE:
<223> OTHER INFORMATION: C08

<400> SEQUENCE: 34
atgcagattt tcgtgaccac cgatatgtgg atgagaatct cactcgaggt tgaaccctcg 60
gatacgatag aaaatgtaaa ggccaagatc caggataagg aaggaattcc tcctgatcag 120
cagagactga tctttggtga caaggatctg gaagatggac gtactttgtc tgactacaat 180
attcaaaagg agtctagcct taatcttgtg ctgaaccttc gtggtggt 228

<210> SEQ ID NO 35
<211> LENGTH: 228
<212> TYPE: RNA
<213> ORGANISM: Artificial Sequence
<220> FEATURE:
<223> OTHER INFORMATION: C08

<400> SEQUENCE: 35
augcagauuu ucgugaccac cgauaugugg augagaaucu cacucgaggu ugaacccucg 60
gauacgauag aaaauguaaa ggccaagauc caggauaagg aaggaauucc uccugaucag 120
cagagacuga ucuuugguga caaggaucug gaagauggac guacuuuguc ugacuacaau 180
auucaaaagg agucuagccu uaaucuugug cugaaccuuc gugguggu 228

<210> SEQ ID NO 36
<211> LENGTH: 76
<212> TYPE: PRT
<213> ORGANISM: Artificial Sequence
<220> FEATURE:
<223> OTHER INFORMATION: C08

<400> SEQUENCE: 36

Met Gln Ile Phe Val Thr Thr Asp Met Trp Met Arg Ile Ser Leu Glu

-continued

```
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Gly Asp Lys
        35                  40                  45

Asp Leu Glu Asp Gly Arg Thr Leu Ser Asp Tyr Asn Ile Gln Lys Glu
    50                  55                  60

Ser Ser Leu Asn Leu Val Leu Asn Leu Arg Gly Gly
65                  70                  75
```

<210> SEQ ID NO 37
<211> LENGTH: 228
<212> TYPE: DNA
<213> ORGANISM: Artificial Sequence
<220> FEATURE:
<223> OTHER INFORMATION: G08

<400> SEQUENCE: 37

```
atgttgattt tcgtgaaaac ccttaccggg aaaaccatca ccctcgaggt tgaaccctcg     60

gatacgatag aaaatgtaaa ggccaagatc caggataagg aaggaattcc tcctgatcag    120

cagagactga tctttgctgg caaatcgctg gaagatggac gtactttgtc tgactacaat    180

attctaaagg actctaaact tcatcctctg ttgagacttc gtggtggt                 228
```

<210> SEQ ID NO 38
<211> LENGTH: 228
<212> TYPE: RNA
<213> ORGANISM: Artificial Sequence
<220> FEATURE:
<223> OTHER INFORMATION: G08

<400> SEQUENCE: 38

```
auguugauuu ucgugaaaac ccuuaccggg aaaaccauca cccucgaggu ugaacccucg     60

gauacgauag aaaauguaaa ggccaagauc caggauaagg aaggaauucc uccugaucag    120

cagagacuga ucuuugcugg caaaucgcug gaagauggac guacuuuguc ugacuacaau    180

auucuaaagg acucuaaacu ucauccucug uugagacuuc gugguggu                 228
```

<210> SEQ ID NO 39
<211> LENGTH: 76
<212> TYPE: PRT
<213> ORGANISM: Artificial Sequence
<220> FEATURE:
<223> OTHER INFORMATION: G08

<400> SEQUENCE: 39

```
Met Leu Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Ser Leu Glu Asp Gly Arg Thr Leu Ser Asp Tyr Asn Ile Leu Lys Asp
    50                  55                  60

Ser Lys Leu His Pro Leu Leu Arg Leu Arg Gly Gly
65                  70                  75
```

<210> SEQ ID NO 40
<211> LENGTH: 228
<212> TYPE: DNA

<213> ORGANISM: Artificial Sequence
<220> FEATURE:
<223> OTHER INFORMATION: H04

<400> SEQUENCE: 40
atgcgaatta tcgtgaaaac ctttatgcgg aagccgatca cgctcgaggt tgaaccctcg 60
gatacgatag aaaatgtaaa ggccaagatc caggataagg aaggaattcc tcctgatcag 120
cagagactgt attttgcggc cagtcagctg gaagatggac gtactttgtc tgactacaat 180
attcaaaagg agtctactct tcttcttgtg gtaaggctgc tccgcgtt 228

<210> SEQ ID NO 41
<211> LENGTH: 228
<212> TYPE: RNA
<213> ORGANISM: Artificial Sequence
<220> FEATURE:
<223> OTHER INFORMATION: H04

<400> SEQUENCE: 41
augcgaauua ucgugaaaac cuuuaugcgg aagccgauca cgcucgaggu ugaacccucg 60
gauacgauag aaaauguaaa ggccaagauc caggauaagg aaggaauucc uccugaucag 120
cagagacugu auuuugcggc cagucagcug gaagauggac guacuuuguc ugacuacaau 180
auucaaaagg agucuacucu ucuucuugug guaaggcugc uccgcguu 228

<210> SEQ ID NO 42
<211> LENGTH: 76
<212> TYPE: PRT
<213> ORGANISM: Artificial Sequence
<220> FEATURE:
<223> OTHER INFORMATION: H04

<400> SEQUENCE: 42

Met Arg Ile Ile Val Lys Thr Phe Met Arg Lys Pro Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Tyr Phe Ala Ala Ser
35 40 45

Gln Leu Glu Asp Gly Arg Thr Leu Ser Asp Tyr Asn Ile Gln Lys Glu
50 55 60

Ser Thr Leu Leu Leu Val Val Arg Leu Leu Arg Val
65 70 75

<210> SEQ ID NO 43
<211> LENGTH: 222
<212> TYPE: RNA
<213> ORGANISM: Artificial Sequence
<220> FEATURE:
<223> OTHER INFORMATION: i53 alt

<400> SEQUENCE: 43
auguugauuu ucgugaaaac ccuuaccggg aaaaccauca cccucgaggu ugaacccucg 60
gauacgauag aaaauguaaa ggccaagauc caggauaagg aaggaauucc uccugaucag 120
cagagacugg ccuuugcugg caaaucgcug gaagauggac guacuuuguc ugacuacaau 180
auucuaaagg acucuaaacu ucauccucug uugagacuuc gu 222

<210> SEQ ID NO 44
<211> LENGTH: 4435
<212> TYPE: DNA

<213> ORGANISM: Artificial Sequence
<220> FEATURE:
<223> OTHER INFORMATION: AAV.323

<400> SEQUENCE: 44

```
cttgctttga caattttggt ctttcagaat actataaata taacctatat tataatttca     60
taaagtctgt gcattttctt tgacccagga tatttgcaaa agacatattc aaacttccgc    120
agaacacttt atttcacata tacatgcctc ttatatcagg gatgtgaaac agggtcttga    180
aaactgtcta aatctaaaac aatgctaatg caggtttaaa tttaataaaa taaaatccaa    240
aatctaacag ccaagtcaaa tctgcatgtt ttaacattta aaatatttta aagacgtctt    300
ttcccaggat tcaacatgtg aaatcttttc tcagggatac acgtgtgcct agatcctcat    360
tgctttagtt ttttacagag gaatgaatat aaaaagaaaa tacttaaatt ttatccctct    420
tacctctata atcatacata ggcataattt tttaacctag gctccagata gccatagaag    480
aaccaaacac tttctgcgtg tgtgagaata atcagagtga gatttttca caagtacctg     540
atgagggttg agacaggtag aaaaagtgag agatctctat ttatttagca ataatagaga    600
aagcatttaa gagaataaag caatggaaat aagaaatttg taaatttcct tctgataact    660
agaaatagag gatccagttt cttttggtta acctaaattt tatttcattt tattgtttta    720
ttttatttta ttttatttta ttttgtgtaa tcgtagtttc agagtgttag agctgaaagg    780
aagaagtagg agaaacatgc aaagtaaaag tataacactt tccttactaa accgacatgg    840
gtttccaggt aggggcagga ttcaggatga ctgacagggc ccttagggaa cactgagacc    900
ctacgctgac ctcataaatg cttgctacct ttgctgtttt aattacatct tttaatagca    960
ggaagcagaa ctctgcactt caaaagtttt tcctcacctg aggagttaat ttagtacaag   1020
gggaaaaagt acagggggat gggagaaagg cgatcacgtt gggaagctat agagaaagaa   1080
gagtaaattt tagtaaagga ggtttaaaca aacaaaatat aaagagaaat aggaacttga   1140
atcaaggaaa tgattttaaa acgcagtatt cttagtggac tagaggaaaa aaataatctg   1200
agccaagtag aagacctttt cccctcctac ccctacttc taagtcacag aggcttttg    1260
ttcccccaga cactcttgca gattagtcca ggcagaaaca gttagatgtc cccagttaac   1320
ctcctatttg acaccactga ttaccccatt gatagtcaca ctttgggttg taagtgactt   1380
tttatttatt tgtatttttg actgcattaa gaggtctcta gttttttatc tcttgtttcc   1440
caaaacctaa taagtaacta atgcacagag cacattgatt tgtatttatt ctatttttag   1500
acataattta ttagcatgca tgagcaaatt aagaaaaaca acaacaaatg aatgcatata   1560
tatgtatatg tatgtgtgta tatatacaca catatatata tatatttttt cttttcttac   1620
cagaaggttt taatccaaat aaggagaaga tatgcttaga accgaggtag agttttcatc   1680
cattctgtcc tgtaagtatt ttgcatattc tggagacgca ggaagagatc catctacata   1740
tcccaaagct gaattatggt agacaaaact cttccacttt tagtgcatca acttcttatt   1800
tgtgtaataa gaaaattggg aaaacgatct tcaatatgct taccaagctg tgattccaaa   1860
tattacgtaa atacacttgc aaaggaggat gtttttagta gcaatttgta ctgatggtat   1920
ggggccaaga gatatatctt agagggaggg ctgagggttt gaagtccaac tcctaagcca   1980
gtgccagaag agccaaggac aggtacggct gtcatcactt agacctcacc ctgtggagcc   2040
acaccctagg gttggccaat ctactcccag gagcagggag ggcaggagcc agggctgggc   2100
ataaaagtca gggcagagcc atctattgct tacatttgct tctgacacaa ctgtgttcac   2160
tagcaacctc aaacagacac catggtgcat ctgactcctg aagaaaaatc cgctgtcact   2220
```

```
gccctgtggg gcaaggtgaa cgtggatgaa gttggtggtg aggccctggg caggttggta   2280
tcaaggttac aagacaggtt taaggagacc aatagaaact gggcatgtgg agacagagaa   2340
gactcttggg tttctgatag gcactgactc tctctgccta ttggtctatt ttcccaccct   2400
taggctgctg gtggtctacc cttggaccca gaggttcttt gagtcctttg gggatctgtc   2460
cactcctgat gctgttatgg gcaaccctaa ggtgaaggct catggcaaga aagtgctcgg   2520
tgcctttagt gatggcctgg ctcacctgga caacctcaag ggcacctttg ccacactgag   2580
tgagctgcac tgtgacaagc tgcacgtgga tcctgagaac ttcagggtga gtctatggga   2640
cgcttgatgt tttctttccc cttcttttct atggttaagt tcatgtcata ggaaggggat   2700
aagtaacagg gtacagttta gaatgggaaa cagacgaatg attgcatcag tgtggaagtc   2760
tcaggatcgt tttagtttct tttatttgct gttcataaca attgttttct tttgtttaat   2820
tcttgctttc tttttttttc ttctccgcaa tttttactat tatacttaat gccttaacat   2880
tgtgtataac aaaaggaaat atctctgaga tacattaagt aacttaaaaa aaaactttac   2940
acagtctgcc tagtacatta ctatttggaa tatatgtgtg cttatttgca tattcataat   3000
ctccctactt tattttcttt tatttttaat tgatacataa tcattataca tatttatggg   3060
ttaaagtgta atgttttaat atgtgtacac atattgacca aatcagggta attttgcatt   3120
tgtaatttta aaaaatgctt tcttctttta atatactttt ttgtttatct tatttctaat   3180
actttcccta atctctttct ttcagggcaa taatgataca atgtatcatg cctctttgca   3240
ccattctaaa gaataacagt gataatttct gggttaaggc aatagcaata tctctgcata   3300
taaatatttc tgcatataaa ttgtaactga tgtaagaggt ttcatattgc taatagcagc   3360
tacaatccag ctaccattct gcttttattt tatggttggg ataaggctgg attattctga   3420
gtccaagcta ggcccttttg ctaatcatgt tcatacctct tatcttcctc ccacagctcc   3480
tgggcaacgt gctggtctgt gtgctggccc atcactttgg caaagaattc accccaccag   3540
tgcaggctgc ctatcagaaa gtggtggctg gtgtggctaa tgccctggcc cacaagtatc   3600
actaagctcg ctttcttgct gtccaatttc tattaaaggt tcctttgttc cctaagtcca   3660
actactaaac tgggggatat tatgaagggc cttgagcatc tggattctgc ctaataaaaa   3720
acatttattt tcattgcaat gatgtattta aattatttct gaatatttta ctaaaaaggg   3780
aatgtgggag gtcagtgcat ttaaaacata aagaaatgaa gagctagttc aaaccttggg   3840
aaaatacact atatcttaaa ctccatgaaa gaaggtgagg ctgcaaacag ctaatgcaca   3900
ttggcaacag cccctgatgc atatgcctta ttcatccctc agaaaaggat tcaagtagag   3960
gcttgatttg gaggttaaag ttttgctatg ctgtatttta cattacttat tgttttagct   4020
gtcctcatga atgtcttttc actacccatt tgcttatcct gcatctctca gccttgactc   4080
cactcagttc tcttgcttag agataccacc tttcccctga agtgttcctt ccatgtttta   4140
cggcgagatg gtttctcctc gcctggccac tcagccttag ttgtctctgt tgtcttatag   4200
aggtctactt gaagaaggaa aaacaggggt catggtttga ctgtcctgtg agcccttctt   4260
ccctgcctcc cccactcaca gtgacccgga atctgcagtg ctagtctccc ggaactatca   4320
ctctttcaca gtctgctttg gaaggactgg gcttagtatg aaaagttagg actgagaaga   4380
atttgaaagg cggctttttg tagcttgata ttcactactg tcttattacc ctgtc        4435
```

<210> SEQ ID NO 45
<211> LENGTH: 16
<212> TYPE: DNA

<213> ORGANISM: Artificial Sequence
<220> FEATURE:
<223> OTHER INFORMATION: Gene-edit (E6V to E6)

<400> SEQUENCE: 45
gaagaaaaat ccgctg 16

<210> SEQ ID NO 46
<211> LENGTH: 4760
<212> TYPE: DNA
<213> ORGANISM: Artificial Sequence
<220> FEATURE:
<223> OTHER INFORMATION: AAV.323 with ITRs

<400> SEQUENCE: 46
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtcttgct ttgacaattt tggtctttca gaatactata 180
aatataacct atattataat ttcataaagt ctgtgcattt tctttgaccc aggatatttg 240
caaaagacat attcaaactt ccgcagaaca ctttatttca catatacatg cctcttatat 300
cagggatgtg aaacagggtc ttgaaaactg tctaaatcta aaacaatgct aatgcaggtt 360
taaatttaat aaaataaaat ccaaaatcta acagccaagt caaatctgca tgttttaaca 420
tttaaaatat tttaaagacg tcttttccca ggattcaaca tgtgaaatct tttctcaggg 480
atacacgtgt gcctagatcc tcattgcttt agttttttac agaggaatga atataaaaag 540
aaaatactta aattttatcc ctcttacctc tataatcata cataggcata atttttttaac 600 ctaggctcca gatagccata gaagaaccaa acactttctg cgtgtgtgag aataatcaga 660
gtgagatttt ttcacaagta cctgatgagg gttgagacag gtagaaaaag tgagagatct 720
ctatttattt agcaataata gagaaagcat ttaagagaat aaagcaatgg aaataagaaa 780
tttgtaaatt tccttctgat aactagaaat agaggatcca gtttcttttg gttaacctaa 840
attttatttc attttattgt ttattttat tttattttat tttattttgt gtaatcgtag 900
tttcagagtg ttagagctga aaggaagaag taggagaaac atgcaaagta aaagtataac 960
actttcctta ctaaaccgac atgggtttcc aggtaggggc aggattcagg atgactgaca 1020
gggcccttag ggaacactga gaccctacgc tgacctcata aatgcttgct acctttgctg 1080
ttttaattac atcttttaat agcaggaagc agaactctgc acttcaaaag tttttcctca 1140
cctgaggagt taatttagta caaggggaaa aagtacaggg ggatgggaga aaggcgatca 1200
cgttgggaag ctatagagaa agaagagtaa attttagtaa aggaggttta aacaaacaaa 1260
atataaagag aaataggaac ttgaatcaag gaaatgattt taaaacgcag tattcttagt 1320
ggactagagg aaaaaaataa tctgagccaa gtagaagacc ttttcccctc ctacccctac 1380
tttctaagtc acagaggctt tttgttcccc cagacactct tgcagattag tccaggcaga 1440
aacagttaga tgtccccagt taacctccta tttgacacca ctgattaccc cattgatagt 1500
cacactttgg gttgtaagtg actttttatt tatttgtatt tttgactgca ttaagaggtc 1560
tctagttttt tatctcttgt ttcccaaaac ctaataagta actaatgcac agagcacatt 1620
gatttgtatt tattctattt ttagacataa tttattagca tgcatgagca aattaagaaa 1680
aacaacaaca aatgaatgca tatatatgta tatgtatgtg tgtatatata cacacatata 1740
tatatatatt ttttcttttc ttaccagaag gttttaatcc aaataaggag aagatatgct 1800
tagaaccgag gtagagtttt catccattct gtcctgtaag tattttgcat attctggaga 1860

-continued

```
cgcaggaaga gatccatcta catatcccaa agctgaatta tggtagacaa aactcttcca   1920
cttttagtgc atcaacttct tatttgtgta ataagaaaat tgggaaaacg atcttcaata   1980
tgcttaccaa gctgtgattc caaatattac gtaaatacac ttgcaaagga ggatgttttt   2040
agtagcaatt tgtactgatg gtatggggcc aagagatata tcttagaggg agggctgagg   2100
gtttgaagtc caactcctaa gccagtgcca gaagagccaa ggacaggtac ggctgtcatc   2160
acttagacct caccctgtgg agccacaccc tagggttggc caatctactc ccaggagcag   2220
ggagggcagg agccagggct gggcataaaa gtcagggcag agccatctat tgcttacatt   2280
tgcttctgac acaactgtgt tcactagcaa cctcaaacag acaccatggt gcatctgact   2340
cctgaagaaa aatccgctgt cactgccctg tggggcaagg tgaacgtgga tgaagttggt   2400
ggtgaggccc tgggcaggtt ggtatcaagg ttacaagaca ggtttaagga gaccaataga   2460
aactgggcat gtggagacag agaagactct tgggtttctg ataggcactg actctctctg   2520
cctattggtc tattttccca cccttaggct gctggtggtc taccettgga cccagaggtt   2580
ctttgagtcc tttggggatc tgtccactcc tgatgctgtt atgggcaacc ctaaggtgaa   2640
ggctcatggc aagaaagtgc tcggtgcctt tagtgatggc ctggctcacc tggacaacct   2700
caagggcacc tttgccacac tgagtgagct gcactgtgac aagctgcacg tggatcctga   2760
gaacttcagg gtgagtctat gggacgcttg atgttttctt tccccttctt ttctatggtt   2820
aagttcatgt cataggaagg ggataagtaa cagggtacag tttagaatgg gaaacagacg   2880
aatgattgca tcagtgtgga agtctcagga tcgttttagt ttcttttatt tgctgttcat   2940
aacaattgtt ttcttttgtt taattcttgc tttctttttt tttcttctcc gcaattttta   3000
ctattatact taatgcctta acattgtgta taacaaaagg aaatatctct gagatacatt   3060
aagtaactta aaaaaaaact ttacacagtc tgcctagtac attactattt ggaatatatg   3120
tgtgcttatt tgcatattca taatctccct actttatttt cttttatttt taattgatac   3180
ataatcatta tacatattta tgggttaaag tgtaatgttt taatatgtgt acacatattg   3240
accaaatcag ggtaattttg catttgtaat tttaaaaaat gctttcttct tttaatatac   3300
tttttttgttt atcttatttc taatactttc cctaatctct ttctttcagg gcaataatga   3360
tacaatgtat catgcctctt tgcaccattc taaagaataa cagtgataat ttctgggtta   3420
aggcaatagc aatatctctg catataaata tttctgcata taaattgtaa ctgatgtaag   3480
aggtttcata ttgctaatag cagctacaat ccagctacca ttctgctttt attttatggt   3540
tgggataagg ctggattatt ctgagtccaa gctaggccct tttgctaatc atgttcatac   3600
ctcttatctt cctcccacag ctcctgggca acgtgctggt ctgtgtgctg gcccatcact   3660
ttggcaaaga attcaccccc ccagtgcagg ctgcctatca gaaagtggtg gctggtgtgg   3720
ctaatgccct ggcccacaag tatcactaag ctcgctttct tgctgtccaa tttctattaa   3780
aggttccttt gttccctaag tccaactact aaactggggg atattatgaa gggccttgag   3840
catctggatt ctgcctaata aaaaacattt attttcattg caatgatgta tttaaattat   3900
ttctgaatat tttactaaaa agggaatgtg ggaggtcagt gcatttaaaa cataaagaaa   3960
tgaagagcta gttcaaacct tgggaaaata cactatatct taaactccat gaaagaaggt   4020
gaggctgcaa acagctaatg cacattggca acagcccctg atgcatatgc cttattcatc   4080
cctcagaaaa ggattcaagt agaggcttga tttggaggtt aaagttttgc tatgctgtat   4140
tttacattac ttattgtttt agctgtcctc atgaatgtct tttcactacc catttgctta   4200
```

-continued

```
tcctgcatct ctcagccttg actccactca gttctcttgc ttagagatac cacctttccc   4260

ctgaagtgtt ccttccatgt tttacggcga gatggtttct cctcgcctgg ccactcagcc   4320

ttagttgtct ctgttgtctt atagaggtct acttgaagaa ggaaaaacag gggtcatggt   4380

ttgactgtcc tgtgagccct tcttccctgc ctcccccact cacagtgacc cggaatctgc   4440

agtgctagtc tcccggaact atcactcttt cacagtctgc tttggaagga ctgggcttag   4500

tatgaaaagt taggactgag aagaatttga aaggcggctt tttgtagctt gatattcact   4560

actgtcttat taccctgtcg gtaaccacgt gcggccgagg ctgcagcgtc gtcctcccta   4620

ggaaccccta gtgatggagt tggccactcc ctctctgcgc gctcgctcgc tcactgaggc   4680

cgggcgacca aaggtcgccc gacgcccggg ctttgcccgg gcggcctcag tgagcgagcg   4740

agcgcgcagc tgcctgcagg                                               4760
```

<210> SEQ ID NO 47
<211> LENGTH: 1421
<212> TYPE: DNA
<213> ORGANISM: Artificial Sequence
<220> FEATURE:
<223> OTHER INFORMATION: HBB exons 1-3

<400> SEQUENCE: 47

```
atggtgcatc tgactcctga agaaaaatcc gctgtcactg ccctgtgggg caaggtgaac     60

gtggatgaag ttggtggtga ggccctgggc aggttggtat caaggttaca agacaggttt    120

aaggagacca atagaaactg ggcatgtgga gacagagaag actcttgggt ttctgatagg    180

cactgactct ctctgcctat tggtctattt tcccaccctt aggctgctgg tggtctaccc    240

ttggacccag aggttctttg agtcctttgg ggatctgtcc actcctgatg ctgttatggg    300

caaccctaag gtgaaggctc atggcaagaa agtgctcggt gcctttagtg atggcctggc    360

tcacctggac aacctcaagg gcacctttgc cacactgagt gagctgcact gtgacaagct    420

gcacgtggat cctgagaact tcagggtgag tctatgggac gcttgatgtt ttctttcccc    480

ttcttttcta tggttaagtt catgtcatag gaaggggata agtaacaggg tacagtttag    540

aatgggaaac agacgaatga ttgcatcagt gtggaagtct caggatcgtt ttagtttctt    600

ttatttgctg ttcataacaa ttgttttctt ttgtttaatt cttgctttct ttttttttct    660

tctccgcaat ttttactatt atacttaatg ccttaacatt gtgtataaca aaaggaaata    720

tctctgagat acattaagta acttaaaaaa aaactttaca cagtctgcct agtacattac    780

tatttggaat atatgtgtgc ttatttgcat attcataatc tccctacttt attttctttt    840

atttttaatt gatacataat cattatacat atttatgggt taaagtgtaa tgttttaata    900

tgtgtacaca tattgaccaa atcagggtaa ttttgcattt gtaattttaa aaaatgcttt    960

cttcttttaa tatacttttt tgtttatctt atttctaata ctttccctaa tctctttctt   1020

tcagggcaat aatgatacaa tgtatcatgc ctctttgcac cattctaaag aataacagtg   1080

ataatttctg ggttaaggca atagcaatat ctctgcatat aaatatttct gcatataaat   1140

tgtaactgat gtaagaggtt tcatattgct aatagcagct acaatccagc taccattctg   1200

cttttatttt atggttggga taaggctgga ttattctgag tccaagctag gccctttttgc  1260

taatcatgtt catacctctt atcttcctcc cacagctcct gggcaacgtg ctggtctgtg   1320

tgctggccca tcactttggc aaagaattca ccccaccagt gcaggctgcc tatcagaaag   1380

tggtggctgg tgtggctaat gccctggccc acaagtatca c                        1421
```

<210> SEQ ID NO 48
<211> LENGTH: 1404
<212> TYPE: PRT
<213> ORGANISM: Streptococcus pyogenes

<400> SEQUENCE: 48

```
Met Ala Pro Lys Lys Lys Arg Lys Val Gly Ser Gly Gly Ser Gly Gly
1               5                   10                  15

Ser Gly Asp Lys Lys Tyr Ser Ile Gly Leu Asp Ile Gly Thr Asn Ser
            20                  25                  30

Val Gly Trp Ala Val Ile Thr Asp Glu Tyr Lys Val Pro Ser Lys Lys
        35                  40                  45

Phe Lys Val Leu Gly Asn Thr Asp Arg His Ser Ile Lys Lys Asn Leu
    50                  55                  60

Ile Gly Ala Leu Leu Phe Asp Ser Gly Glu Thr Ala Glu Ala Thr Arg
65                  70                  75                  80

Leu Lys Arg Thr Ala Arg Arg Arg Tyr Thr Arg Arg Lys Asn Arg Ile
                85                  90                  95

Cys Tyr Leu Gln Glu Ile Phe Ser Asn Glu Met Ala Lys Val Asp Asp
            100                 105                 110

Ser Phe Phe His Arg Leu Glu Glu Ser Phe Leu Val Glu Glu Asp Lys
        115                 120                 125

Lys His Glu Arg His Pro Ile Phe Gly Asn Ile Val Asp Glu Val Ala
    130                 135                 140

Tyr His Glu Lys Tyr Pro Thr Ile Tyr His Leu Arg Lys Lys Leu Val
145                 150                 155                 160

Asp Ser Thr Asp Lys Ala Asp Leu Arg Leu Ile Tyr Leu Ala Leu Ala
                165                 170                 175

His Met Ile Lys Phe Arg Gly His Phe Leu Ile Glu Gly Asp Leu Asn
            180                 185                 190

Pro Asp Asn Ser Asp Val Asp Lys Leu Phe Ile Gln Leu Val Gln Thr
        195                 200                 205

Tyr Asn Gln Leu Phe Glu Glu Asn Pro Ile Asn Ala Ser Gly Val Asp
    210                 215                 220

Ala Lys Ala Ile Leu Ser Ala Arg Leu Ser Lys Ser Arg Arg Leu Glu
225                 230                 235                 240

Asn Leu Ile Ala Gln Leu Pro Gly Glu Lys Lys Asn Gly Leu Phe Gly
                245                 250                 255

Asn Leu Ile Ala Leu Ser Leu Gly Leu Thr Pro Asn Phe Lys Ser Asn
            260                 265                 270

Phe Asp Leu Ala Glu Asp Ala Lys Leu Gln Leu Ser Lys Asp Thr Tyr
        275                 280                 285

Asp Asp Asp Leu Asp Asn Leu Leu Ala Gln Ile Gly Asp Gln Tyr Ala
    290                 295                 300

Asp Leu Phe Leu Ala Ala Lys Asn Leu Ser Asp Ala Ile Leu Leu Ser
305                 310                 315                 320

Asp Ile Leu Arg Val Asn Thr Glu Ile Thr Lys Ala Pro Leu Ser Ala
                325                 330                 335

Ser Met Ile Lys Arg Tyr Asp Glu His His Gln Asp Leu Thr Leu Leu
            340                 345                 350

Lys Ala Leu Val Arg Gln Gln Leu Pro Glu Lys Tyr Lys Glu Ile Phe
        355                 360                 365

Phe Asp Gln Ser Lys Asn Gly Tyr Ala Gly Tyr Ile Asp Gly Gly Ala
    370                 375                 380
```

```
Ser Gln Glu Glu Phe Tyr Lys Phe Ile Lys Pro Ile Leu Glu Lys Met
385                 390                 395                 400

Asp Gly Thr Glu Glu Leu Leu Val Lys Leu Asn Arg Glu Asp Leu Leu
                405                 410                 415

Arg Lys Gln Arg Thr Phe Asp Asn Gly Ser Ile Pro His Gln Ile His
            420                 425                 430

Leu Gly Glu Leu His Ala Ile Leu Arg Arg Gln Glu Asp Phe Tyr Pro
        435                 440                 445

Phe Leu Lys Asp Asn Arg Glu Lys Ile Glu Lys Ile Leu Thr Phe Arg
    450                 455                 460

Ile Pro Tyr Tyr Val Gly Pro Leu Ala Arg Gly Asn Ser Arg Phe Ala
465                 470                 475                 480

Trp Met Thr Arg Lys Ser Glu Glu Thr Ile Thr Pro Trp Asn Phe Glu
                485                 490                 495

Glu Val Val Asp Lys Gly Ala Ser Ala Gln Ser Phe Ile Glu Arg Met
            500                 505                 510

Thr Asn Phe Asp Lys Asn Leu Pro Asn Glu Lys Val Leu Pro Lys His
        515                 520                 525

Ser Leu Leu Tyr Glu Tyr Phe Thr Val Tyr Asn Glu Leu Thr Lys Val
    530                 535                 540

Lys Tyr Val Thr Glu Gly Met Arg Lys Pro Ala Phe Leu Ser Gly Glu
545                 550                 555                 560

Gln Lys Lys Ala Ile Val Asp Leu Leu Phe Lys Thr Asn Arg Lys Val
                565                 570                 575

Thr Val Lys Gln Leu Lys Glu Asp Tyr Phe Lys Lys Ile Glu Cys Phe
            580                 585                 590

Asp Ser Val Glu Ile Ser Gly Val Glu Asp Arg Phe Asn Ala Ser Leu
        595                 600                 605

Gly Thr Tyr His Asp Leu Leu Lys Ile Ile Lys Asp Lys Asp Phe Leu
    610                 615                 620

Asp Asn Glu Glu Asn Glu Asp Ile Leu Glu Asp Ile Val Leu Thr Leu
625                 630                 635                 640

Thr Leu Phe Glu Asp Arg Glu Met Ile Glu Glu Arg Leu Lys Thr Tyr
                645                 650                 655

Ala His Leu Phe Asp Asp Lys Val Met Lys Gln Leu Lys Arg Arg Arg
            660                 665                 670

Tyr Thr Gly Trp Gly Arg Leu Ser Arg Lys Leu Ile Asn Gly Ile Arg
        675                 680                 685

Asp Lys Gln Ser Gly Lys Thr Ile Leu Asp Phe Leu Lys Ser Asp Gly
    690                 695                 700

Phe Ala Asn Arg Asn Phe Met Gln Leu Ile His Asp Asp Ser Leu Thr
705                 710                 715                 720

Phe Lys Glu Asp Ile Gln Lys Ala Gln Val Ser Gly Gln Gly Asp Ser
                725                 730                 735

Leu His Glu His Ile Ala Asn Leu Ala Gly Ser Pro Ala Ile Lys Lys
            740                 745                 750

Gly Ile Leu Gln Thr Val Lys Val Val Asp Glu Leu Val Lys Val Met
        755                 760                 765

Gly Arg His Lys Pro Glu Asn Ile Val Ile Glu Met Ala Arg Glu Asn
    770                 775                 780

Gln Thr Thr Gln Lys Gly Gln Lys Asn Ser Arg Glu Arg Met Lys Arg
785                 790                 795                 800

Ile Glu Glu Gly Ile Lys Glu Leu Gly Ser Gln Ile Leu Lys Glu His
```

-continued

```
                805                 810                 815

Pro Val Glu Asn Thr Gln Leu Gln Asn Glu Lys Leu Tyr Leu Tyr Tyr
            820                 825                 830

Leu Gln Asn Gly Arg Asp Met Tyr Val Asp Gln Glu Leu Asp Ile Asn
        835                 840                 845

Arg Leu Ser Asp Tyr Asp Val Asp His Ile Val Pro Gln Ser Phe Leu
    850                 855                 860

Lys Asp Asp Ser Ile Asp Asn Lys Val Leu Thr Arg Ser Asp Lys Asn
865                 870                 875                 880

Arg Gly Lys Ser Asp Asn Val Pro Ser Glu Glu Val Val Lys Lys Met
                885                 890                 895

Lys Asn Tyr Trp Arg Gln Leu Leu Asn Ala Lys Leu Ile Thr Gln Arg
            900                 905                 910

Lys Phe Asp Asn Leu Thr Lys Ala Glu Arg Gly Gly Leu Ser Glu Leu
        915                 920                 925

Asp Lys Ala Gly Phe Ile Lys Arg Gln Leu Val Glu Thr Arg Gln Ile
    930                 935                 940

Thr Lys His Val Ala Gln Ile Leu Asp Ser Arg Met Asn Thr Lys Tyr
945                 950                 955                 960

Asp Glu Asn Asp Lys Leu Ile Arg Glu Val Lys Val Ile Thr Leu Lys
                965                 970                 975

Ser Lys Leu Val Ser Asp Phe Arg Lys Asp Phe Gln Phe Tyr Lys Val
            980                 985                 990

Arg Glu Ile Asn Asn Tyr His His  Ala His Asp Ala Tyr  Leu Asn Ala
        995                 1000                1005

Val Val  Gly Thr Ala Leu Ile  Lys Lys Tyr Pro Lys  Leu Glu Ser
    1010                1015                1020

Glu Phe  Val Tyr Gly Asp Tyr  Lys Val Tyr Asp Val  Arg Lys Met
    1025                1030                1035

Ile Ala  Lys Ser Glu Gln Glu  Ile Gly Lys Ala Thr  Ala Lys Tyr
    1040                1045                1050

Phe Phe  Tyr Ser Asn Ile Met  Asn Phe Phe Lys Thr  Glu Ile Thr
    1055                1060                1065

Leu Ala  Asn Gly Glu Ile Arg  Lys Arg Pro Leu Ile  Glu Thr Asn
    1070                1075                1080

Gly Glu  Thr Gly Glu Ile Val  Trp Asp Lys Gly Arg  Asp Phe Ala
    1085                1090                1095

Thr Val  Arg Lys Val Leu Ser  Met Pro Gln Val Asn  Ile Val Lys
    1100                1105                1110

Lys Thr  Glu Val Gln Thr Gly  Gly Phe Ser Lys Glu  Ser Ile Leu
    1115                1120                1125

Pro Lys  Arg Asn Ser Asp Lys  Leu Ile Ala Arg Lys  Lys Asp Trp
    1130                1135                1140

Asp Pro  Lys Lys Tyr Gly Gly  Phe Asp Ser Pro Thr  Val Ala Tyr
    1145                1150                1155

Ser Val  Leu Val Val Ala Lys  Val Glu Lys Gly Lys  Ser Lys Lys
    1160                1165                1170

Leu Lys  Ser Val Lys Glu Leu  Leu Gly Ile Thr Ile  Met Glu Arg
    1175                1180                1185

Ser Ser  Phe Glu Lys Asn Pro  Ile Asp Phe Leu Glu  Ala Lys Gly
    1190                1195                1200

Tyr Lys  Glu Val Lys Lys Asp  Leu Ile Ile Lys Leu  Pro Lys Tyr
    1205                1210                1215
```

```
Ser Leu  Phe Glu Leu Glu Asn  Gly Arg Lys Arg Met  Leu Ala Ser
    1220                 1225                 1230

Ala Gly  Glu Leu Gln Lys Gly  Asn Glu Leu Ala Leu  Pro Ser Lys
    1235                 1240                 1245

Tyr Val  Asn Phe Leu Tyr Leu  Ala Ser His Tyr Glu  Lys Leu Lys
    1250                 1255                 1260

Gly Ser  Pro Glu Asp Asn Glu  Gln Lys Gln Leu Phe  Val Glu Gln
    1265                 1270                 1275

His Lys  His Tyr Leu Asp Glu  Ile Ile Glu Gln Ile  Ser Glu Phe
    1280                 1285                 1290

Ser Lys  Arg Val Ile Leu Ala  Asp Ala Asn Leu Asp  Lys Val Leu
    1295                 1300                 1305

Ser Ala  Tyr Asn Lys His Arg  Asp Lys Pro Ile Arg  Glu Gln Ala
    1310                 1315                 1320

Glu Asn  Ile Ile His Leu Phe  Thr Leu Thr Asn Leu  Gly Ala Pro
    1325                 1330                 1335

Ala Ala  Phe Lys Tyr Phe Asp  Thr Thr Ile Asp Arg  Lys Arg Tyr
    1340                 1345                 1350

Thr Ser  Thr Lys Glu Val Leu  Asp Ala Thr Leu Ile  His Gln Ser
    1355                 1360                 1365

Ile Thr  Gly Leu Tyr Glu Thr  Arg Ile Asp Leu Ser  Gln Leu Gly
    1370                 1375                 1380

Gly Asp  Gly Ser Ala Gly Ser  Gly Gly Ser Gly Gly  Ser Gly Pro
    1385                 1390                 1395

Lys Lys  Lys Arg Lys Val
    1400
```

<210> SEQ ID NO 49
<211> LENGTH: 20
<212> TYPE: DNA
<213> ORGANISM: Artificial Sequence
<220> FEATURE:
<223> OTHER INFORMATION: HBB Target Sequence

<400> SEQUENCE: 49
taaggagacc aatagaaact 20

<210> SEQ ID NO 50
<211> LENGTH: 23
<212> TYPE: DNA
<213> ORGANISM: Artificial Sequence
<220> FEATURE:
<223> OTHER INFORMATION: HBB Target Sequence with PAM

<400> SEQUENCE: 50
taaggagacc aatagaaact ggg 23

<210> SEQ ID NO 51
<211> LENGTH: 20
<212> TYPE: RNA
<213> ORGANISM: Artificial Sequence
<220> FEATURE:
<223> OTHER INFORMATION: T223 Spacer Sequence

<400> SEQUENCE: 51
uaaggagacc aauagaaacu 20

<210> SEQ ID NO 52
<211> LENGTH: 100

<212> TYPE: RNA
<213> ORGANISM: Artificial Sequence
<220> FEATURE:
<223> OTHER INFORMATION: T223 sgRNA
<220> FEATURE:
<221> NAME/KEY: misc_feature
<222> LOCATION: (1)..(3)
<223> OTHER INFORMATION: 2' O-methyl phosphorothioate nucleotide
<220> FEATURE:
<221> NAME/KEY: misc_feature
<222> LOCATION: (1)..(4)
<223> OTHER INFORMATION: joined by phosphorothioate bond
<220> FEATURE:
<221> NAME/KEY: misc_feature
<222> LOCATION: (97)..(99)
<223> OTHER INFORMATION: 2' O-methyl phosphorothioate nucleotide
<220> FEATURE:
<221> NAME/KEY: misc_feature
<222> LOCATION: (97)..(100)
<223> OTHER INFORMATION: joined by phosphorothioate bond

<400> SEQUENCE: 52
uaaggagacc aauagaaacu guuuuagagc uagaaauagc aaguuaaaau aaggcuaguc 60
cguuaucaac uugaaaaagu ggcaccgagu cggugcuuuu 100

<210> SEQ ID NO 53
<211> LENGTH: 139
<212> TYPE: DNA
<213> ORGANISM: Artificial Sequence
<220> FEATURE:
<223> OTHER INFORMATION: Segment of wild-type HBB gene

<400> SEQUENCE: 53
catctgactc ctgaggagaa gtctgccgtt actgccctgt ggggcaaggt gaacgtggat 60
gaagttggtg gtgaggccct gggcaggttg gtatcaaggt tacaagacag gtttaaggag 120
accaatagaa actgggcat 139

<210> SEQ ID NO 54
<211> LENGTH: 139
<212> TYPE: DNA
<213> ORGANISM: Artificial Sequence
<220> FEATURE:
<223> OTHER INFORMATION: Segment of HBB gene with beta-thal mutation

<400> SEQUENCE: 54
catctgactc ctgaggagaa gtctgcagtt actgccctgt ggggcaaggt gaacgtggat 60
gaagttggag gtgaggccct gggcaggttg gtatcaaggt tacaagacag gtttaaggag 120
accaatagaa actgggcat 139

<210> SEQ ID NO 55
<211> LENGTH: 1178
<212> TYPE: DNA
<213> ORGANISM: Artificial Sequence
<220> FEATURE:
<223> OTHER INFORMATION: EF1a promoter

<400> SEQUENCE: 55
ggctccggtg cccgtcagtg ggcagagcgc acatcgccca cagtccccga gaagttgggg 60
ggaggggtcg gcaattgaac cggtgcctag agaaggtggc gcggggtaaa ctgggaaagt 120
gatgtcgtgt actggctccg cctttttccc gagggtgggg gagaaccgta tataagtgca 180
gtagtcgccg tgaacgttct ttttcgcaac gggtttgccg ccagaacaca ggtaagtgcc 240
gtgtgtggtt cccgcgggcc tggcctcttt acgggttatg gcccttgcgt gccttgaatt 300
acttccactg gctgcagtac gtgattcttg atcccgagct tcgggttgga agtgggtggg 360
agagttcgag gccttgcgct taaggagccc cttcgcctcg tgcttgagtt gaggcctggc 420
ctgggcgctg gggccgccgc gtgcgaatct ggtggcacct tcgcgcctgt ctcgctgctt 480
tcgataagtc tctagccatt taaaattttt gatgacctgc tgcgacgctt tttttctggc 540
aagatagtct tgtaaatgcg ggccaagatc tgcacactgg tatttcggtt tttggggccg 600
cgggcggcga cggggcccgt gcgtcccagc gcacatgttc ggcgaggcgg ggcctgcgag 660
cgcggccacc gagaatcgga cgggggtagt ctcaagctgg ccggcctgct ctggtgcctg 720
gcctcgcgcc gccgtgtatc gccccgccct gggcggcaag gctggcccgg tcggcaccag 780
ttgcgtgagc ggaaagatgg ccgcttcccg gccctgctgc agggagctca aaatggagga 840
cgcggcgctc gggagagcgg gcgggtgagt cacccacaca aaggaaaagg gcctttccgt 900
cctcagccgt cgcttcatgt gactccacgg agtaccgggc gccgtccagg cacctcgatt 960
agttctcgag cttttggagt acgtcgtctt taggttgggg ggaggggttt tatgcgatgg 1020
agtttcccca cactgagtgg gtggagactg aagttaggcc agcttggcac ttgatgtaat 1080
tctccttgga atttgccctt tttgagtttg gatcttggtt cattctcaag cctcagacag 1140
tggttcaaag ttttttctt ccatttcagg tgtcgtga 1178

<210> SEQ ID NO 56
<211> LENGTH: 112
<212> TYPE: DNA
<213> ORGANISM: Artificial Sequence
<220> FEATURE:
<223> OTHER INFORMATION: AAV.320 sequence with correction to GAA

<400> SEQUENCE: 56
gaagagaaaa gcgctgtgac cgcactctgg ggtaaagtga acgtcgacga ggtgggcggt 60
gaagctctcg gaaggttggt atcaaggtta caagacaggt ttaaggagac ga 112

<210> SEQ ID NO 57
<211> LENGTH: 4435
<212> TYPE: DNA
<213> ORGANISM: Artificial Sequence
<220> FEATURE:
<223> OTHER INFORMATION: AAV.320 with correction to GAA

<400> SEQUENCE: 57
cttgctttga caattttggt ctttcagaat actataaata taacctatat tataatttca 60
taaagtctgt gcattttctt tgacccagga tatttgcaaa agacatattc aaacttccgc 120
agaacacttt atttcacata tacatgcctc ttatatcagg gatgtgaaac agggtcttga 180
aaactgtcta aatctaaaac aatgctaatg caggtttaaa tttaataaaa taaaatccaa 240
aatctaacag ccaagtcaaa tctgcatgtt ttaacattta aaatatttta aagacgtctt 300
ttcccaggat tcaacatgtg aaatcttttc tcagggatac acgtgtgcct agatcctcat 360
tgctttagtt ttttacagag gaatgaatat aaaaagaaaa tacttaaatt ttatccctct 420
tacctctata atcatacata ggcataattt tttaacctag gctccagata gccatagaag 480
aaccaaacac tttctgcgtg tgtgagaata atcagagtga gattttttca caagtacctg 540
atgagggttg agacaggtag aaaaagtgag agatctctat ttatttagca ataatagaga 600
aagcatttaa gagaataaag caatggaaat aagaaatttg taaatttcct tctgataact 660
agaaatagag gatccagttt cttttggtta acctaaattt tatttcattt tattgtttta 720
ttttatttta ttttatttta ttttgtgtaa tcgtagtttc agagtgttag agctgaaagg 780

```
aagaagtagg agaaacatgc aaagtaaaag tataacactt tccttactaa accgacatgg    840
gtttccaggt aggggcagga ttcaggatga ctgacagggc ccttagggaa cactgagacc    900
ctacgctgac ctcataaatg cttgctacct ttgctgtttt aattacatct tttaatagca    960
ggaagcagaa ctctgcactt caaaagtttt tcctcacctg aggagttaat ttagtacaag   1020
gggaaaaagt acagggggat gggagaaagg cgatcacgtt gggaagctat agagaaagaa   1080
gagtaaattt tagtaaagga ggtttaaaca aacaaaatat aaagagaaat aggaacttga   1140
atcaaggaaa tgattttaaa acgcagtatt cttagtggac tagaggaaaa aaataatctg   1200
agccaagtag aagacctttt cccctcctac ccctactttc taagtcacag aggctttttg   1260
ttcccccaga cactcttgca gattagtcca ggcagaaaca gttagatgtc cccagttaac   1320
ctcctatttg acaccactga ttaccccatt gatagtcaca ctttgggttg taagtgactt   1380
tttatttatt tgtatttttg actgcattaa gaggtctcta gtttttttatc tcttgtttcc   1440
caaaacctaa taagtaacta atgcacagag cacattgatt tgtatttatt ctatttttag   1500
acataattta ttagcatgca tgagcaaatt aagaaaaaca acaacaaatg aatgcatata   1560
tatgtatatg tatgtgtgta tatatacaca catatatata tatatttttt cttttcttac   1620
cagaaggttt taatccaaat aaggagaaga tatgcttaga accgaggtag agttttcatc   1680
cattctgtcc tgtaagtatt ttgcatattc tggagacgca ggaagagatc catctacata   1740
tcccaaagct gaattatggt agacaaaact cttccacttt tagtgcatca acttcttatt   1800
tgtgtaataa gaaaattggg aaaacgatct tcaatatgct taccaagctg tgattccaaa   1860
tattacgtaa atacacttgc aaaggaggat gtttttagta gcaatttgta ctgatggtat   1920
ggggccaaga gatatatctt agagggaggg ctgagggttt gaagtccaac tcctaagcca   1980
gtgccagaag agccaaggac aggtacggct gtcatcactt agacctcacc ctgtggagcc   2040
acaccctagg gttggccaat ctactcccag gagcagggag ggcaggagcc agggctgggc   2100
ataaaagtca gggcagagcc atctattgct tacatttgct tctgacacaa ctgtgttcac   2160
tagcaacctc aaacagacac catggtgcat ctgactcctg aagagaaaag cgctgtgacc   2220
gcactctggg gtaaagtgaa cgtcgacgag gtgggcggtg aagctctcgg aaggttggta   2280
tcaaggttac aagacaggtt taaggagacg aatagaaact gggcatgtgg agacagagaa   2340
gactcttggg tttctgatag gcactgactc tctctgccta ttggtctatt ttcccaccct   2400
taggctgctg gtggtctacc cttggaccca gaggttcttt gagtcctttg gggatctgtc   2460
cactcctgat gctgttatgg gcaaccctaa ggtgaaggct catggcaaga aagtgctcgg   2520
tgcctttagt gatggcctgg ctcacctgga caacctcaag ggcacctttg ccacactgag   2580
tgagctgcac tgtgacaagc tgcacgtgga tcctgagaac ttcagggtga gtctatggga   2640
cgcttgatgt tttctttccc cttcttttct atggttaagt tcatgtcata ggaaggggat   2700
aagtaacagg gtacagttta gaatgggaaa cagacgaatg attgcatcag tgtggaagtc   2760
tcaggatcgt tttagtttct tttatttgct gttcataaca attgttttct tttgtttaat   2820
tcttgctttc ttttttttc ttctccgcaa tttttactat tatacttaat gccttaacat   2880
tgtgtataac aaaaggaaat atctctgaga tacattaagt aacttaaaaa aaaactttac   2940
acagtctgcc tagtacatta ctatttggaa tatatgtgtg cttatttgca tattcataat   3000
ctccctactt tattttcttt tatttttaat tgatacataa tcattataca tatttatggg   3060
ttaaagtgta atgttttaat atgtgtacac atattgacca aatcagggta attttgcatt   3120
```

```
tgtaatttta aaaaatgctt tcttctttta atatactttt ttgtttatct tatttctaat   3180
actttcccta atctctttct ttcagggcaa taatgataca atgtatcatg cctctttgca   3240
ccattctaaa gaataacagt gataatttct gggttaaggc aatagcaata tctctgcata   3300
taaatatttc tgcatataaa ttgtaactga tgtaagaggt ttcatattgc taatagcagc   3360
tacaatccag ctaccattct gcttttattt tatggttggg ataaggctgg attattctga   3420
gtccaagcta ggcccttttg ctaatcatgt tcatacctct tatcttcctc ccacagctcc   3480
tgggcaacgt gctggtctgt gtgctggccc atcactttgg caaagaattc accccaccag   3540
tgcaggctgc ctatcagaaa gtggtggctg gtgtggctaa tgccctggcc cacaagtatc   3600
actaagctcg ctttcttgct gtccaatttc tattaaaggt tcctttgttc cctaagtcca   3660
actactaaac tgggggatat tatgaagggc cttgagcatc tggattctgc ctaataaaaa   3720
acatttattt tcattgcaat gatgtattta aattatttct gaatatttta ctaaaaaggg   3780
aatgtgggag gtcagtgcat ttaaaacata aagaaatgaa gagctagttc aaaccttggg   3840
aaaatacact atatcttaaa ctccatgaaa gaaggtgagg ctgcaaacag ctaatgcaca   3900
ttggcaacag cccctgatgc atatgcctta ttcatccctc agaaaaggat tcaagtagag   3960
gcttgatttg gaggttaaag ttttgctatg ctgtatttta cattacttat tgttttagct   4020
gtcctcatga atgtcttttc actacccatt tgcttatcct gcatctctca gccttgactc   4080
cactcagttc tcttgcttag agataccacc tttcccctga agtgttcctt ccatgtttta   4140
cggcgagatg gtttctcctc gcctggccac tcagccttag ttgtctctgt tgtcttatag   4200
aggtctactt gaagaaggaa aaacaggggt catggtttga ctgtcctgtg agcccttctt   4260
ccctgcctcc cccactcaca gtgacccgga atctgcagtg ctagtctccc ggaactatca   4320
ctctttcaca gtctgctttg gaaggactgg gcttagtatg aaaagttagg actgagaaga   4380
atttgaaagg cggctttttg tagcttgata ttcactactg tcttattacc ctgtc        4435
```

<210> SEQ ID NO 58
<211> LENGTH: 4760
<212> TYPE: DNA
<213> ORGANISM: Artificial Sequence
<220> FEATURE:
<223> OTHER INFORMATION: AAV 320 with ITRs and correction to GAA

<400> SEQUENCE: 58

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtcttgct ttgacaattt tggtctttca gaatactata    180
aatataacct atattataat ttcataaagt ctgtgcattt tctttgaccc aggatatttg    240
caaaagacat attcaaactt ccgcagaaca ctttatttca catatacatg cctcttatat    300
cagggatgtg aaacagggtc ttgaaaactg tctaaatcta aaacaatgct aatgcaggtt    360
taaatttaat aaaataaaat ccaaaatcta acagccaagt caaatctgca tgttttaaca    420
tttaaaatat tttaaagacg tcttttccca ggattcaaca tgtgaaatct tttctcaggg    480
atacacgtgt gcctagatcc tcattgcttt agttttttac agaggaatga atataaaaag    540
aaaatactta aattttatcc ctcttacctc tataatcata catagcata atttttttaac    600
ctaggctcca gatagccata gaagaaccaa acactttctg cgtgtgtgag aataatcaga    660
gtgagatttt ttcacaagta cctgatgagg gttgagacag gtagaaaaag tgagagatct    720
ctatttattt agcaataata gagaaagcat ttaagagaat aaagcaatgg aaataagaaa    780
```

```
tttgtaaatt tccttctgat aactagaaat agaggatcca gtttcttttg gttaacctaa    840
attttatttc attttattgt tttattttat tttattttat tttattttgt gtaatcgtag    900
tttcagagtg ttagagctga aaggaagaag taggagaaac atgcaaagta aaagtataac    960
actttcctta ctaaaccgac atgggtttcc aggtaggggc aggattcagg atgactgaca   1020
gggcccttag ggaacactga gaccctacgc tgacctcata aatgcttgct acctttgctg   1080
ttttaattac atcttttaat agcaggaagc agaactctgc acttcaaaag tttttcctca   1140
cctgaggagt taatttagta caaggggaaa aagtacaggg ggatgggaga aaggcgatca   1200
cgttgggaag ctatagagaa agaagagtaa attttagtaa aggaggttta aacaaacaaa   1260
atataaagag aaataggaac ttgaatcaag gaaatgattt taaaacgcag tattcttagt   1320
ggactagagg aaaaaaataa tctgagccaa gtagaagacc ttttcccctc ctacccctac   1380
tttctaagtc acagaggctt tttgttcccc cagacactct tgcagattag tccaggcaga   1440
aacagttaga tgtccccagt taacctccta tttgacacca ctgattaccc cattgatagt   1500
cacactttgg gttgtaagtg actttttatt tatttgtatt tttgactgca ttaagaggtc   1560
tctagttttt tatctcttgt ttcccaaaac ctaataagta actaatgcac agagcacatt   1620
gatttgtatt tattctattt ttagacataa tttattagca tgcatgagca aattaagaaa   1680
aacaacaaca aatgaatgca tatatatgta tatgtatgtg tgtatatata cacacatata   1740
tatatatatt ttttcttttc ttaccagaag gttttaatcc aaataaggag aagatatgct   1800
tagaaccgag gtagagtttt catccattct gtcctgtaag tattttgcat attctggaga   1860
cgcaggaaga gatccatcta catatcccaa agctgaatta tggtagacaa aactcttcca   1920
cttttagtgc atcaacttct tatttgtgta ataagaaaat tgggaaaacg atcttcaata   1980
tgcttaccaa gctgtgattc caaatattac gtaaatacac ttgcaaagga ggatgttttt   2040
agtagcaatt tgtactgatg gtatggggcc aagagatata tcttagaggg agggctgagg   2100
gtttgaagtc caactcctaa gccagtgcca gaagagccaa ggacaggtac ggctgtcatc   2160
acttagacct caccctgtgg agccacaccc tagggttggc caatctactc ccaggagcag   2220
ggagggcagg agccagggct gggcataaaa gtcagggcag agccatctat tgcttacatt   2280
tgcttctgac acaactgtgt tcactagcaa cctcaaacag acaccatggt gcatctgact   2340
cctgaagaga aaagcgctgt gaccgcactc tggggtaaag tgaacgtcga cgaggtgggc   2400
ggtgaagctc tcggaaggtt ggtatcaagg ttacaagaca ggtttaagga gacgaataga   2460
aactgggcat gtggagacag agaagactct tgggtttctg ataggcactg actctctctg   2520
cctattggtc tattttccca cccttaggct gctggtggtc tacccttgga cccagaggtt   2580
ctttgagtcc tttggggatc tgtccactcc tgatgctgtt atgggcaacc ctaaggtgaa   2640
ggctcatggc aagaaagtgc tcggtgcctt tagtgatggc ctggctcacc tggacaacct   2700
caagggcacc tttgccacac tgagtgagct gcactgtgac aagctgcacg tggatcctga   2760
gaacttcagg gtgagtctat gggacgcttg atgttttctt tccccttctt ttctatggtt   2820
aagttcatgt cataggaagg ggataagtaa cagggtacag tttagaatgg gaaacagacg   2880
aatgattgca tcagtgtgga agtctcagga tcgttttagt ttcttttatt tgctgttcat   2940
aacaattgtt ttcttttgtt taattcttgc tttctttttt tttcttctcc gcaattttta   3000
ctattatact taatgcctta acattgtgta taacaaaagg aaatatctct gagatacatt   3060
aagtaactta aaaaaaaact ttacacagtc tgcctagtac attactattt ggaatatatg   3120
```

-continued

```
tgtgcttatt tgcatattca taatctccct actttatttt cttttatttt taattgatac   3180

ataatcatta tacatattta tgggttaaag tgtaatgttt taatatgtgt acacatattg   3240

accaaatcag ggtaattttg catttgtaat tttaaaaaat gctttcttct tttaatatac   3300

tttttgttt atcttatttc taatactttc cctaatctct ttctttcagg gcaataatga    3360

tacaatgtat catgcctctt tgcaccattc taaagaataa cagtgataat ttctgggtta   3420

aggcaatagc aatatctctg catataaata tttctgcata taaattgtaa ctgatgtaag   3480

aggtttcata ttgctaatag cagctacaat ccagctacca ttctgctttt attttatggt   3540

tgggataagg ctggattatt ctgagtccaa gctaggccct tttgctaatc atgttcatac   3600

ctcttatctt cctcccacag ctcctgggca acgtgctggt ctgtgtgctg gcccatcact   3660

ttggcaaaga attcacccca ccagtgcagg ctgcctatca gaaagtggtg gctggtgtgg   3720

ctaatgccct ggcccacaag tatcactaag ctcgctttct tgctgtccaa tttctattaa   3780

aggttccttt gttccctaag tccaactact aaactggggg atattatgaa gggccttgag   3840

catctggatt ctgcctaata aaaaacattt attttcattg caatgatgta tttaaattat   3900

ttctgaatat tttactaaaa agggaatgtg ggaggtcagt gcatttaaaa cataaagaaa   3960

tgaagagcta gttcaaacct tgggaaaata cactatatct taaactccat gaaagaaggt   4020

gaggctgcaa acagctaatg cacattggca acagcccctg atgcatatgc cttattcatc   4080

cctcagaaaa ggattcaagt agaggcttga tttggaggtt aaagttttgc tatgctgtat   4140

tttacattac ttattgtttt agctgtcctc atgaatgtct tttcactacc catttgctta   4200

tcctgcatct ctcagccttg actccactca gttctcttgc ttagagatac cacctttccc   4260

ctgaagtgtt ccttccatgt tttacggcga gatggtttct cctcgcctgg ccactcagcc   4320

ttagttgtct ctgttgtctt atagaggtct acttgaagaa ggaaaaacag ggtcatggt    4380

ttgactgtcc tgtgagccct tcttccctgc ctcccccact cacagtgacc cggaatctgc   4440

agtgctagtc tcccggaact atcactcttt cacagtctgc tttggaagga ctgggcttag   4500

tatgaaaagt taggactgag aagaatttga aaggcggctt tttgtagctt gatattcact   4560

actgtcttat taccctgtcg gtaaccacgt gcggccgagg ctgcagcgtc gtcctcccta   4620

ggaacccta gtgatggagt tggccactcc ctctctgcgc gctcgctcgc tcactgaggc    4680

cgggcgacca aaggtcgccc gacgcccggg ctttgcccgg gcggcctcag tgagcgagcg   4740

agcgcgcagc tgcctgcagg                                               4760
```